(12) United States Patent
Song et al.

(10) Patent No.: US 12,167,685 B2
(45) Date of Patent: Dec. 10, 2024

(54) ORGANIC COMPOUNDS AND ORGANIC LIGHT EMITTING DISPLAY DEVICE USING THE SAME

(71) Applicant: LG Display Co., Ltd., Seoul (KR)

(72) Inventors: InBum Song, Seoul (KR); SangBeom Kim, Paju-si (KR); Sunghoon Kim, Seoul (KR); Sang-hoon Hong, Seoul (KR); Seong-min Park, Seoul (KR); TaeWan Lee, Seoul (KR); SunJae Kim, Goyang-si (KR); DongHun Lee, Seoul (KR); Jeonghoe Heo, Seoul (KR)

(73) Assignee: LG Display Co., Ltd., Seoul (KR)

( * ) Notice: Subject to any disclaimer, the term of this patent is extended or adjusted under 35 U.S.C. 154(b) by 570 days.

(21) Appl. No.: 17/078,155

(22) Filed: Oct. 23, 2020

(65) Prior Publication Data
US 2021/0126200 A1    Apr. 29, 2021

(30) Foreign Application Priority Data

Oct. 23, 2019 (KR) .......................... 10-2019-0132197
Sep. 28, 2020 (KR) .......................... 10-2020-0125521

(51) Int. Cl.
*H01L 51/00* (2006.01)
*C07D 311/96* (2006.01)
(Continued)

(52) U.S. Cl.
CPC ......... *H10K 85/636* (2023.02); *C07D 311/96* (2013.01); *C07D 407/12* (2013.01);
(Continued)

(58) Field of Classification Search
None
See application file for complete search history.

(56) References Cited

U.S. PATENT DOCUMENTS

2012/0112173 A1\* 5/2012 Matsumoto .......... H10K 85/615
257/E51.026
2015/0333277 A1\* 11/2015 Kim ..................... C07D 335/04
546/14
(Continued)

FOREIGN PATENT DOCUMENTS

CN    108137527 A    6/2018
WO    2019/054633 A1    3/2019

OTHER PUBLICATIONS

First Office Action and Search Report issued in corresponding CN Application No. 202011150407.4, dated Apr. 27, 2023.

*Primary Examiner* — Jay Yang
(74) *Attorney, Agent, or Firm* — Morgan, Lewis & Bockius LLP

(57) ABSTRACT

The present disclosure relates to organic compounds and an organic light emitting display device using the same and more particularly, to an organic light emitting display in which an organic compound represented by the following Chemical Formula 1 is used for a hole transport layer or an electron blocking layer of the organic light emitting element to easily transport holes injected from an anode to a light emitting layer and suppress the leakage of electrons from the light emitting layer. Therefore, it is possible to provide an organic light emitting display device with high luminous efficiency and long lifetime.

(Continued)

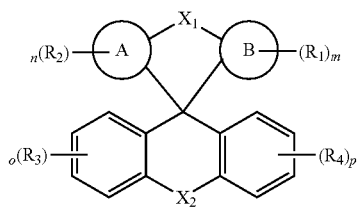

[Chemical Formula 1]

20 Claims, 2 Drawing Sheets

(51) Int. Cl.
C07D 407/12 (2006.01)
C09K 11/06 (2006.01)
H10K 85/60 (2023.01)
H10K 50/15 (2023.01)
H10K 50/18 (2023.01)

(52) U.S. Cl.
CPC ............ *C09K 11/06* (2013.01); *H10K 85/633* (2023.02); *C09K 2211/1018* (2013.01); *H10K 50/15* (2023.02); *H10K 50/18* (2023.02); *H10K 85/615* (2023.02); *H10K 85/626* (2023.02); *H10K 85/6574* (2023.02)

(56) References Cited

U.S. PATENT DOCUMENTS

2018/0287068 A1   10/2018  Ha et al.
2019/0363263 A1*  11/2019  Uno ................. C07F 7/0816
2021/0013420 A1*   1/2021  So .................... C07D 411/12

* cited by examiner

ORGANIC COMPOUNDS AND ORGANIC LIGHT EMITTING DISPLAY DEVICE USING THE SAME

CROSS-REFERENCE TO RELATED APPLICATIONS

This application claims the priority of Korean Patent Application No. 10-2019-0132197 filed on Oct. 23, 2019, and NO. 10-2020-0125521 filed on Sep. 28, 2020, in the Korean Intellectual Property Office, the disclosure of which is incorporated herein by reference.

BACKGROUND

Technical Field

The present disclosure relates to organic compounds and an organic light emitting display device using the same. More particularly, the present disclosure relates to novel organic compounds with hole transport properties and electron blocking properties and an organic light emitting display device which can have high efficiency and long lifetime by applying the organic compounds to an organic layer.

Discussion of the Related Art

An organic light emitting display device (OLED) uses an organic light emitting element that is a self-light emitting element. Thus, the organic light emitting display device does not need an additional light source unlike a liquid crystal display device (LCD) using a backlight unit. Therefore, the organic light emitting display device has a simple structure and is easy to manufacture. Further, the organic light emitting display device is advantageous in terms of power consumption since it is driven with a low voltage. Also, the organic light emitting display device has excellent color expression ability, high luminance, wide viewing angle, high response speed, and high contrast ratio. Therefore, the organic light emitting display device is being actively developed as a next-generation display device.

When a voltage is applied to an organic light emitting element, holes injected from an anode and electrons injected from a cathode recombine in a light emitting layer to form excitons. The organic light emitting element emits light when the excitons thus formed transit from an unstable excited state to a stable ground state.

In general, the organic light emitting element includes various layers to improve luminous efficiency in addition to an anode that supplies holes, a cathode that supplies electrons and a light emitting layer (EML). For example, the organic light emitting element has a structure in which an anode, a hole injection layer (HIL), a hole transport layer (HTL), a light emitting layer, an electron transport layer (ETL) and an electron injection layer (EIL) are laminated.

In recent years, displays using organic light emitting elements have been scaled up and thinned. In line with this trend, the displays have been required to be driven with low power while having lifetime and luminous efficiency equal to or greater than those of conventional displays.

SUMMARY

Accordingly, embodiments of the present disclosure are directed to organic compounds and an organic light emitting display device using the same that substantially obviate one or more of the problems due to limitations and disadvantages of the related art.

To achieve high efficiency and long lifetime with a low voltage, a light emitting layer of an organic light emitting element needs to be designed so that holes and electrons can be smoothly transferred, and charges injected into the light emitting layer do not leak to an adjacent layer.

An object to be achieved by the present disclosure is to provide organic compounds that have hole transport properties and electron blocking properties and thus can be used in a hole transport layer or an electron blocking layer of an organic light emitting display device.

Another object to be achieved by the present disclosure is to provide an organic light emitting display device with high luminous efficiency and long lifetime.

Additional features and aspects will be set forth in the description that follows, and in part will be apparent from the description, or may be learned by practice of the inventive concepts provided herein: Other features and aspects of the inventive concepts may be realized and attained by the structure particularly pointed out in the written description, or derivable therefrom, and the claims hereof as well as the appended drawings.

According to an aspect of the present disclosure, an organic compound is represented by the following Chemical Formula 1:

[Chemical Formula 1]

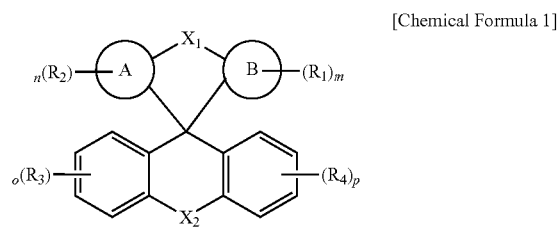

wherein in the above Chemical Formula 1,
a ring A and a ring B are different from each other and each independently substituted or unsubstituted $C_6$-$C_{10}$ arylene groups,
$X_1$ and $X_2$ are the same as or different from each other, and each independently selected from the group consisting of a single bond, $C(R_5)(R_6)$, O and S, and at least one of $X_1$ and $X_2$ is O or S,
$R_1$, $R_2$, $R_3$ and $R_4$ are the same as or different from each other, and each independently selected from the group consisting of a functional group represented by the following Chemical Formula 2, hydrogen, deuterium, substituted or unsubstituted $C_1$-$C_{20}$ alkyl groups, substituted or unsubstituted $C_2$-$C_{20}$ alkenyl groups, substituted or unsubstituted $C_2$-$C_{24}$ alkynyl groups, substituted or unsubstituted $C_1$-$C_{20}$ alkoxy groups; substituted or unsubstituted $C_1$-$C_{20}$ alkyl amine groups, substituted or unsubstituted $C_1$-$C_{20}$ alkyl silyl groups, substituted or unsubstituted $C_1$-$C_{20}$ alkoxy silyl groups, substituted or unsubstituted $C_3$-$C_{30}$ cycloalkyl silyl groups, substituted or unsubstituted $C_5$-$C_{30}$ aryl silyl groups, substituted or unsubstituted $C_5$-$C_{30}$ aryl groups, substituted or unsubstituted $C_5$-$C_{30}$ aryl amine groups, substituted or unsubstituted $C_3$-$C_{30}$ heteroaryl groups, a halogen group, a cyano group, a carboxyl group, a carbonyl group, an amine group, a nitro group, and combinations thereof, one or two of $R_1$, $R_2$, $R_3$ and $R_4$ are the functional group represented by the following Chemical Formula 2, $R_5$ and $R_6$ are the same as or different from each other, and each independently selected from the group consisting of hydrogen, deuterium, substituted or unsubstituted $C_1$-$C_{20}$ alkyl groups, substituted or unsubstituted $C_2$-$C_{20}$ alkenyl groups, substituted or unsubstituted $C_2$-$C_{24}$ alkynyl groups, substituted or unsubstituted $C_1$-$C_{20}$ alkoxy groups, substituted or unsubstituted $C_1$-$C_{20}$ alkyl amine groups, substituted or unsubstituted $C_1$-$C_{20}$ alkyl silyl groups, substituted or unsubstituted $C_1$-$C_{20}$ alkoxy silyl groups, substituted or unsubstituted $C_3$-$C_{30}$ cycloalkyl silyl groups, substituted or unsubstituted $C_5$-$C_{30}$ aryl silyl groups, substituted or unsubstituted $C_5$-$C_{30}$ aryl groups, substituted or unsubstituted $C_5$-$C_{30}$ aryl amine groups, substituted or unsubstituted $C_3$-$C_{30}$ heteroaryl groups, a halogen group, a cyano group, a carboxyl group, a carbonyl group, an amine group, a nitro group, and combinations thereof, m and n are each independently an integer of 0 to 6, and p are each independently an integer of 0 to 4, a sum of m, n, o and p is equal to or more than 1,

[Chemical Formula 2]

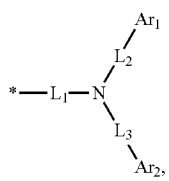

and in the above Chemical Formula 2, $L_1$, $L_2$ and $L_3$ are the same as or different from each other, and each independently selected from the group consisting of a single bond, substituted or unsubstituted $C_5$-$C_{30}$ arylene groups, substituted or unsubstituted $C_3$-$C_{30}$ heteroarylene groups, substituted or unsubstituted $C_1$-$C_{20}$ alkylene groups, substituted or unsubstituted $C_3$-$C_{20}$ cycloalkylene groups, substituted or unsubstituted. $C_2$-$C_{20}$ alkenylene groups, substituted or unsubstituted $C_3$-$C_{20}$ cycloalkenylene groups, substituted or unsubstituted $C_1$-$C_{20}$ heteroalkylene groups, substituted or unsubstituted $C_3$-$C_{20}$ heterocycloalkylene groups, substituted or unsubstituted $C_2$-$C_{20}$ heteroalkenylene groups and substituted or unsubstituted $C_3$-$C_{20}$ heterocycloalkenylene groups, and $Ar_1$ and $Ar_2$ are the same as or different from each other, and each independently selected from the group consisting of substituted or unsubstituted $C_5$-$C_{30}$ aryl groups, substituted or unsubstituted $C_3$-$C_{30}$ heteroaryl groups, substituted or unsubstituted $C_3$-$C_{20}$ cycloalkyl groups, substituted or unsubstituted $C_6$-$C_{30}$ aralkyl groups, substituted or unsubstituted $C_6$-$C_{30}$ heteroaralkyl groups and substituted or unsubstituted $C_5$-$C_{30}$ arylamino groups.

According to another aspect of the present disclosure, an organic light emitting display device, comprising:

a plurality of sub-pixels, wherein at least one of the plurality of sub-pixels includes an organic light emitting element including: an anode; a plurality of organic layers disposed on the anode; and a cathode disposed on the plurality of organic layers, wherein at least one of the plurality of organic layers contains an organic compound represented by Chemical Formula 1. The organic light emitting display device includes an organic layer that contains an organic compound represented by Chemical Formula 1 and thus can easily transport holes injected from an anode to a light emitting layer and effectively trap electrons in the light emitting layer.

Therefore, the recombination efficiency of holes and electrons in the light emitting layer can be improved, which results in high luminous efficiency and long lifetime of the organic light emitting display device.

According to the present disclosure, it is possible to provide a hole transport and electron blocking organic compound having a specific structure. The organic compound of the present disclosure is used in an organic layer, specifically a hole transport layer or an electron blocking layer, of an organic light emitting display device. Thus, it is possible to easily transport holes injected from an anode to a light emitting layer and effectively suppress the leakage of electrons from the light emitting layer. Therefore, it is possible to provide a display device which has an improved recombination efficiency of holes and electrons in the light emitting layer and thus has high luminous efficiency and long lifetime.

The effects according to the present disclosure are not limited to the contents exemplified above, and more various effects are included in the present specification.

BRIEF DESCRIPTION OF THE DRAWINGS

The accompanying drawings, which are included to provide a further understanding of the disclosure and are incorporated in and constitute a part of this application, illustrate embodiments of the disclosure and together with the description serve to explain various principles. In the drawings.

DETAILED DESCRIPTION

Figure 1:
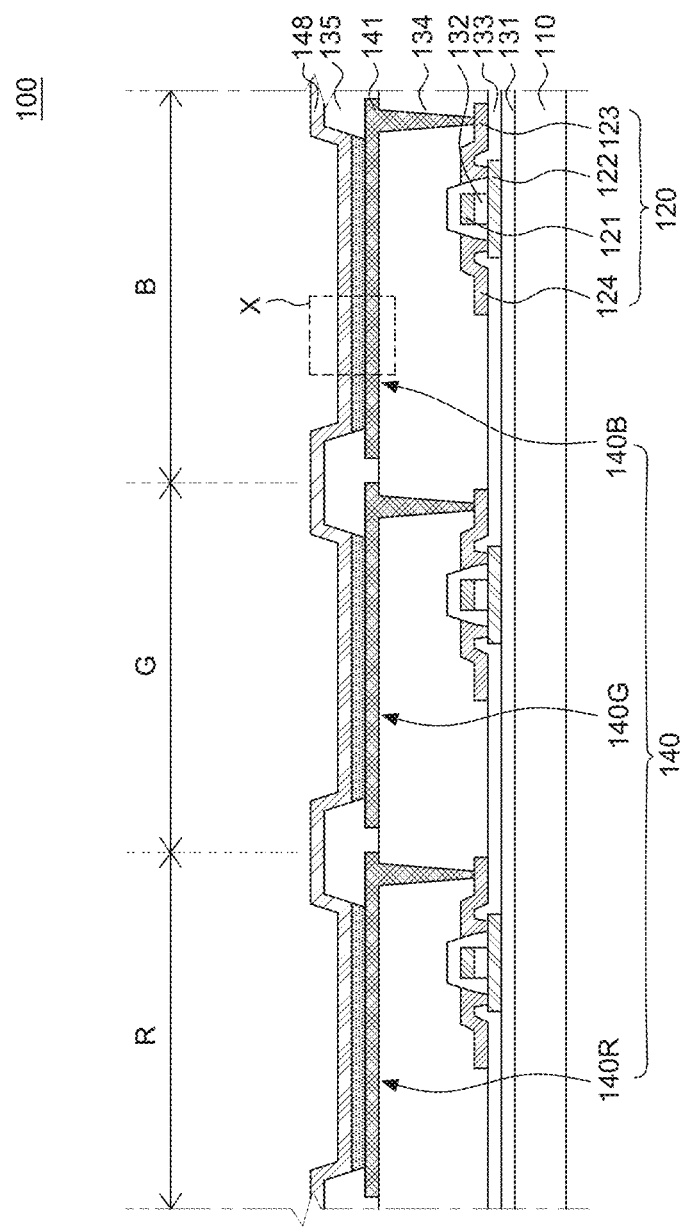
FIG. 1 is a schematic cross-sectional view of an organic light emitting display device according to an exemplary embodiment of the present disclosure.

Advantages and characteristics of the present disclosure and a method of achieving the advantages and characteristics will be clear by referring to exemplary embodiments described below in detail together with the accompanying drawings. However, the present disclosure is not limited to the exemplary embodiments disclosed herein but will be implemented in various forms. The exemplary embodiments are provided by way of example only so that those skilled in the art can fully understand the disclosures of the present disclosure and the scope of the present disclosure. Therefore, the present disclosure will be defined only by the scope of the appended claims.

The shapes, sizes, ratios, angles, numbers, and the like illustrated in the accompanying drawings for describing the exemplary embodiments of the present disclosure are merely examples, and the present disclosure is not limited thereto. Like reference numerals generally denote like elements throughout the specification. Further, in the following description of the present disclosure, a detailed explanation of known related technologies may be omitted to avoid unnecessarily obscuring the subject matter of the present disclosure. The terms such as "including," "having," and "consist of" used herein are generally intended to allow other-components to be added unless the terms are used with the term "only". Any references to singular may include plural unless expressly stated otherwise.

Components are interpreted to include an ordinary error range even if not expressly stated.

When the position relation between two parts is described using the terms such as "on", "above", "below", and "next", one or more parts may be positioned between the two parts unless the terms are used with the term "immediately" or "directly".

When an element or layer is disposed "on" another element or layer, another layer or another element may be interposed directly on the other element or therebetween.

Although the terms "first", "second", and the like are used for describing various components, these components are not confined by these terms. These terms are merely used for distinguishing one component from the other components. Therefore, a first component to be mentioned below may be a second component in a technical concept of the present disclosure.

Like reference numerals generally denote like elements throughout the specification.

A size and a thickness of each component illustrated in the drawing are illustrated for convenience of description, and the present disclosure is not limited to the size and the thickness of the component illustrated.

The features of various embodiments of the present disclosure can be partially or entirely adhered to or combined with each other and can be interlocked and operated in technically various ways, and the embodiments can be carried out independently of or in association with each other.

As used herein, the term "unsubstituted" means that a hydrogen atom is not substituted or the hydrogen atom is substituted by an isotope selected from protium, deuterium and tritium.

As used herein, the term "substituted" means that a hydrogen atom or atom group of a compound is substituted by a substituent. For example, the substituent may be selected from $C_1$-$C_{30}$ alkyl groups, $C_2$-$C_{30}$ alkenyl groups, $C_2$-$C_{24}$ alkynyl groups, $C_3$-$C_{12}$ cycloalkyl groups, $C_2$-$C_{30}$ heterocycloalkyl groups, $C_7$-$C_{30}$ aralkyl groups, $C_6$-$C_{30}$ aryl groups, $C_5$-$C_{30}$ heteroaralkyl groups, $C_1$-$C_{30}$ alkoxy groups, $C_1$-$C_{30}$ alkylamino groups, $C_6$-$C_{30}$ arylamino groups, $C_7$-$C_{30}$ aralkylamino groups, $C_2$-$C_{24}$ heteroarylamino groups, $C_1$-$C_{30}$ alkylsilyl groups, $C_6$-$C_{30}$ arylsilyl groups, $C_6$-$C_{30}$ aryloxy groups, $C_1$-$C_{30}$ alkyl halide groups, a cyano group, a halogen group, a carboxyl group, a hydroxyl group, a carbonyl group, an amine group, a nitro group, and combinations thereof, but may not be limited thereto.

As used herein, the term "hetero" means that at least one of carbon atoms constituting a cyclic saturated or unsaturated hydrocarbon is substituted by a heteroatom such as N, O, S and Se.

As used herein, the term "alkyl" refers to a monovalent substituent derived from linear or branched saturated hydrocarbons. For example, the alkyl may include methyl, ethyl, propyl, n-butyl, iso-butyl, n-pentyl, hexyl, and the like, but may not be limited thereto.

As used herein, the term "alkenyl" refers to a monovalent substituent derived from linear or branched unsaturated hydrocarbons having two or more carbon atoms with at least one C=C bond. For example, the alkenyl may include vinyl, allyl, iso-propenyl, 2-butenyl, and the like, but may not be limited thereto.

As used herein, the term "alkynyl" refers to a monovalent substituent derived from linear or branched unsaturated hydrocarbons having two or more carbon atoms with at least one carbon-carbon triple bond. For example, the alkynyl may include ethynyl, 2-propanyl, and the like, but may not be limited thereto.

As used herein, the term "aryl" refers to a monovalent substituent derived from aromatic hydrocarbons and may have a form in which two or more rings are simply connected to each other in a pendant form or are condensed with each other. For example, the aryl may include phenyl, naphthyl, phenanthryl, and the like, but may not be limited thereto.

As used herein, the term "heteroaryl" refers to a monovalent substituent derived from aromatic hydrocarbons of which at least one carbon in a ring is substituted by a heteroatom such as N, O, S or Se. Furthermore, the heteroaryl may have a form in which two or more rings are simply connected to each other in a pendant form, are condensed with each other, or are condensed with an aryl group. For example, the heteroaryl may include pyridyl, pyrazinyl, pyrimidinyl, pyridazinyl, triazinyl, phenoxathienyl, indolizinyl, indolyl, purinyl, quinolyl, benzothiazole, carbazolyl, N-imidazolyl, 2-pyridinyl, 2-pyrimidinyl, and the like, but may not be limited thereto.

As used herein, the term "aryloxy" refers to a monovalent substituent represented by General Formula, ArO—, in which Ar represents aryl. For example, the aryloxy may include phenyloxy, naphthyloxy, diphenyloxy, and the like, but may not be limited thereto.

As used herein, the term "alkoxy" refers to a monovalent substituent represented by General Formula, RO—, in which R represents linear, branched or cycloalkyl having at least one carbon atom. For example, the alkyloxy may include methoxy, ethoxy, n-propoxy, t-butoxy, n-butoxy, and the like, but may not be limited thereto.

As used herein, the term "cycloalkyl" refers to a monovalent substituent derived from cyclic saturated hydrocarbons having three or more carbon atoms and may include polycyclic saturated hydrocarbons having two or more carbon atoms. Also, the cycloalkyl may be condensed with a cyclic compound. For example, the cycloalkyl may include cyclopropyl, cyclopentyl, cyclohexyl, norbornyl, adamantine, and the like, but may not be limited thereto.

As used herein, the term "heterocycloalkyl" refers to a monovalent substituent derived from cyclic saturated hydrocarbons of which at least one carbon atom in a ring is substituted by a heteroatom such as N, O, S or Se and may include polycyclic saturated hydrocarbons having two or more carbon atoms. For example, the heterocycloalkyl may include morpholine, piperazine, and the like, but may not be limited thereto.

As used herein, the terms "alkyl amine" and "aryl amine" refer to amine substituted by an alkyl group and an aryl group, respectively.

As used herein, the terms "alkyl silyl", "aryl silyl" "alkoxy silyl" and "cycloalkyl silyl" refer to silyl substituted by an alkyl group, an aryl group, an alkoxy group and a cycloalkyl group, respectively.

Hereinafter, the present disclosure will be described with reference to Chemical Formulas and the accompanying drawings.

According to an aspect of the present disclosure, an organic compound is represented by the following Chemical Formula 1:

[Chemical Formula 1]

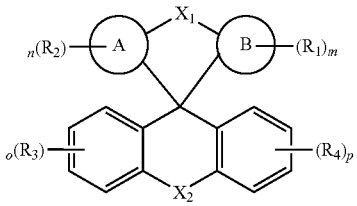

In Chemical Formula 1, a ring A and a ring B are different from each other and each independently substituted or unsubstituted $C_6$-$C_{10}$ arylene groups.

In Chemical Formula 1, $X_1$ and $X_2$ are the same as or different from each other, and each independently selected from the group consisting of a single bond, $C(R_5)(R_6)$, O and S, and at least one of $X_1$ and $X_2$ is O or S.

In Chemical Formula 1, $R_1$, $R_2$, $R_3$ and $R_4$ are the same as or different from each other, and each independently selected from the group consisting of a functional group represented by the following Chemical Formula 2, hydrogen, deuterium, substituted or unsubstituted $C_1$-$C_{20}$ alkyl groups, substituted or unsubstituted $C_2$-$C_{20}$ alkenyl groups, substituted or unsubstituted $C_2$-$C_{24}$ alkynyl groups, substituted or unsubstituted $C_1$-$C_{20}$ alkoxy groups, substituted or unsubstituted $C_1$-$C_{20}$ alkyl amine groups, substituted or unsubstituted $C_1$-$C_{20}$ alkyl silyl groups, substituted or unsubstituted $C_1$-$C_{20}$ alkoxy silyl groups, substituted or unsubstituted $C_3$-$C_{30}$ cycloalkyl silyl groups, substituted or unsubstituted $C_5$-$C_{30}$ aryl silyl groups, substituted or unsubstituted $C_5$-$C_{30}$ aryl groups, substituted or unsubstituted $C_5$-$C_{30}$ aryl amine groups, substituted or unsubstituted $C_3$-$C_{30}$ heteroaryl groups, a halogen group, a cyano group, a carboxyl group, a carbonyl group, an amine group, a nitro group, and combinations thereof.

In Chemical Formula 1, one or two of $R_1$, $R_2$, $R_3$ and $R_4$ are the functional group represented by the following Chemical Formula 2.

In Chemical Formula 1, $R_y$ and $R_6$ are the same as or different from each other, and each independently selected from the group consisting of hydrogen, deuterium, substituted or unsubstituted $C_1$-$C_{20}$ alkyl groups, substituted or unsubstituted $C_2$-$C_{20}$ alkenyl groups, substituted or unsubstituted $C_2$-$C_{24}$ alkynyl groups, substituted or unsubstituted $C_1$-$C_{20}$ alkoxy groups, substituted or unsubstituted $C_1$-$C_{20}$ alkyl amine groups, substituted or unsubstituted $C_1$-$C_{20}$ alkyl silyl groups, substituted or unsubstituted, $C_1$-$C_{20}$ alkoxy silyl groups, substituted or unsubstituted $C_3$-$C_{30}$ cycloalkyl silyl groups, substituted or unsubstituted $C_5$-$C_{30}$ aryl silyl groups, substituted or unsubstituted $C_5$-$C_{30}$ aryl groups, substituted or unsubstituted $C_5$-$C_{30}$ aryl amine groups, substituted or unsubstituted $C_3$-$C_{30}$ heteroaryl groups, a halogen group, a cyano group, a carboxyl group, a carbonyl group, an amine group, a nitro group, and combinations thereof.

In Chemical Formula 1, m and n are each independently an integer of 0 to 6.

In Chemical Formula 1, o and p are each independently an integer of 0 to 4.

In Chemical Formula 1, the sum of m, n, o and p is equal to or more than 1.

[Chemical Formula 2]

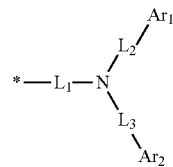

In Chemical Formula 2, $L_1$, $L_2$ and La are the same as or different from each other, and each independently selected from the group consisting of a single bond, substituted or unsubstituted $C_5$-$C_{30}$ arylene groups, substituted or unsubstituted $C_3$-$C_{30}$ heteroarylene groups, substituted or unsubstituted $C_1$-$C_{20}$ alkylene groups, substituted or unsubstituted $C_3$-$C_{20}$ cycloalkylene groups, substituted or unsubstituted $C_2$-$C_{20}$ alkenylene groups, substituted or unsubstituted $C_3$-$C_{20}$ cycloalkenylene groups, substituted or unsubstituted $C_1$-$C_{20}$ heteroalkylene groups, substituted or unsubstituted $C_3$-$C_{20}$ heterocycloalkylene groups, substituted or unsubstituted $C_2$-$C_{20}$ heteroalkenylene groups and substituted or unsubstituted $C_3$-$C_{20}$ heterocycloalkenylene groups.

In Chemical Formula 2, Ar and $Ar_2$ are the same as or different from each other, and each independently selected from the group consisting of substituted or unsubstituted $C_5$-$C_{30}$ aryl groups, substituted or unsubstituted $C_3$-$C_{30}$ heteroaryl groups, substituted or unsubstituted $C_3$-$C_{20}$ cycloalkyl groups, substituted or unsubstituted $C_6$-$C_{30}$ aralkyl groups, substituted or unsubstituted $C_6$-$C_{30}$ heteroaralkyl groups and substituted or unsubstituted $C_5$-$C_{30}$ arylamino groups.

For example, in Chemical Formula 1, the ring A and the ring B are different from each other and each selected from substituted or unsubstituted naphthalene or phenylene. Preferably, the ring A and the ring B may be selected from unsubstituted naphthalene or phenylene.

For example, in Chemical Formula 1, $R_1$, $R_2$, $R_3$ and $R_4$ may be the same as or different from each other, and each independently selected from the functional group represented by Chemical Formula 2, hydrogen, deuterium, $C_1$-$C_{20}$ alkyl groups which are unsubstituted or substituted by a halogen group, $C_1$-$C_{20}$ alkoxy groups which are unsubstituted or substituted by a halogen group, a halogen group, a cyano group, a carboxyl group, a carbonyl group, an amine group, a nitro group, $C_1$-$C_{20}$ alkyl silyl groups, $C_1$-$C_{20}$ alkoxy silyl groups, $C_3$-$C_{30}$ cycloalkyl silyl groups, $C_5$-$C_{30}$ aryl silyl groups, $C_5$-$C_{30}$ aryl groups, $C_5$-$C_{30}$ aryl amine groups and $C_3$-$C_{30}$ heteroaryl groups, and one or two of $R_1$, $R_2$, $R_3$ and $R_4$ are the functional group represented by the following Chemical Formula 2.

For example, in Chemical Formula 2, $L_1$, $L_2$ and $L_3$ are the same as or different from each other, and each independently selected from a single bond, substituted or unsubstituted $C_6$-$C_{18}$ arylene groups and substituted or unsubstituted $C_5$-$C_{12}$ heteroarylene groups.

For example, in Chemical Formula 2, $L_1$, $L_2$ and $L_3$ are the same as or different from each other, and each independently selected from a single bond, phenylene, biphenylene, terphenylene, naphthylene, phenanthrenylene, anthracenylene and carbazolylene, but may not be limited thereto.

For example, in Chemical Formula 2, $Ar_1$ and $Ar_2$ are the same as or different from each other, and each independently selected from substituted or unsubstituted $C_6$-$C_{30}$ aryl groups, substituted or unsubstituted $C_5$-$C_{30}$ heteroaryl groups and substituted or unsubstituted $C_3$-$C_{20}$ cycloalkyl groups.

For example, in Chemical Formula 2, $Ar_1$ and $Ar_2$ are the same as or different from each other, and each independently selected from the group represented by the following Chemical Formulas but may not be limited thereto.

In Chemical Formulas described herein, "*" refers to a bonding site:

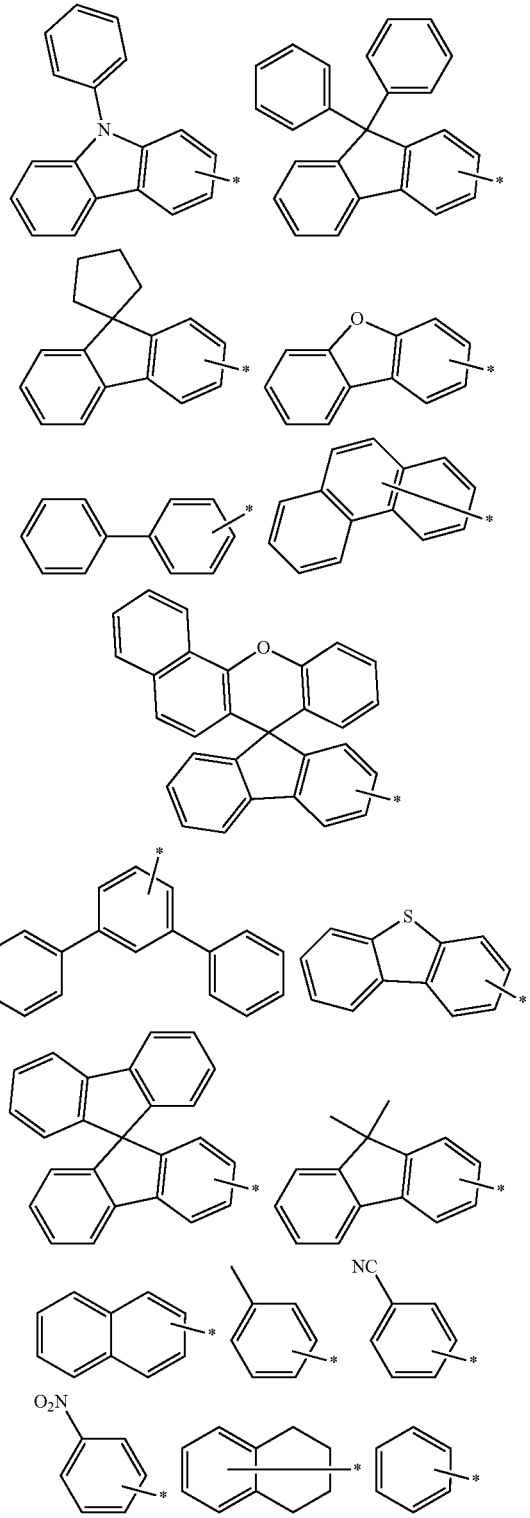

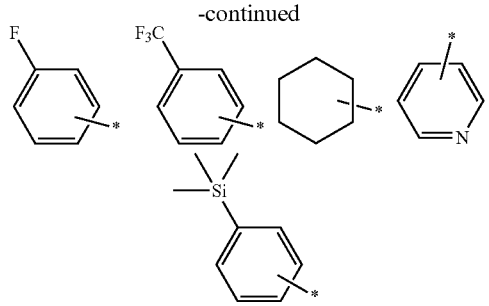

For example, the organic compound represented by Chemical Formula 1 may be selected from compounds represented by the following Chemical Formulas 3-1, 3-2 and 3-3, but may not be limited thereto.

[Chemical Formula 3-1]

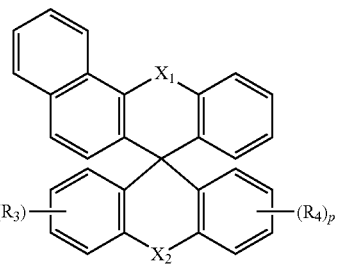

[Chemical Formula 3-2]

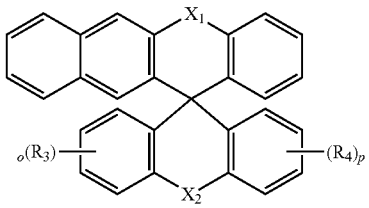

[Chemical Formula 3-3]

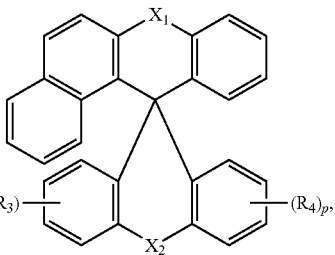

In Chemical Formulas 3-1, 3-2 and 3-3, one of $X_1$ and $X_2$ is O or S, and the other one is selected from the group consisting of a single bond, $C(R_5)(R_6)$, O and S.

In Chemical Formulas 3-1, 3-2 and 3-3, at least one of $R_3$ and Ry are the functional group represented by Chemical Formula 2.

In Chemical Formulas 3-1, 3-2 and 3-3, $R_3$, $R_4$, $R_5$, $R_6$, O and p are identical to those defined in Chemical Formula 1.

In Chemical Formula 2, $L_1$, $L_2$ and $L_3$ are single bonds, and $Ar_1$ and $Ar_2$ are connected to each other to form a hetero condensation ring (a fused ring). For example, a group in which $Ar_1$ and $Ar_2$ are connected to each other to form a fused ring may be represented by the following Chemical Formula 4 but may not be limited thereto.

[Chemical Formula 4]

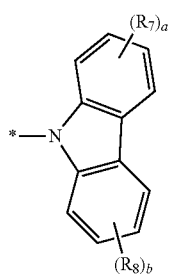

In Chemical Formula 4, Ry and $R_5$ are the same as or different from each other, and each independently selected from the group consisting of hydrogen, deuterium, substituted or unsubstituted $C_1$-$C_{20}$ alkyl groups, substituted or unsubstituted $C_2$-$C_{20}$ alkenyl groups, substituted or unsubstituted $C_2$-$C_{24}$ alkynyl groups, substituted or unsubstituted $C_1$-$C_{20}$ alkoxy groups, substituted or unsubstituted $C_1$-$C_{20}$ alkyl amine groups, substituted or unsubstituted $C_1$-$C_{20}$ alkyl silyl groups, substituted or unsubstituted $C_1$-$C_{20}$ alkoxy silyl groups, substituted or unsubstituted $C_3$-$C_{30}$ cycloalkyl silyl groups, substituted or unsubstituted $C_5$-$C_{30}$ aryl silyl groups, substituted or unsubstituted $C_5$-$C_{30}$ aryl groups, substituted or unsubstituted $C_5$-$C_{30}$ aryl amine groups, substituted or unsubstituted $C_3$-$C_{30}$ heteroaryl groups, a halogen group, a cyano group, a carboxyl group, a carbonyl group, an amine group, a nitro group, and combinations thereof.

In Chemical Formula 4, a and b are each independently an integer of 0 to 4.

In Chemical Formula 1 of the present disclosure, one of $X_1$ and $X_2$ may be O or S and the other one may be a single bond. For example, $X_1$ may be O or S and $X_2$ may be a single bond, and such an organic compound may be selected from the following group.

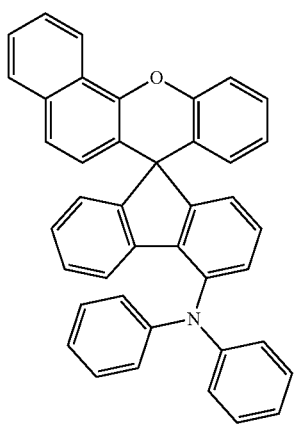

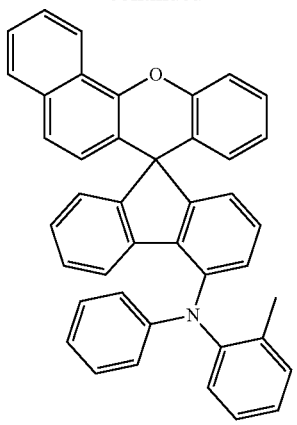

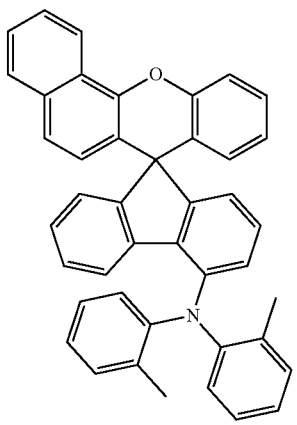

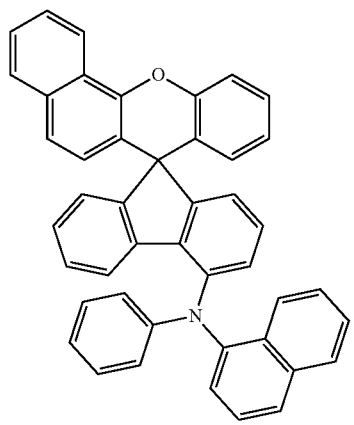

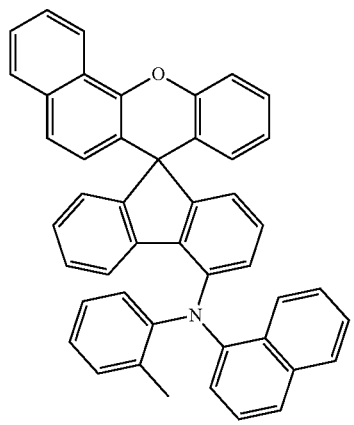

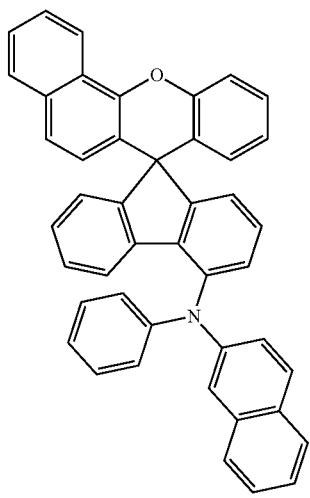
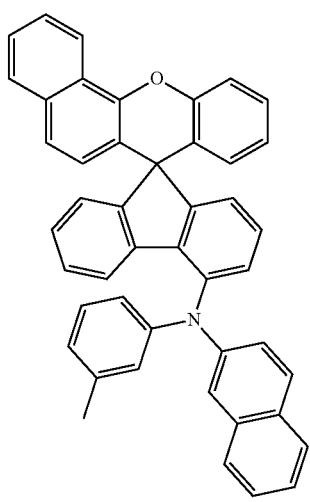
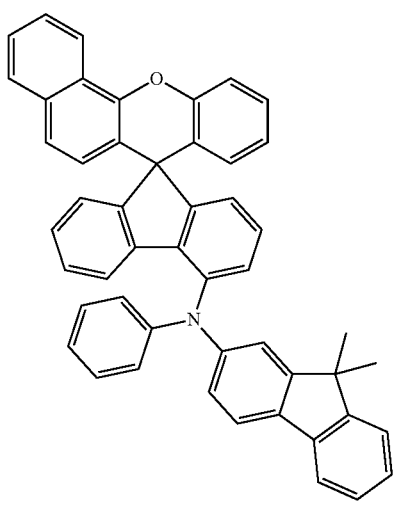
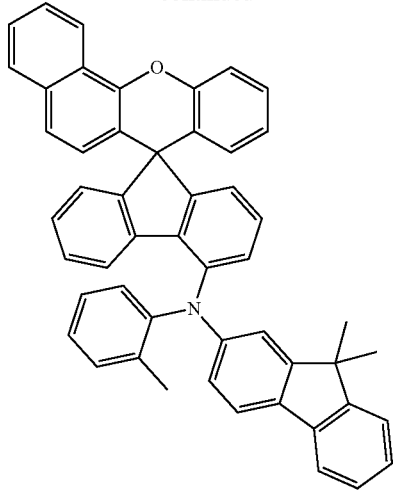
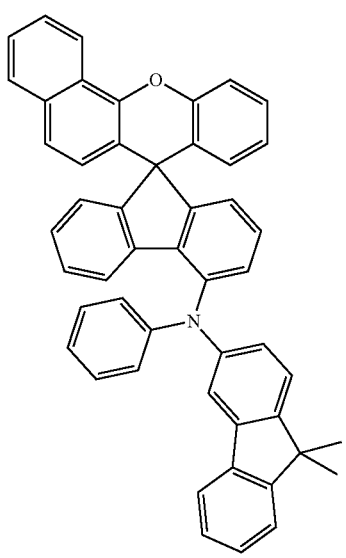
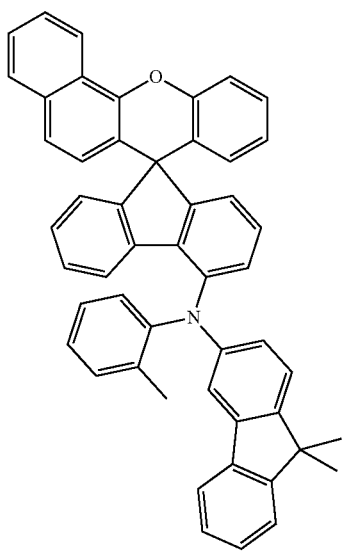

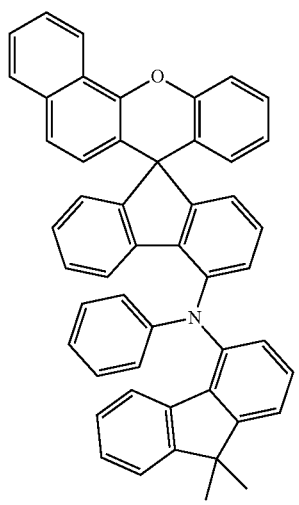
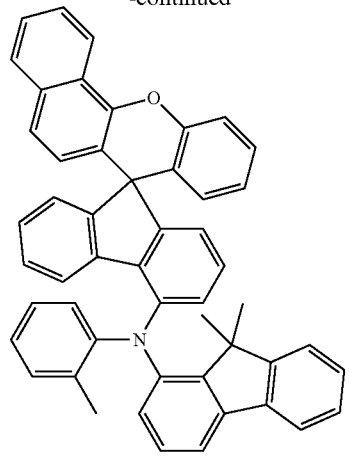
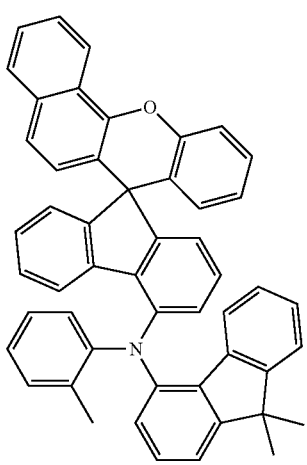
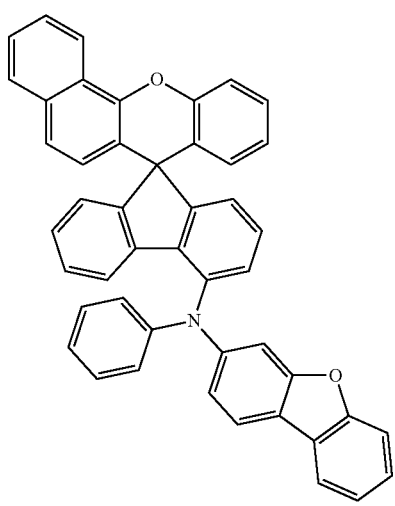
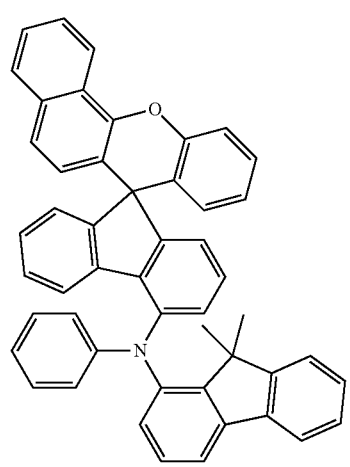
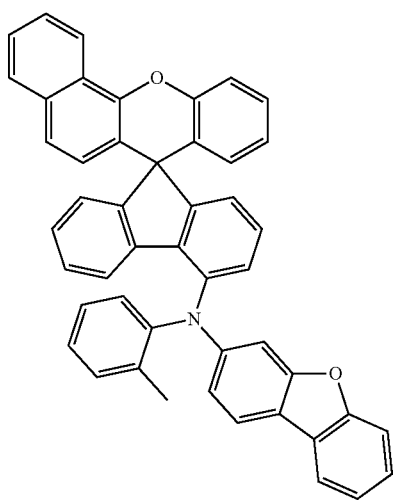

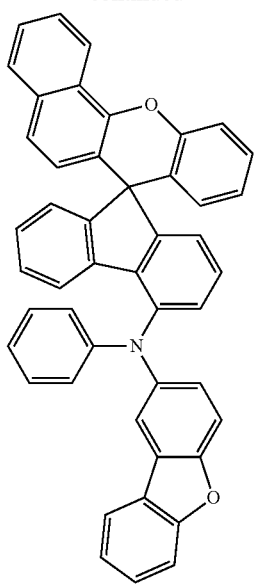
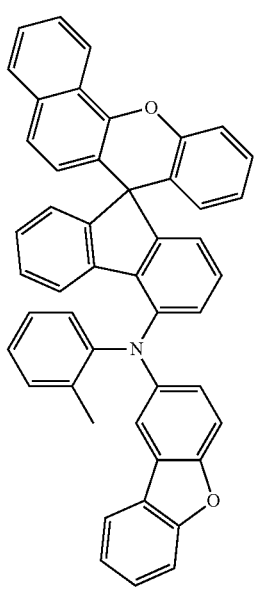
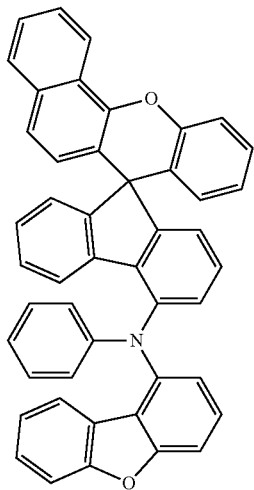
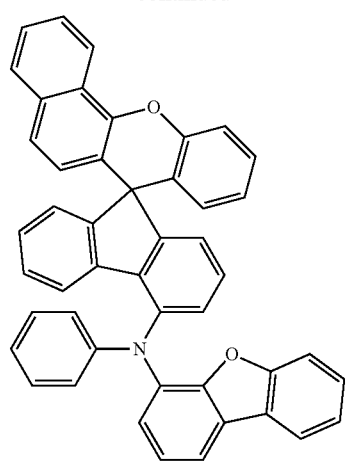
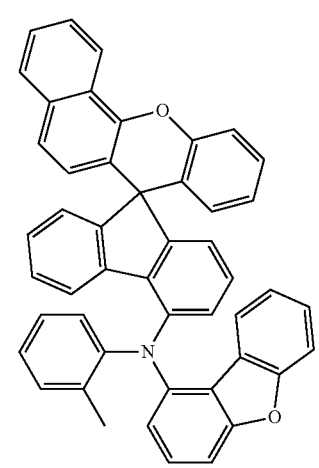
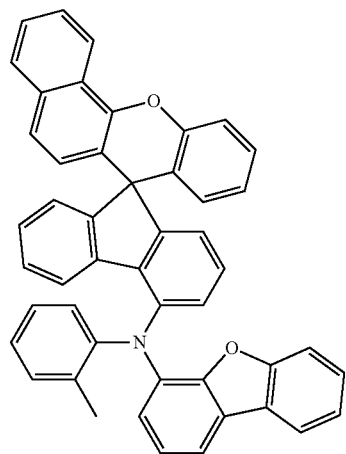

-continued
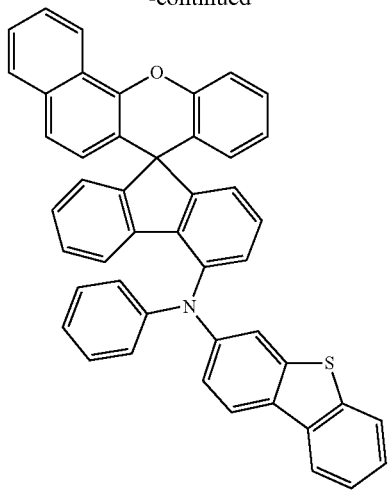
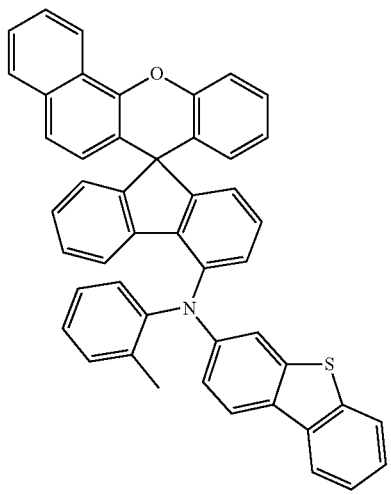
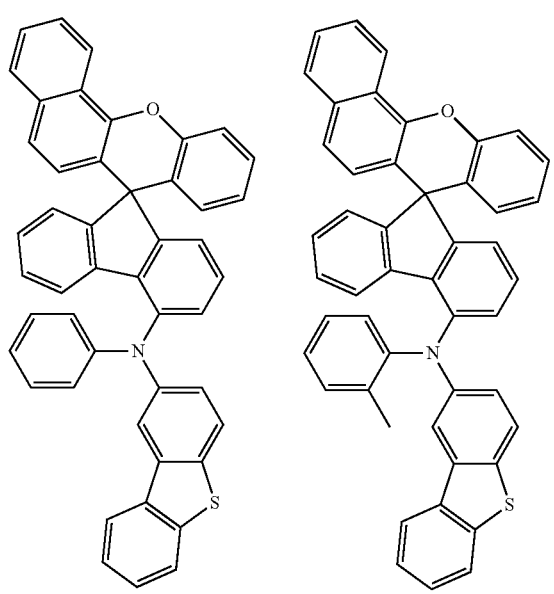
-continued
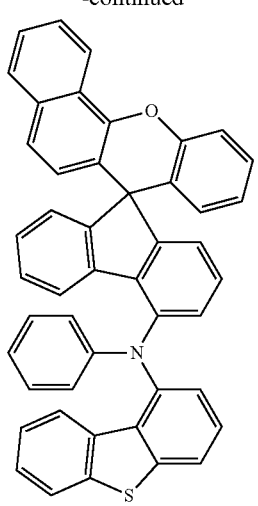
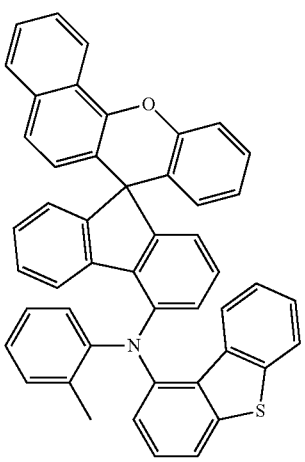
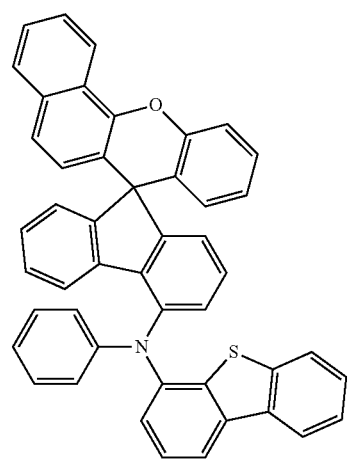

-continued
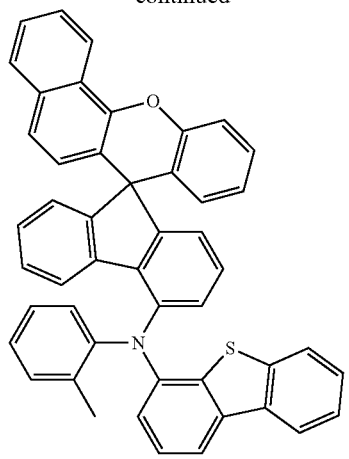
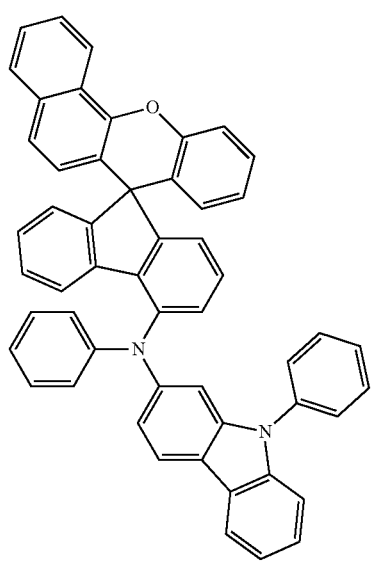
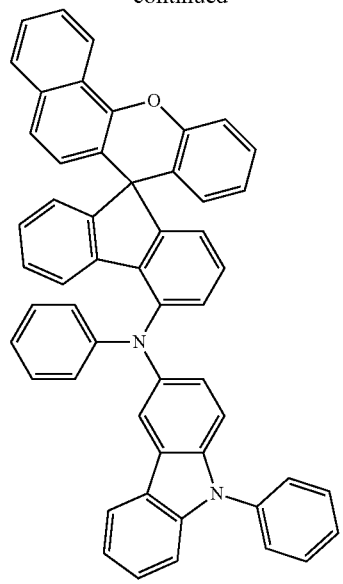
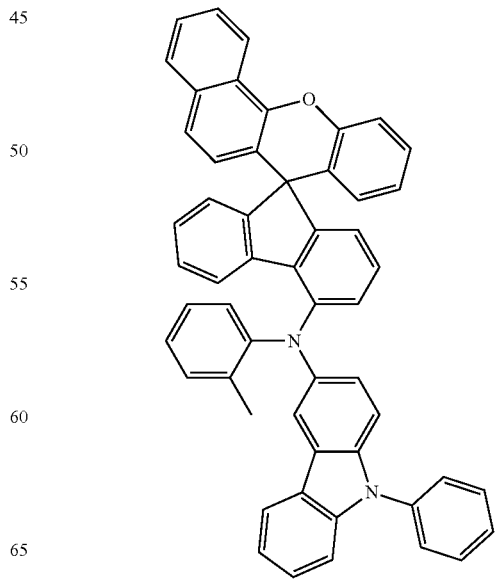

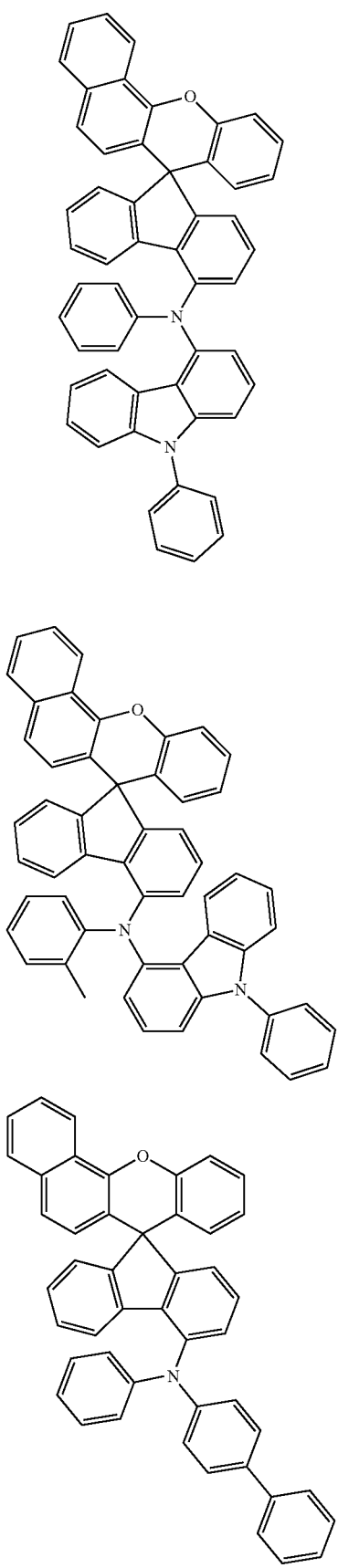
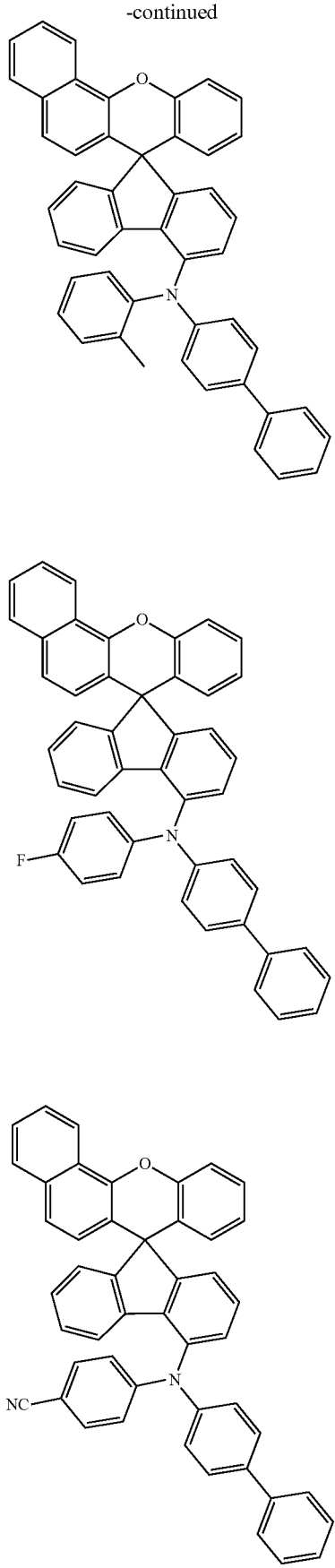

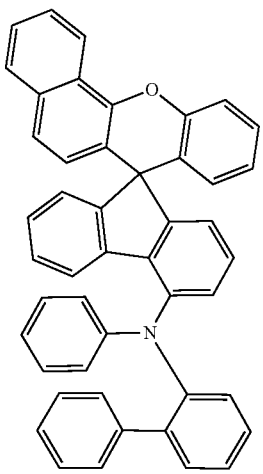
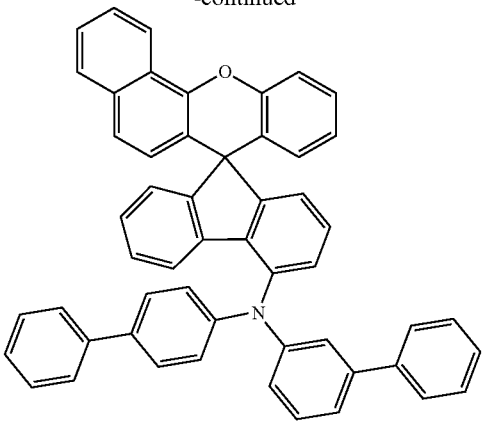
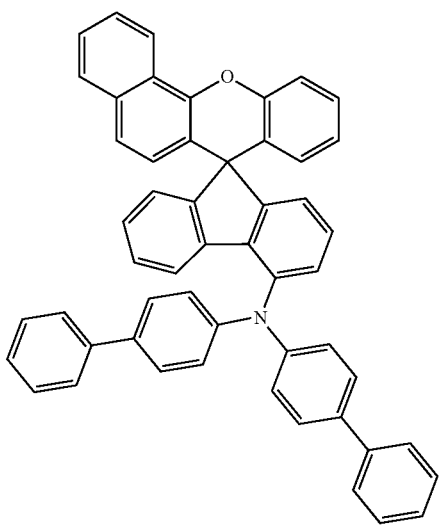
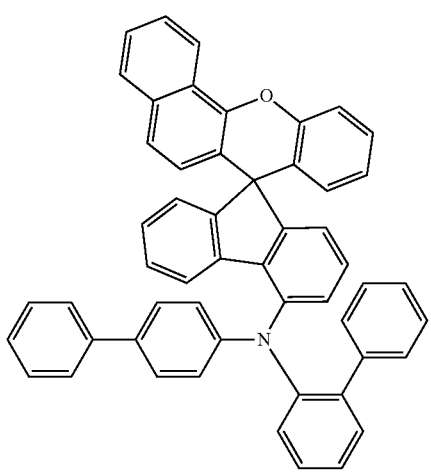
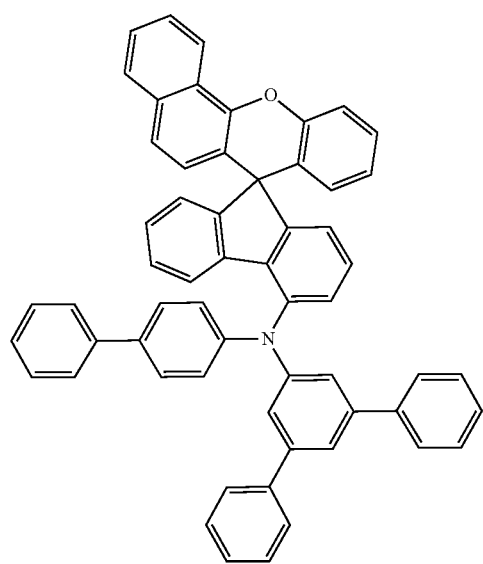

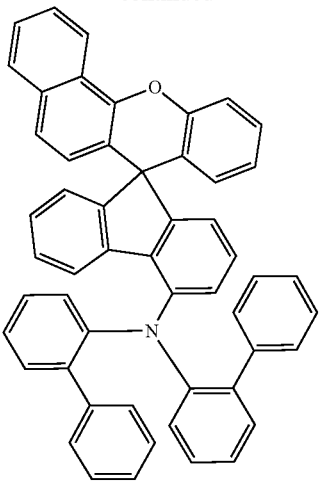
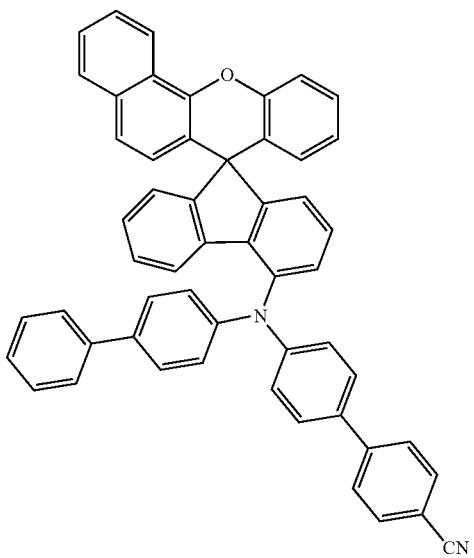
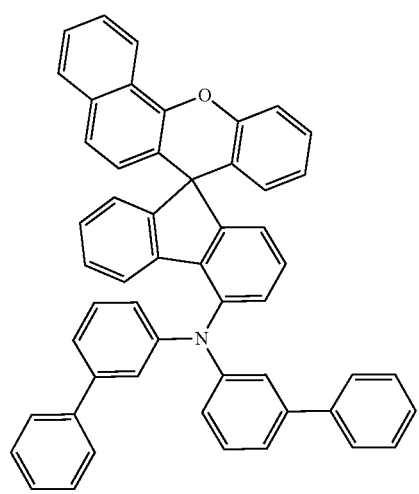
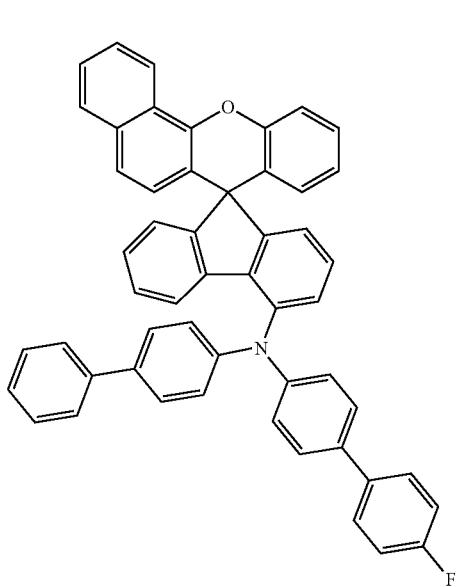
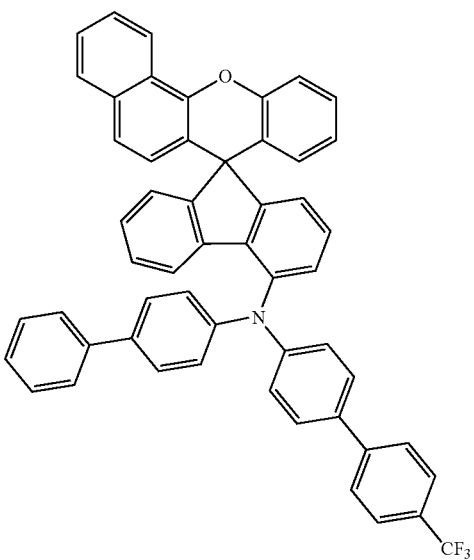

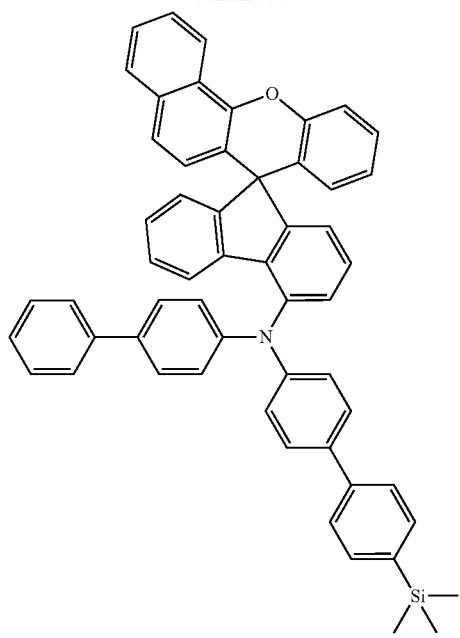
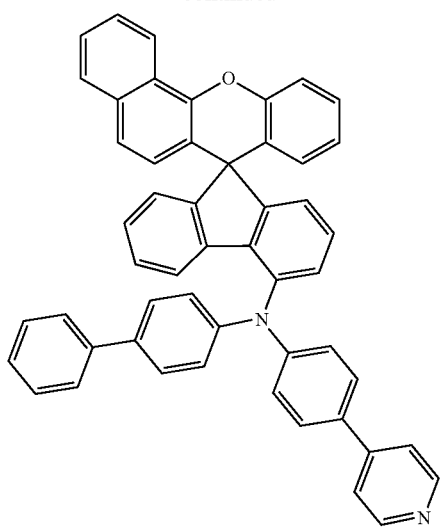
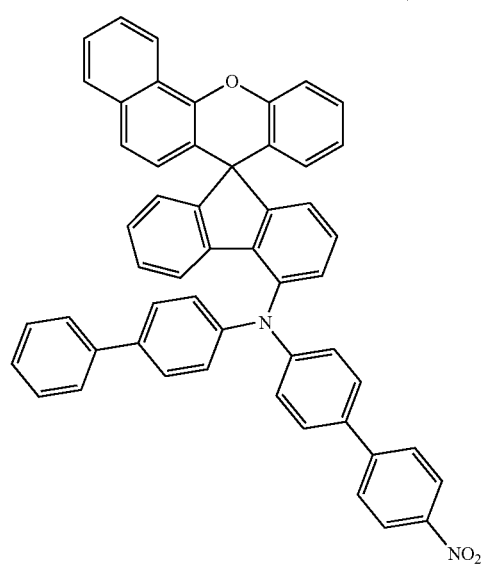
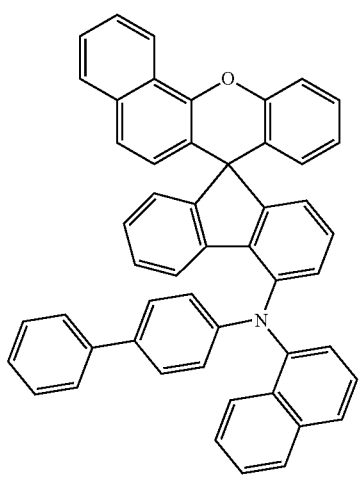
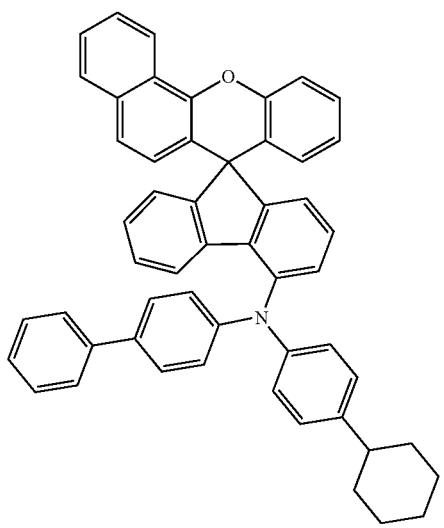
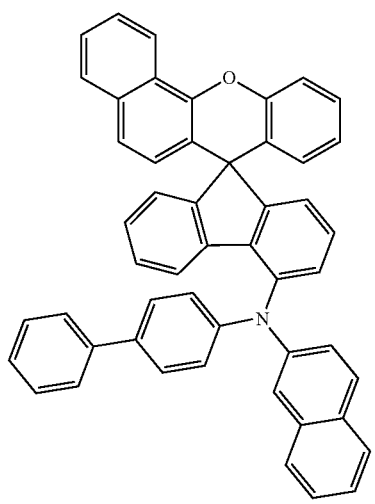

31
-continued
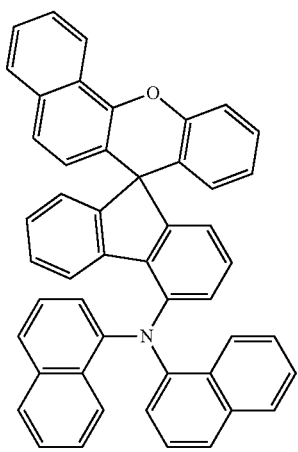
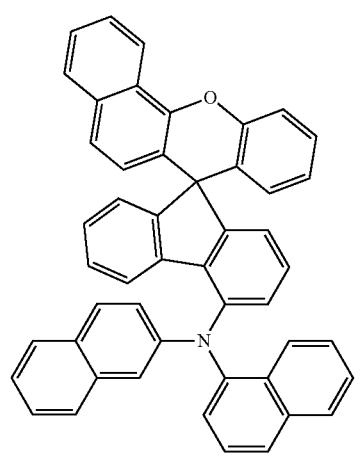
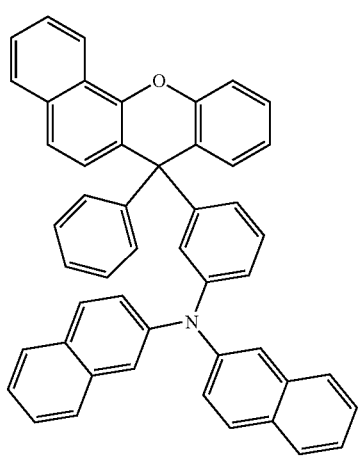
32
-continued
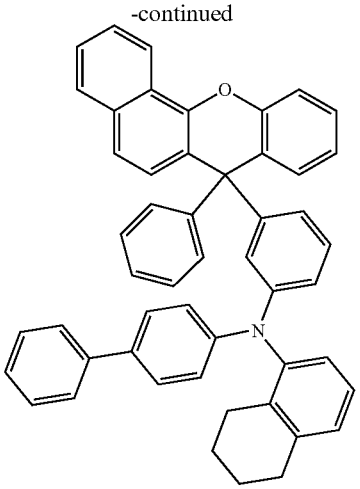
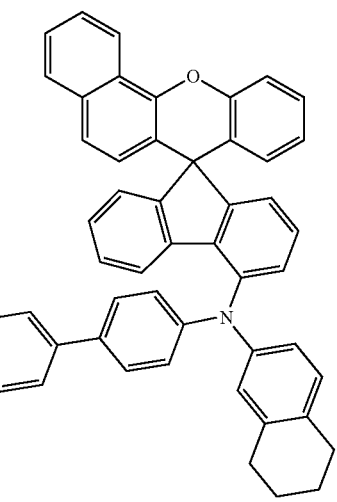
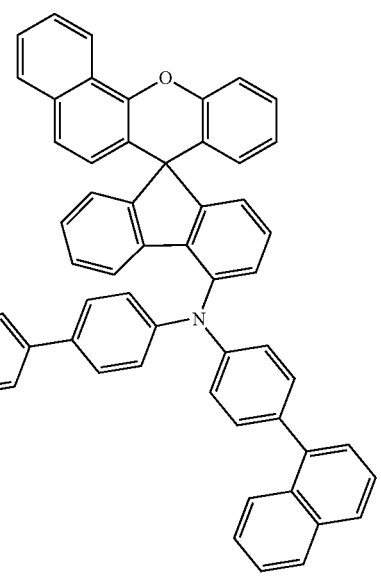

33
-continued
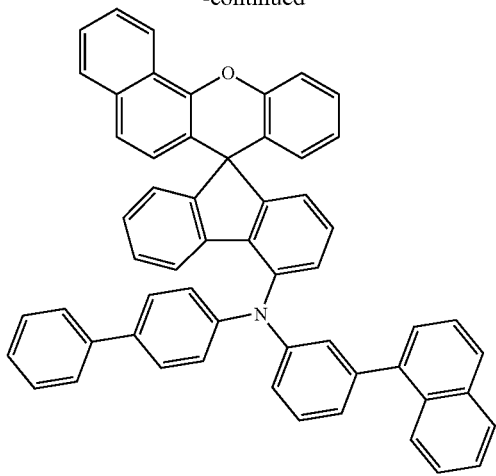
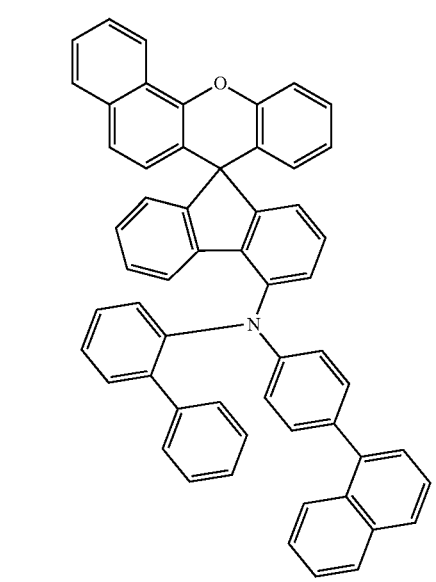
34
-continued
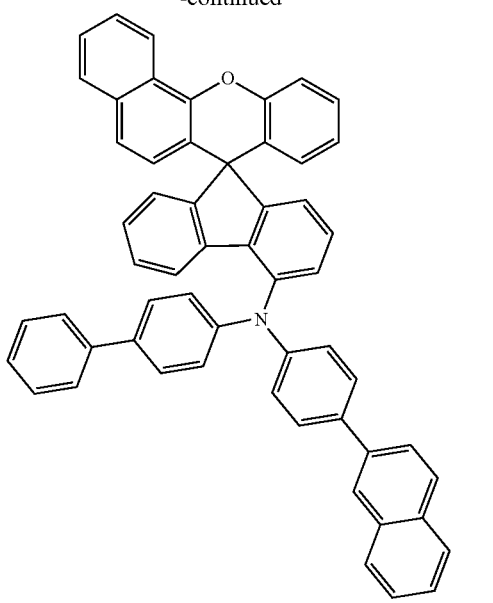
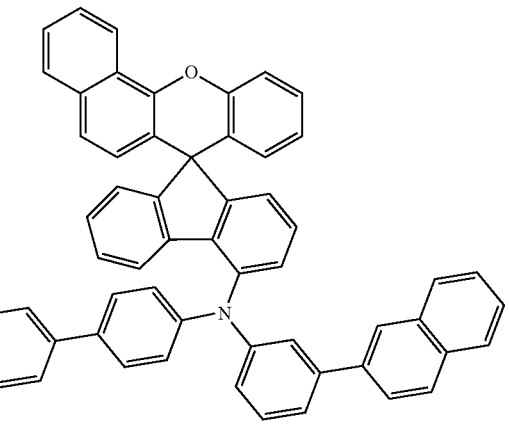
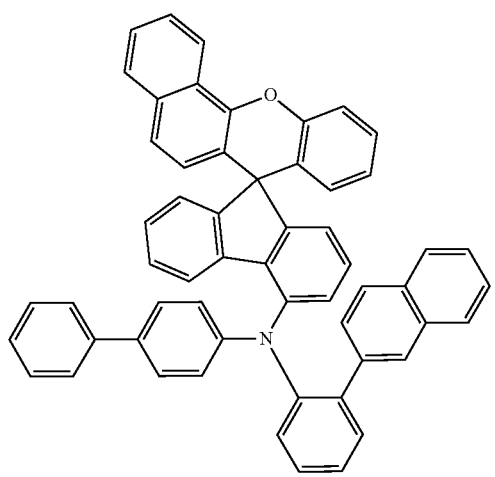

-continued
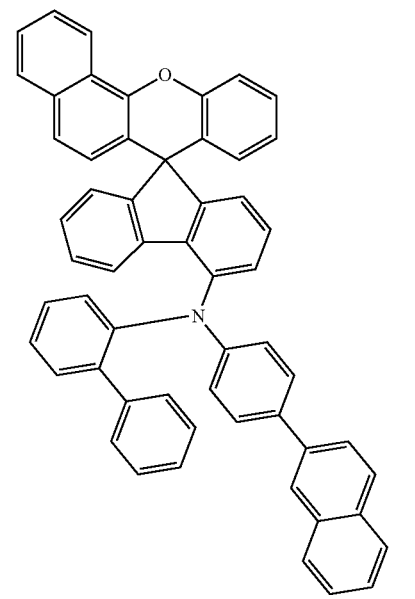
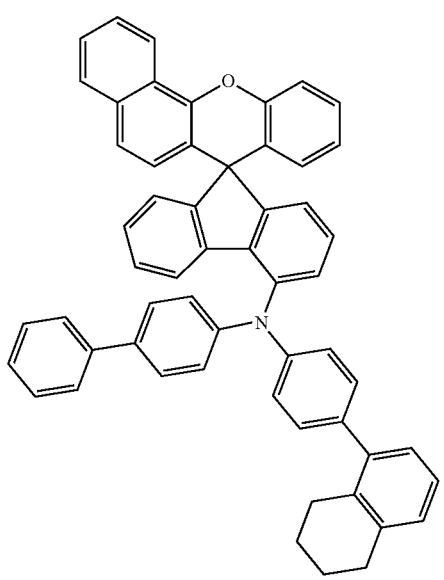
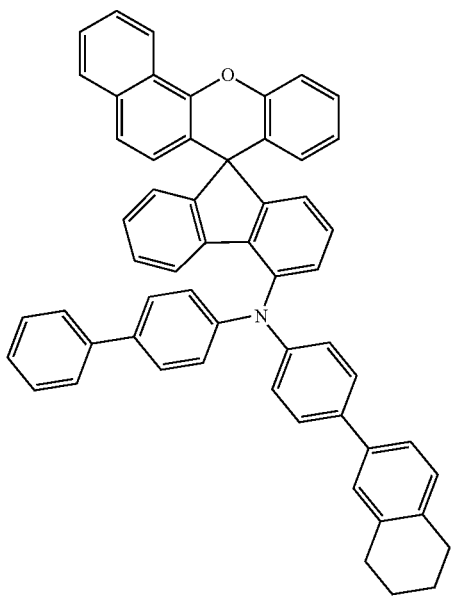
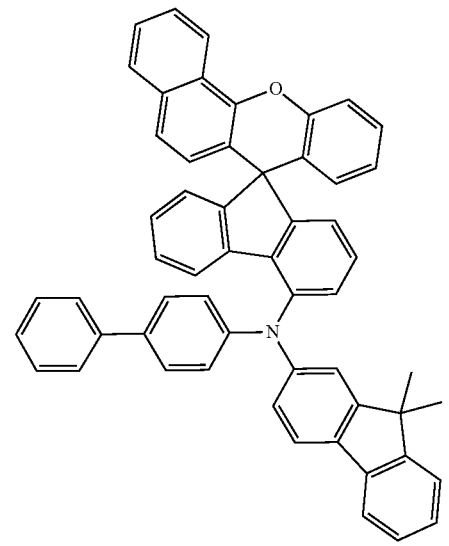

37
-continued
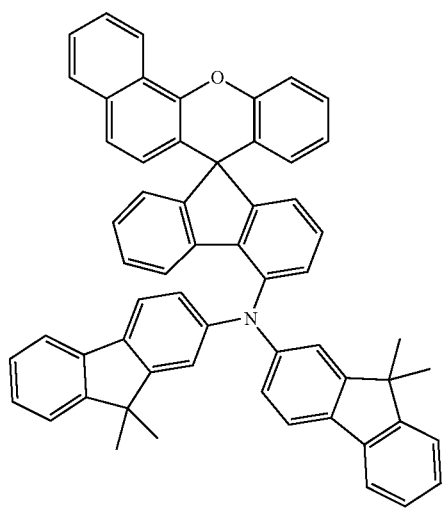
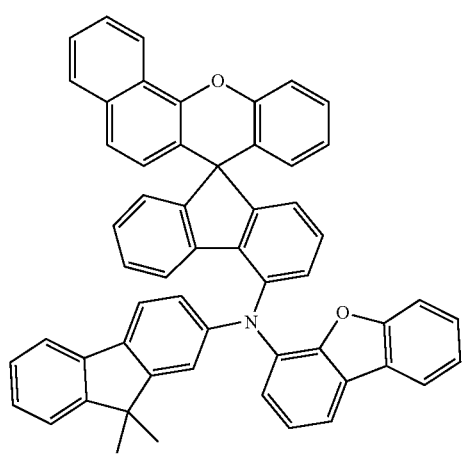
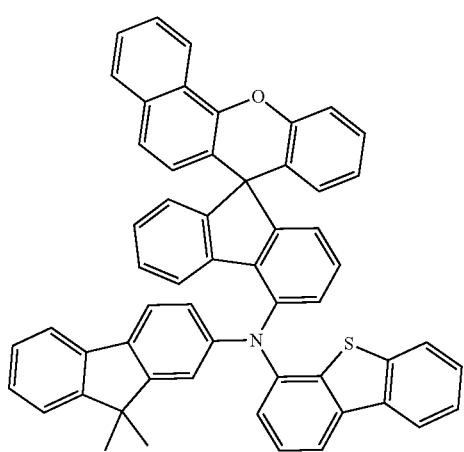
38
-continued
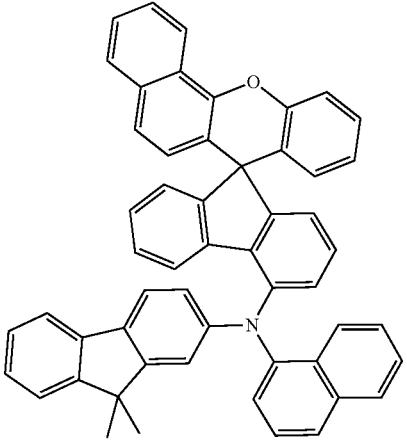
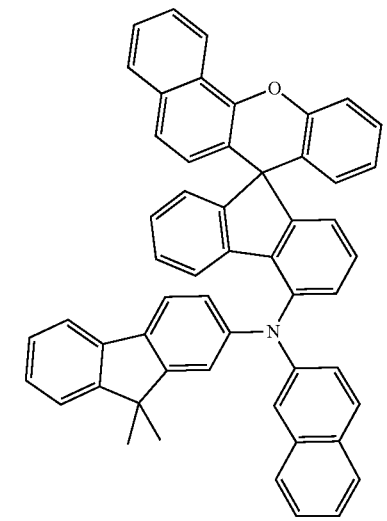
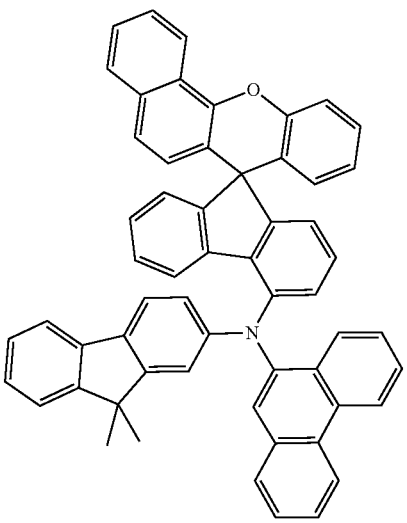

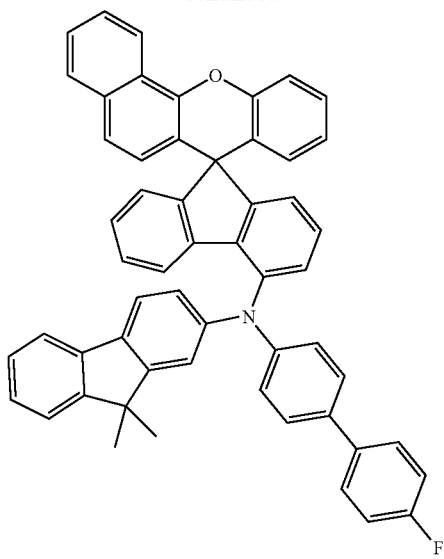
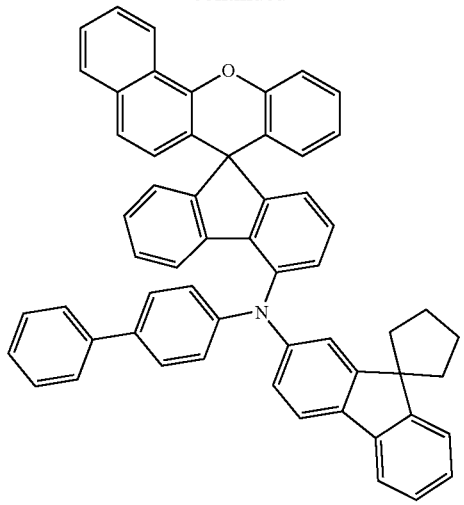
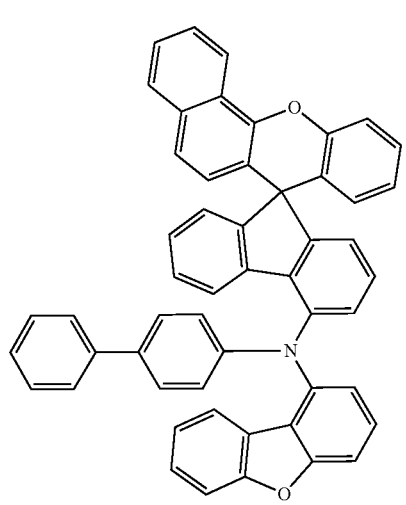

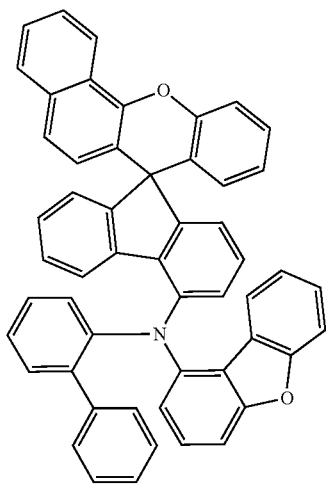
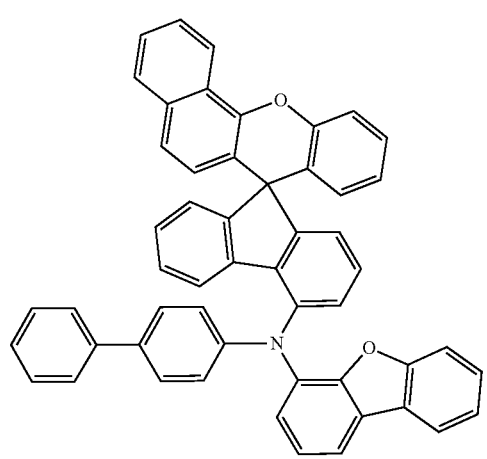
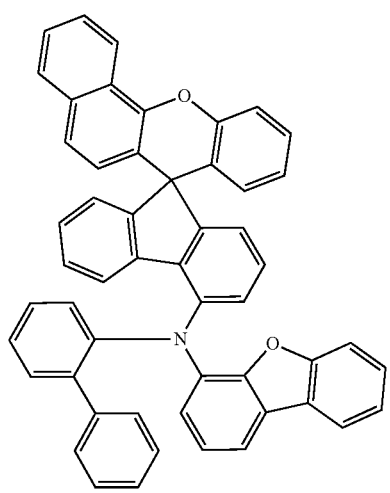
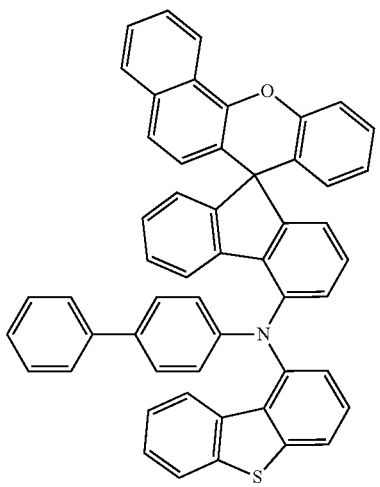
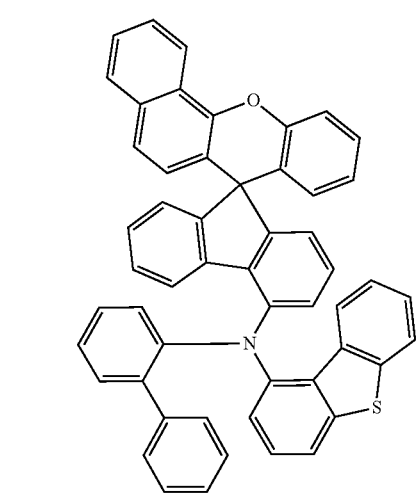
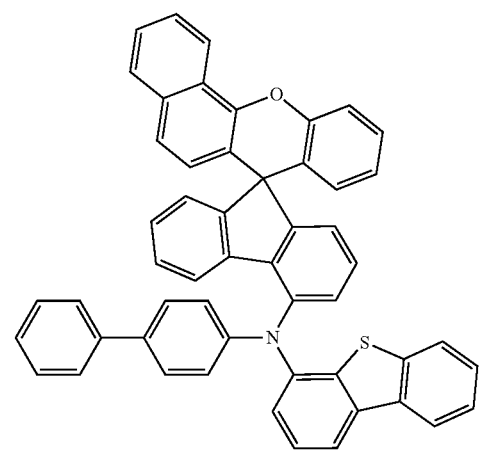

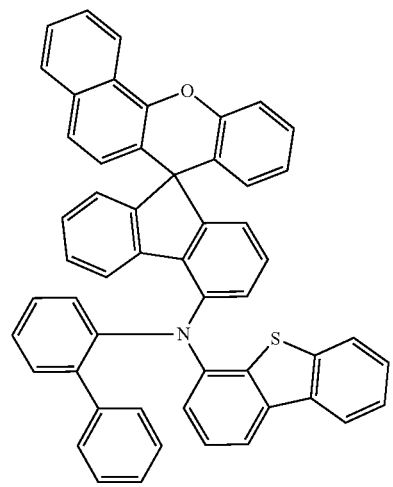
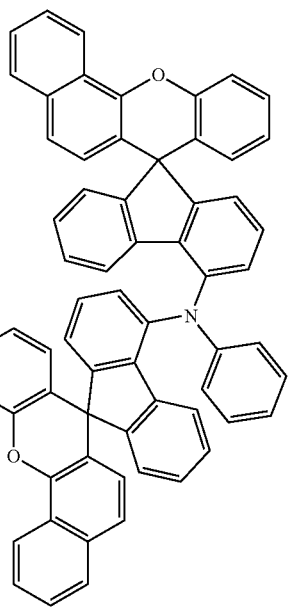
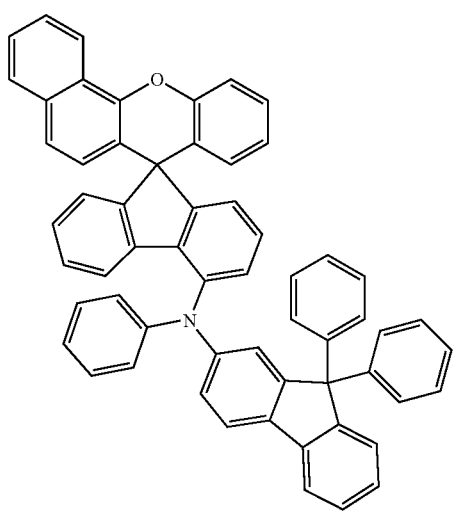
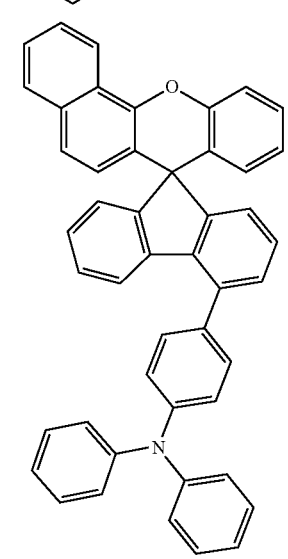
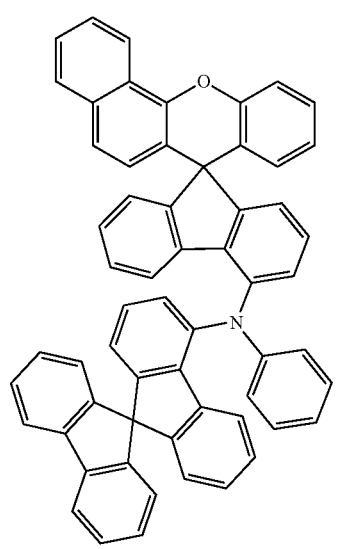
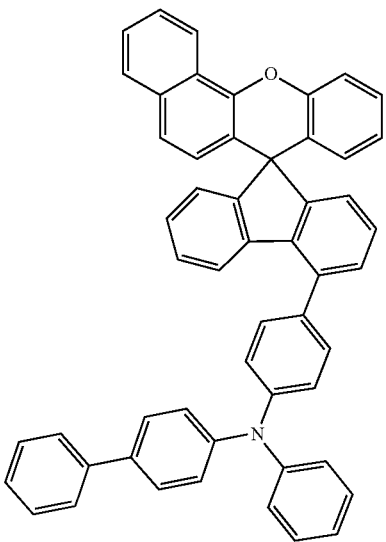

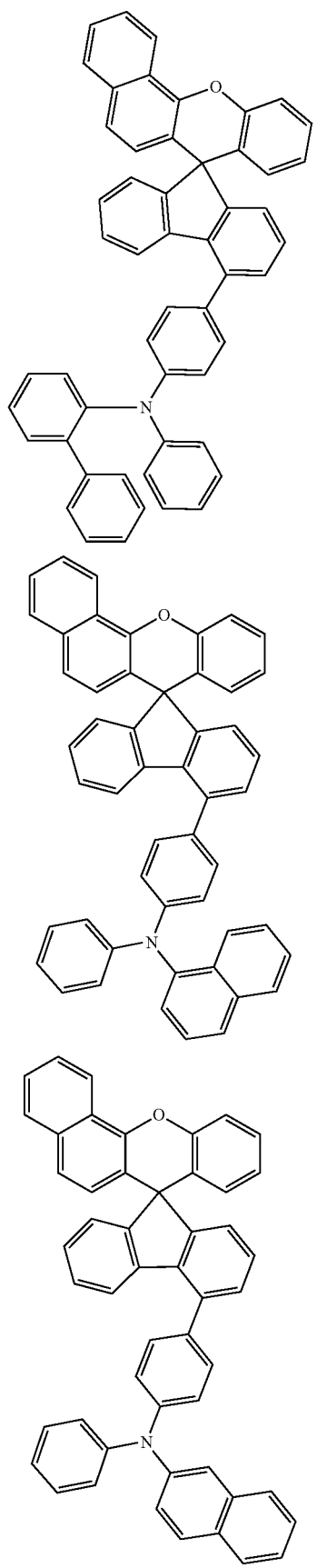

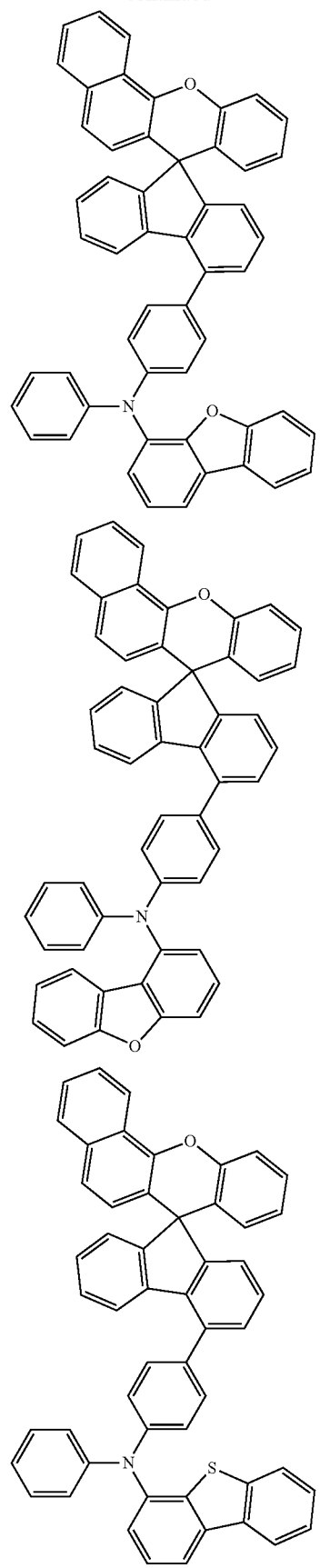

49
-continued
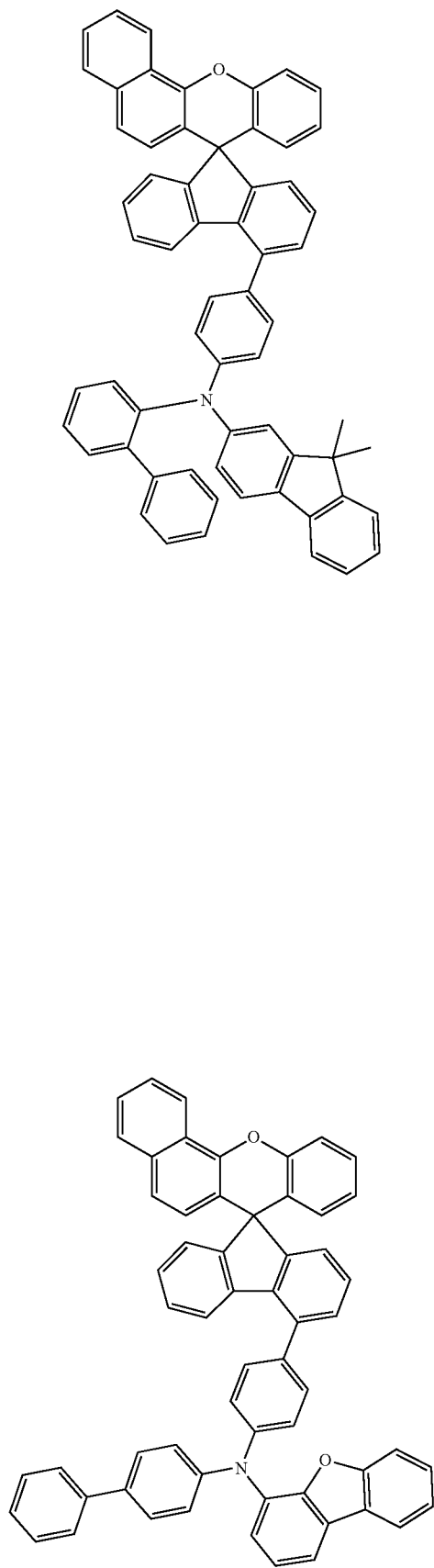
50
-continued
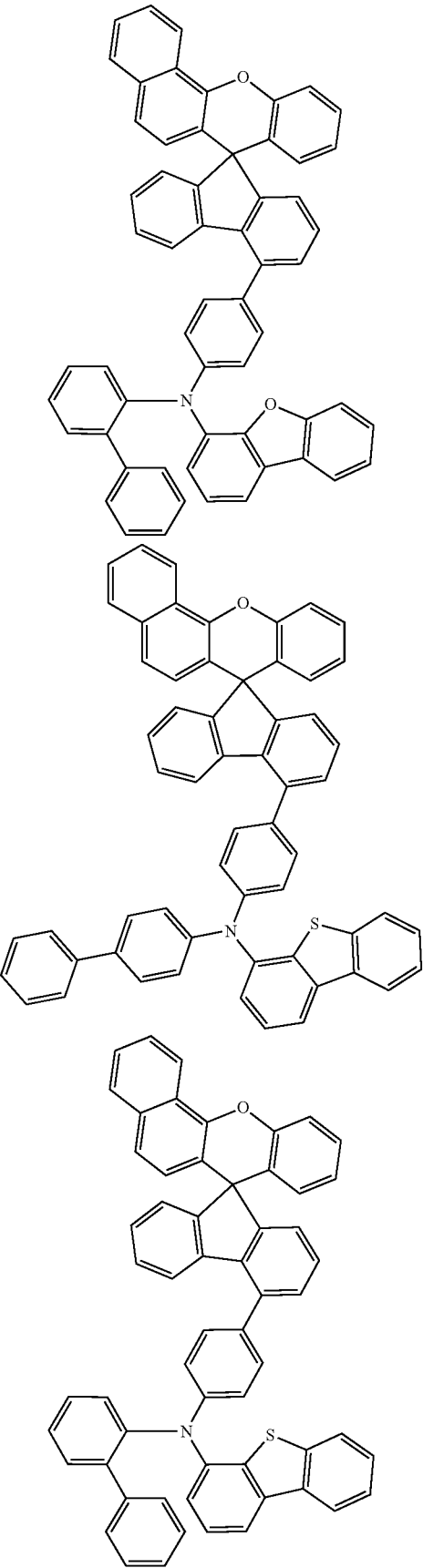

51
-continued
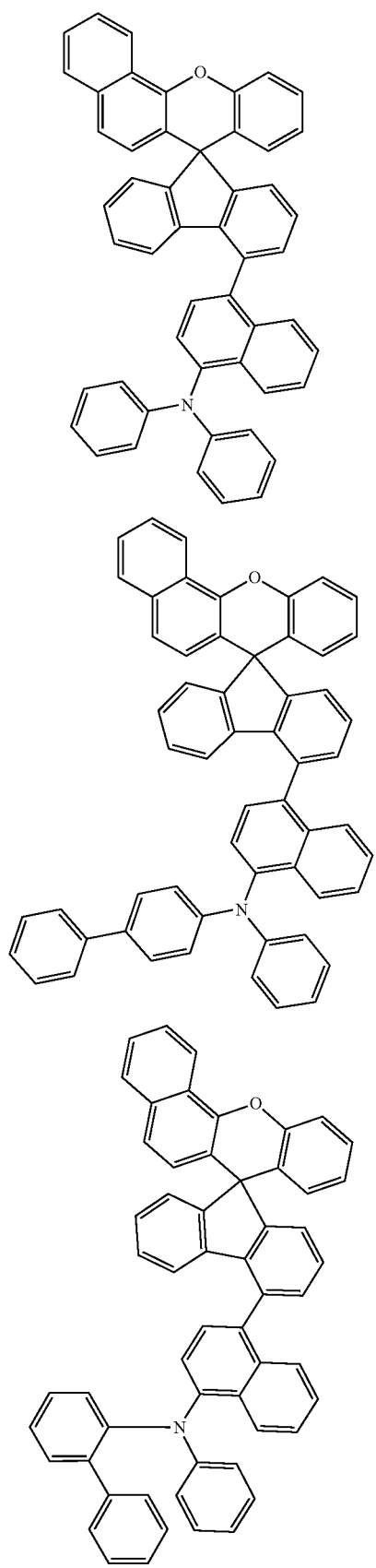
52
-continued
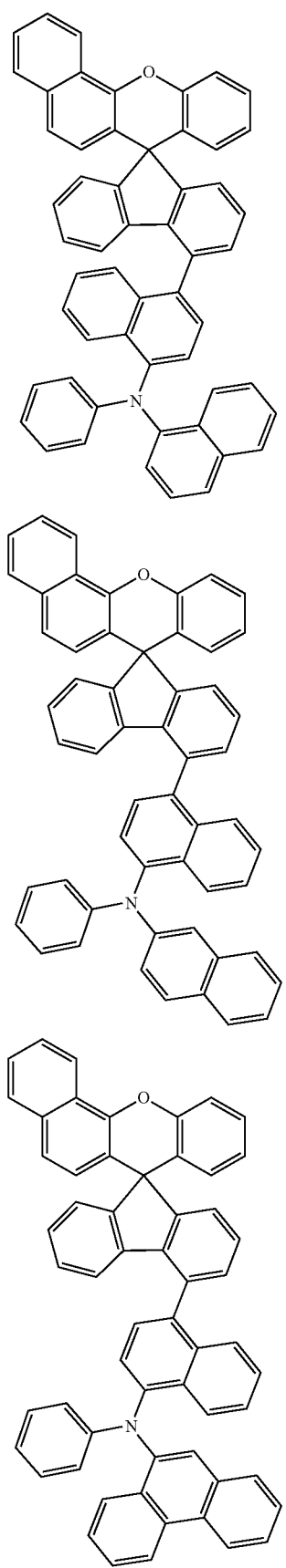

53
-continued
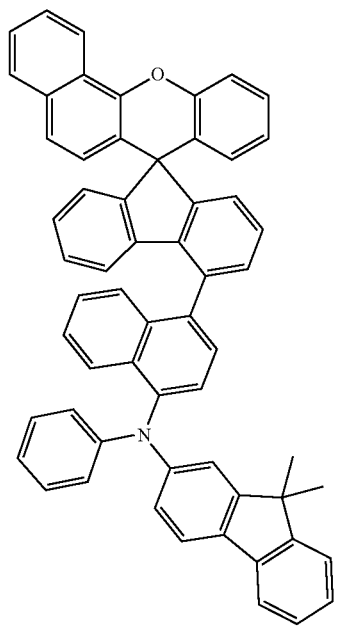
54
-continued
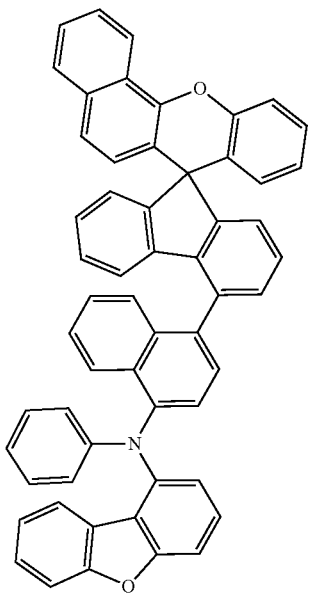
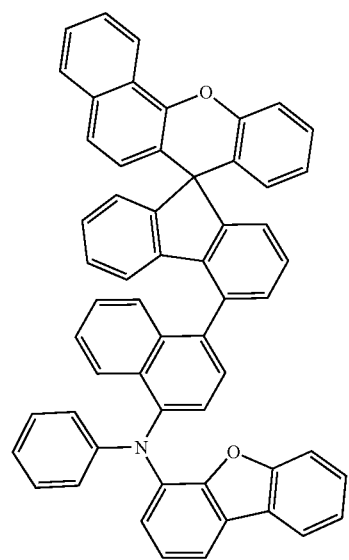
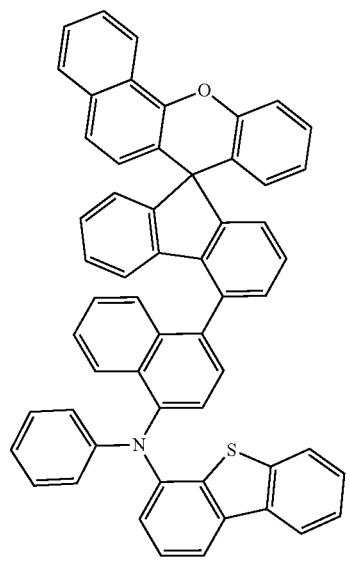

55
-continued
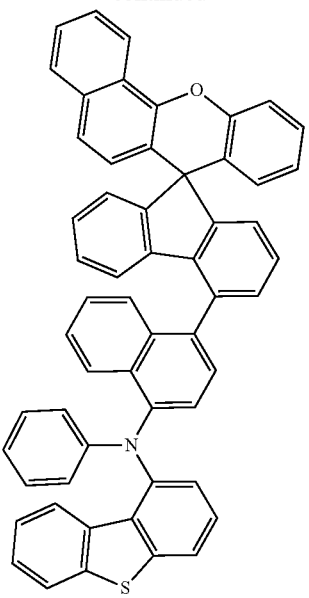
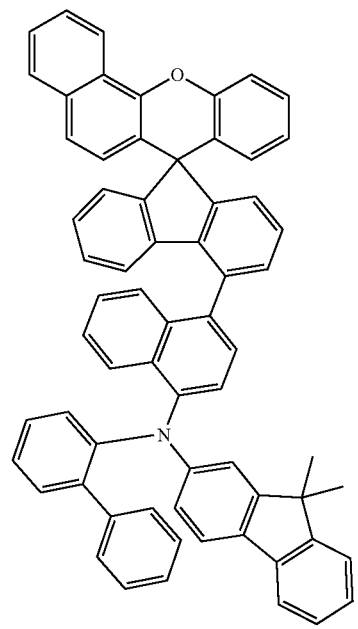
56
-continued
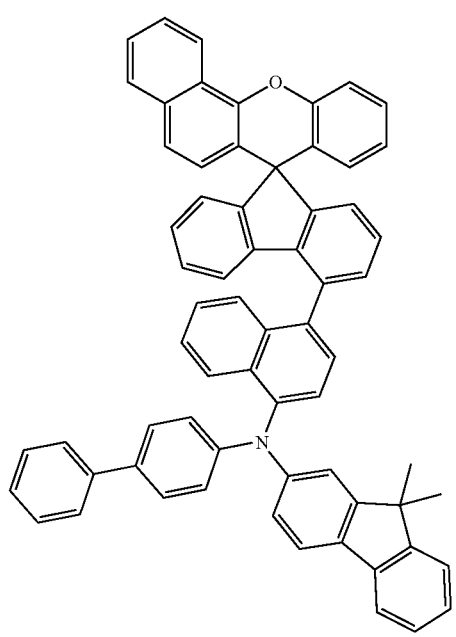
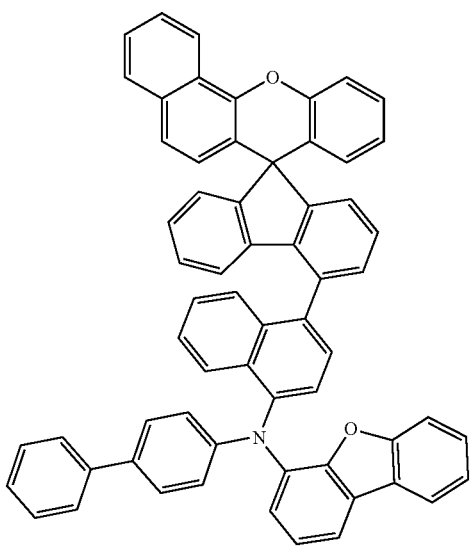

57
-continued
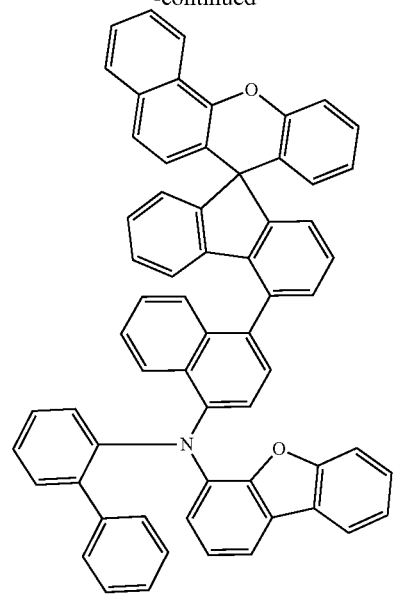
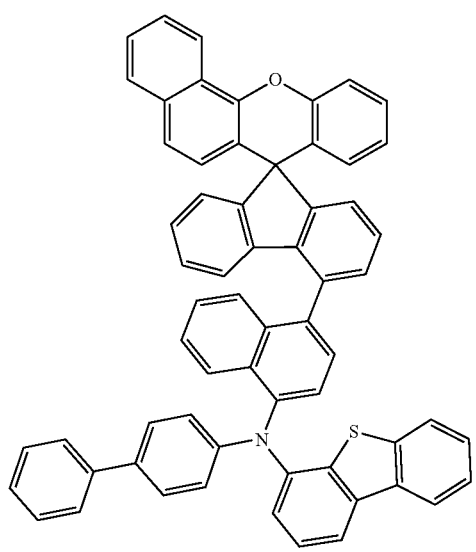
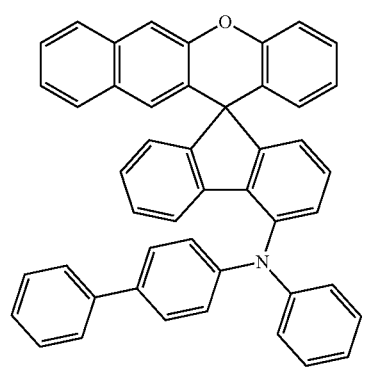
58
-continued
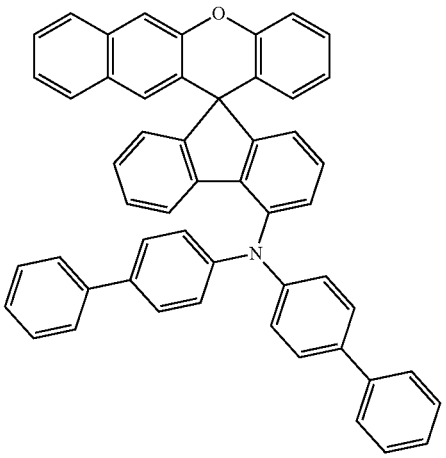
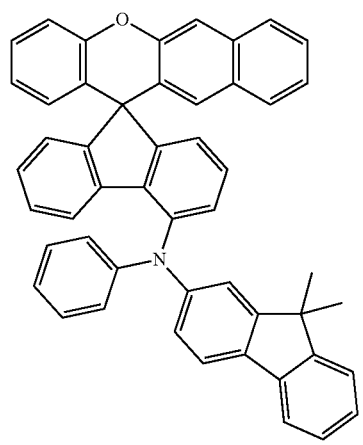
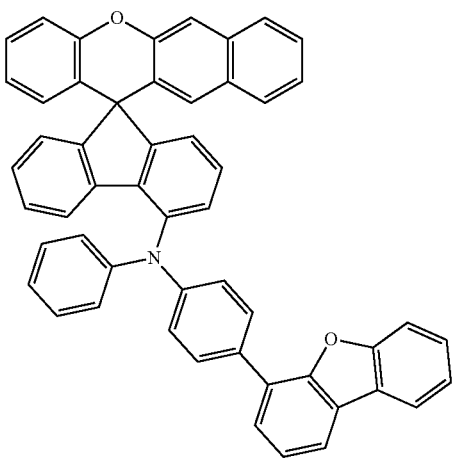

59
-continued
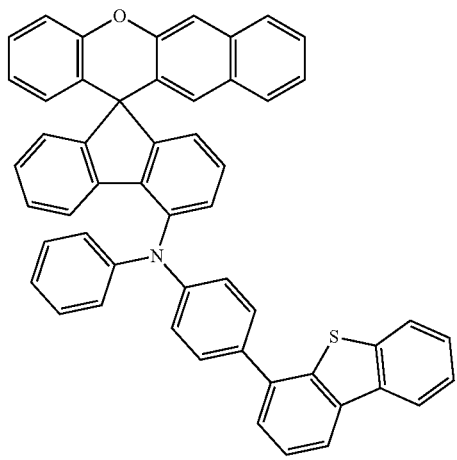
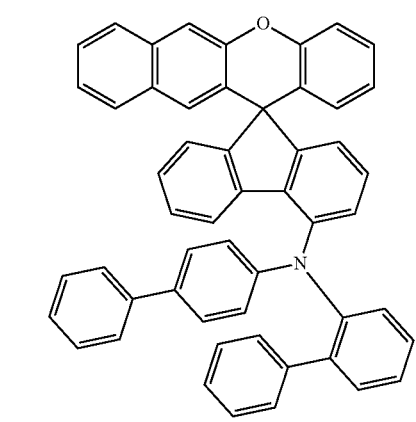
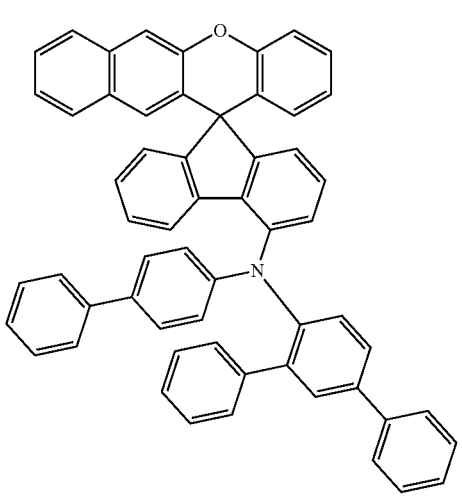
60
-continued
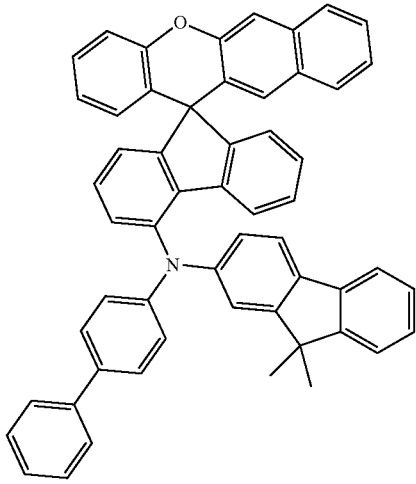
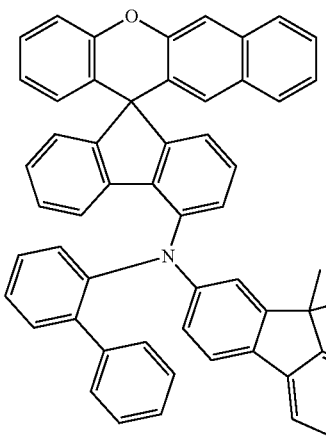
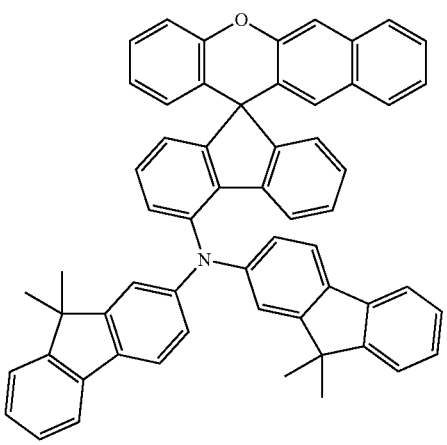

61
-continued
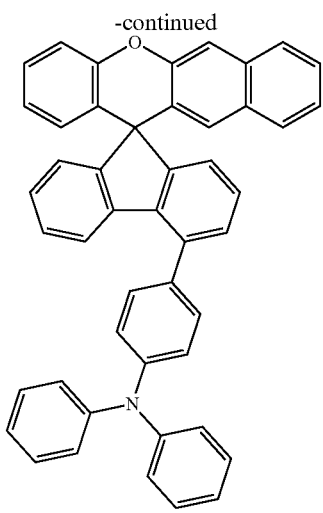
62
-continued
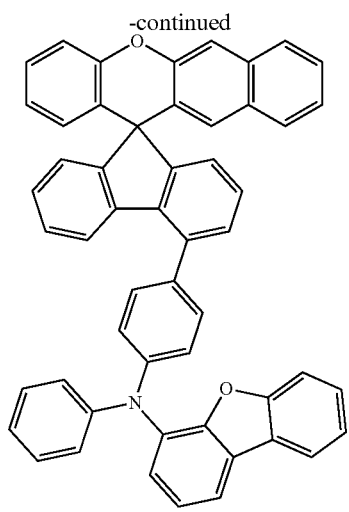
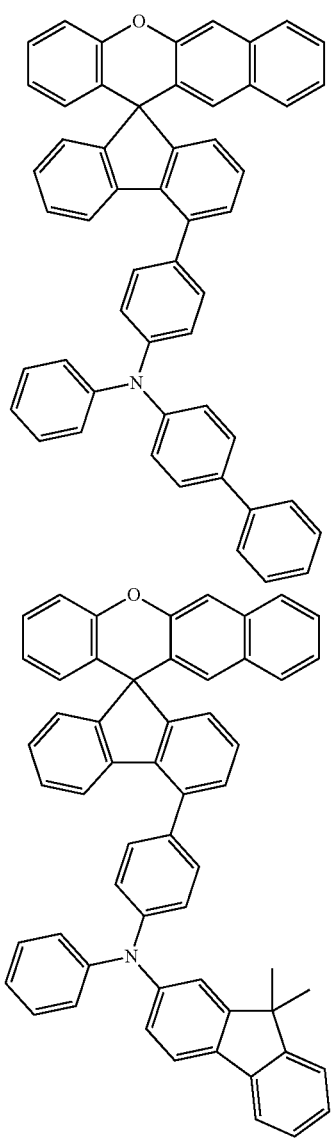
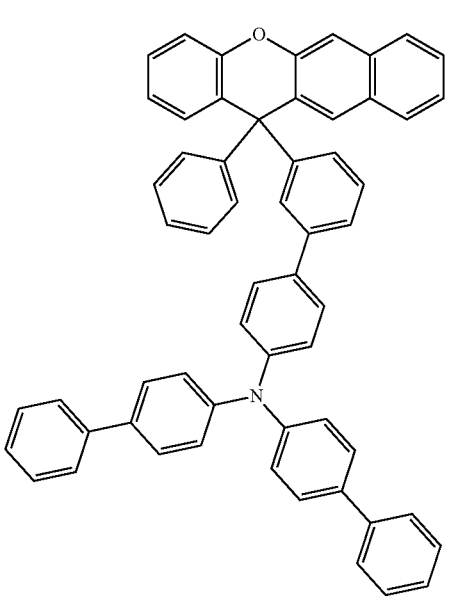
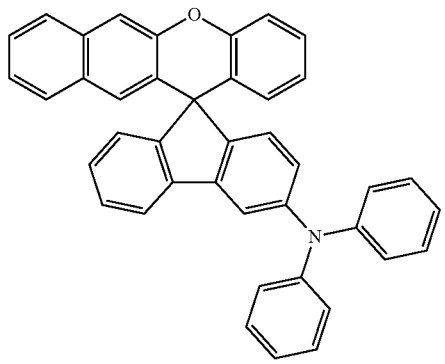

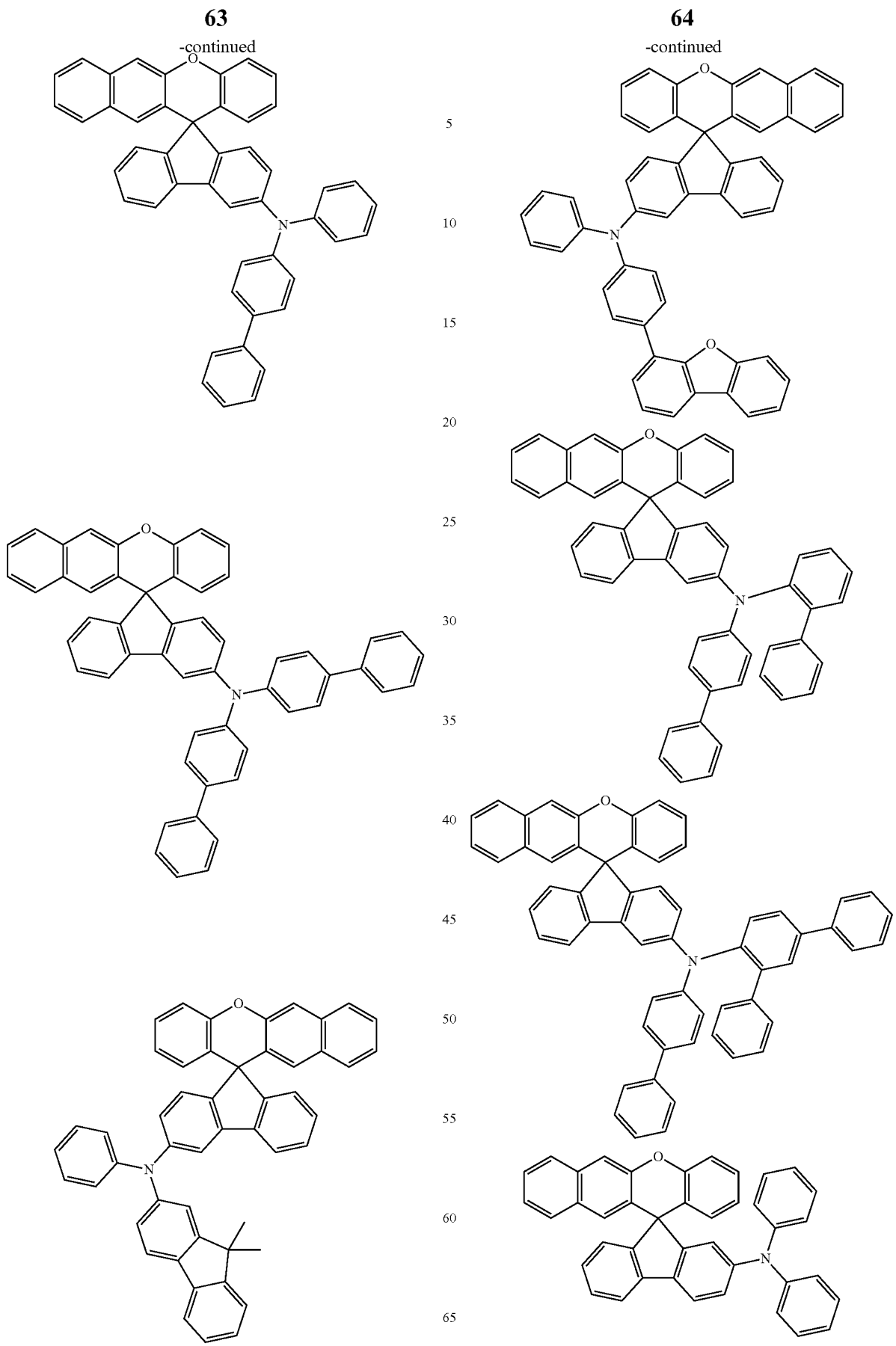

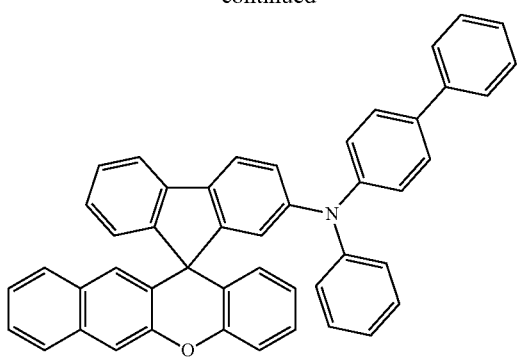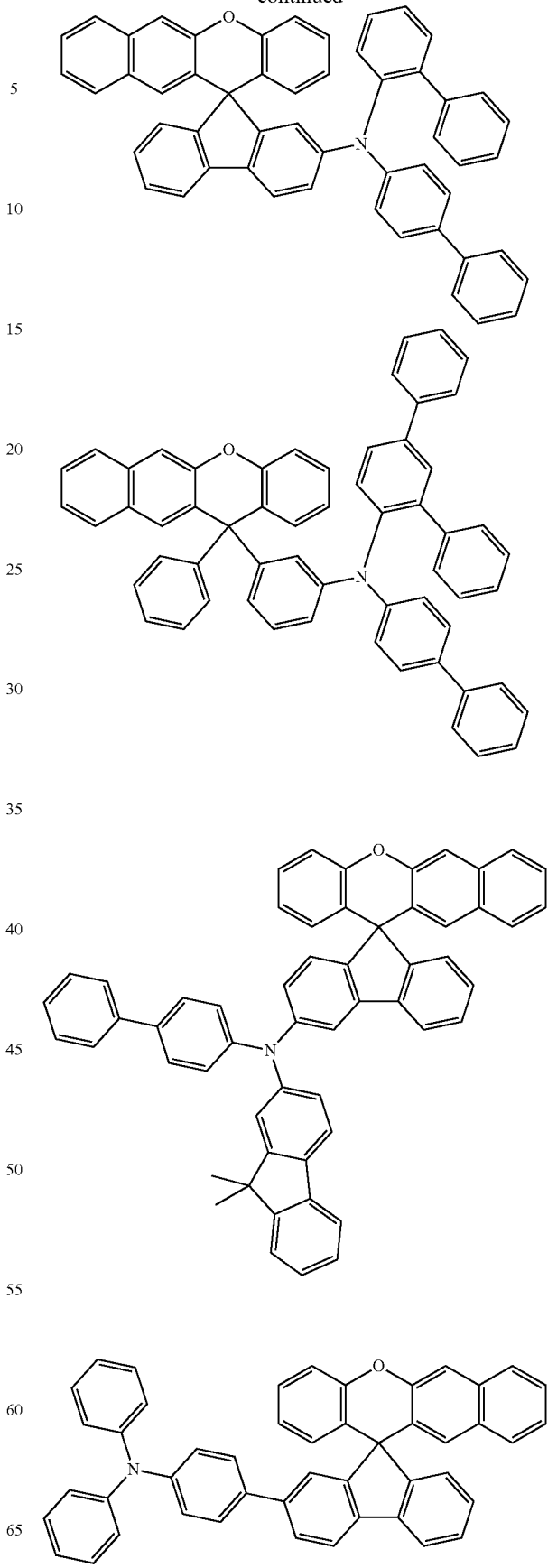

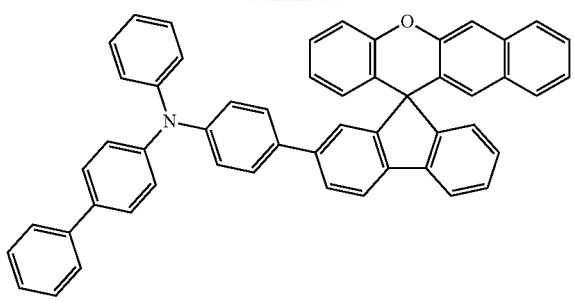
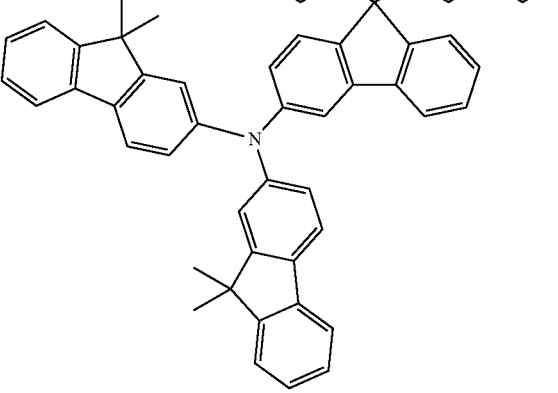
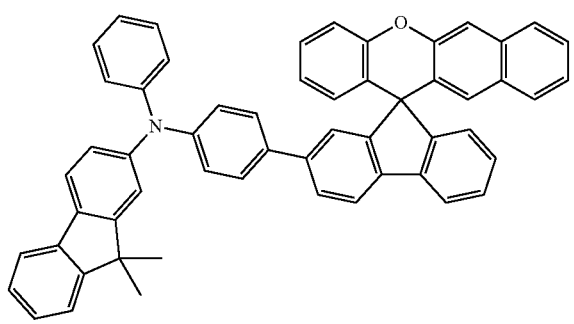
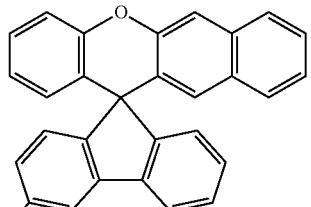
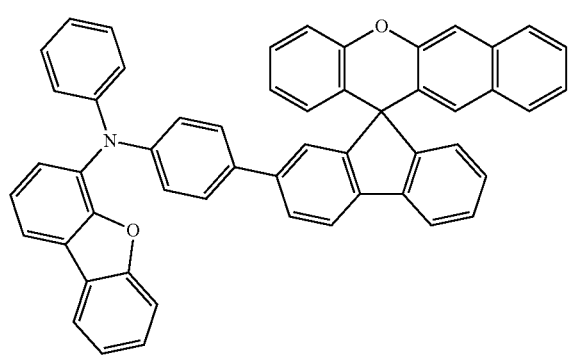
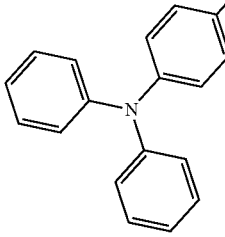
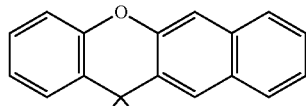
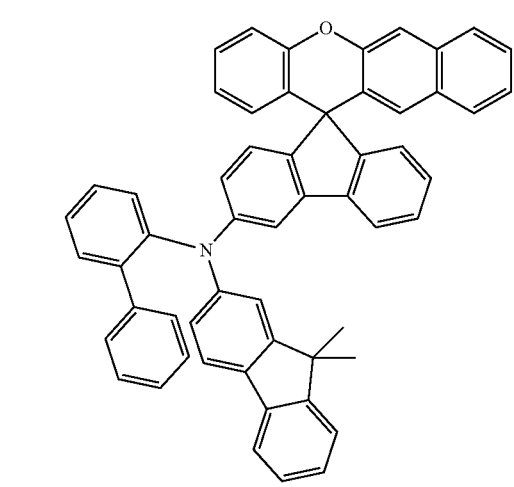
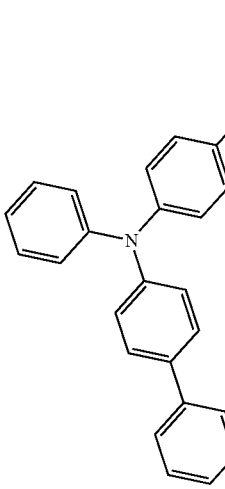

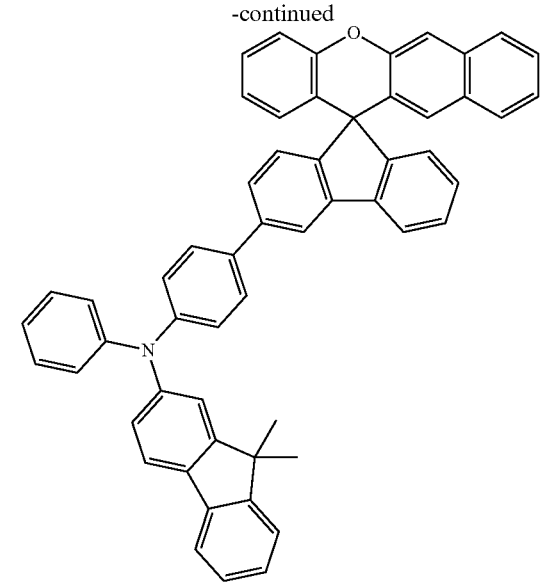
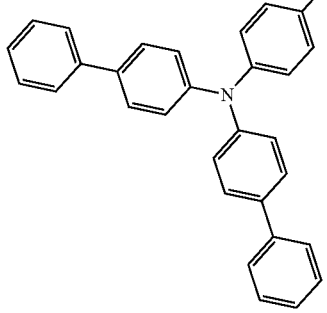
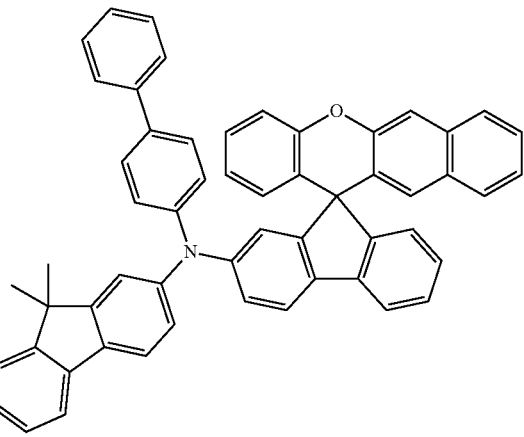
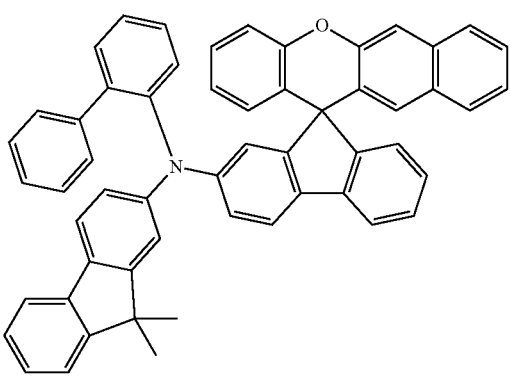
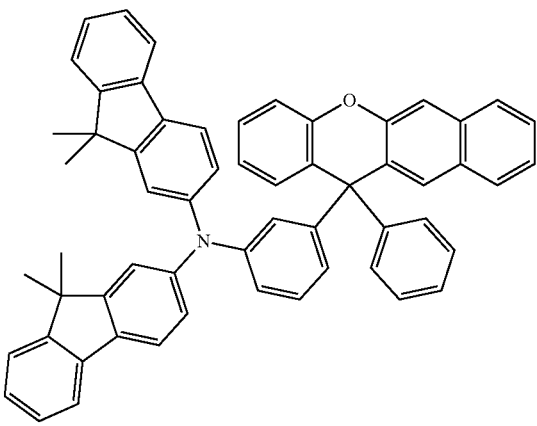
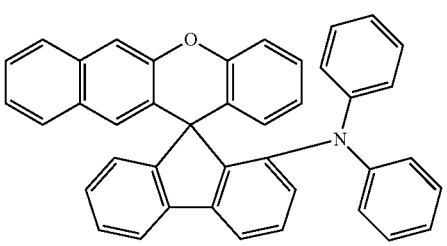

71
-continued
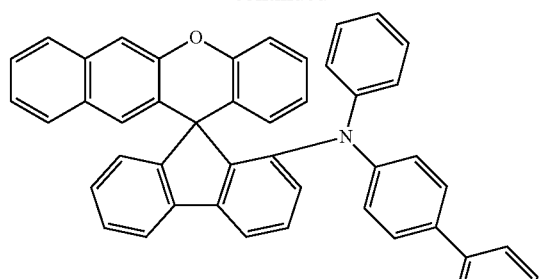
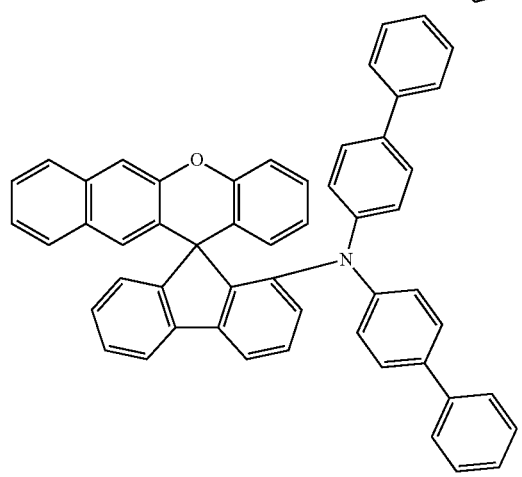
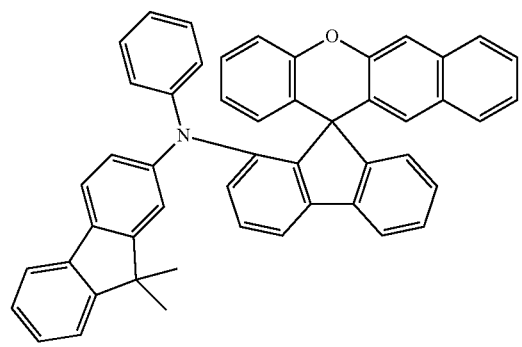
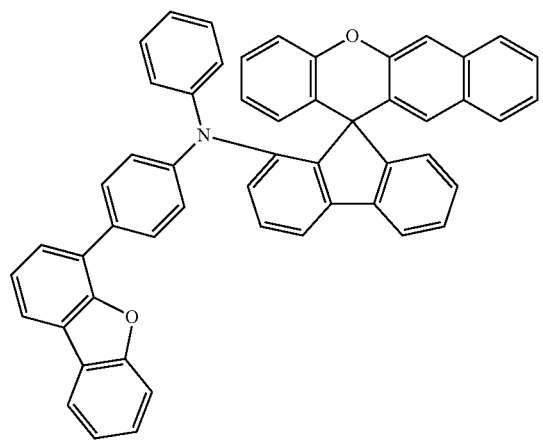
72
-continued
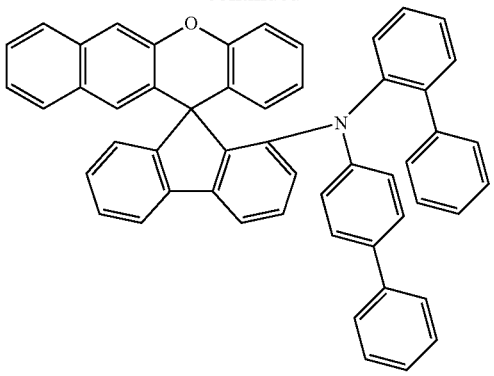
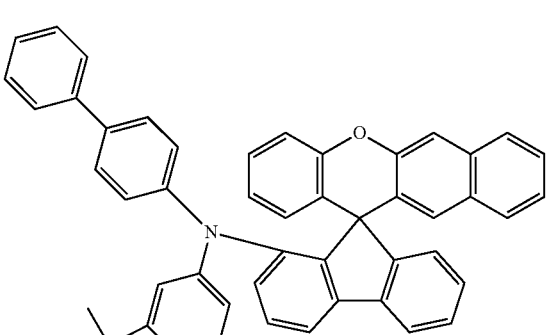
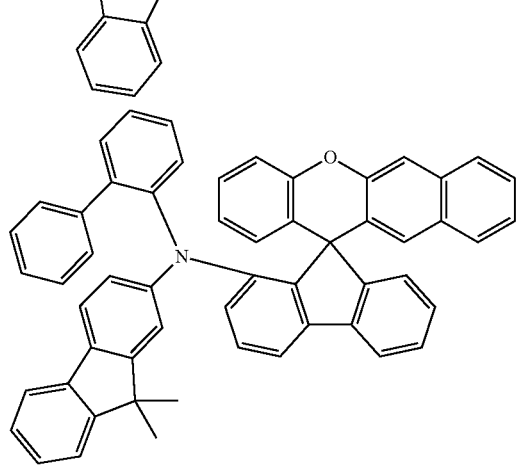

73
-continued
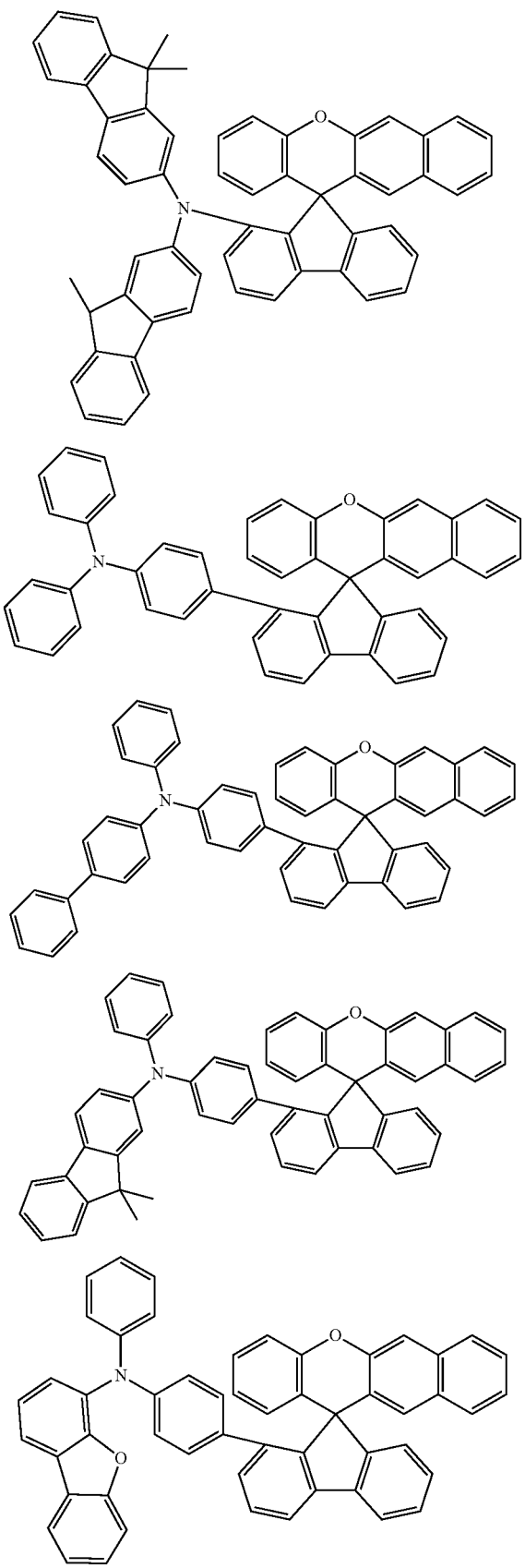
74
-continued
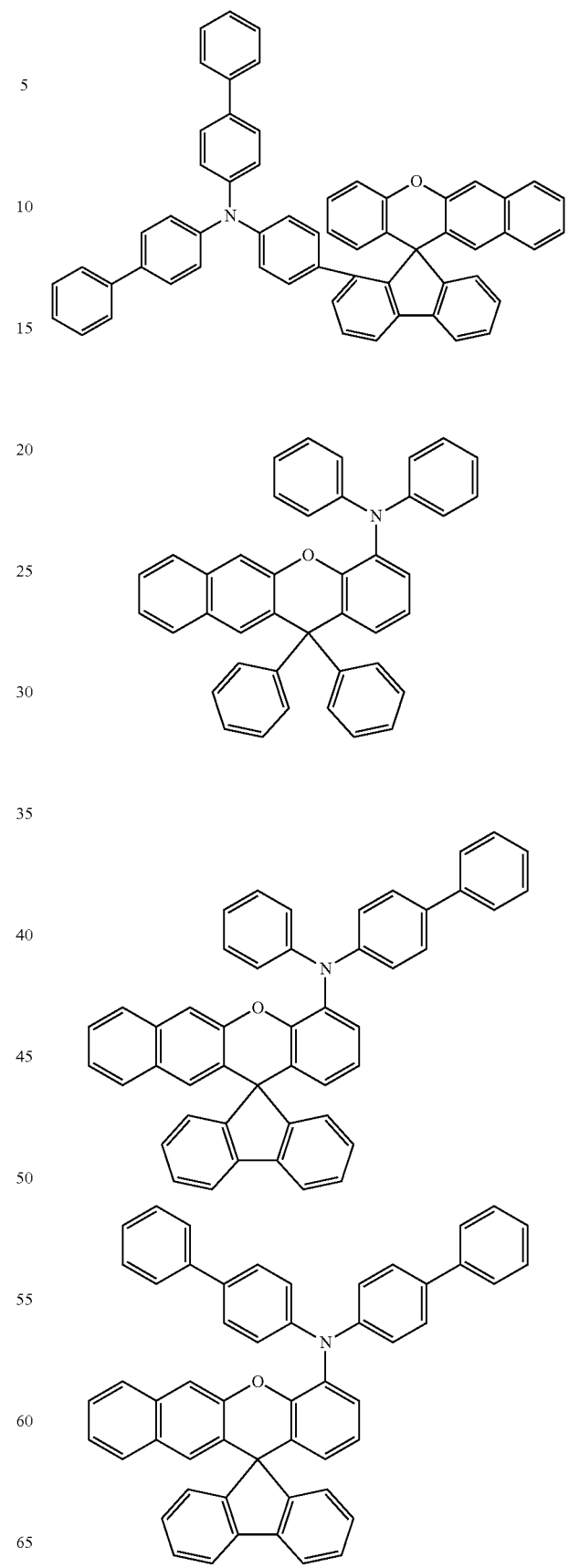

75
76
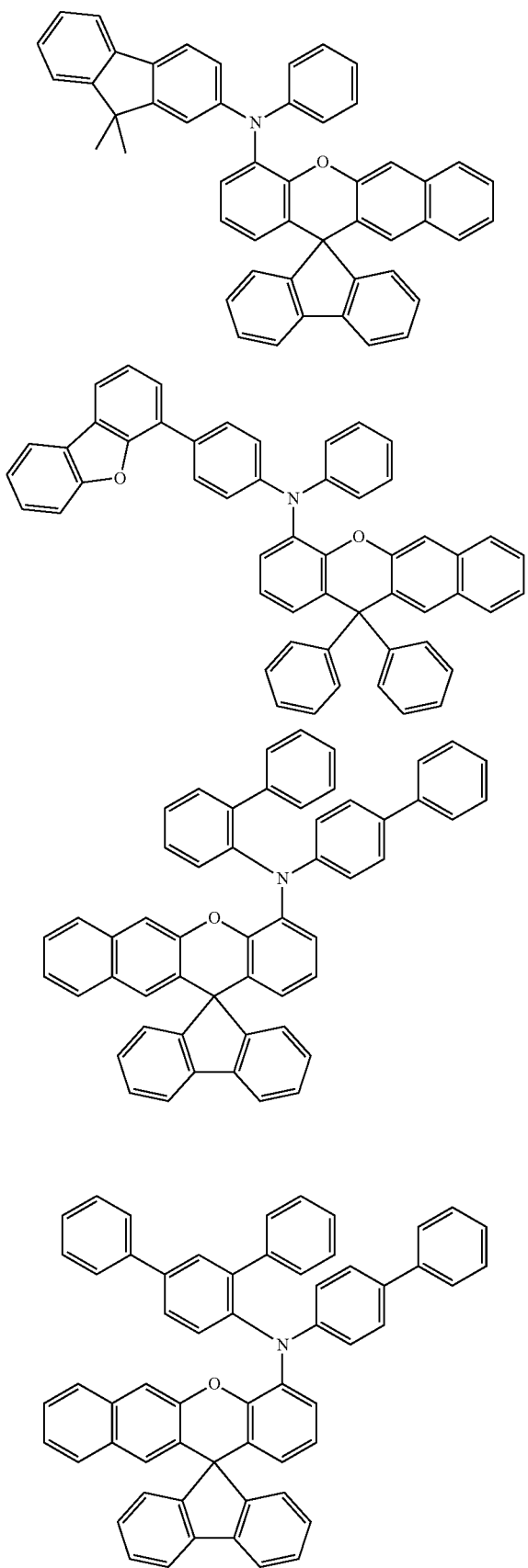
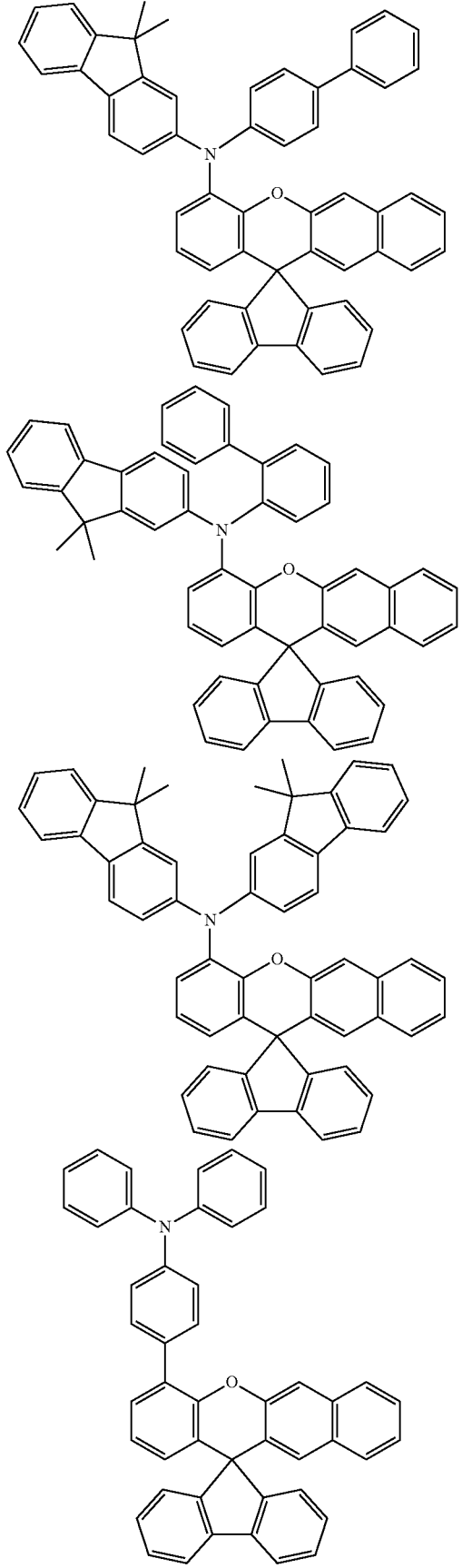

77
-continued
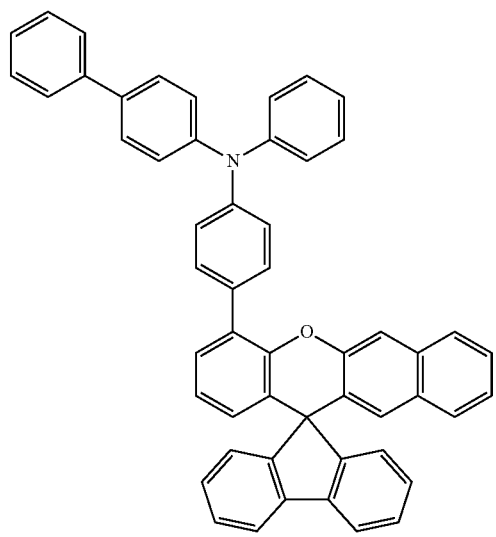
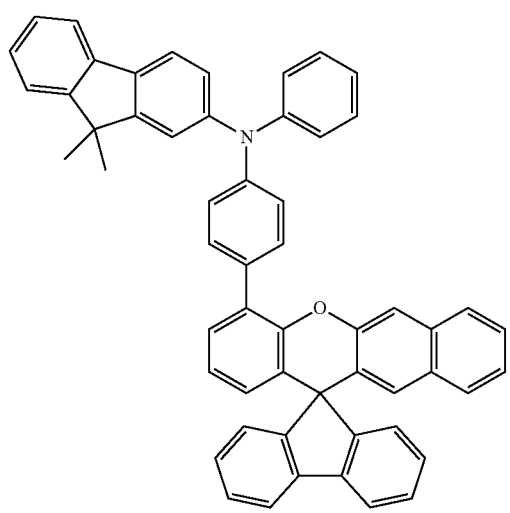
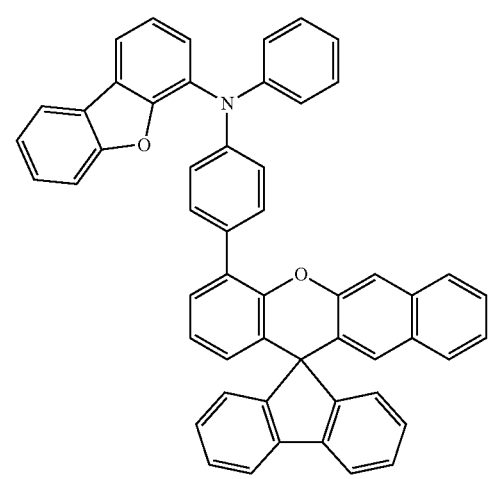
78
-continued
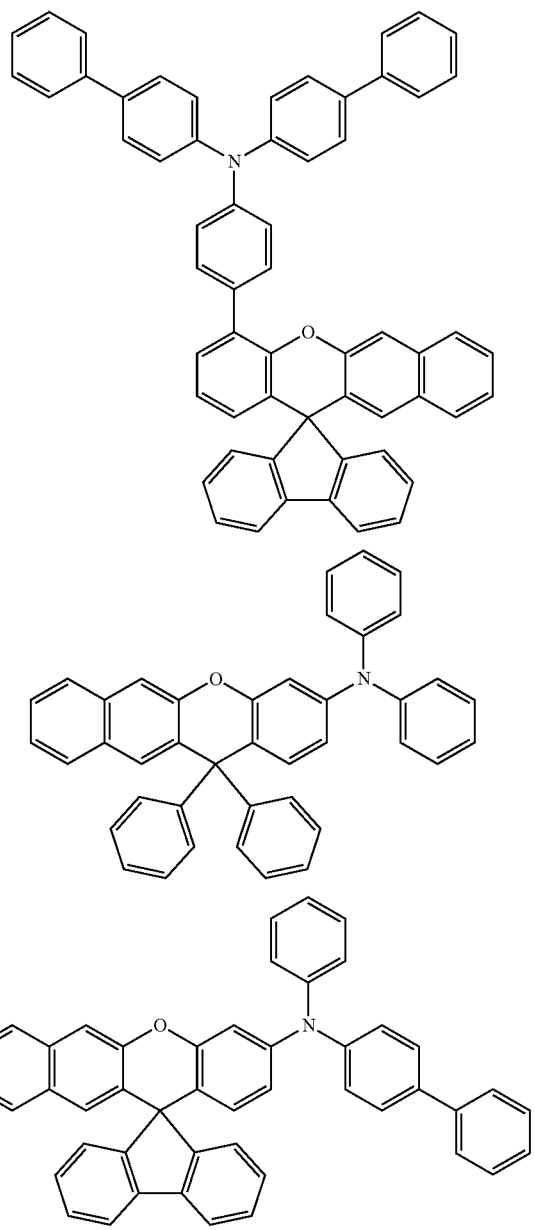
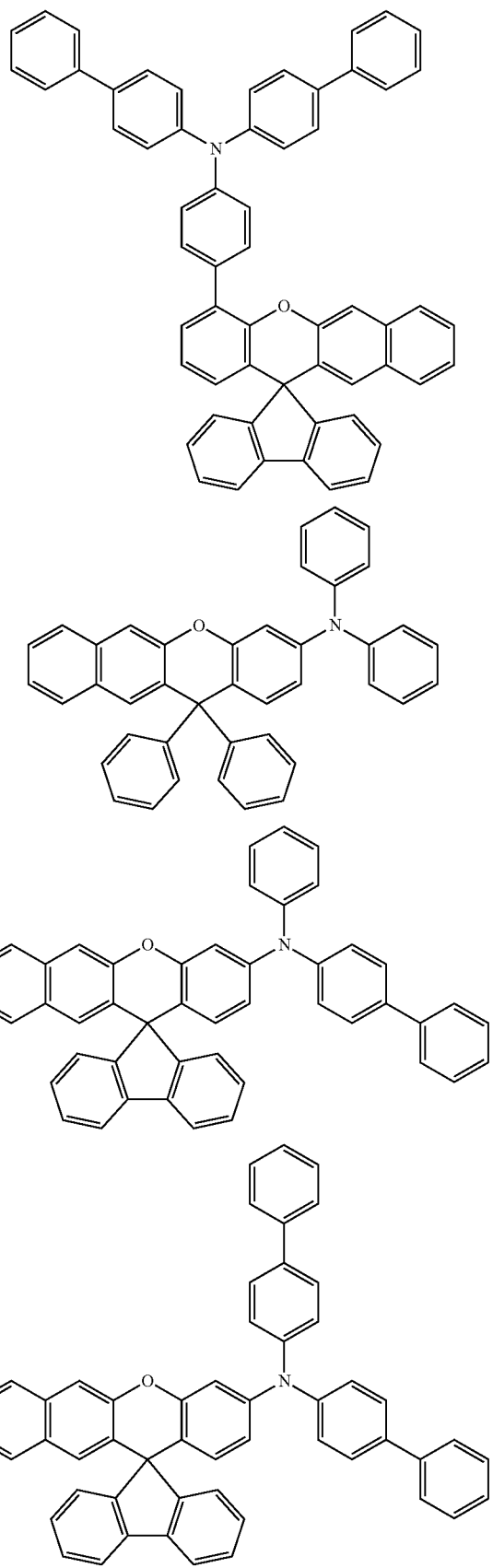

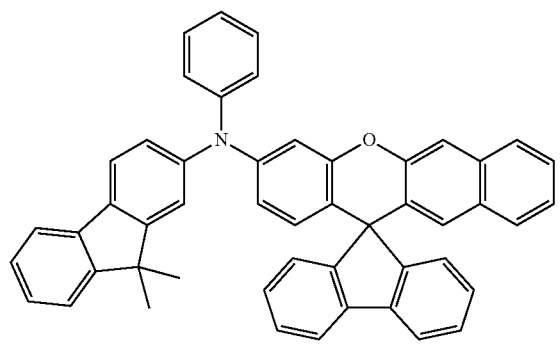
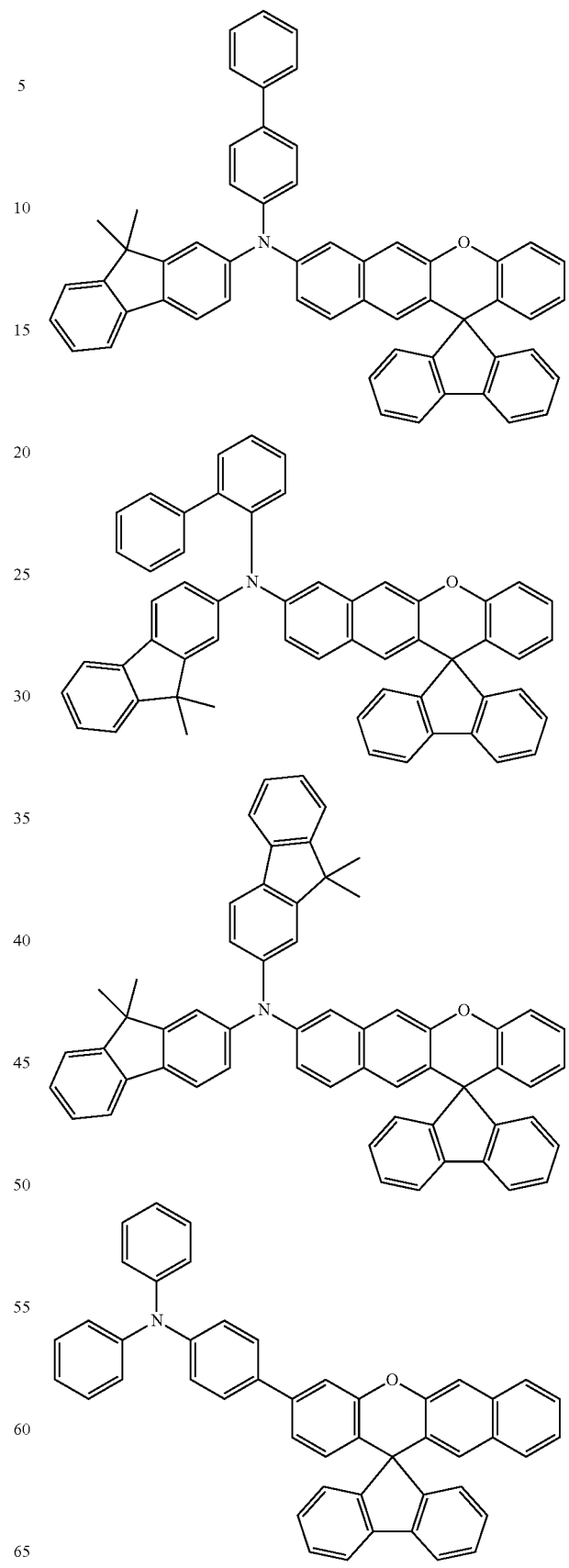

81
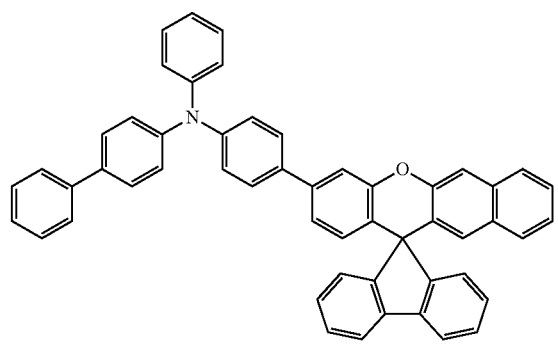
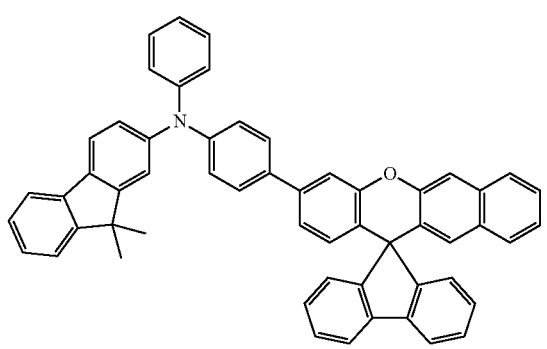
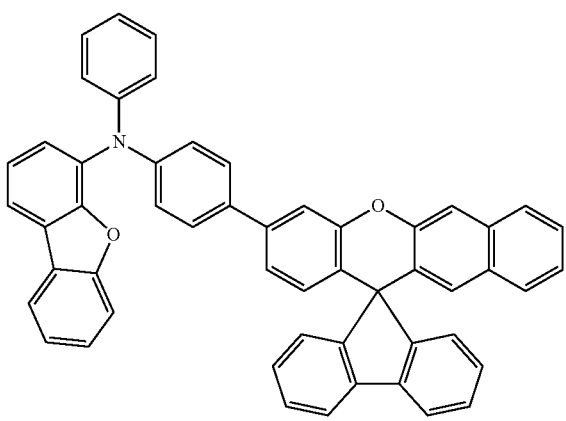
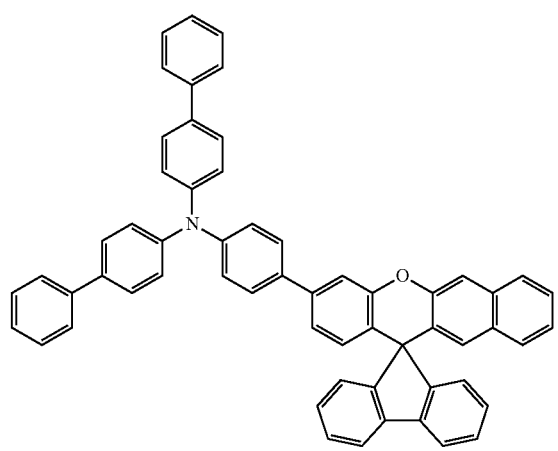
82
-continued
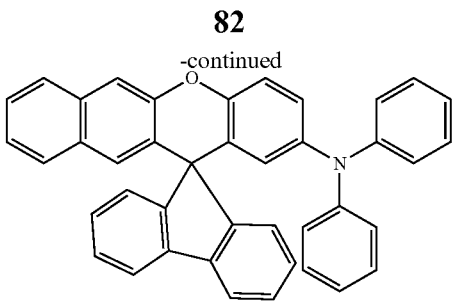
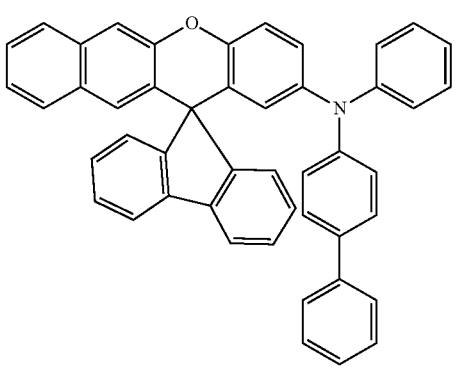
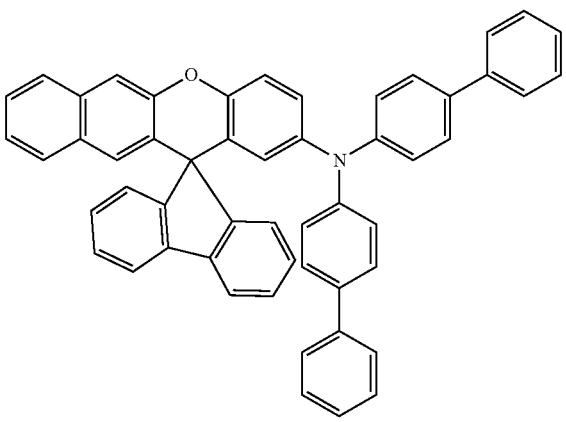
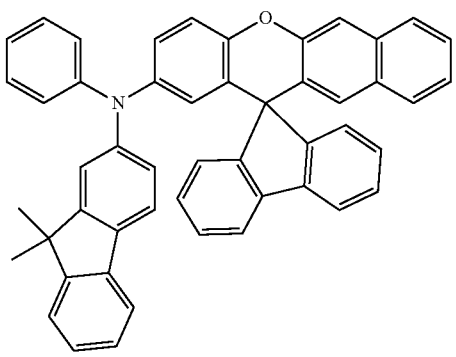

83
-continued
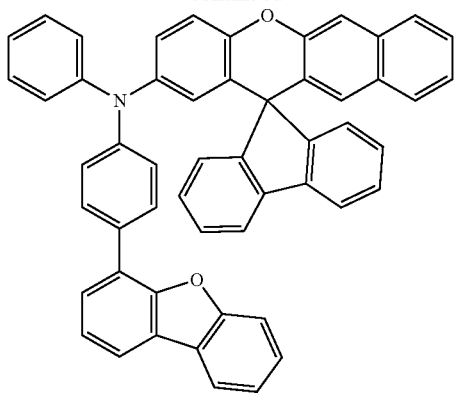
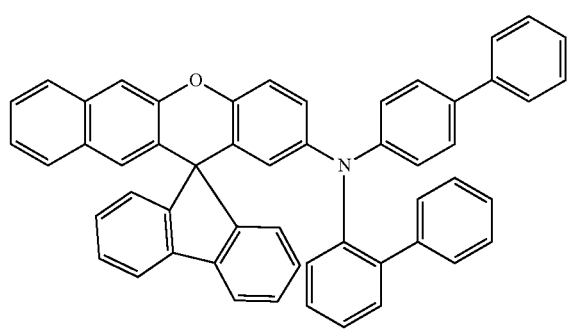
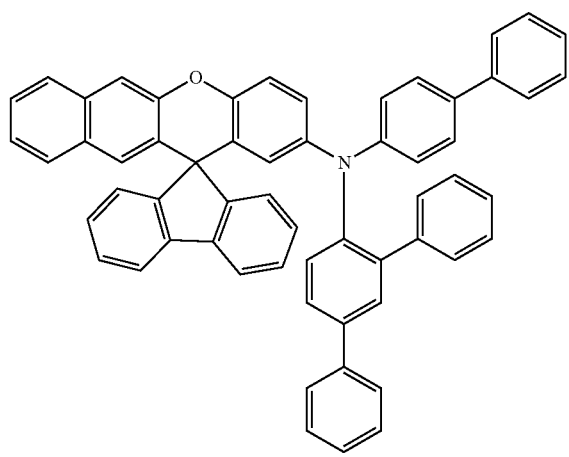
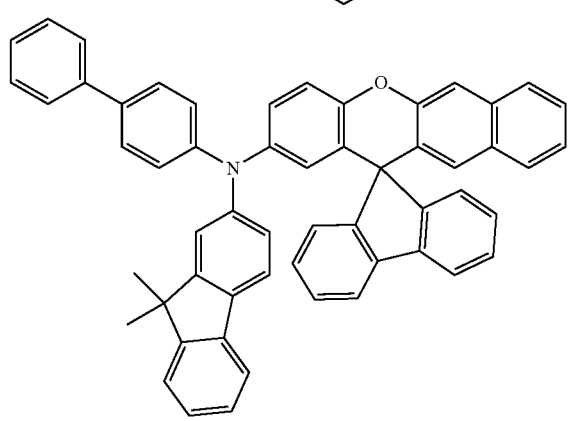
84
-continued
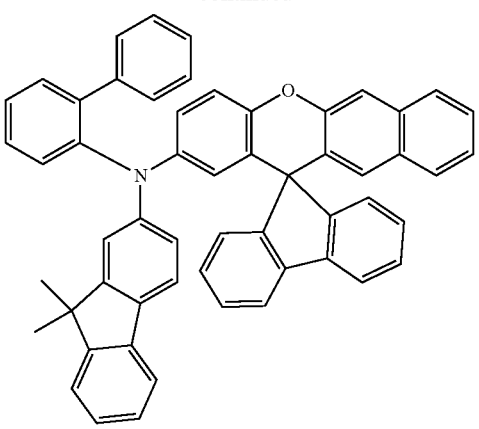
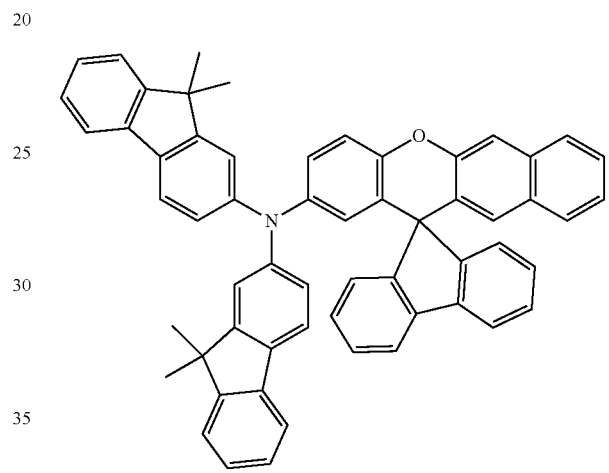
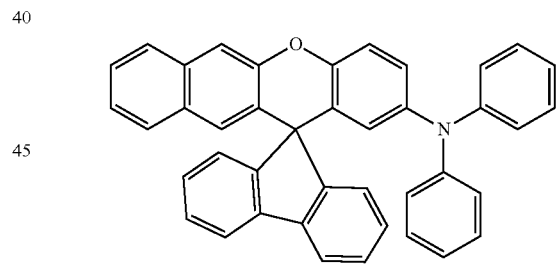
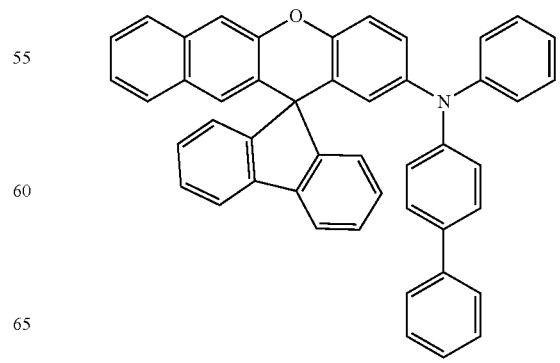

85
-continued
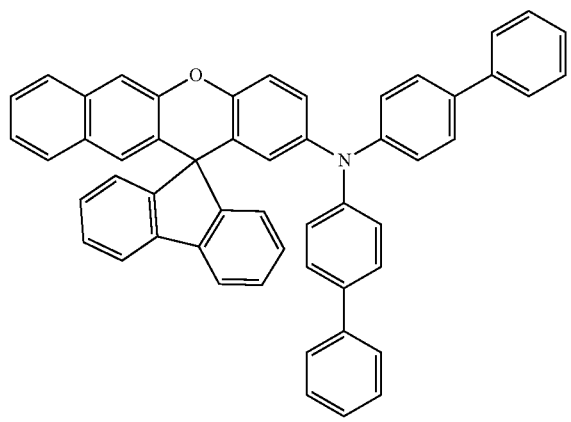
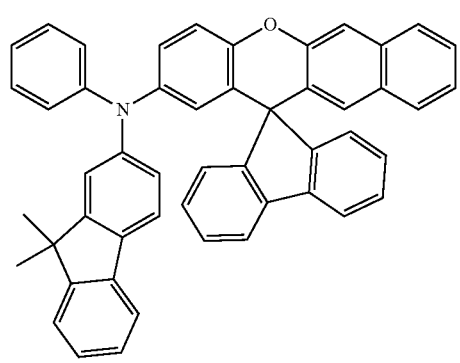
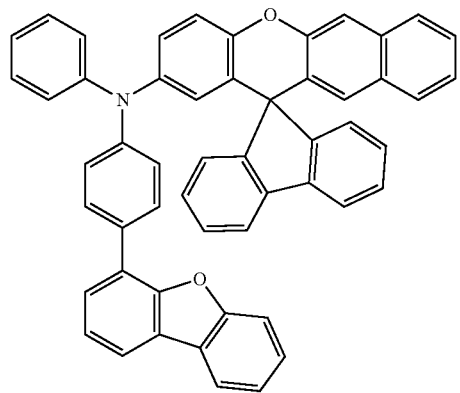
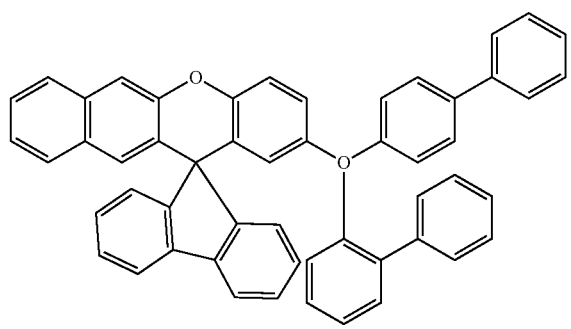
86
-continued
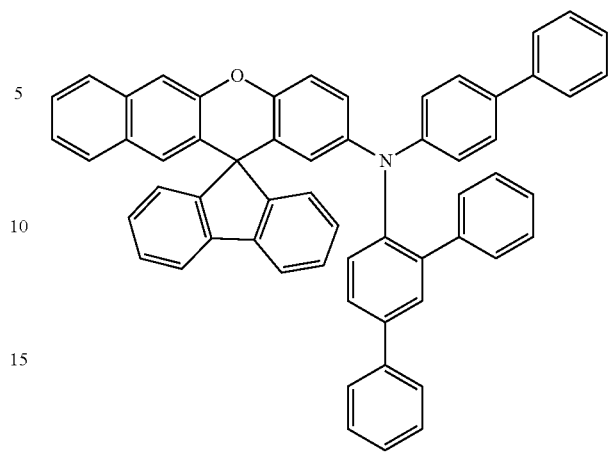
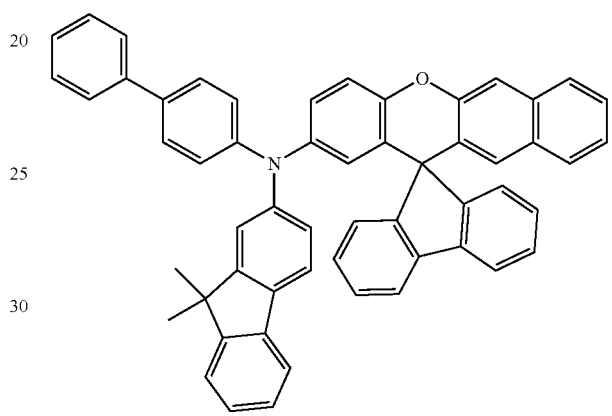
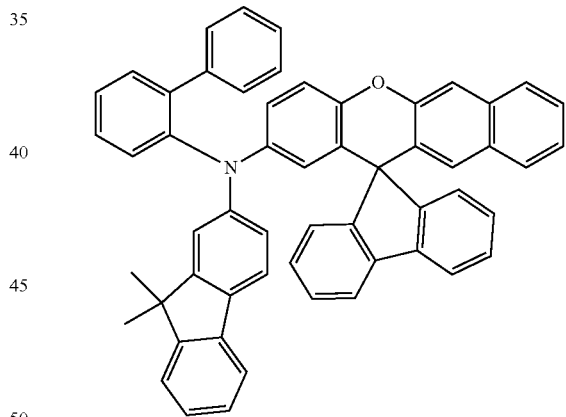
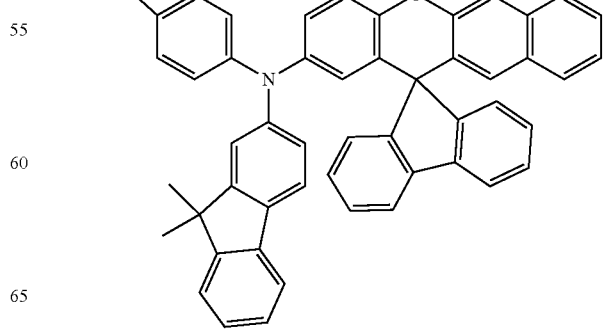

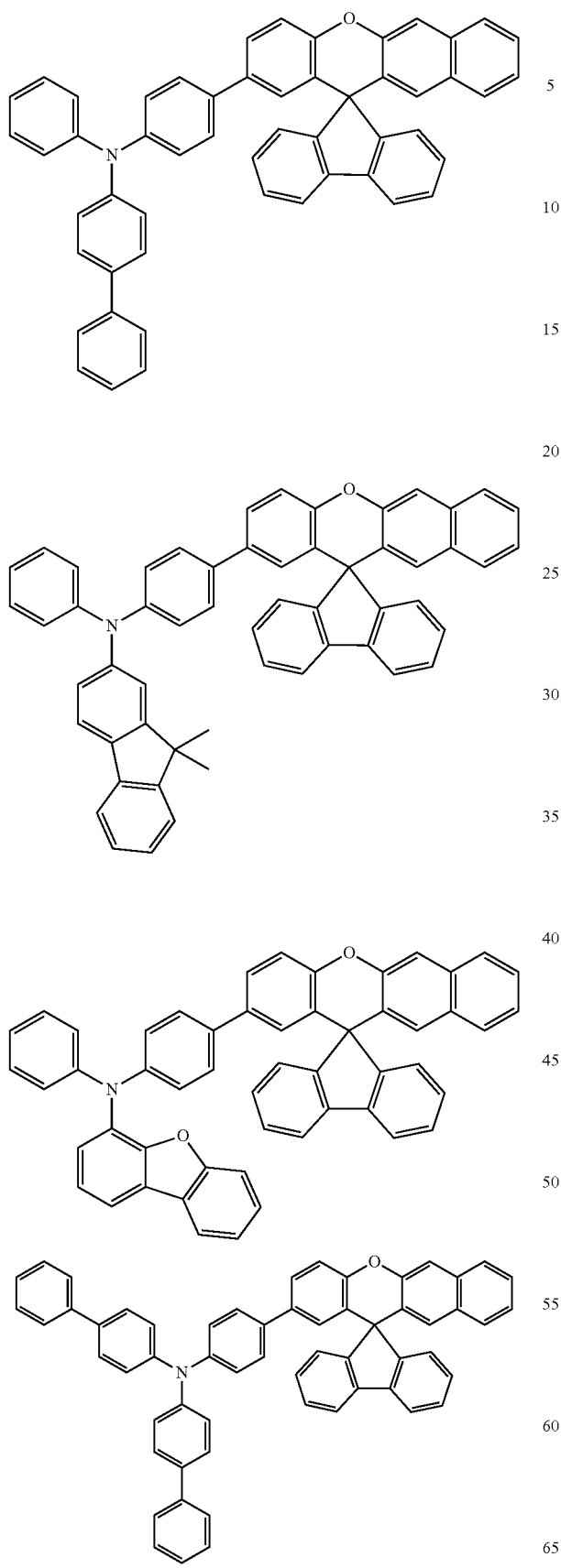
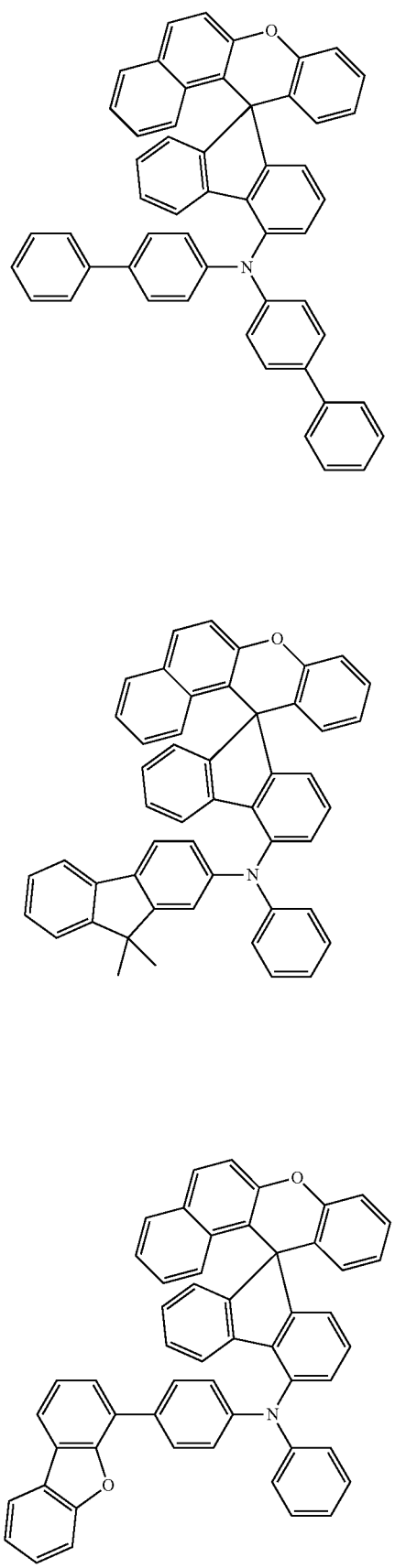

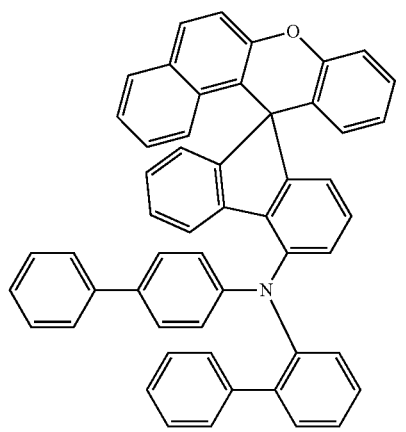
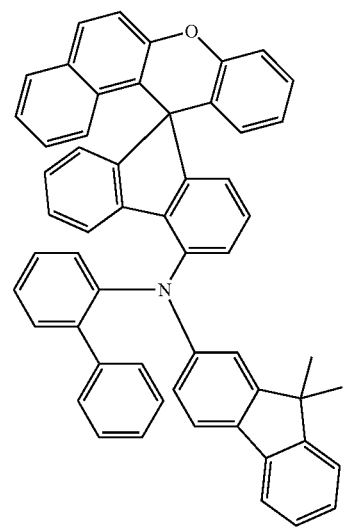
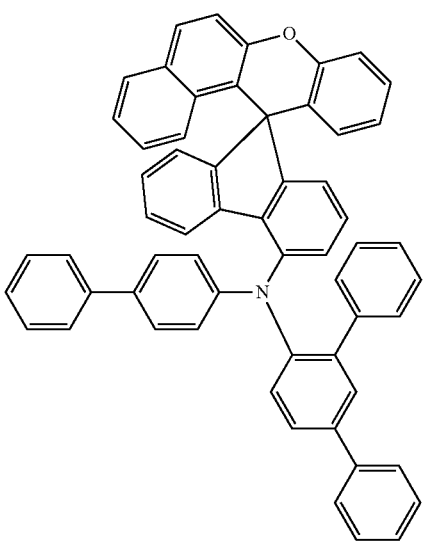
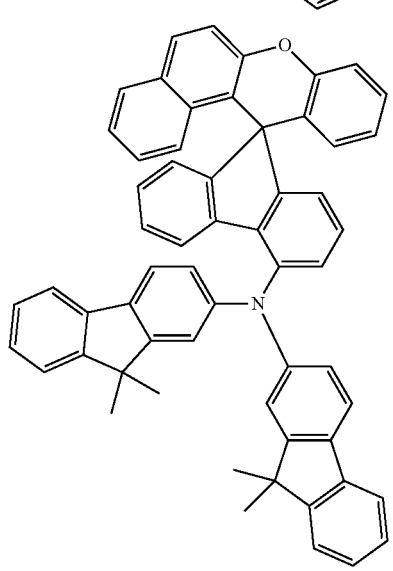
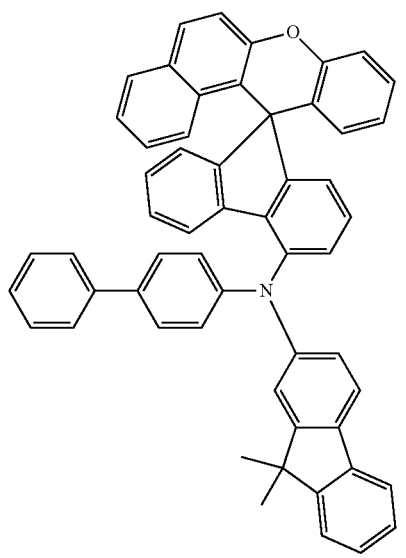
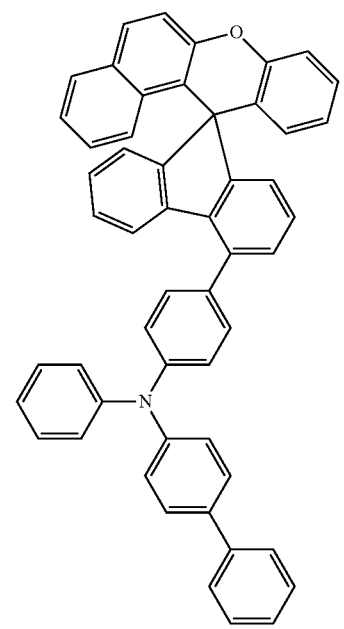 [SMILES: c1ccc(-c2ccc(N(c3ccccc3)c3ccc(-c4cccc5c4-c4ccccc4C54c5ccccc5Sc5ccc6ccccc6c54)cc3)cc2)cc1]

91
-continued
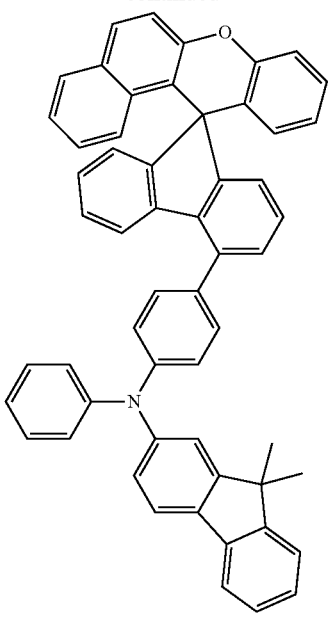
92
-continued
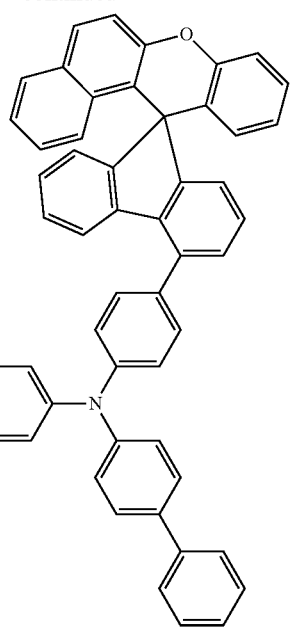
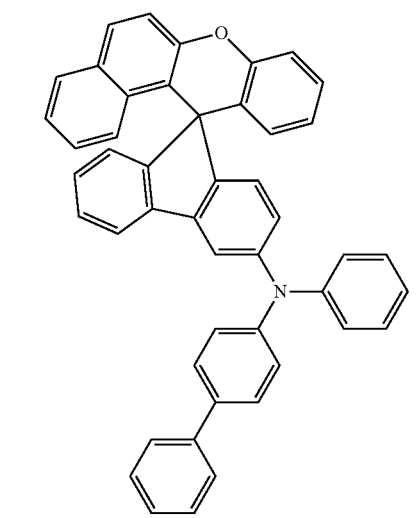
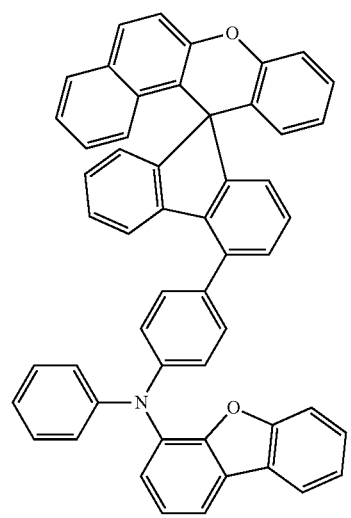
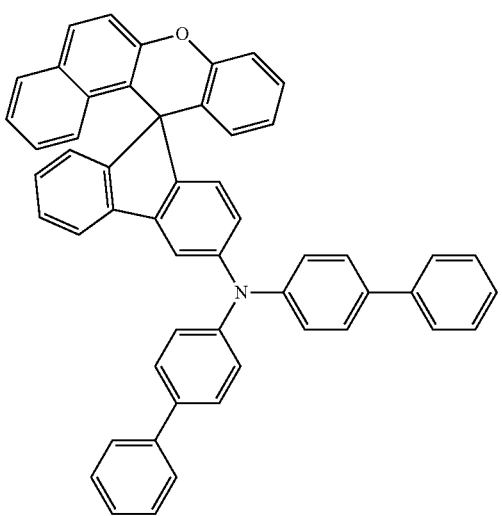

93
-continued
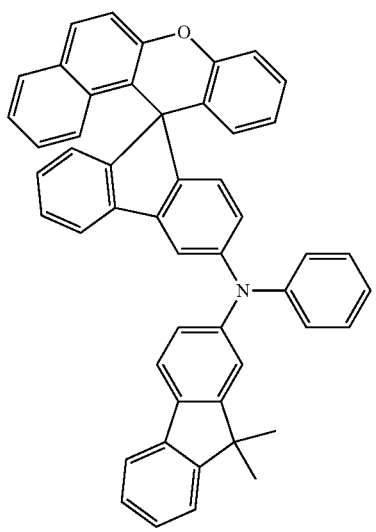
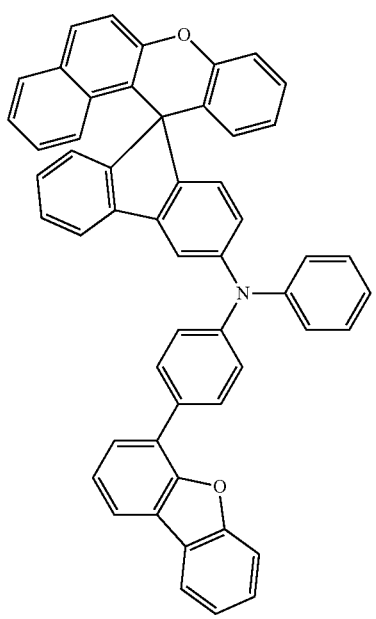
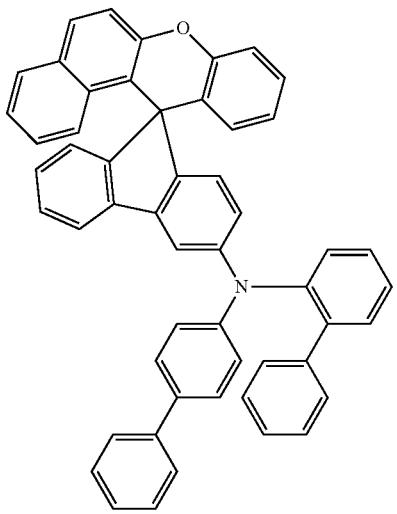
94
-continued
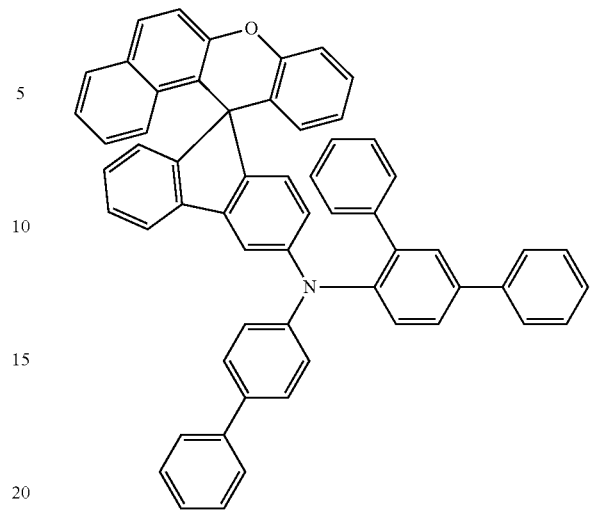
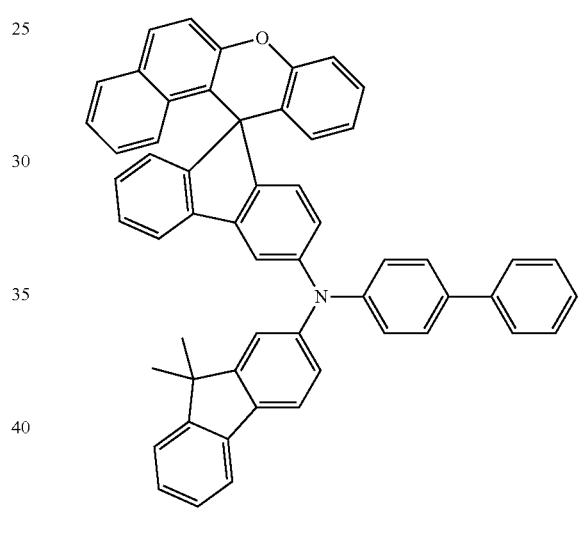
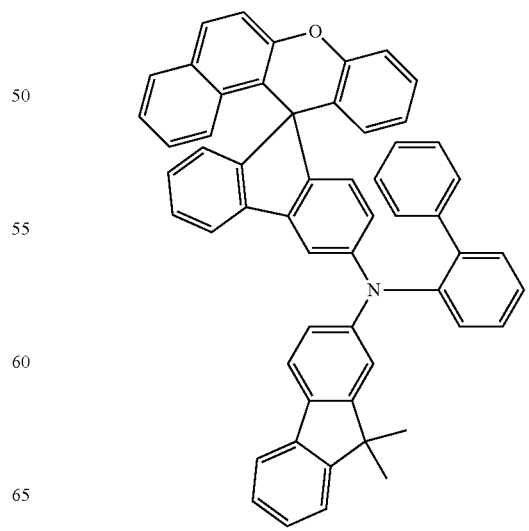

95
-continued
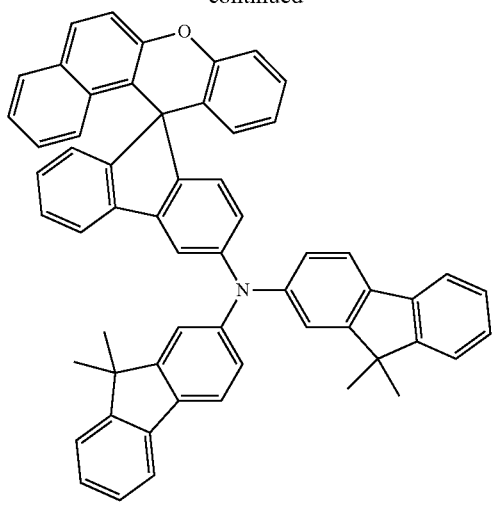
96
-continued
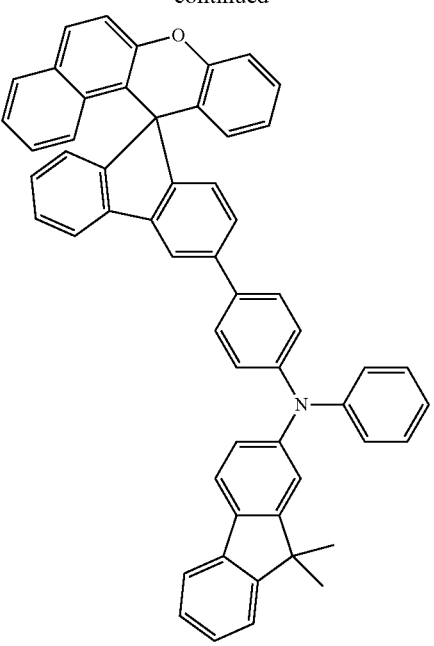
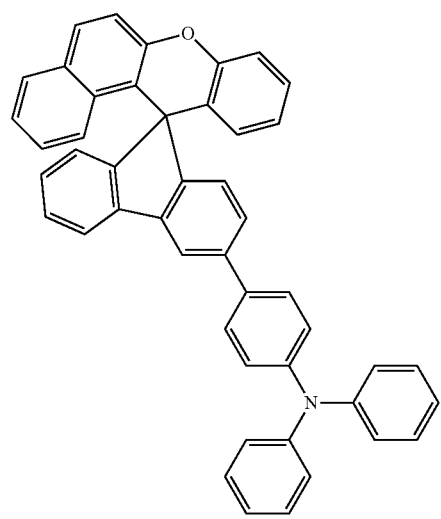
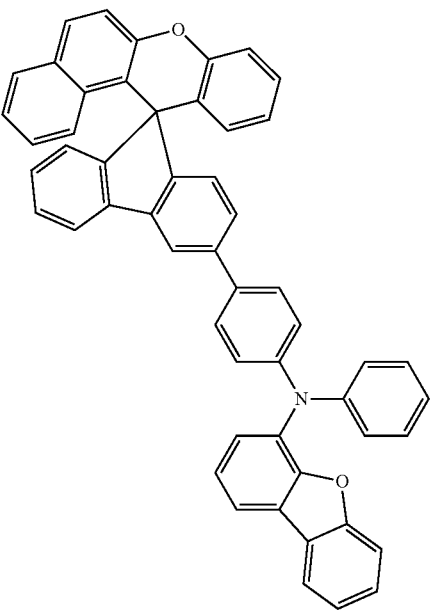

97
-continued
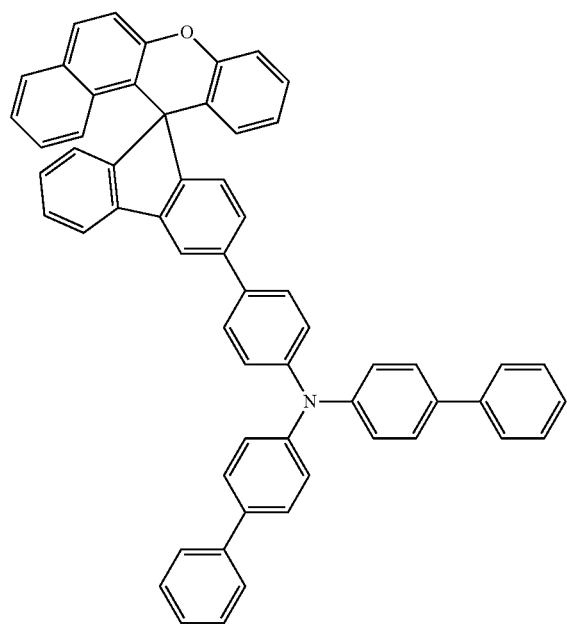
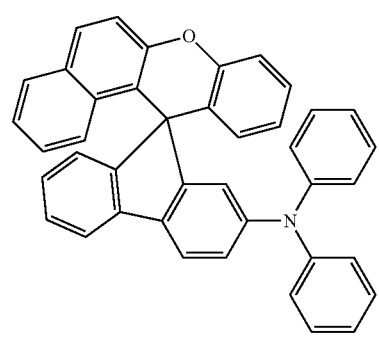
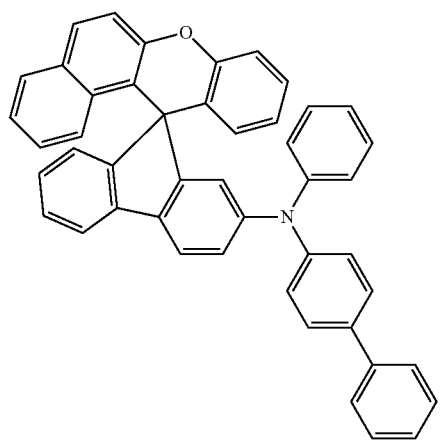
98
-continued
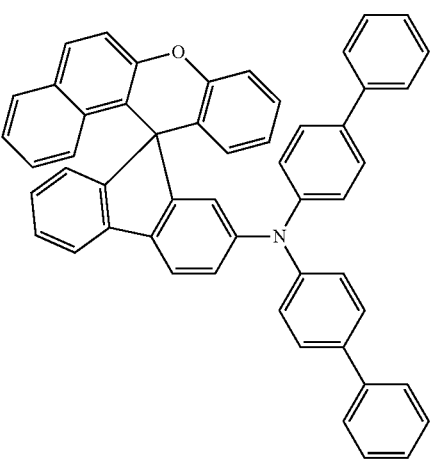
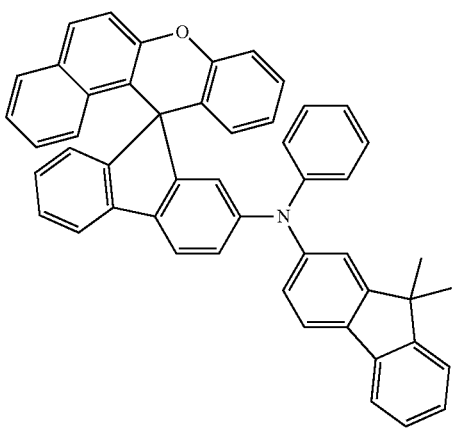
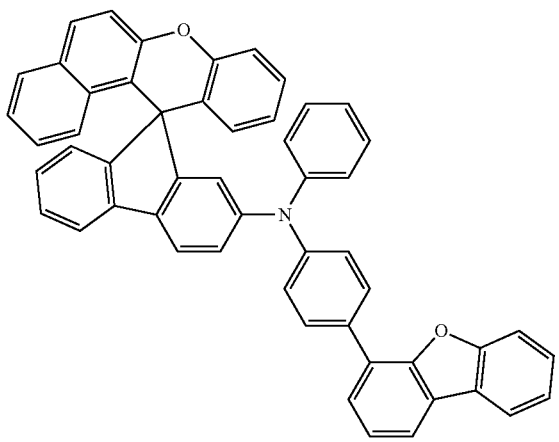

99
-continued
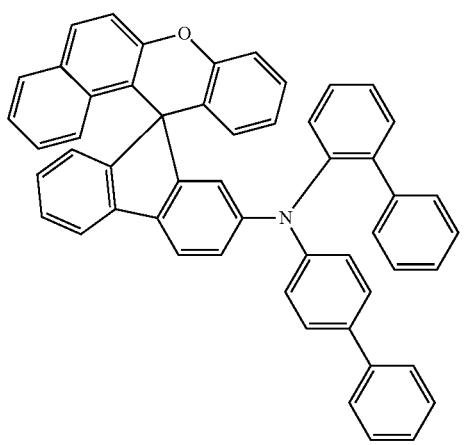
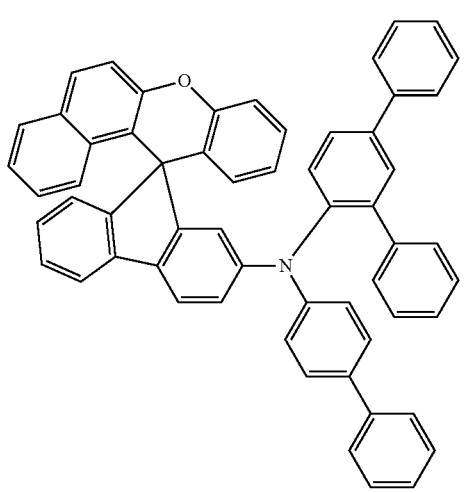
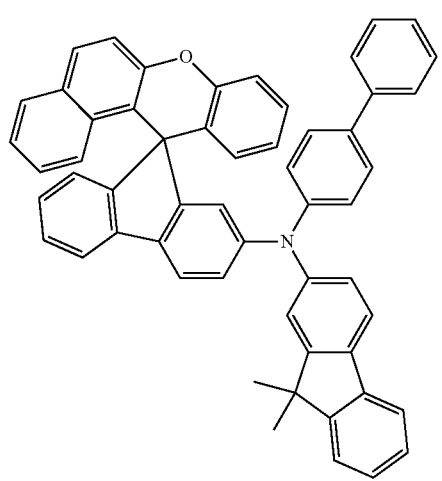
100
-continued
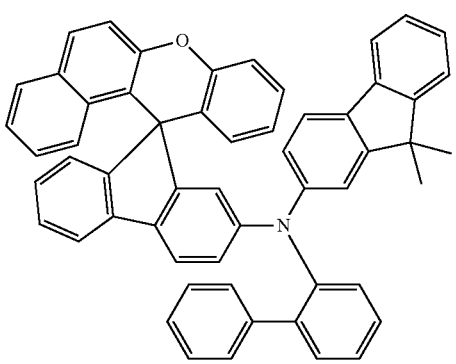
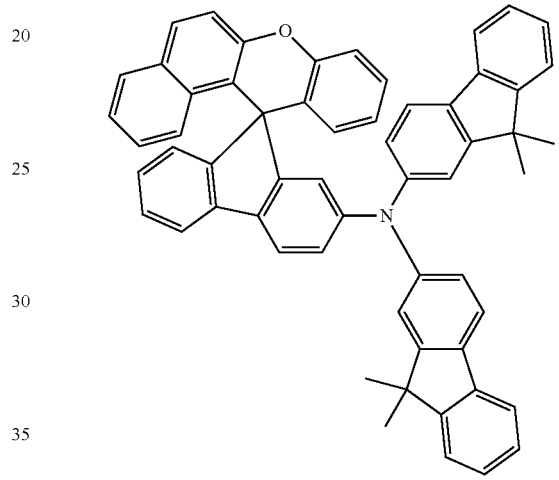
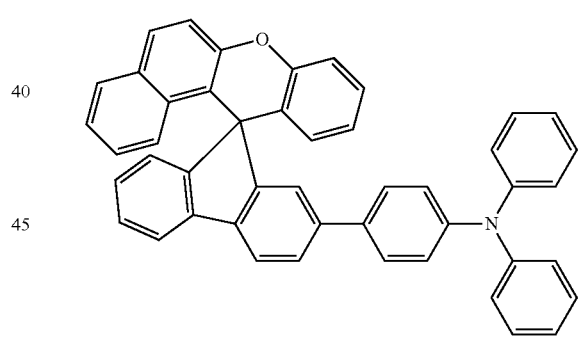
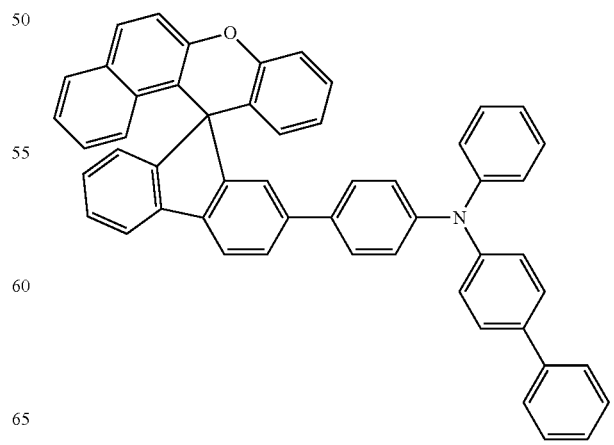

101
-continued
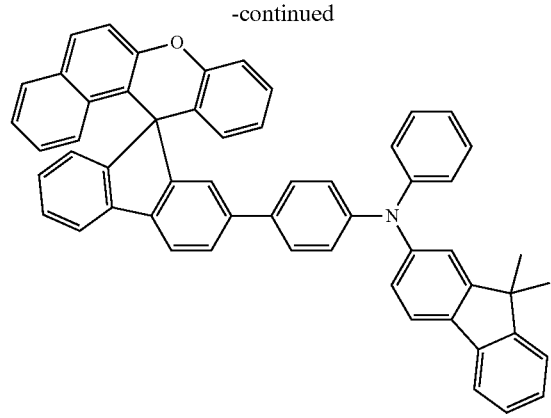
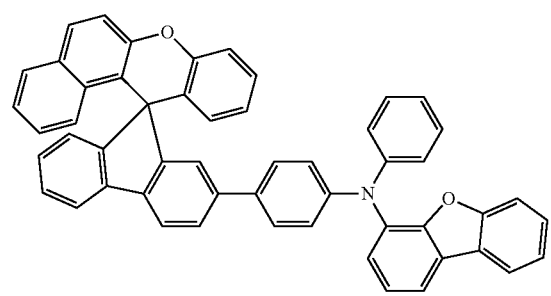
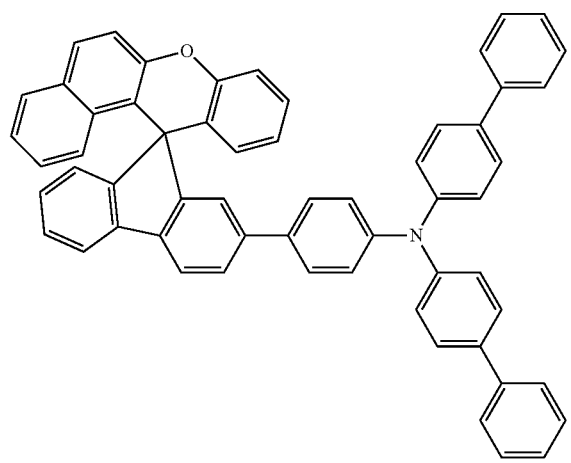
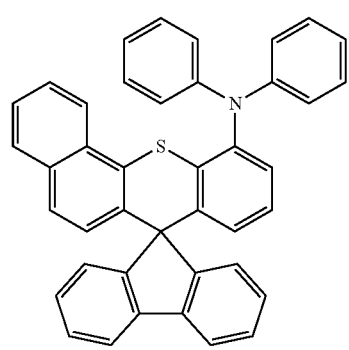
102
-continued
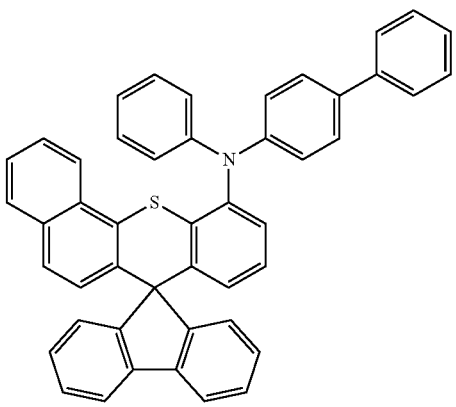
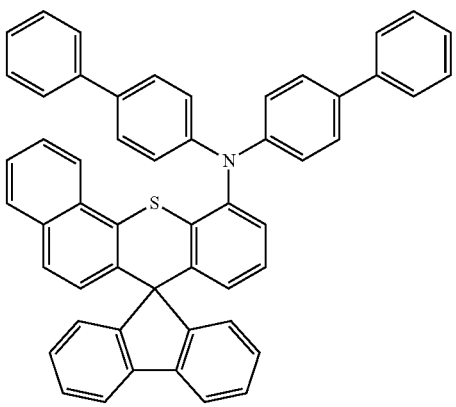
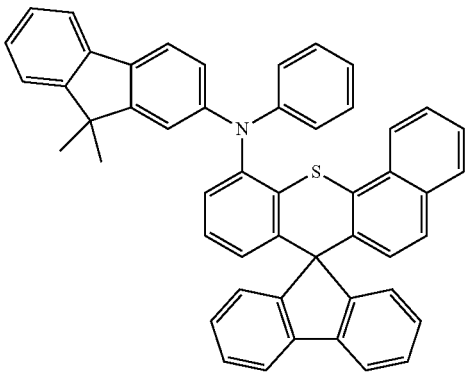
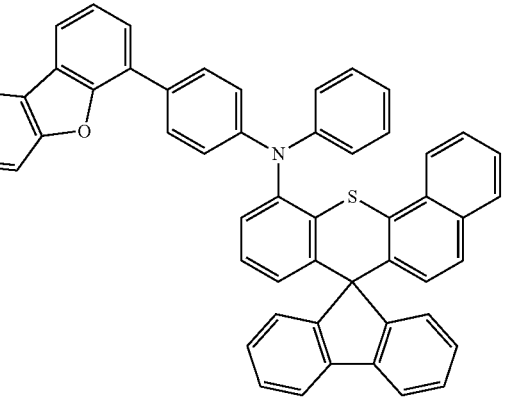

103
-continued
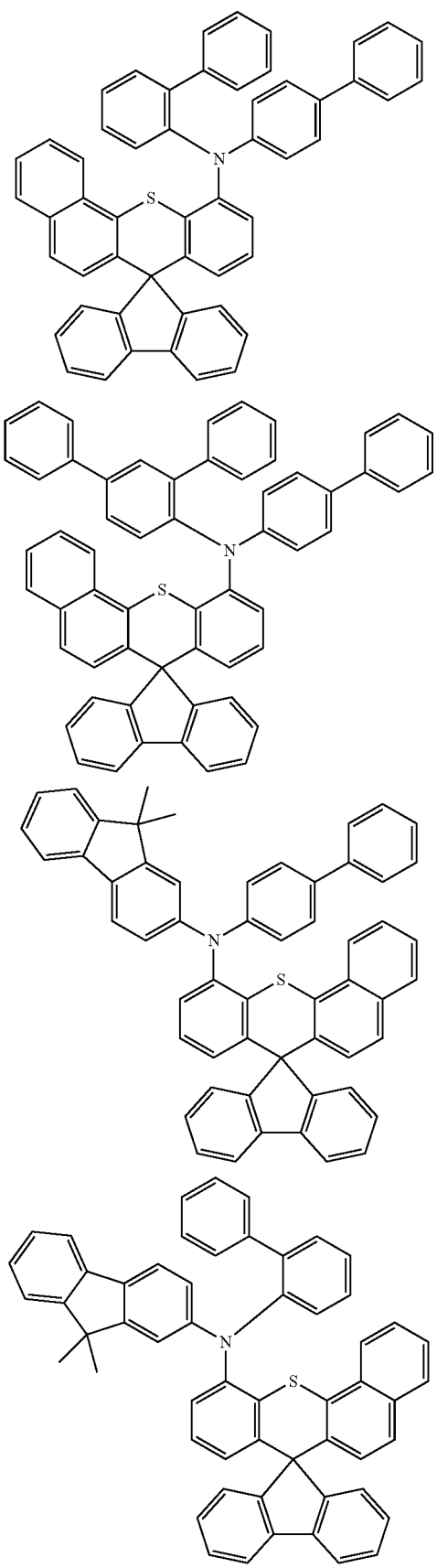
104
-continued
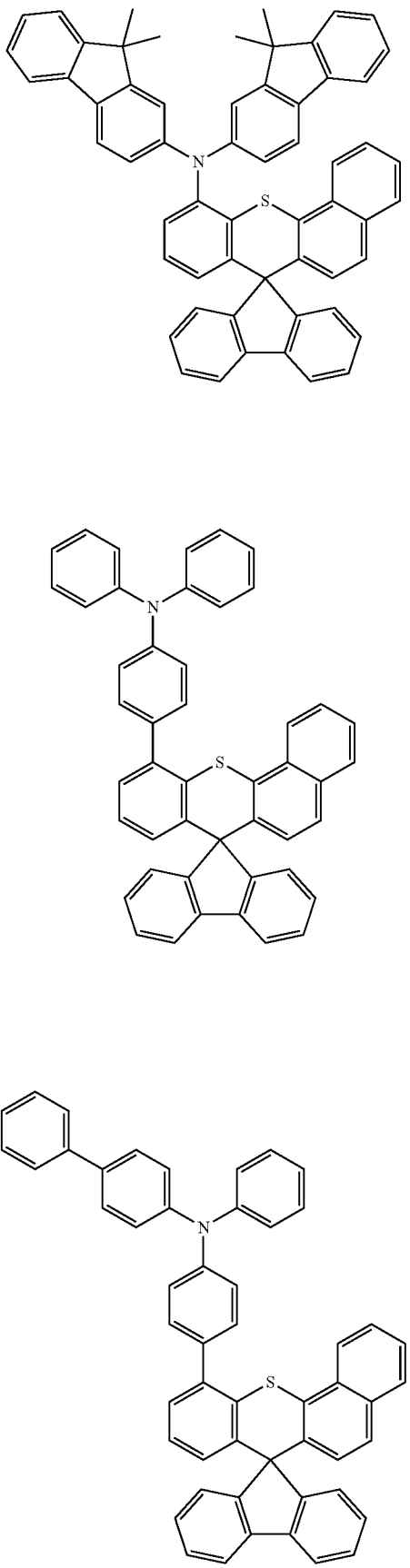

105
-continued
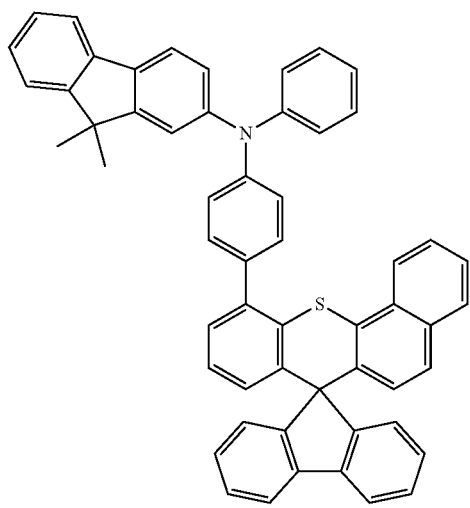
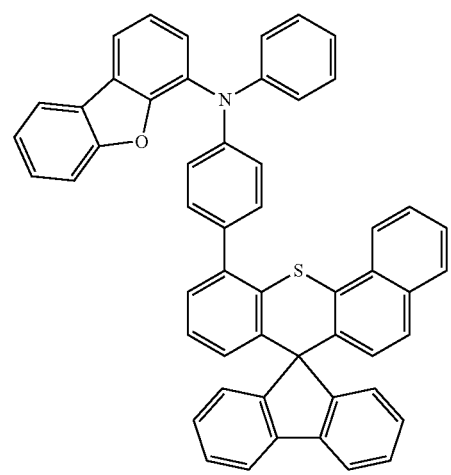
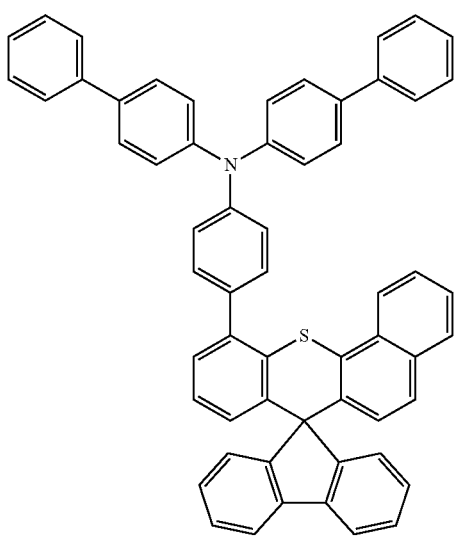
106
-continued
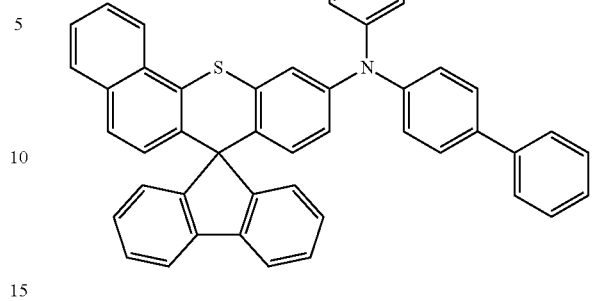
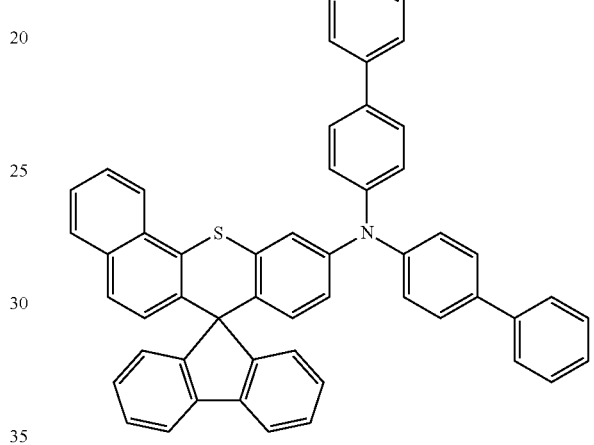
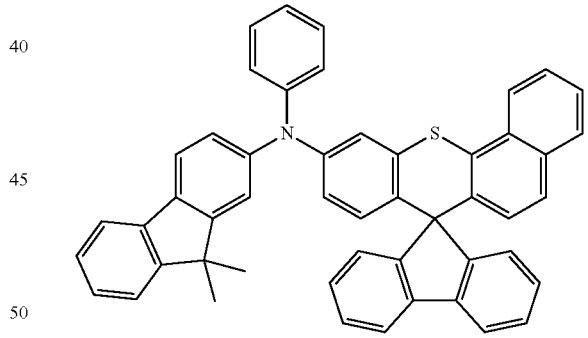
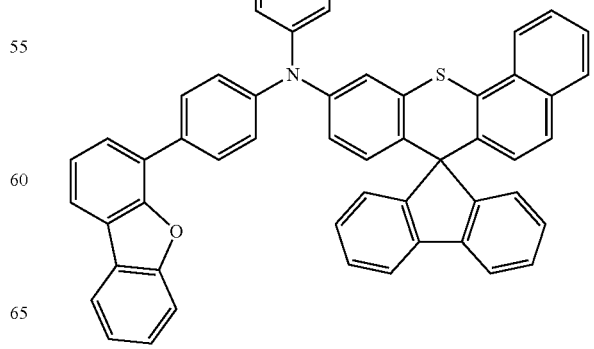

107
-continued
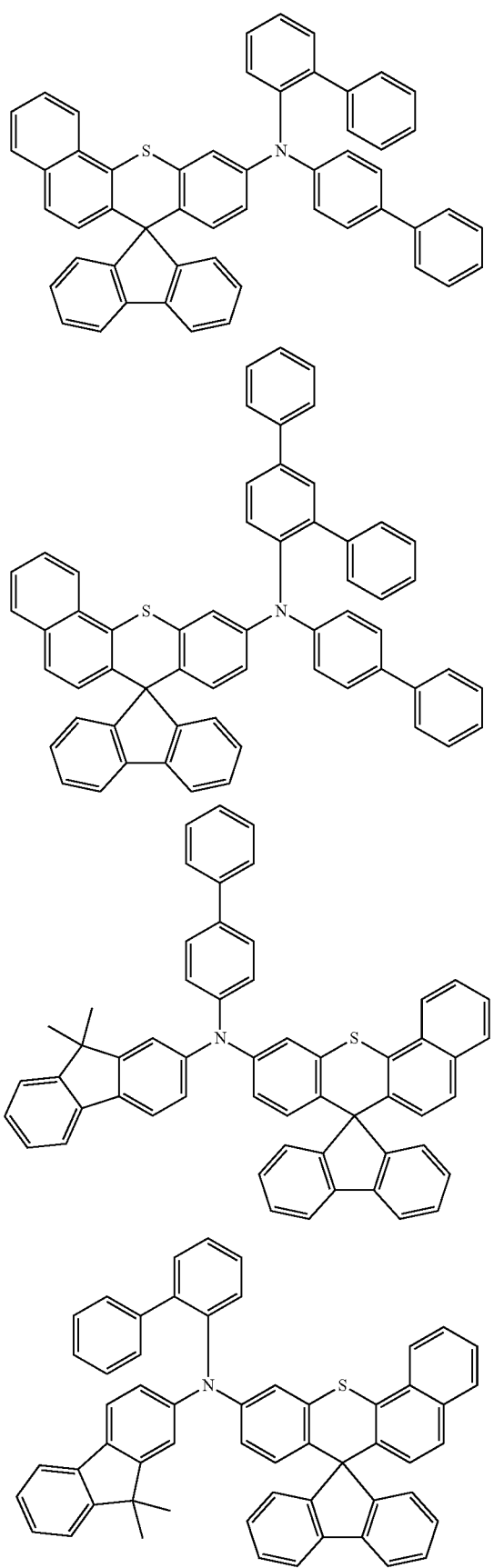
108
-continued
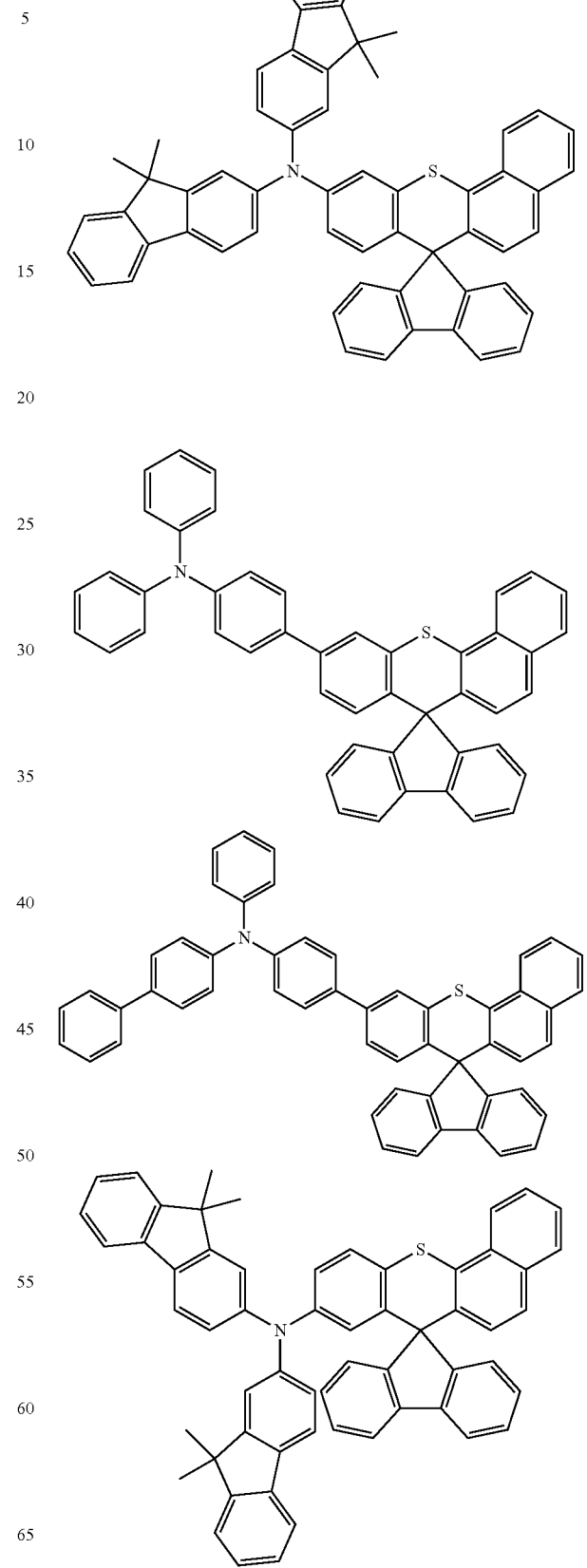

109
-continued
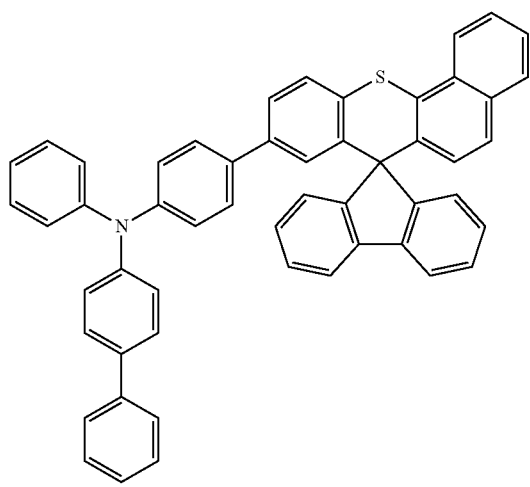
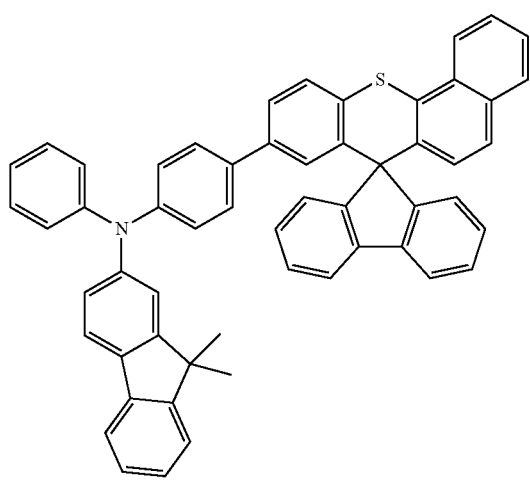
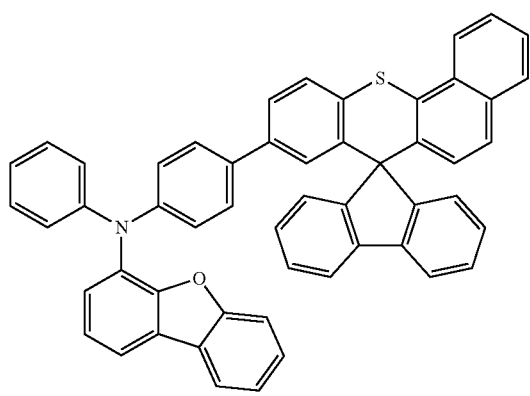
110
-continued
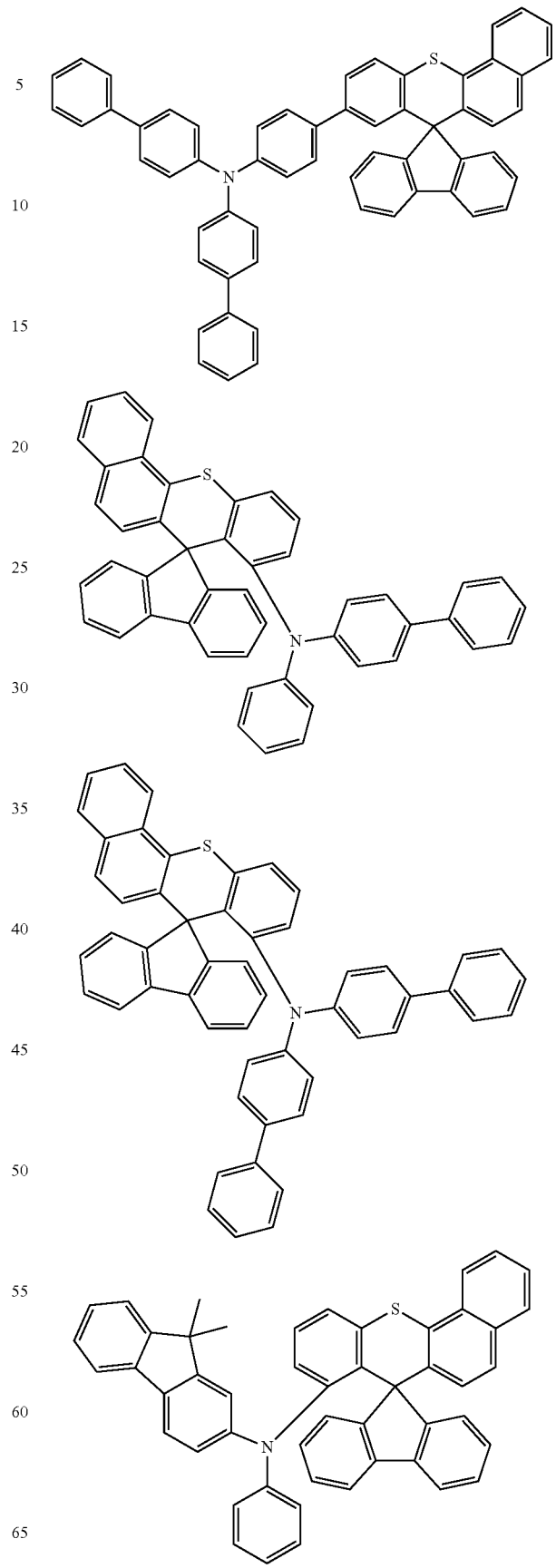

111
-continued
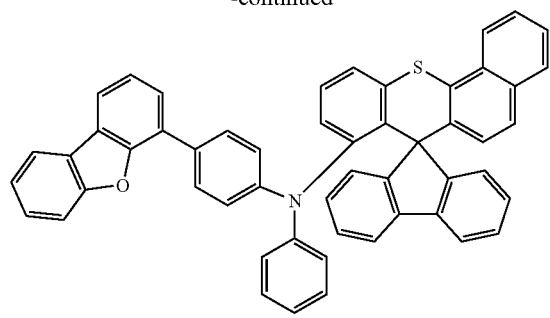
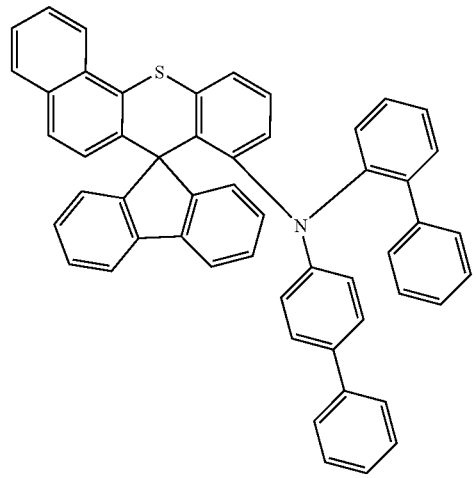
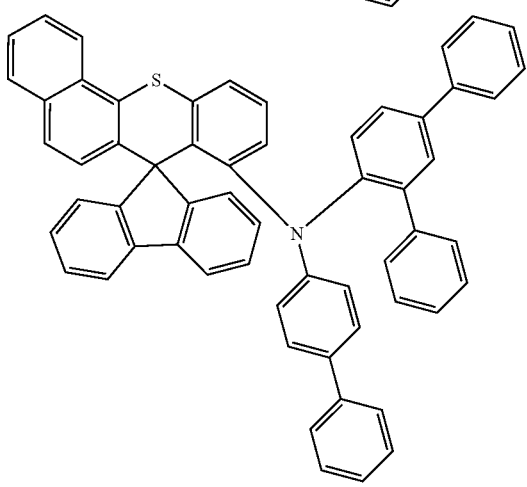
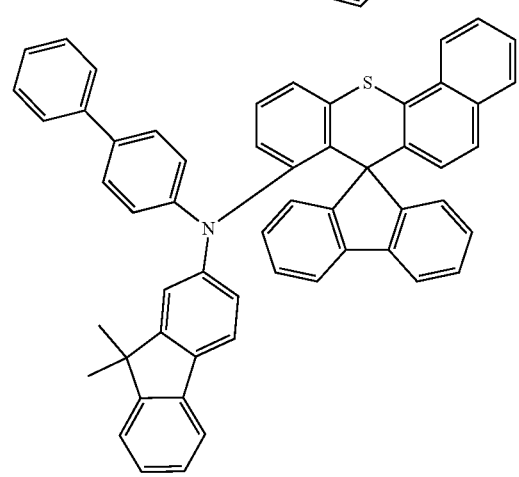
112
-continued
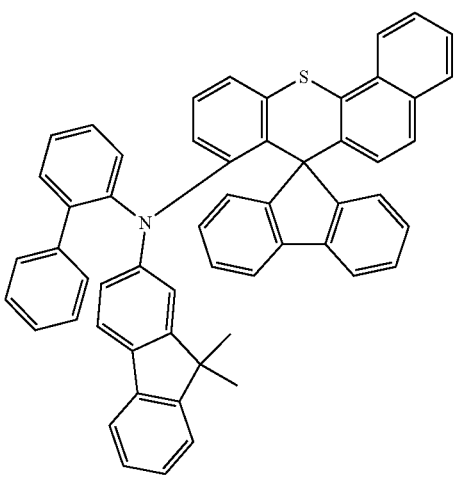
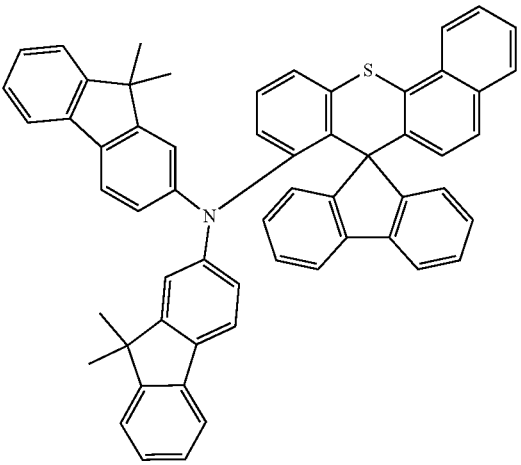
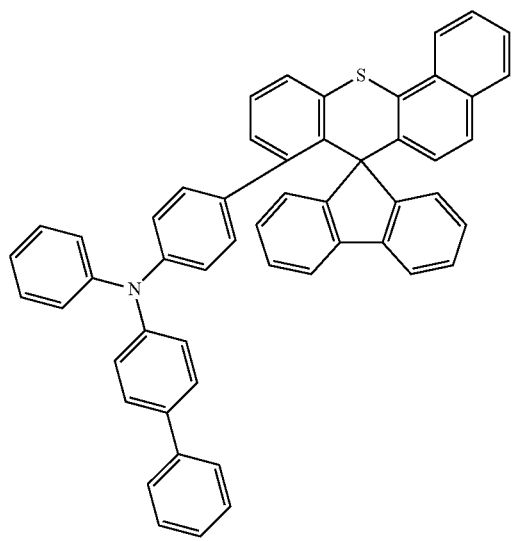

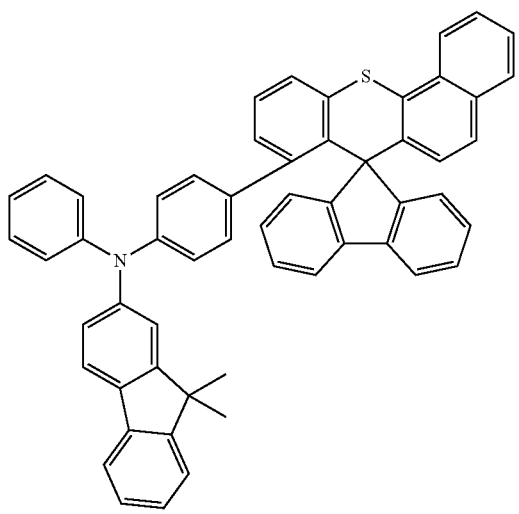
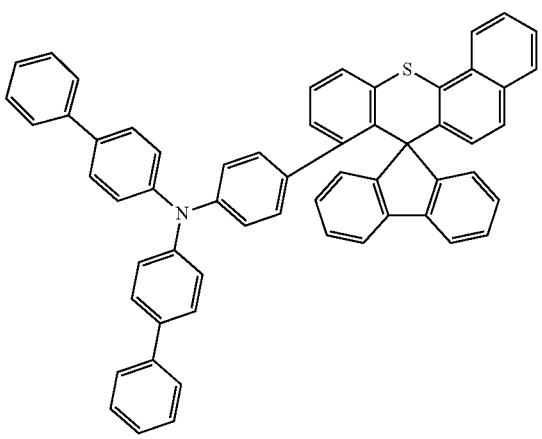
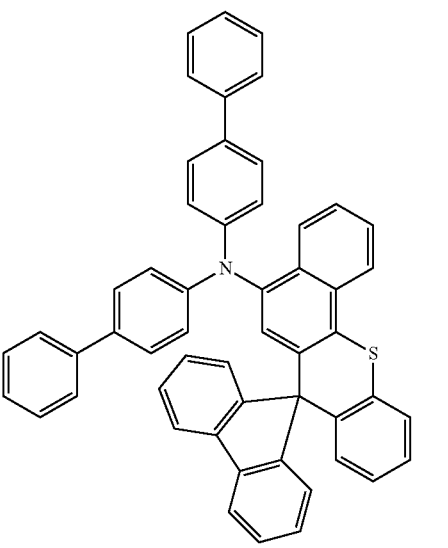
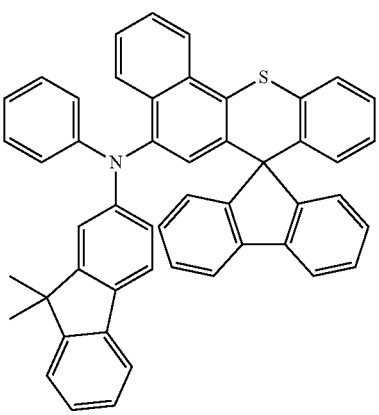
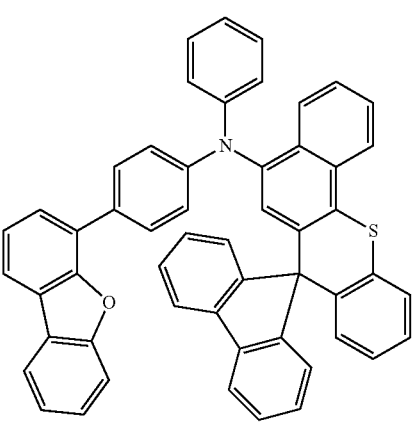
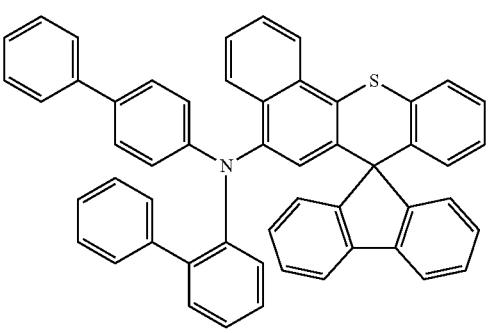

115
-continued
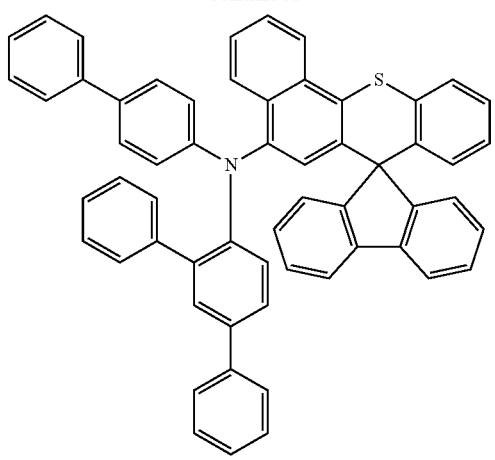
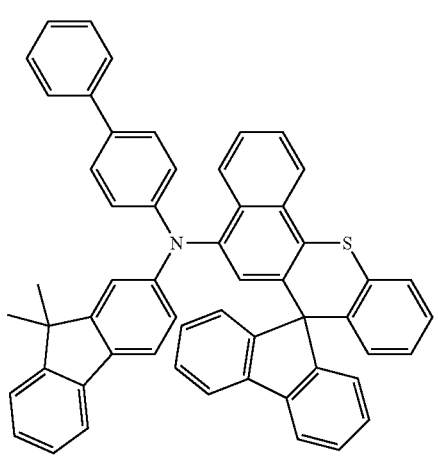
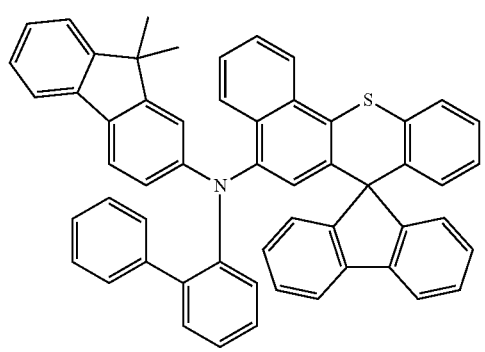
116
-continued
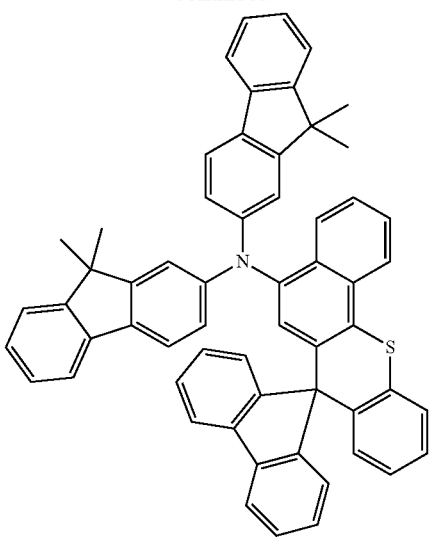
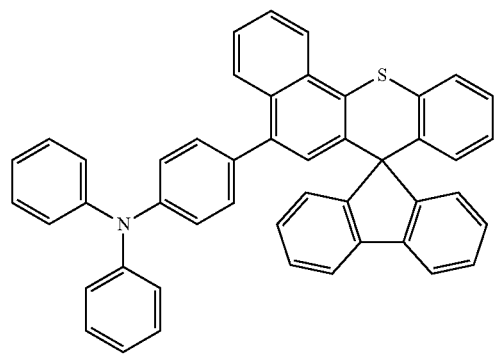
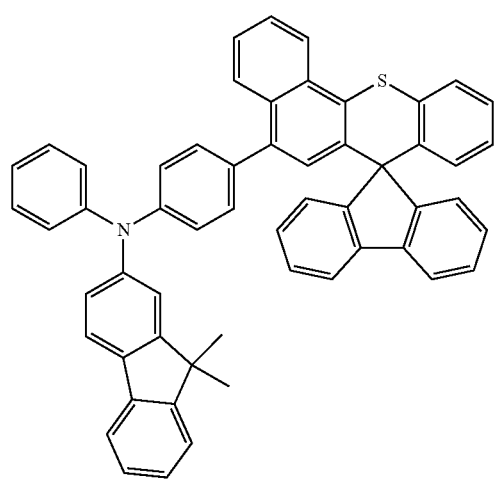

117
-continued
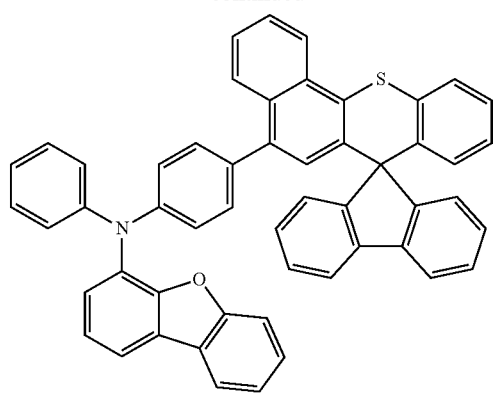
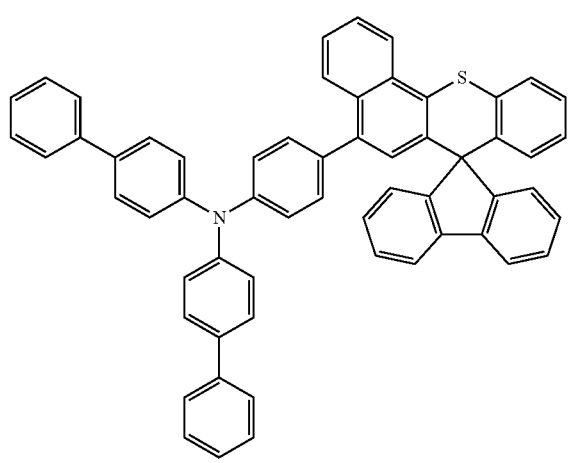
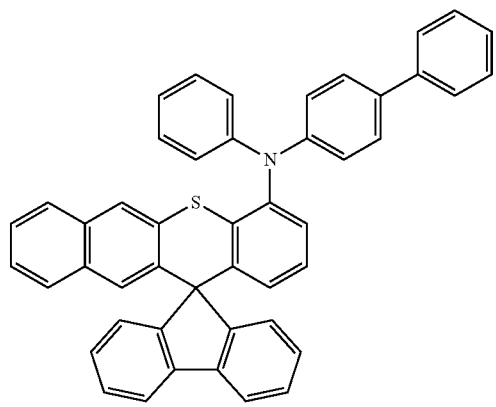
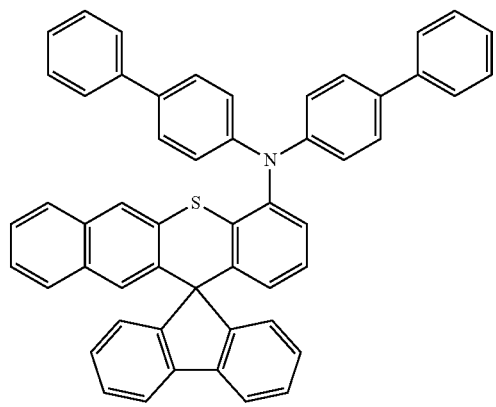
118
-continued
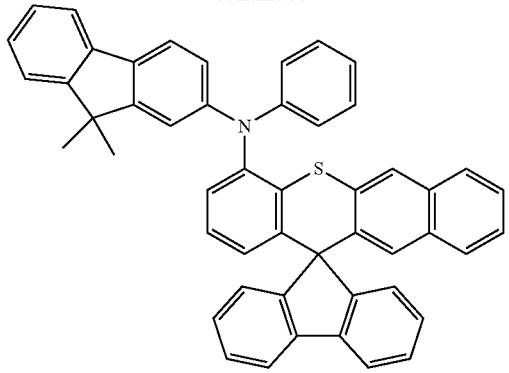
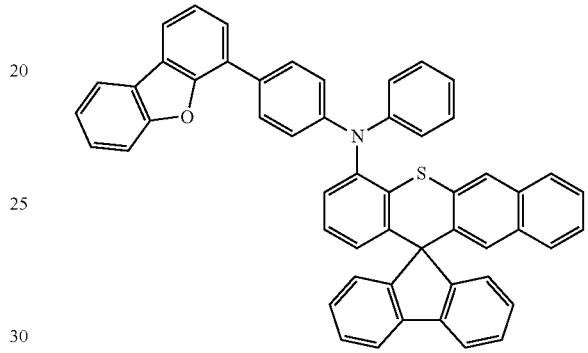
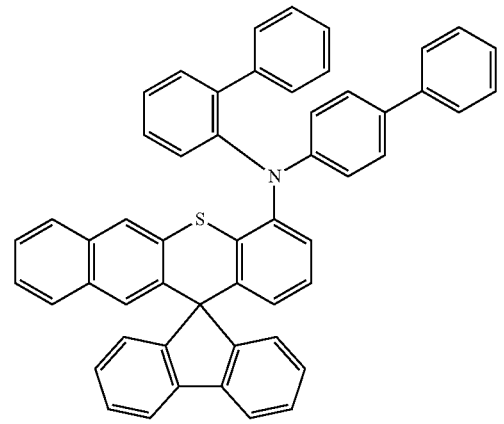
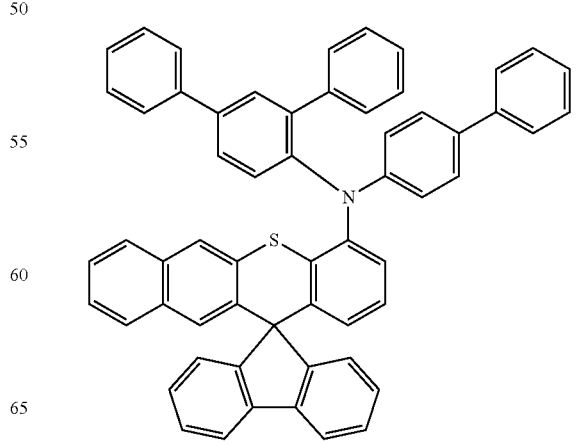

119
-continued
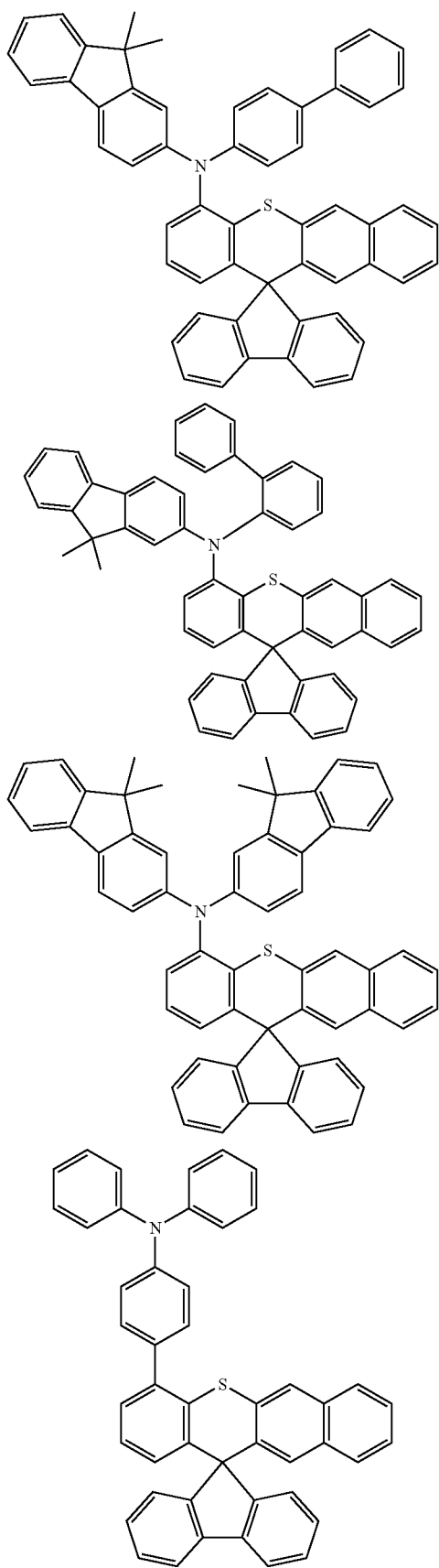
120
-continued
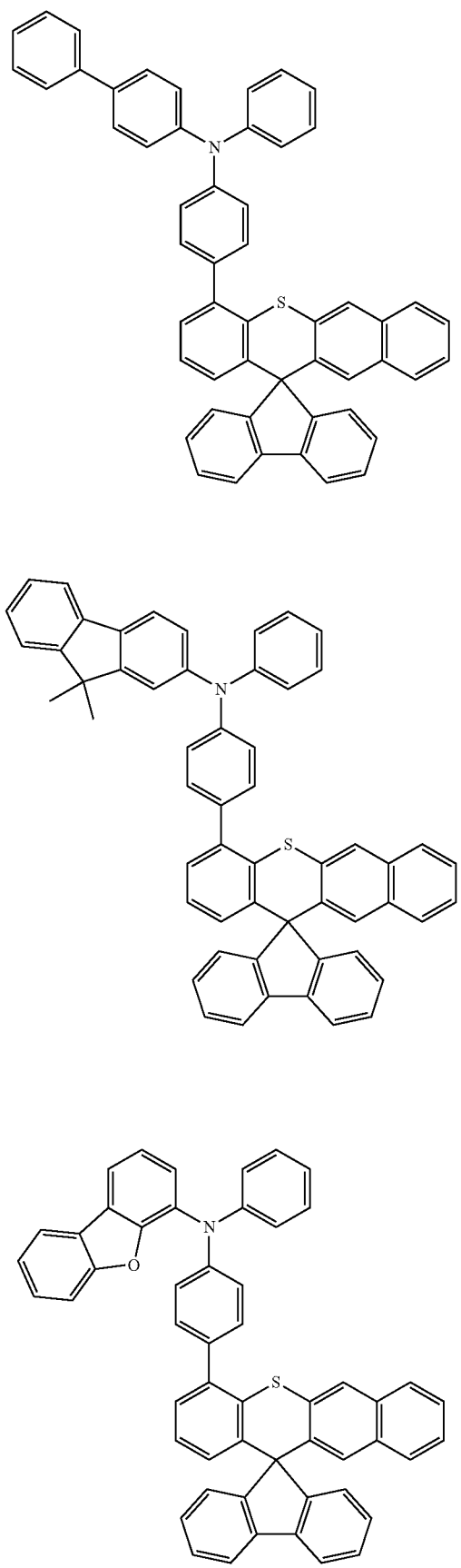

121
-continued
122
-continued
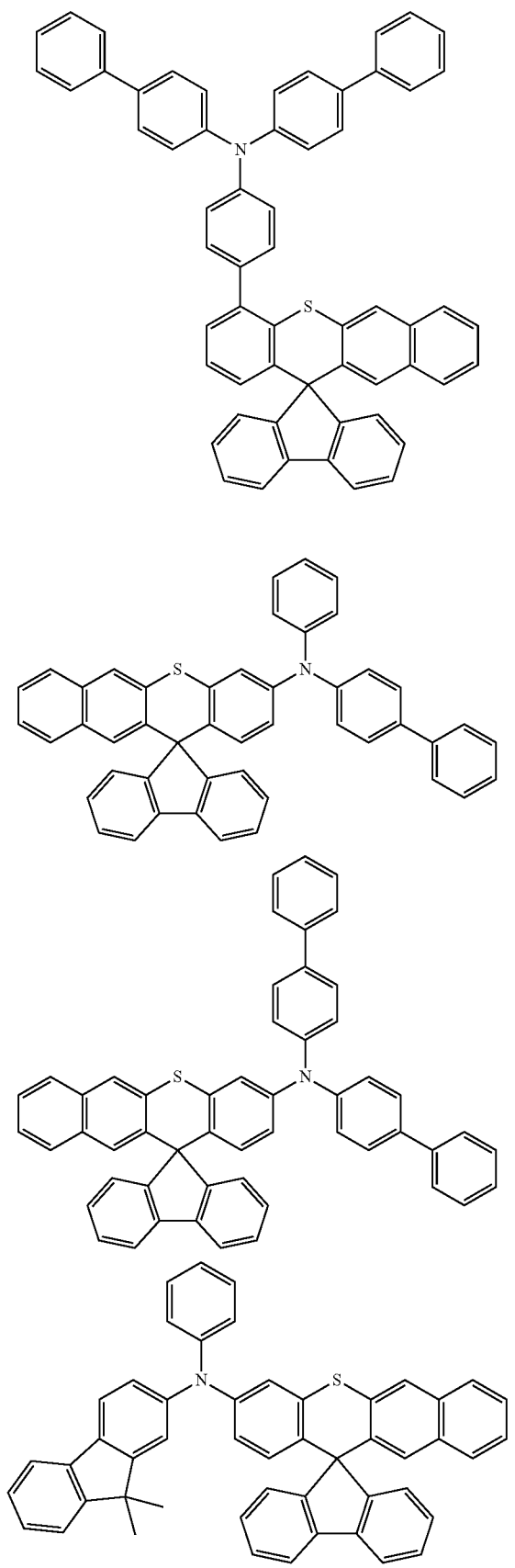
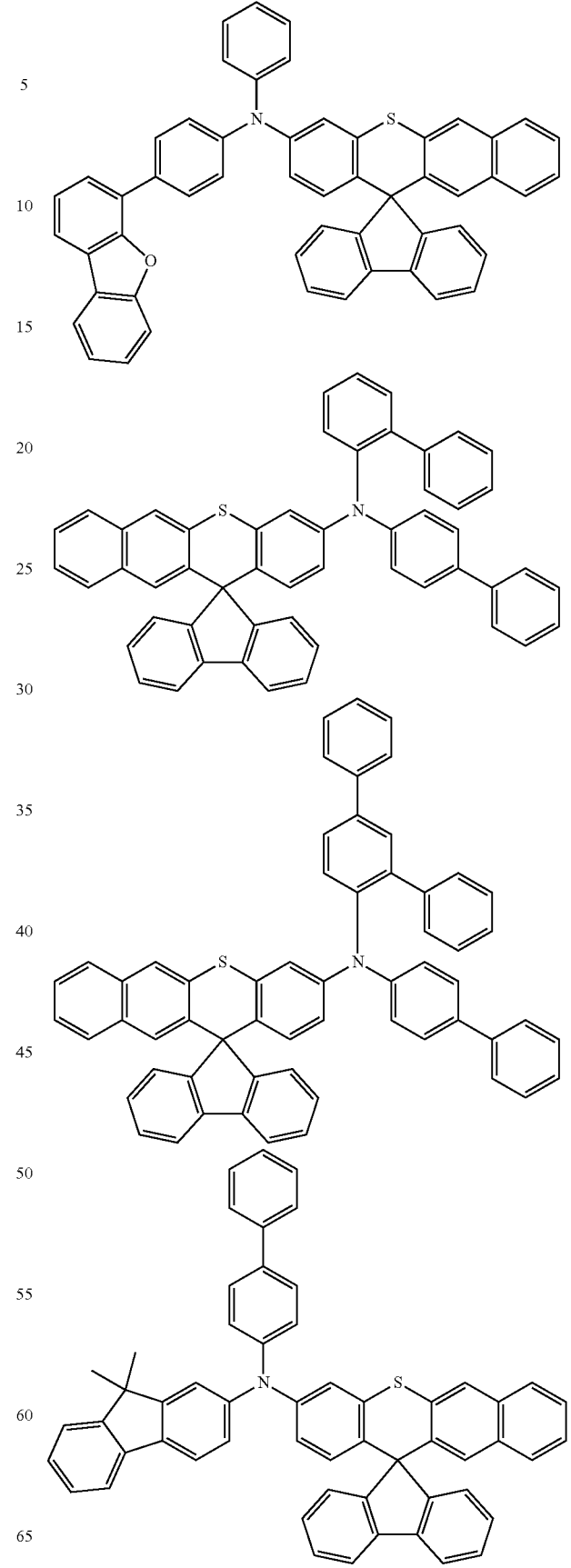

123
-continued
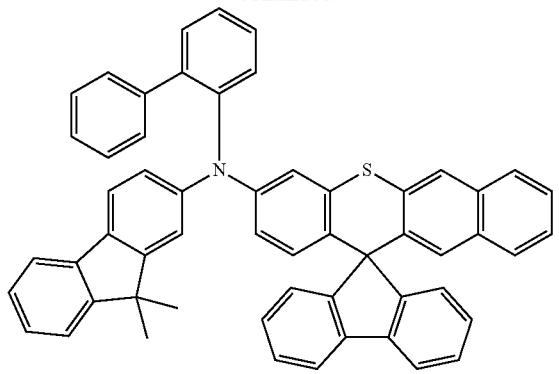
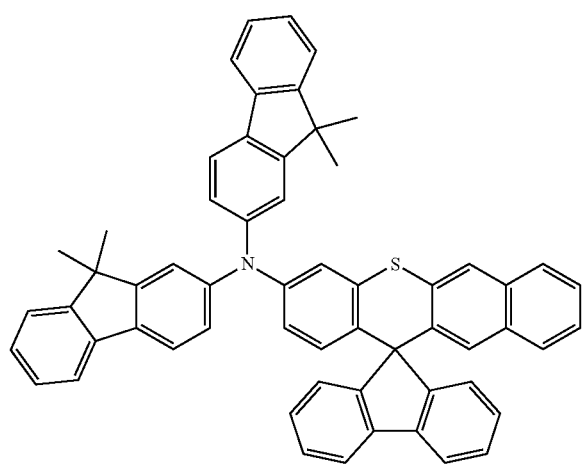
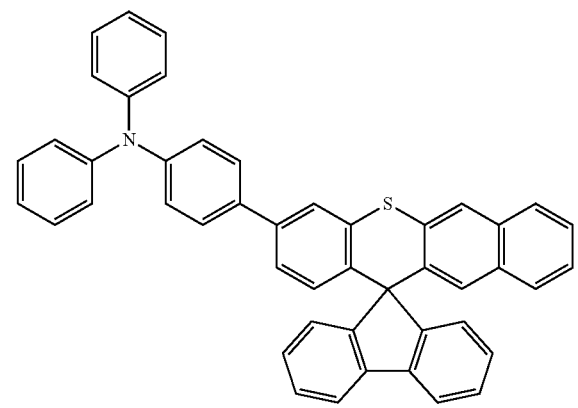
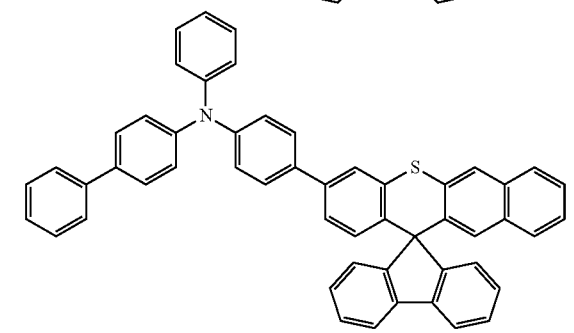
124
-continued
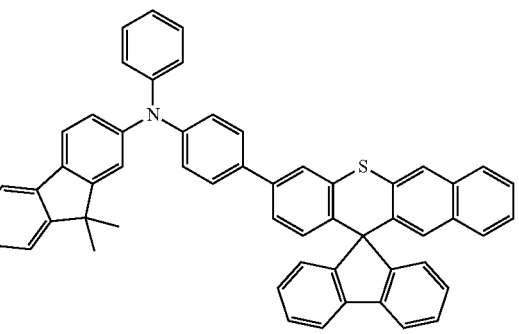
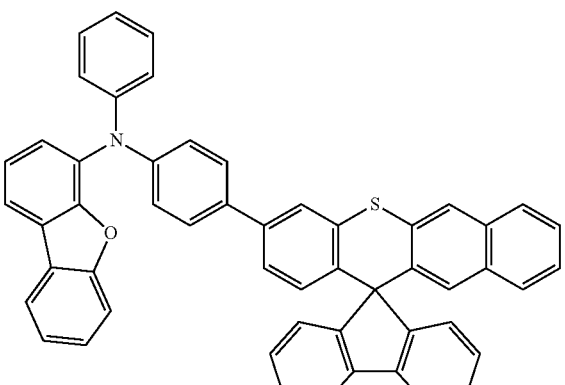
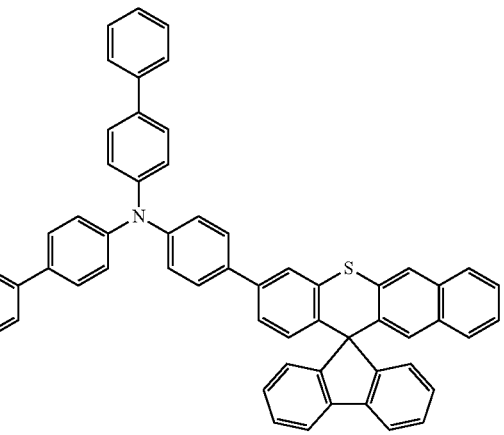
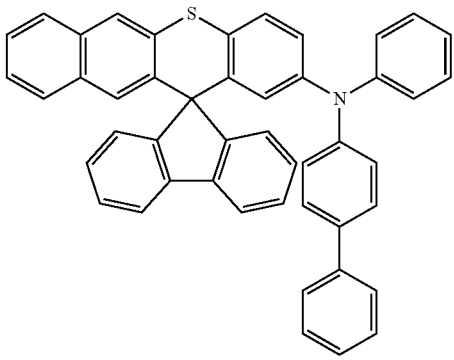

125
-continued
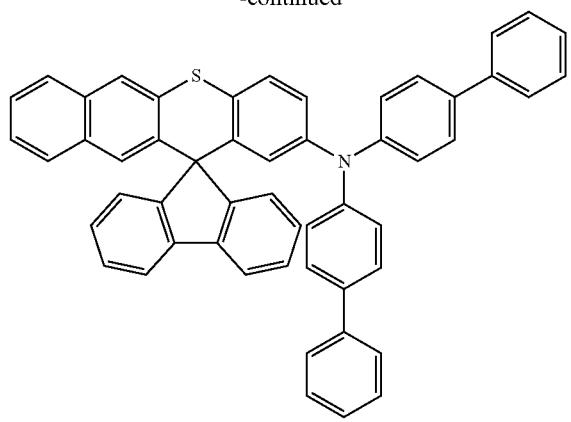
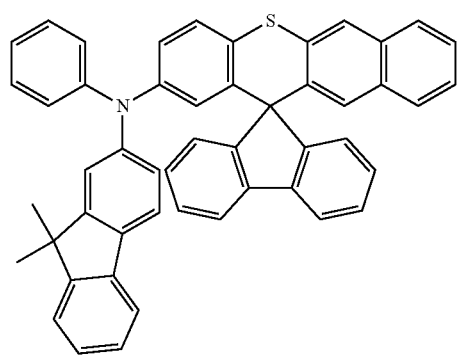
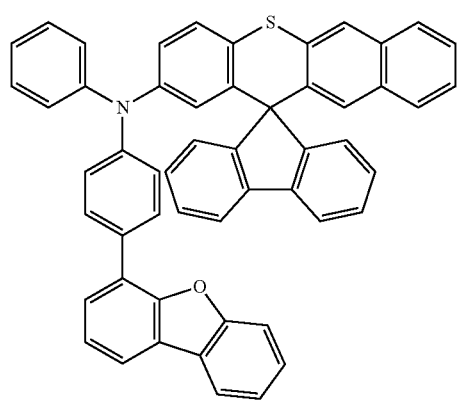
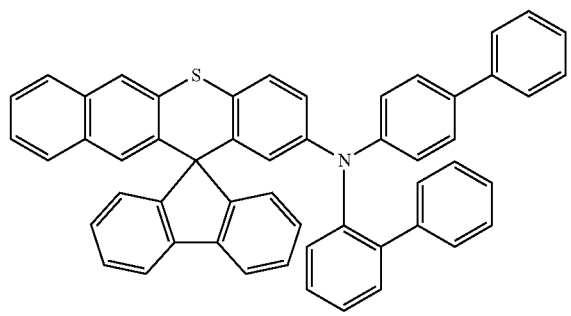
126
-continued
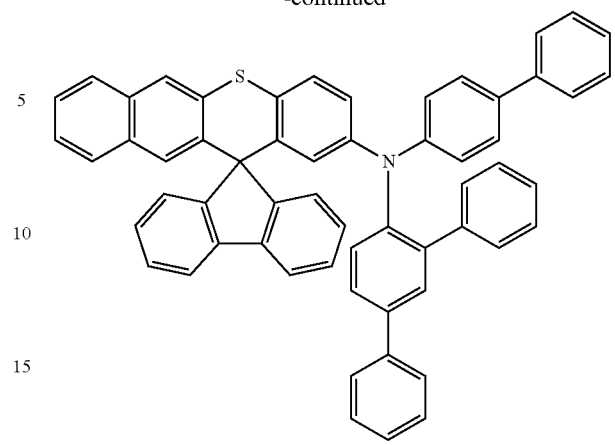
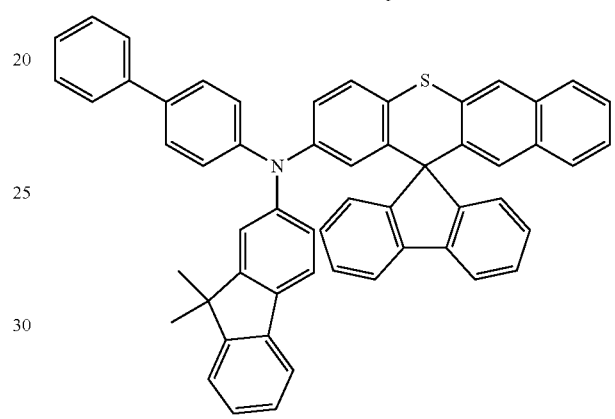
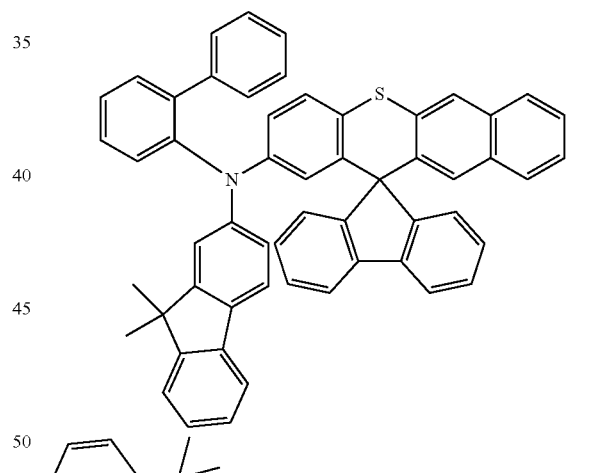
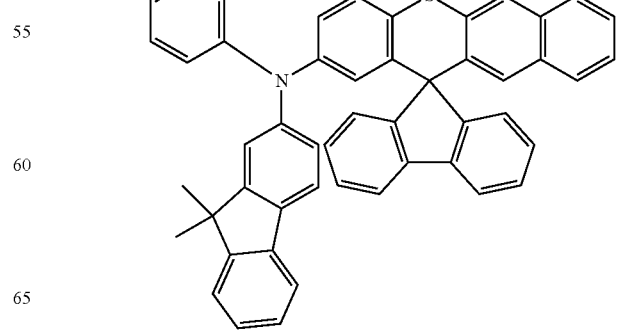

127
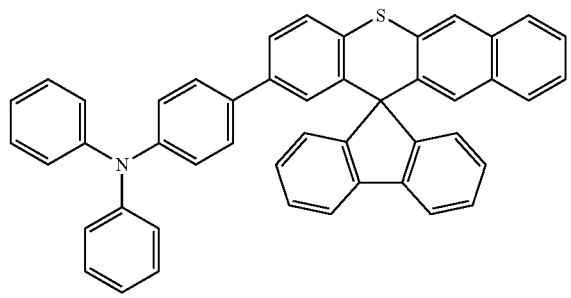
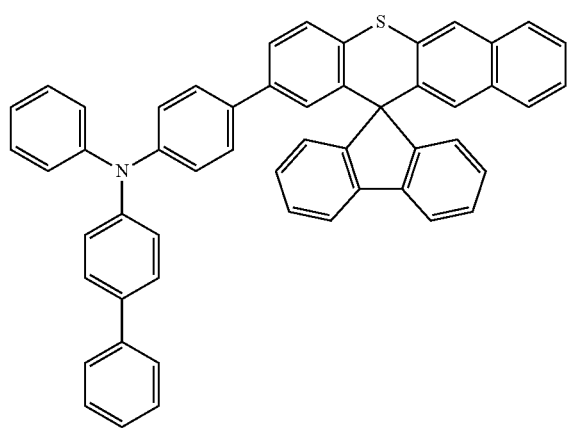
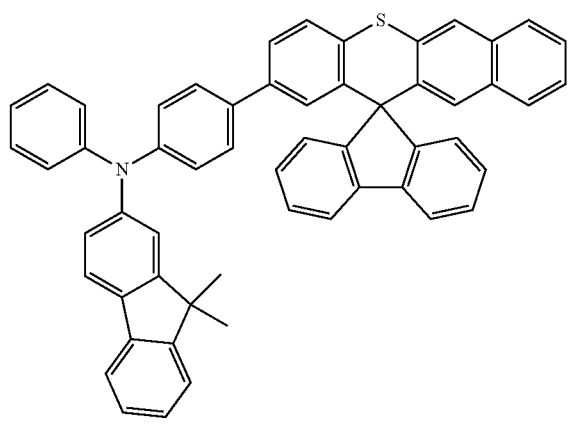
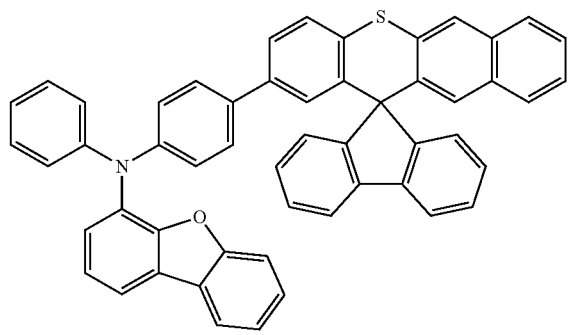
128
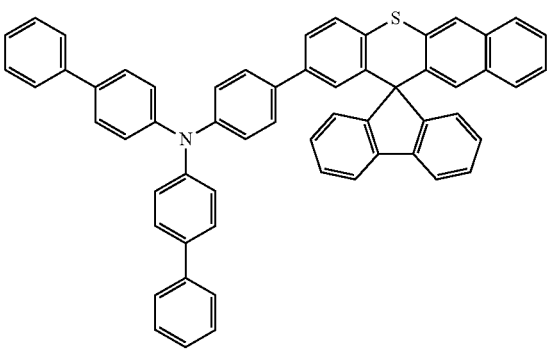
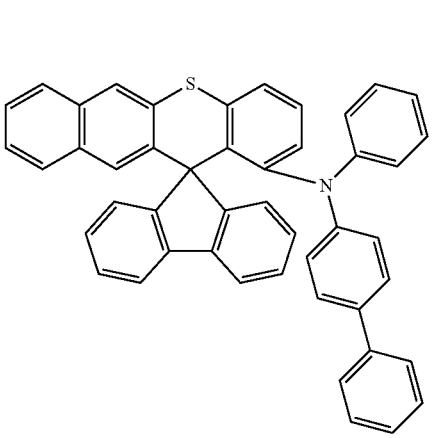
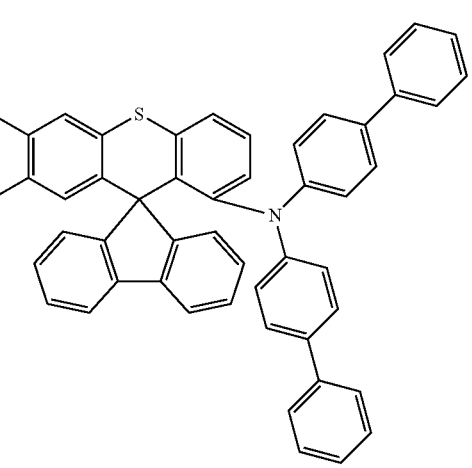
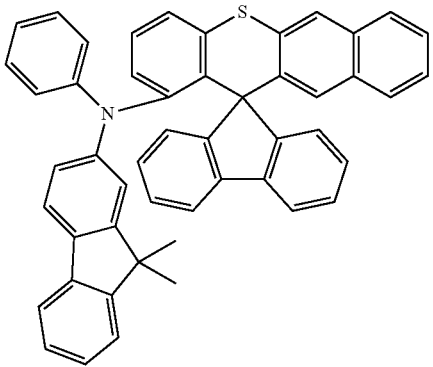

129
-continued
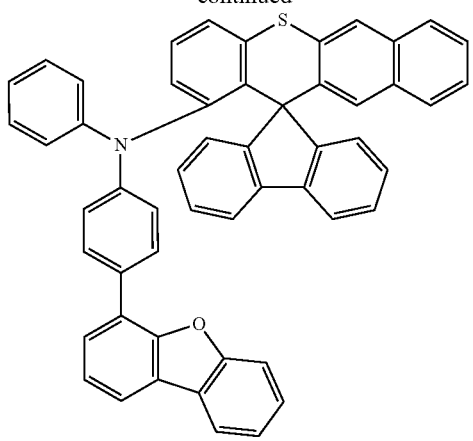
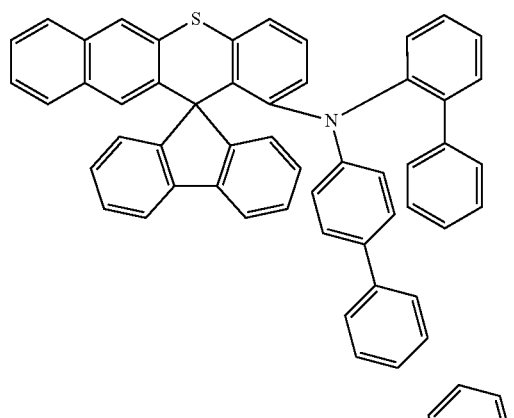
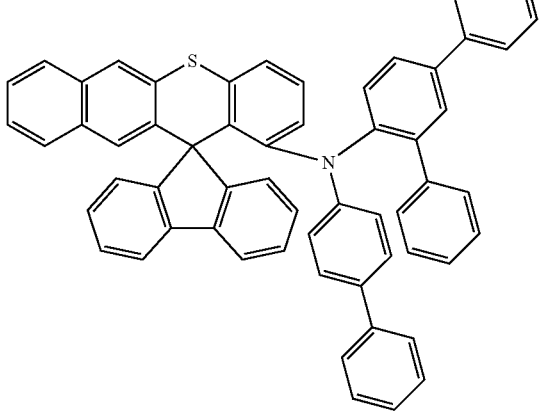
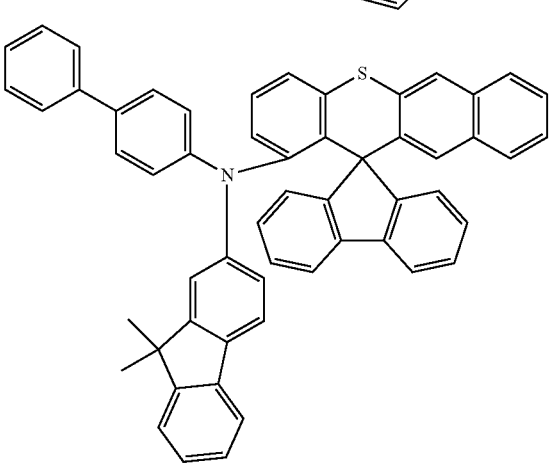
130
-continued
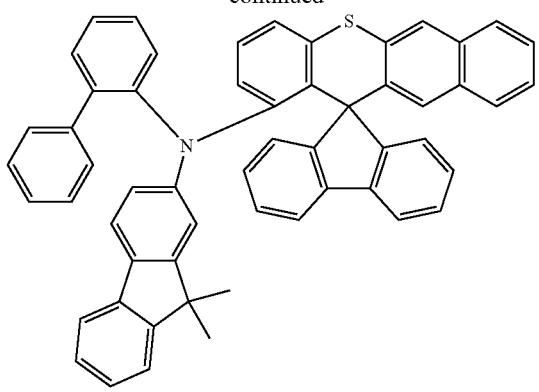
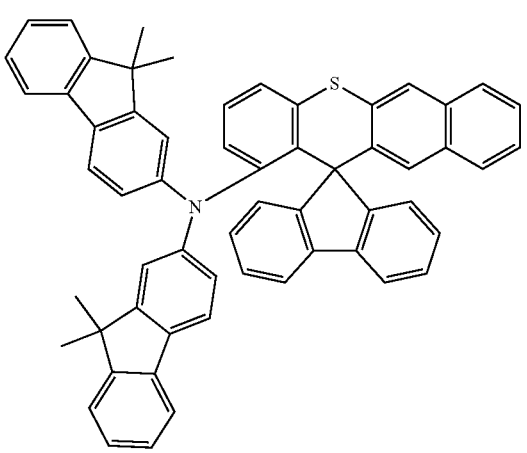
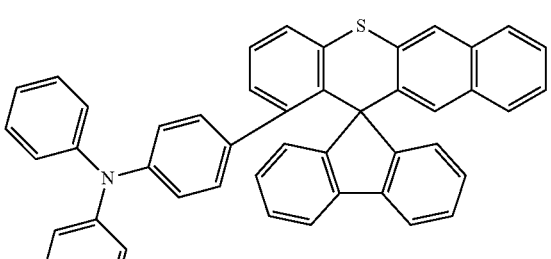
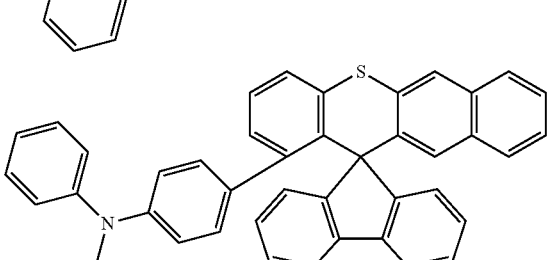

-continued
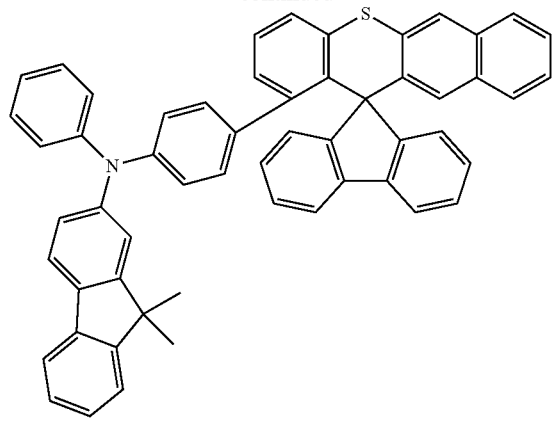
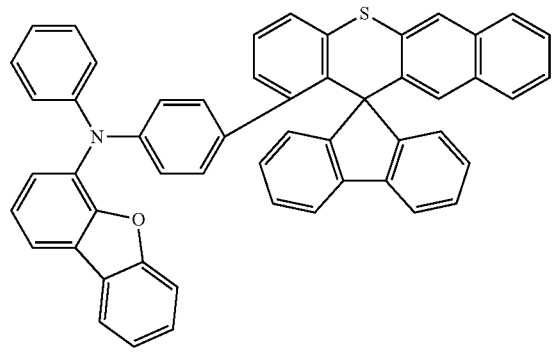
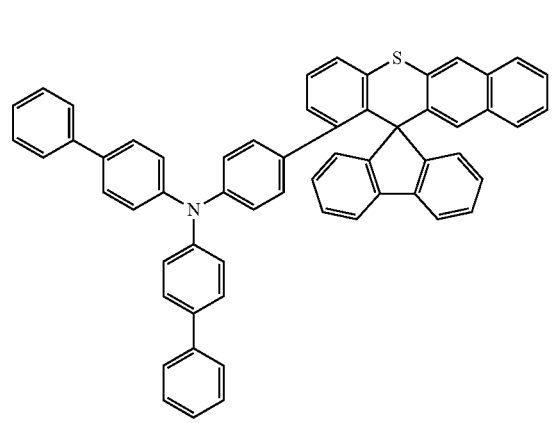
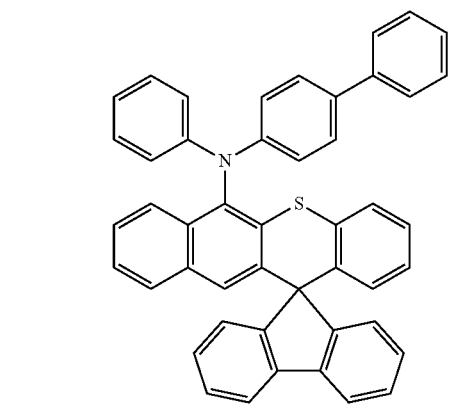
-continued
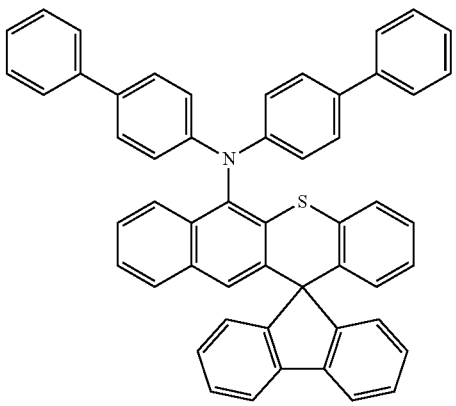
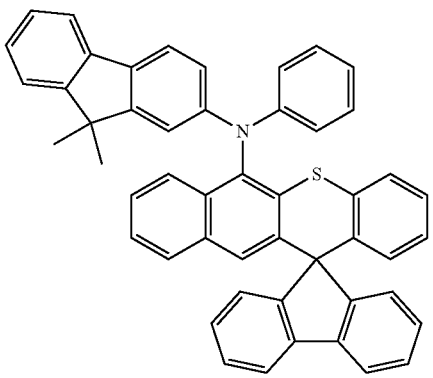
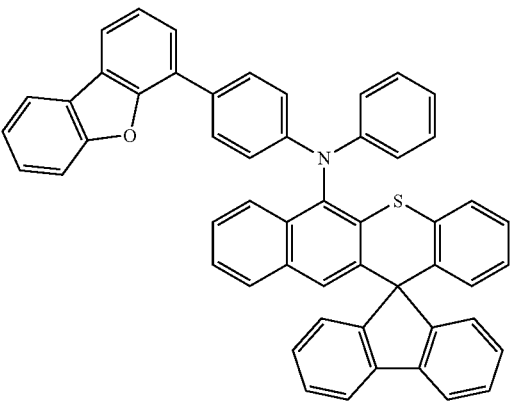
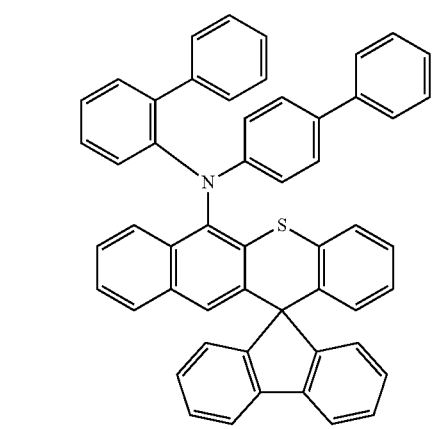

133
-continued
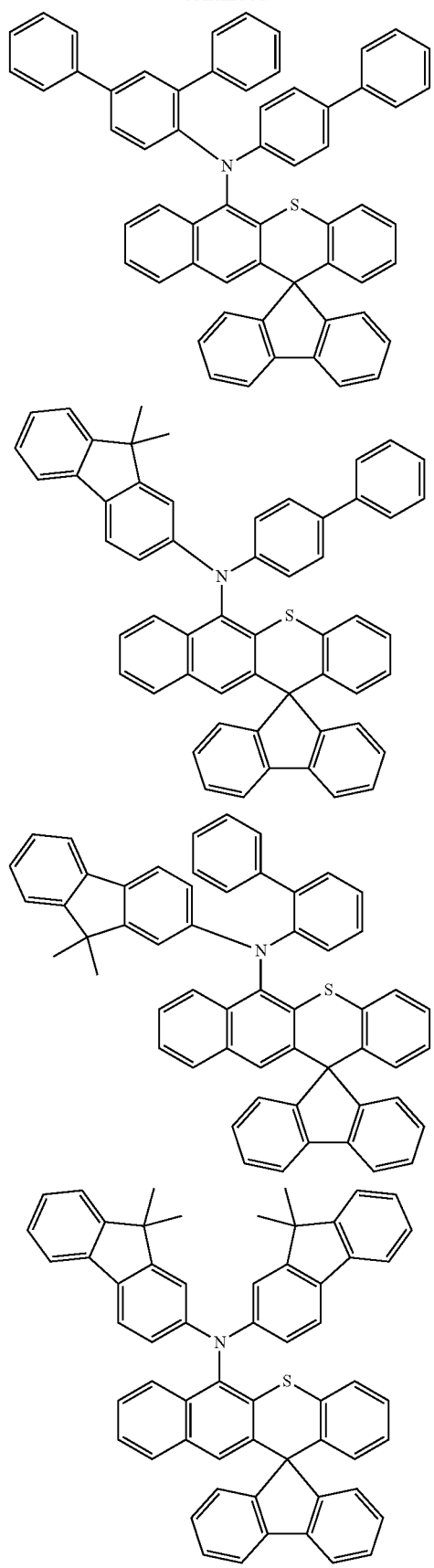
134
-continued
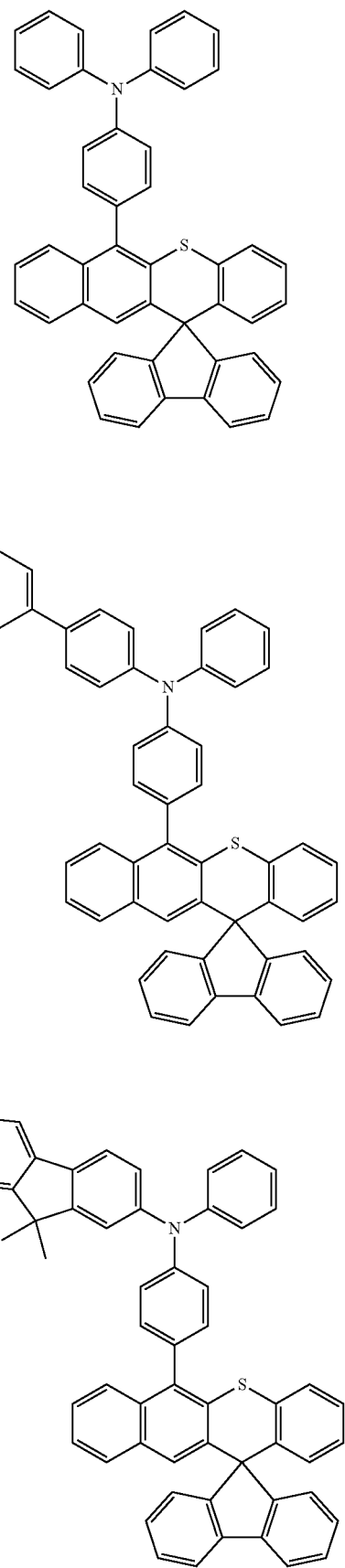

135
-continued
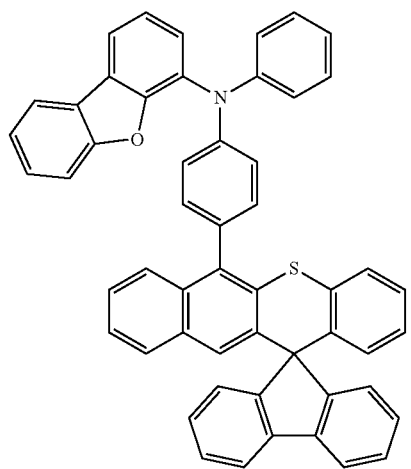
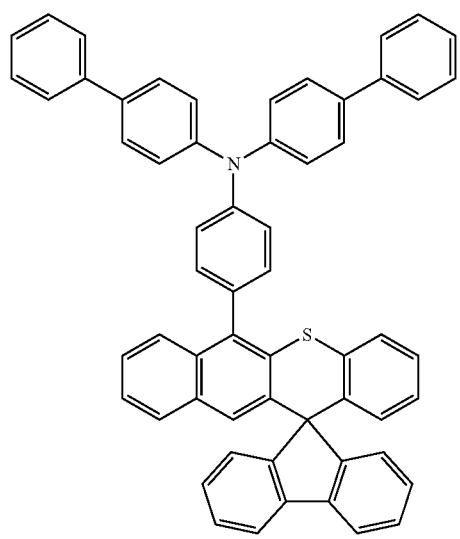
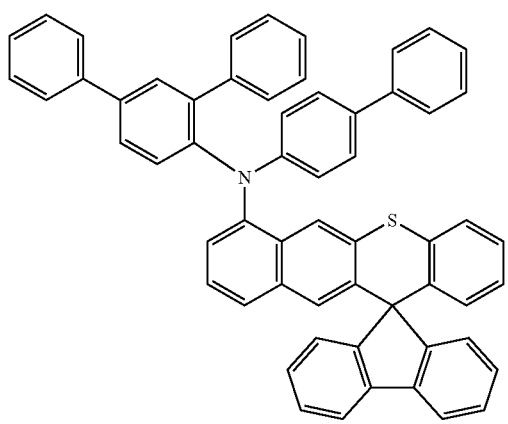
136
-continued
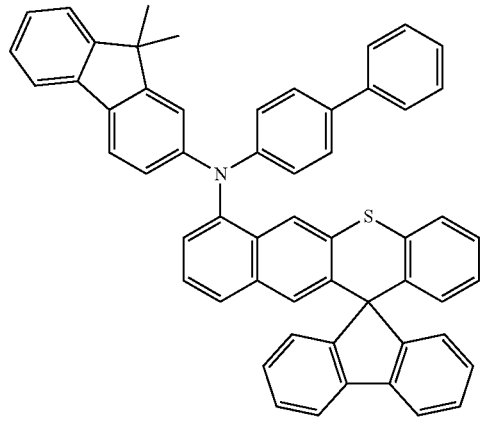
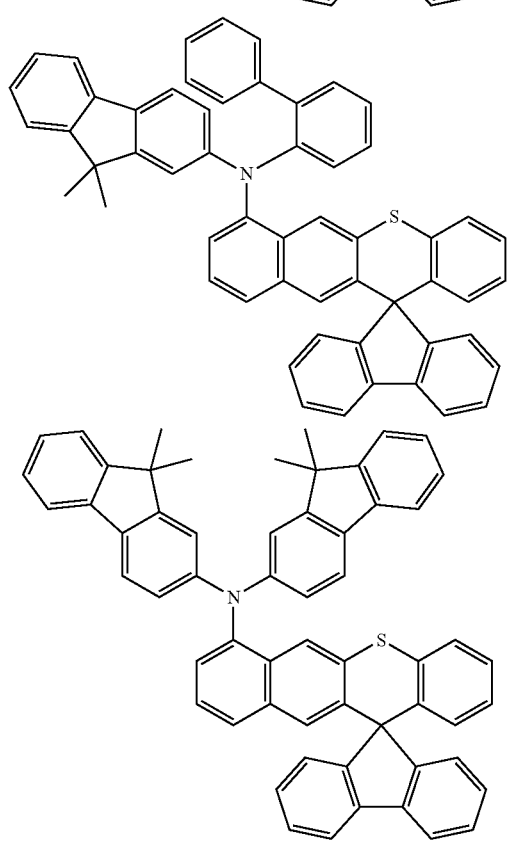
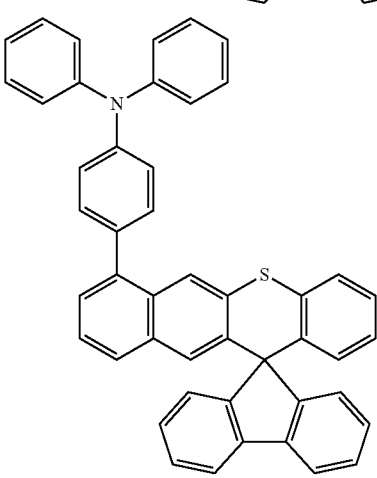

137
-continued
138
-continued
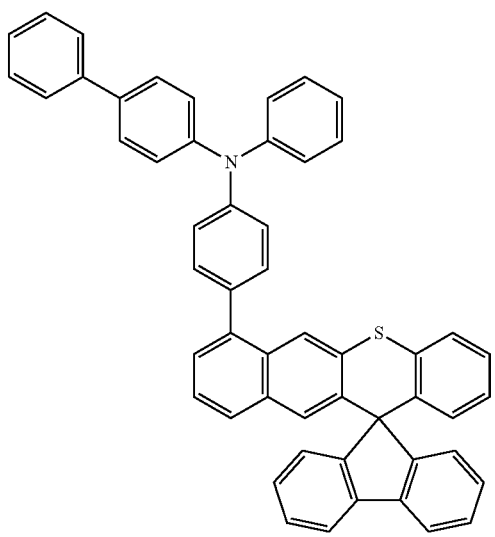
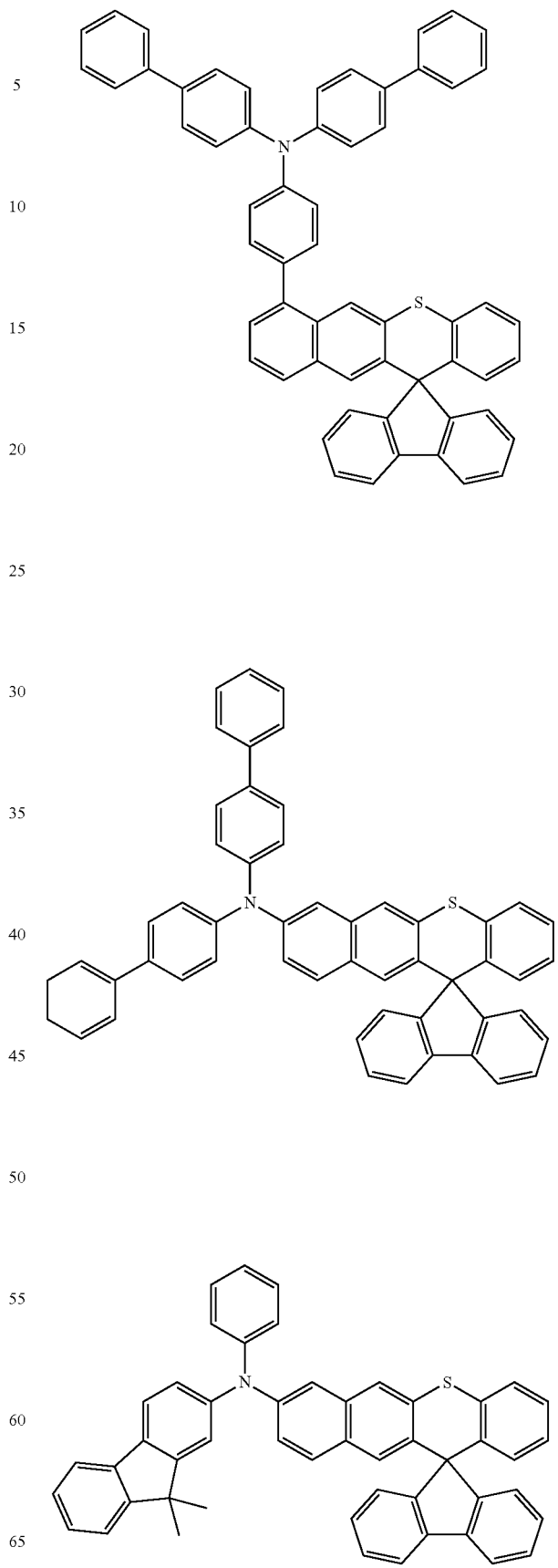

139
-continued
140
-continued
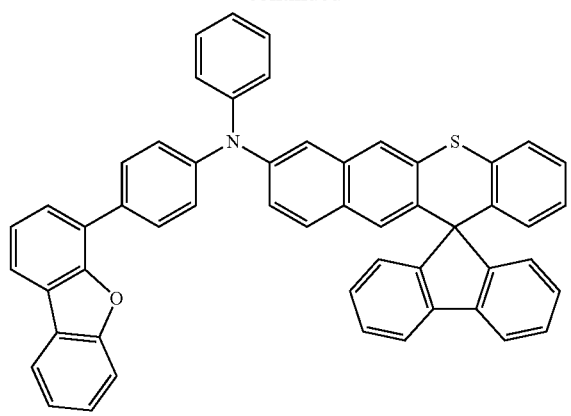
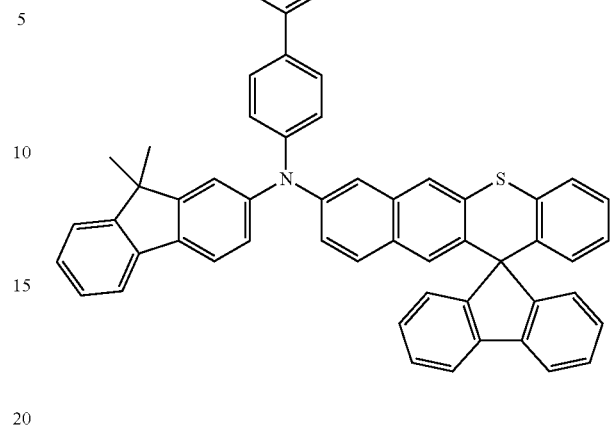
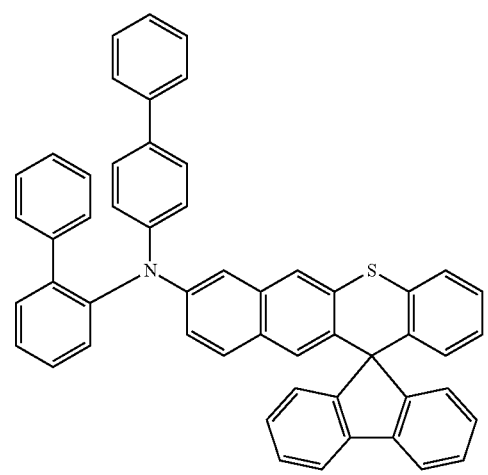
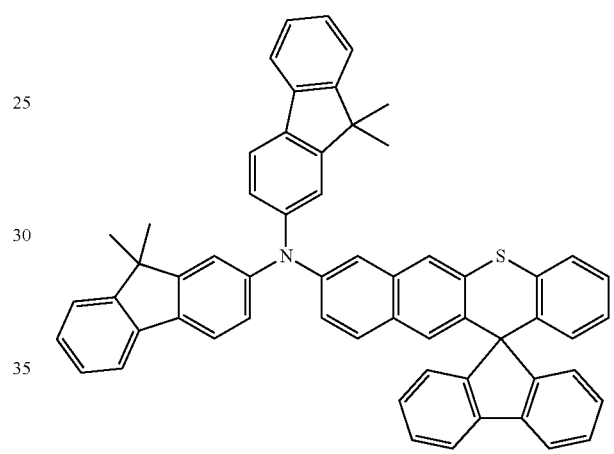
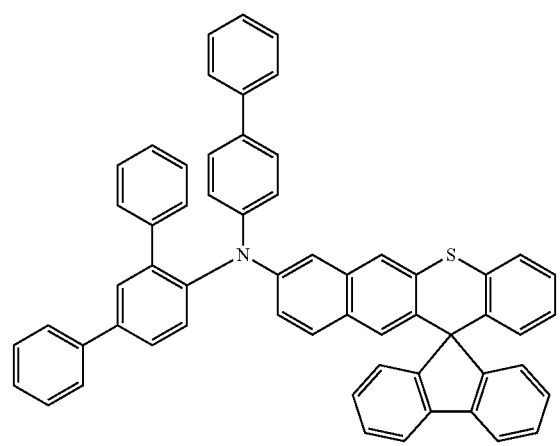
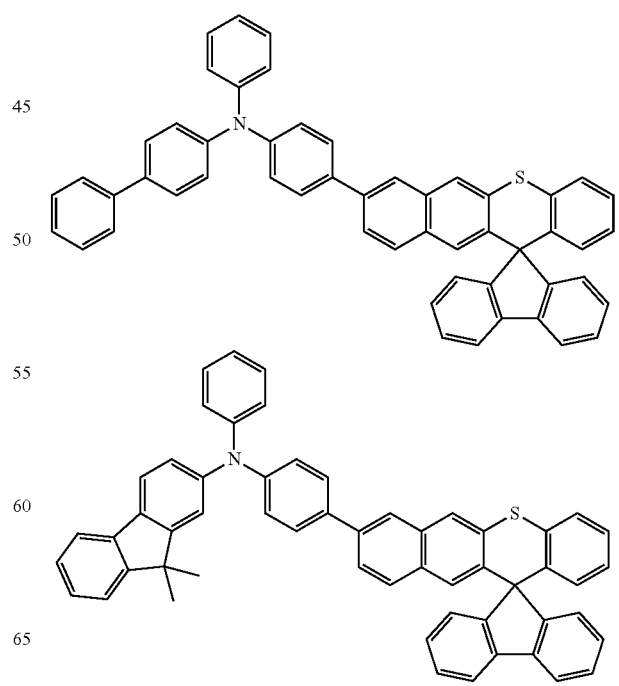

141
-continued
142
-continued
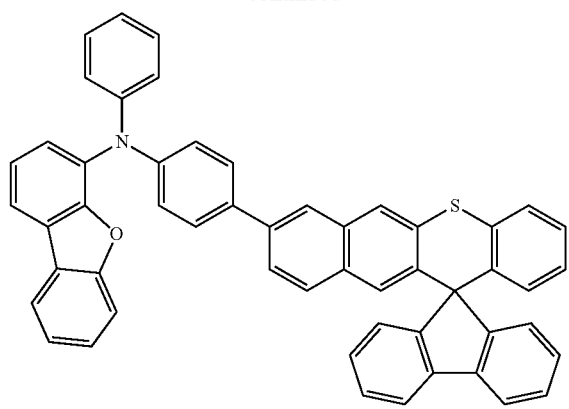
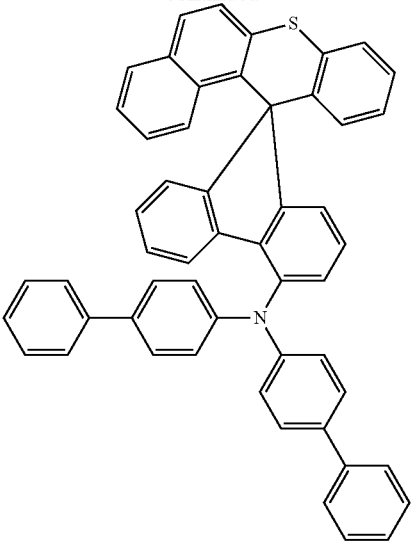
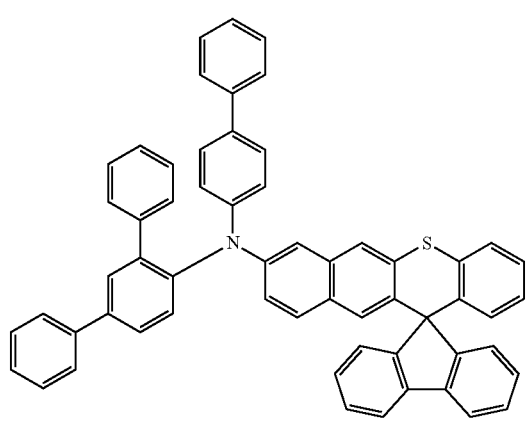
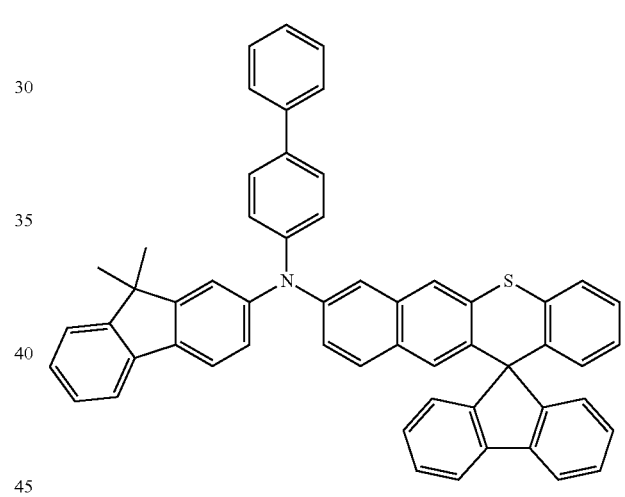
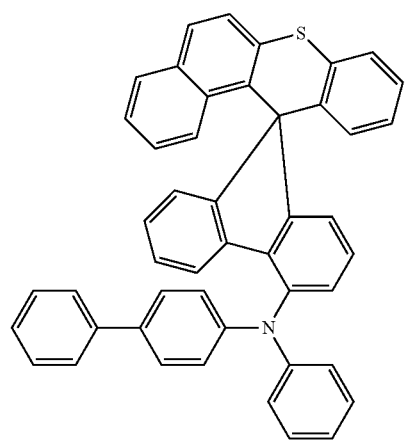
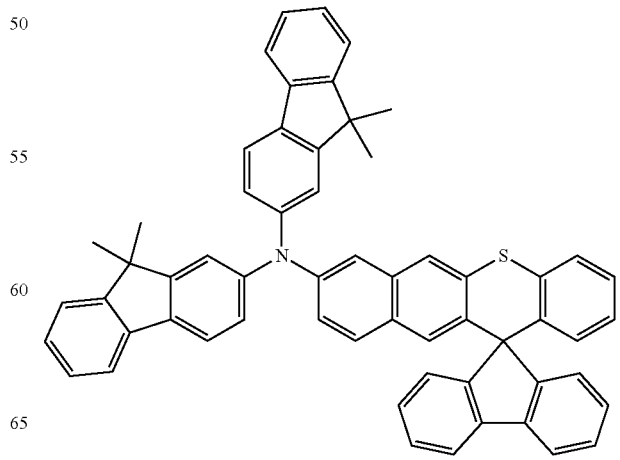

143
-continued
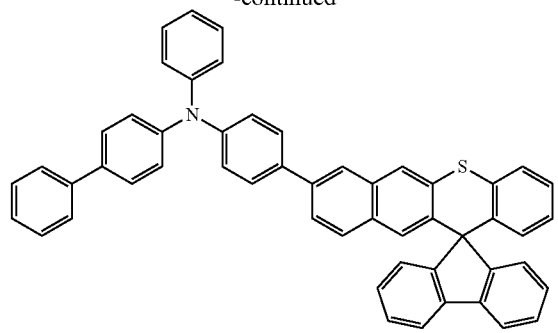
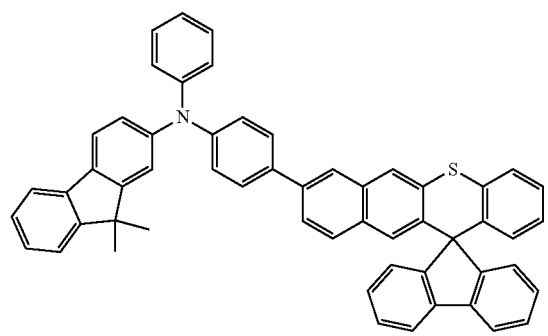
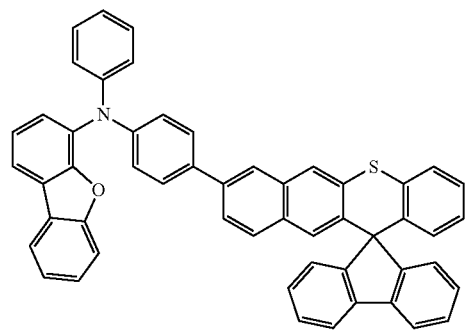
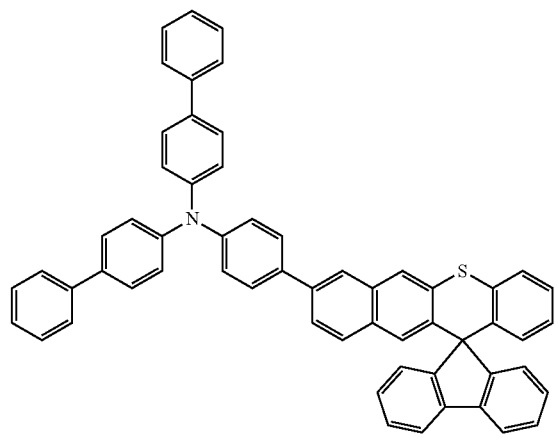
144
-continued
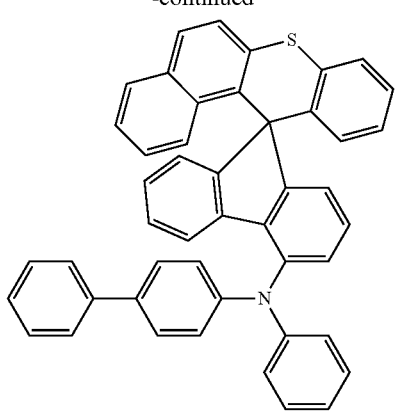
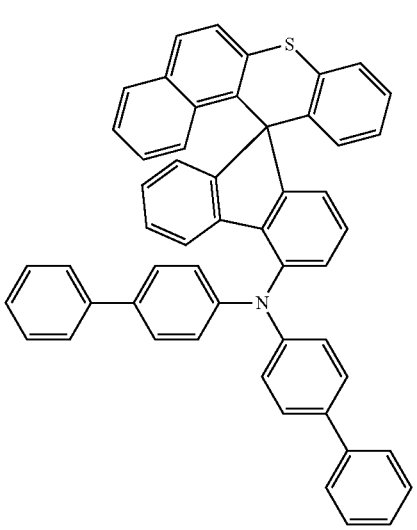
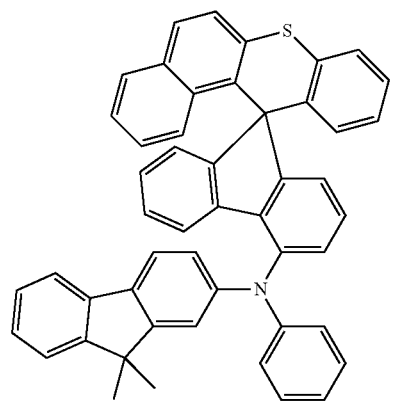

-continued
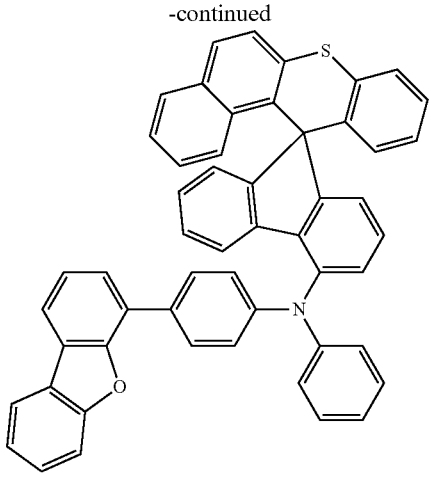
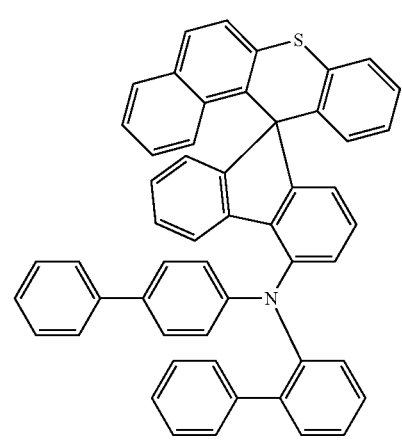
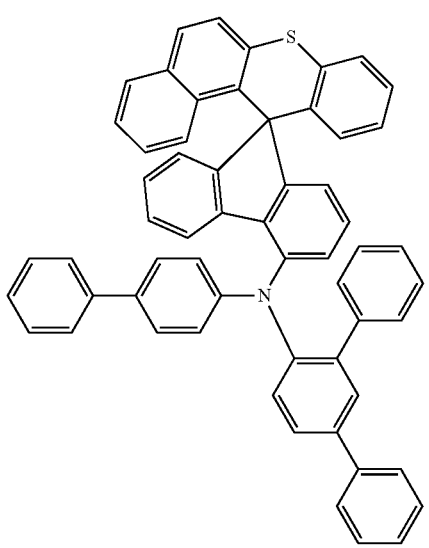
-continued
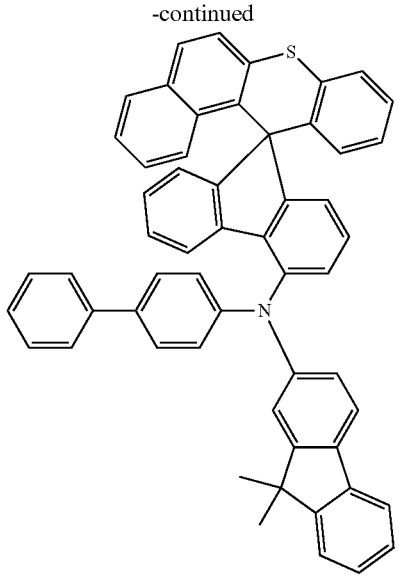
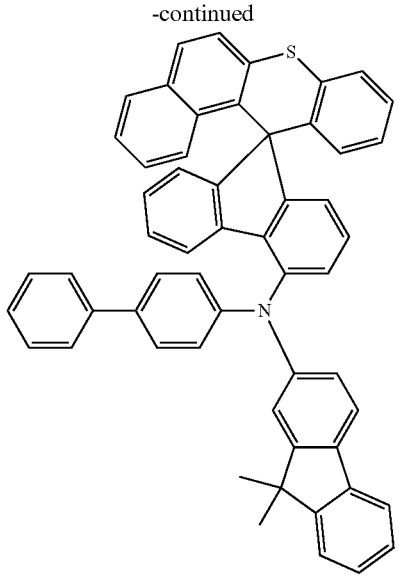
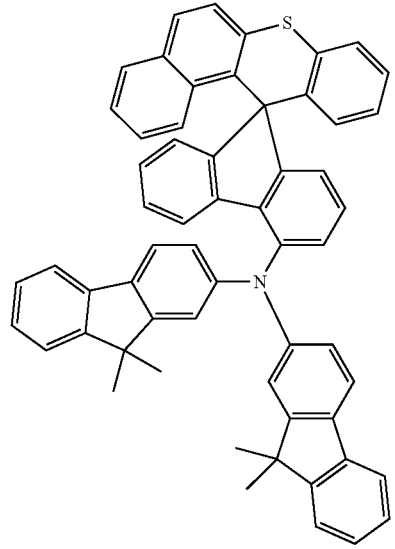

147
-continued
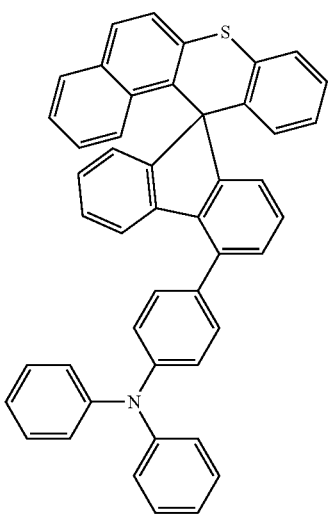
148
-continued
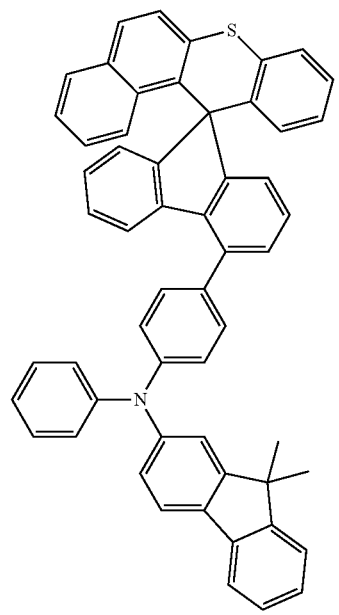
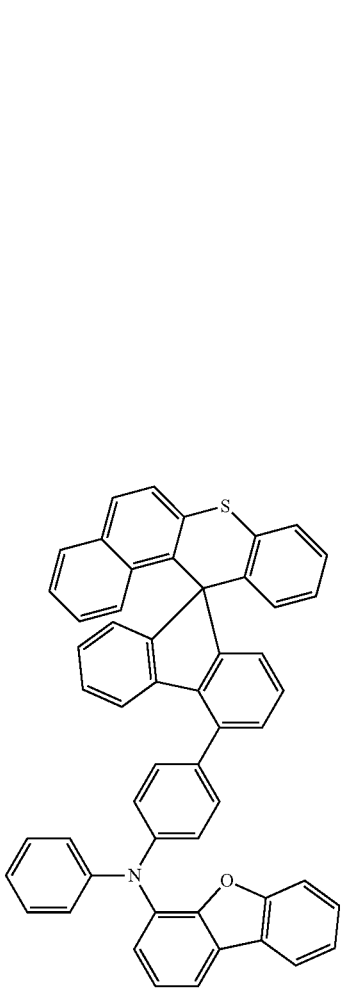

149
-continued
150
-continued
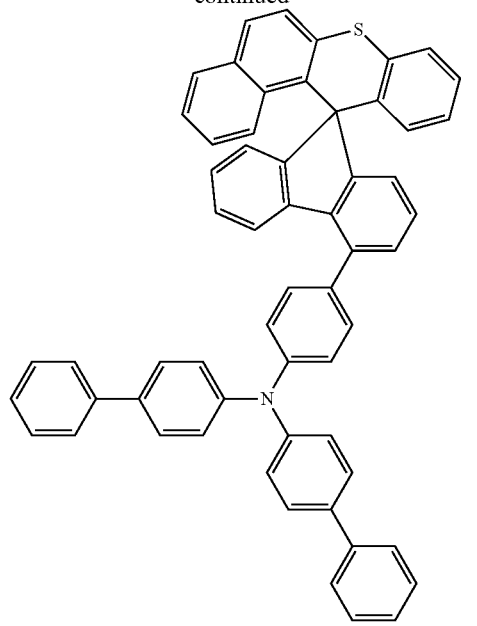
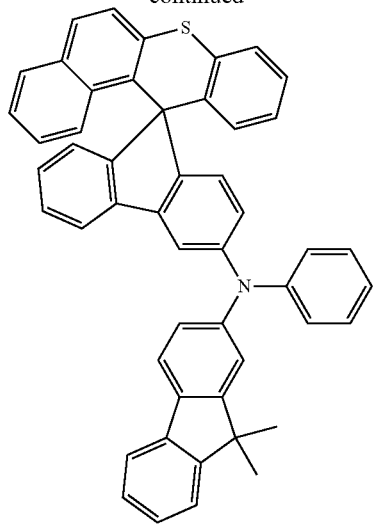
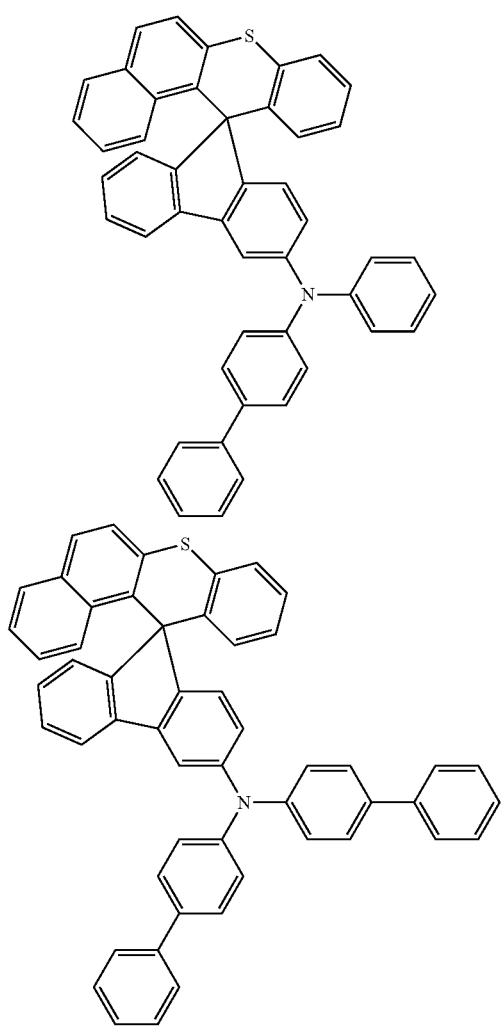
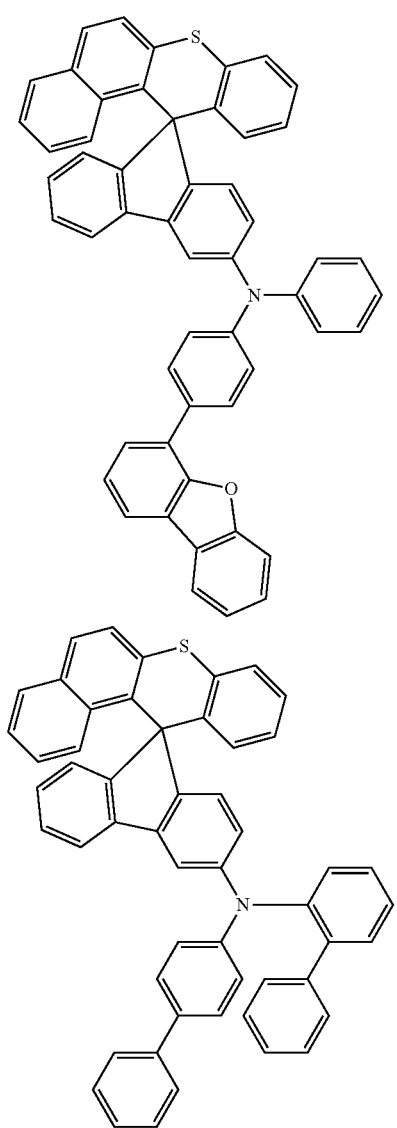

151
-continued
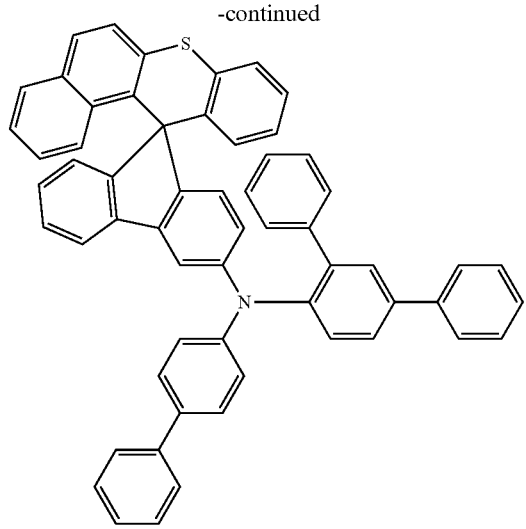
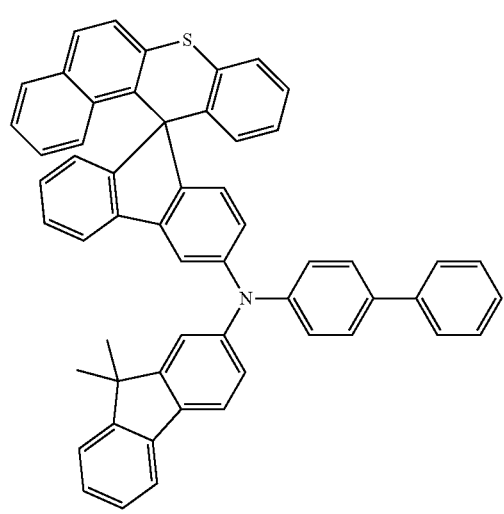
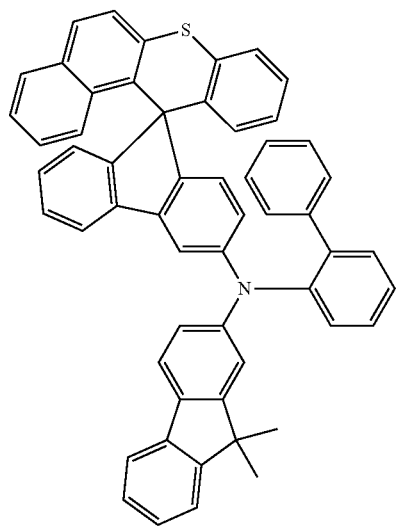
152
-continued
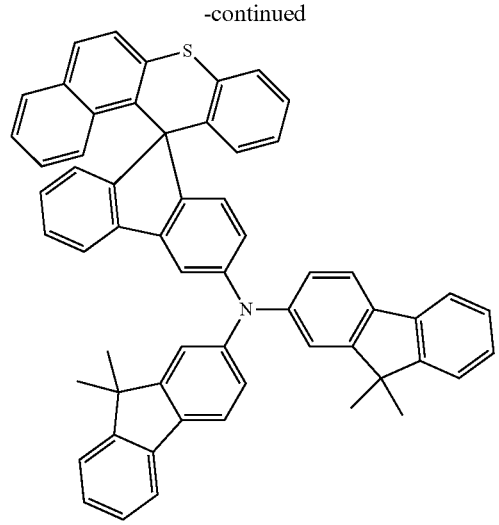
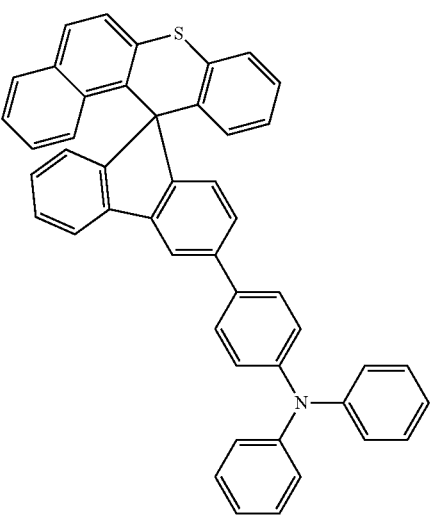
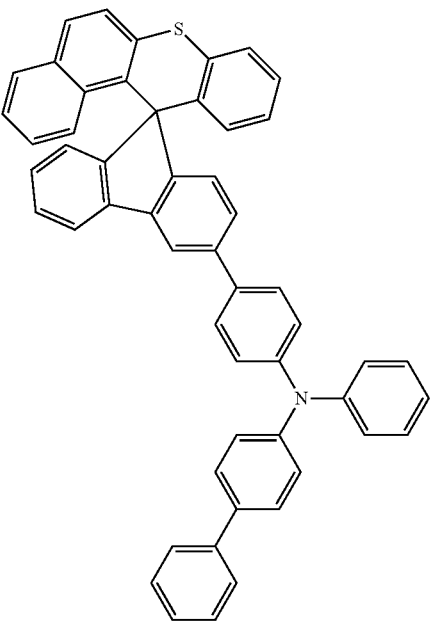

153
-continued
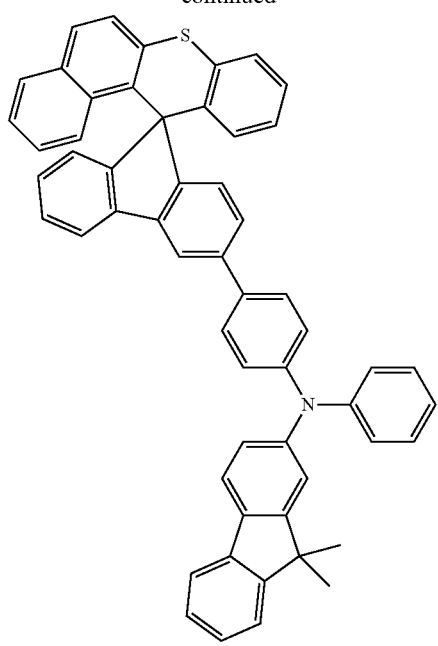
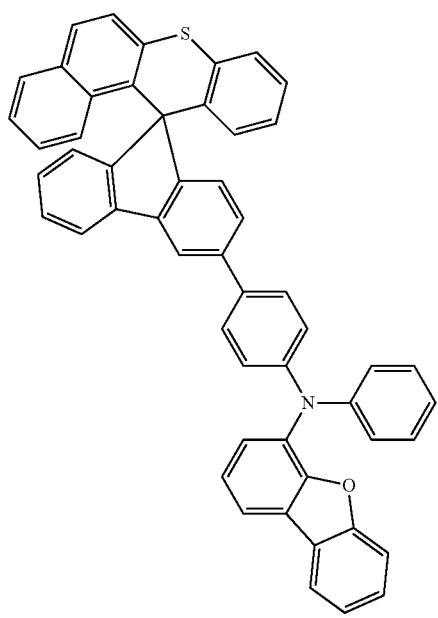
154
-continued
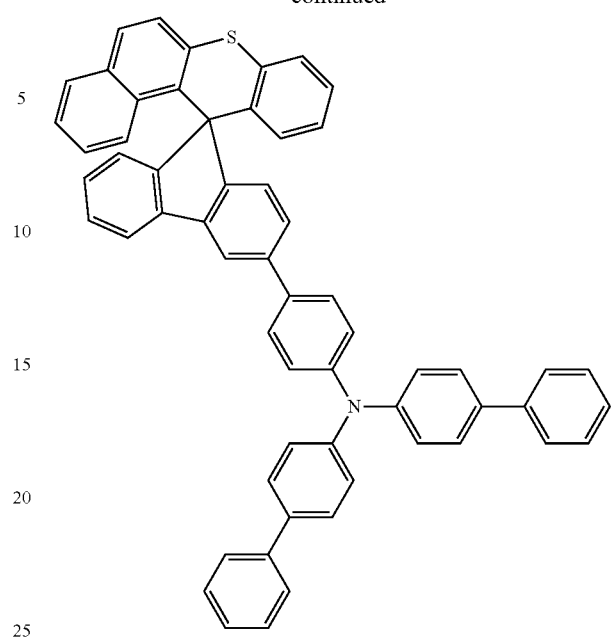
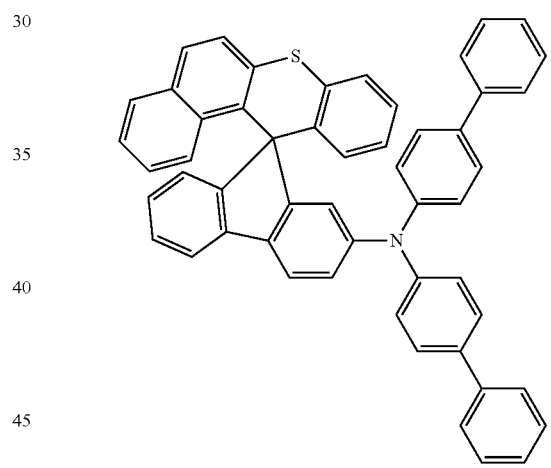
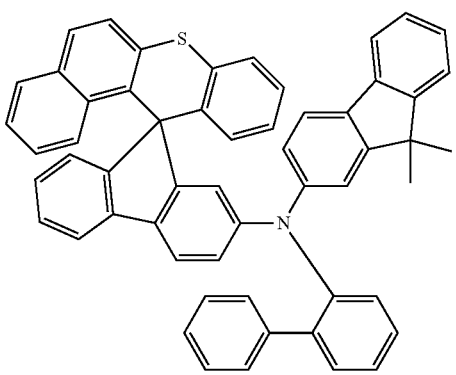

155
-continued
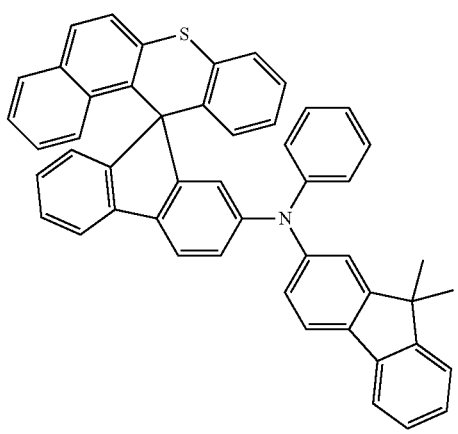
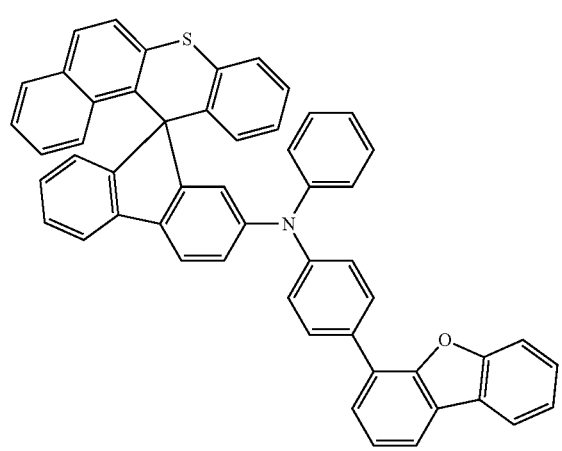
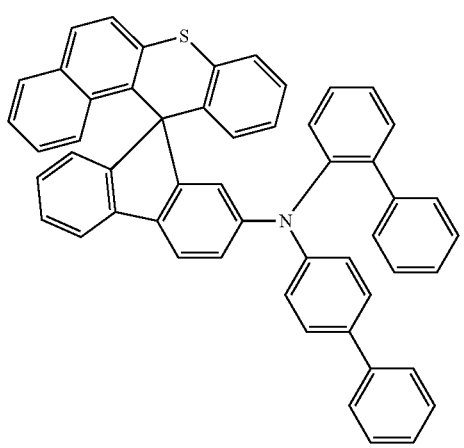
156
-continued
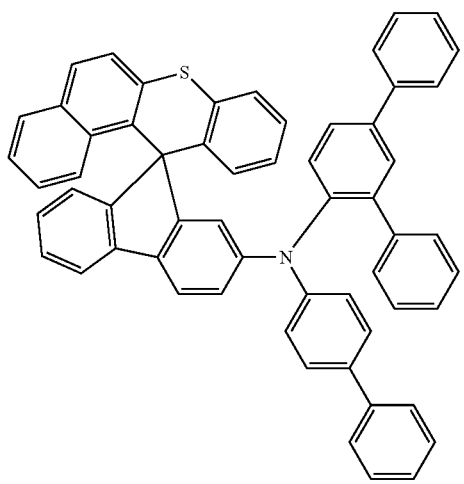
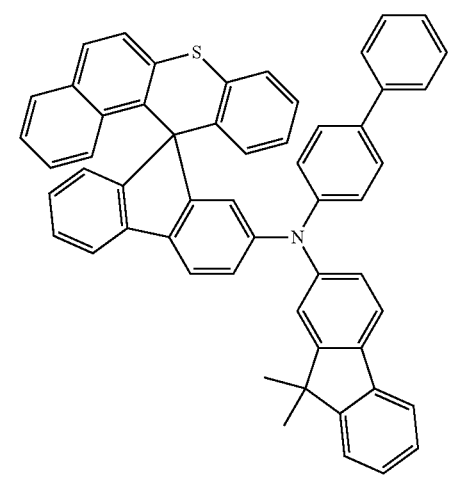
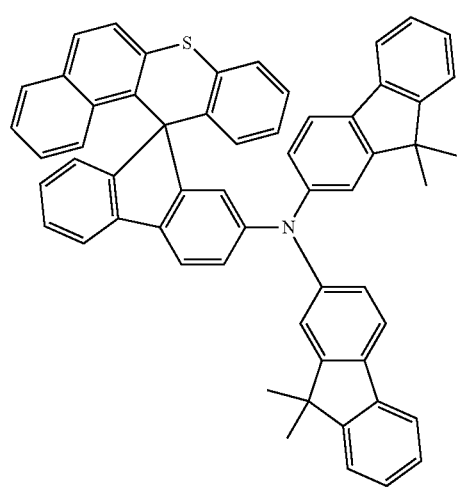

157
-continued
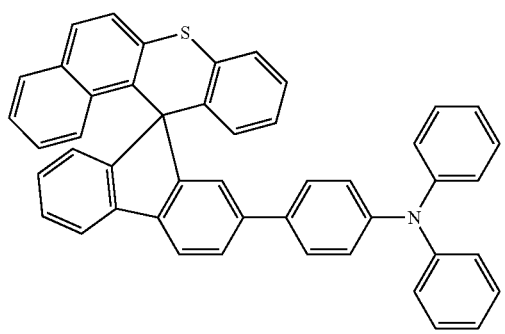
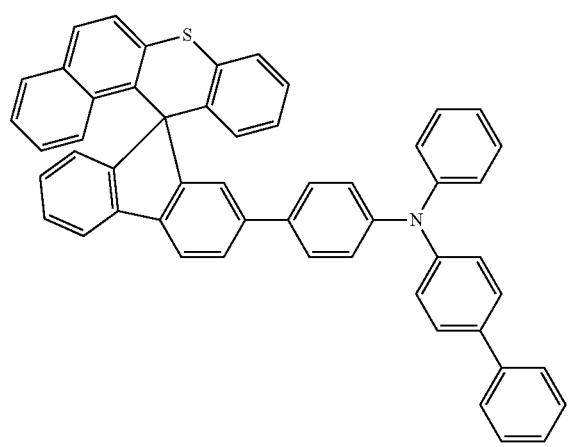
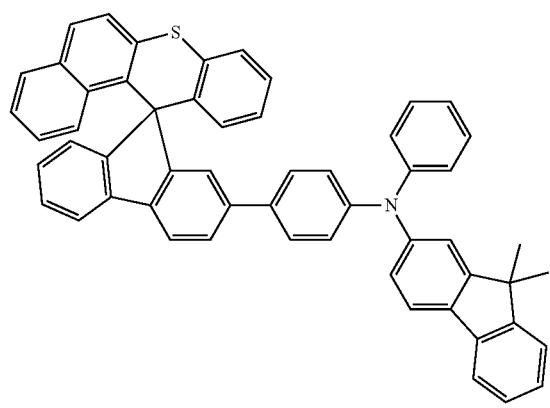
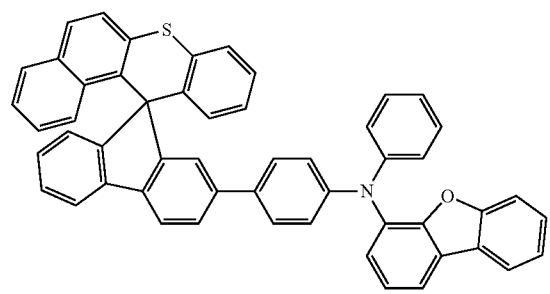
158
-continued
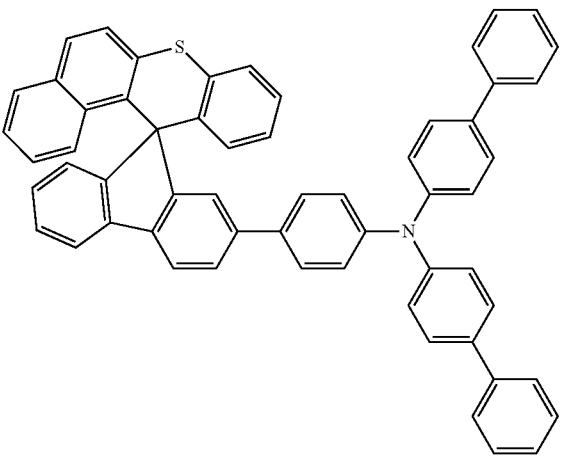
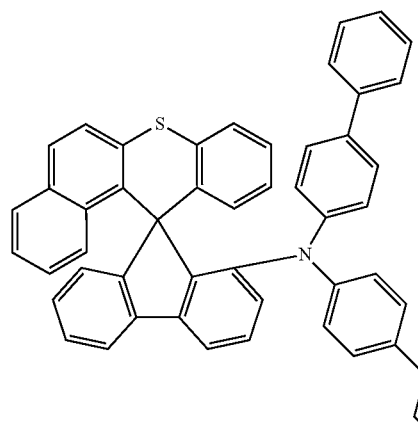
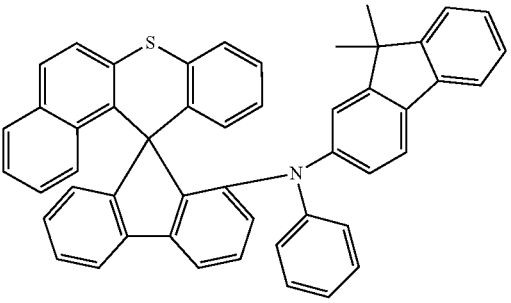

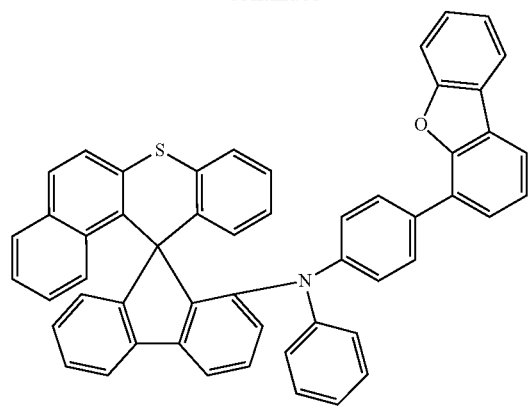
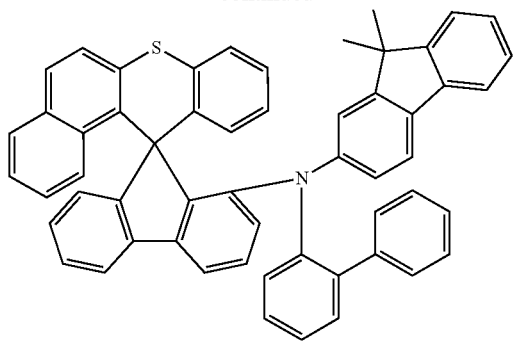
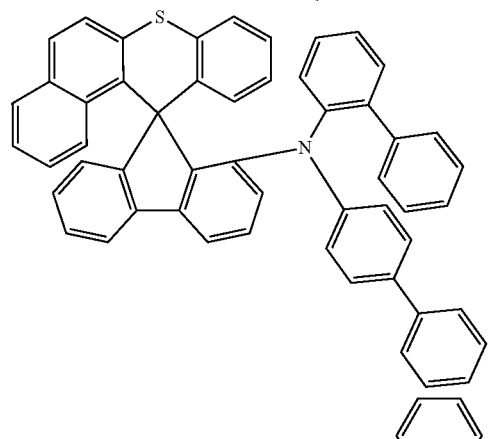
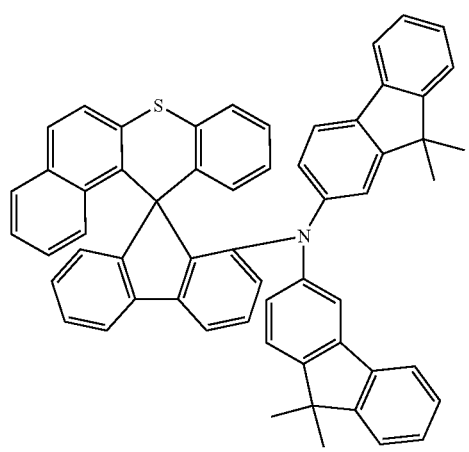
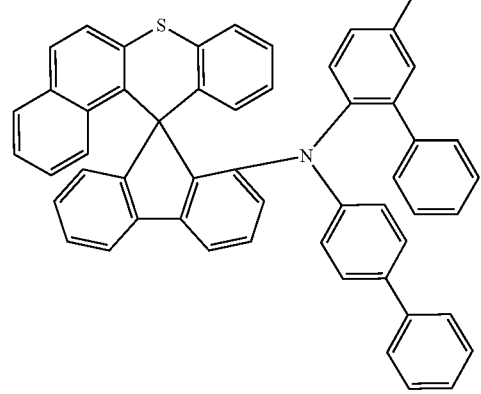
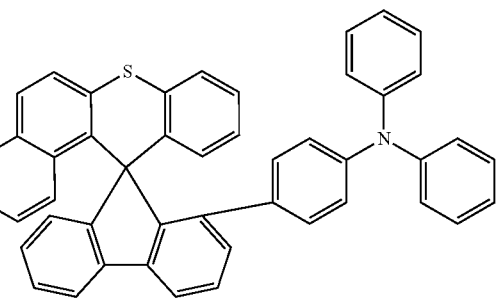
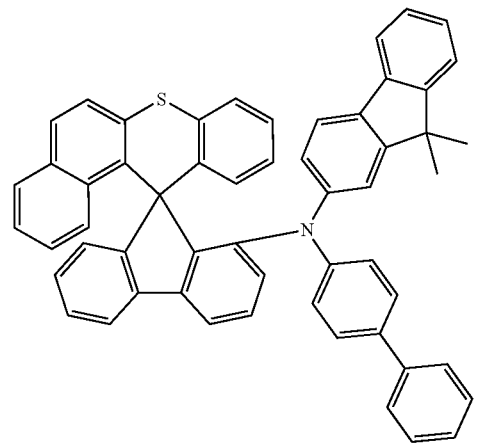
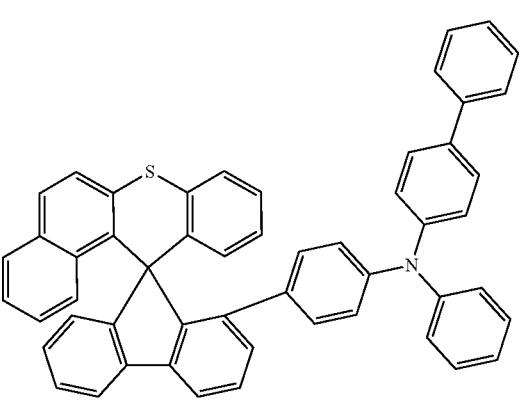

161
-continued
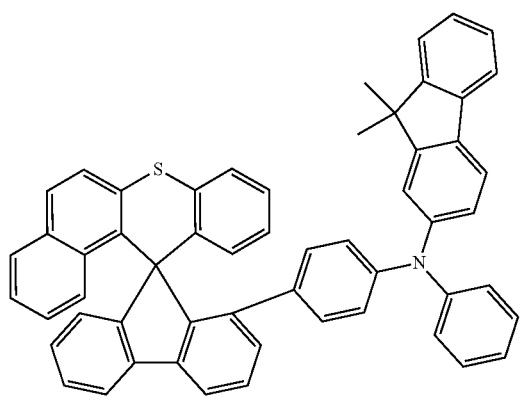
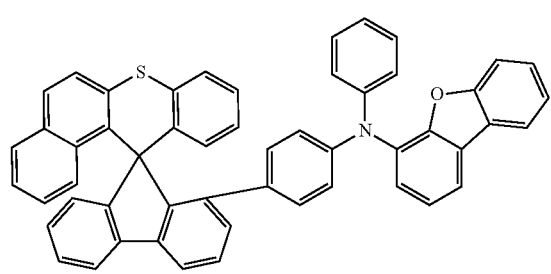
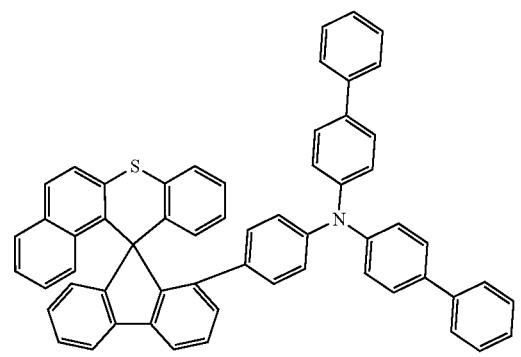
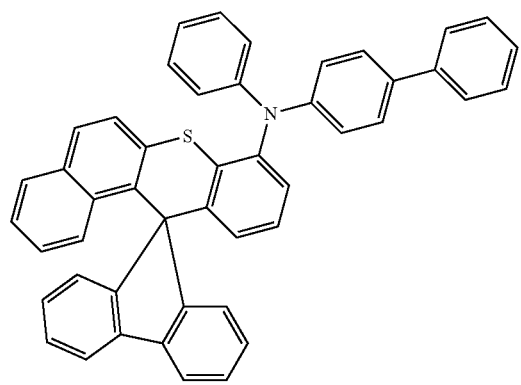
162
-continued
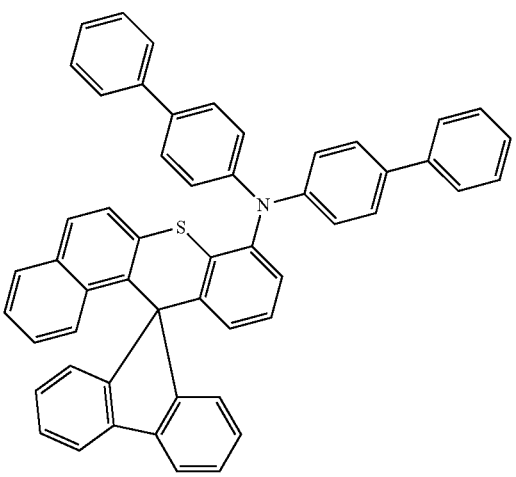
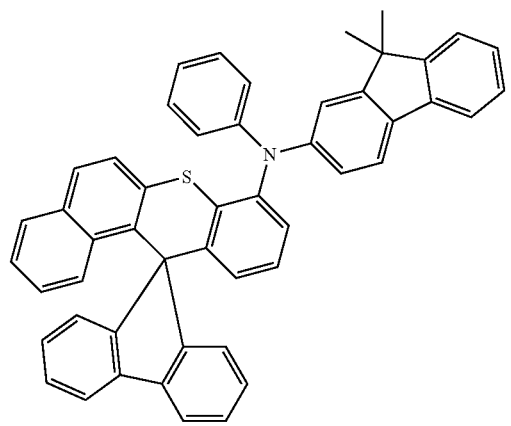
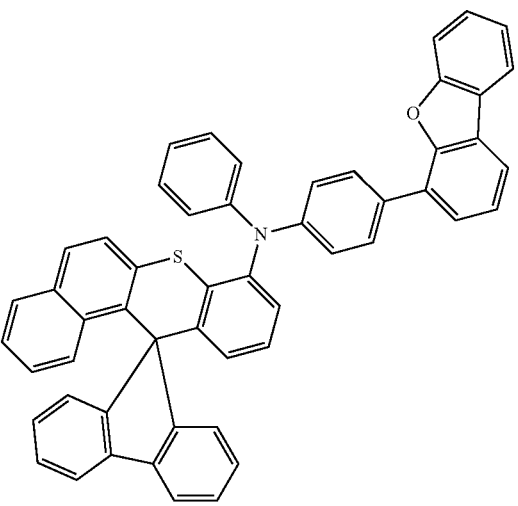

163
-continued
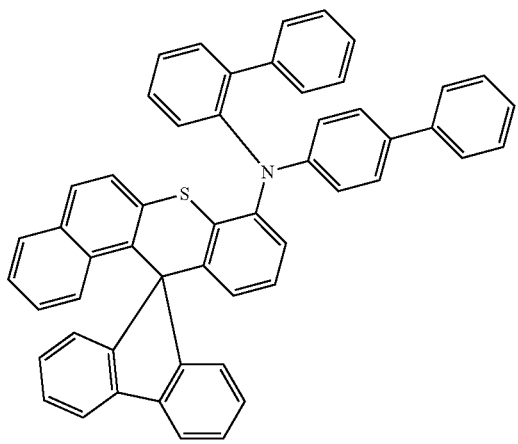
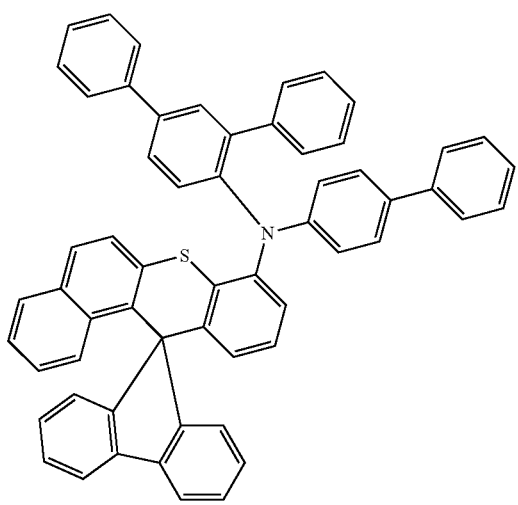
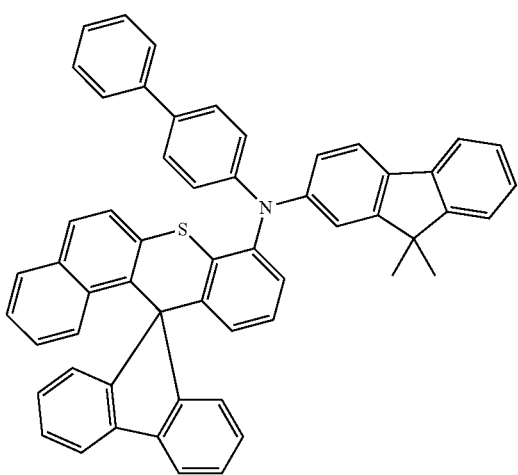
164
-continued
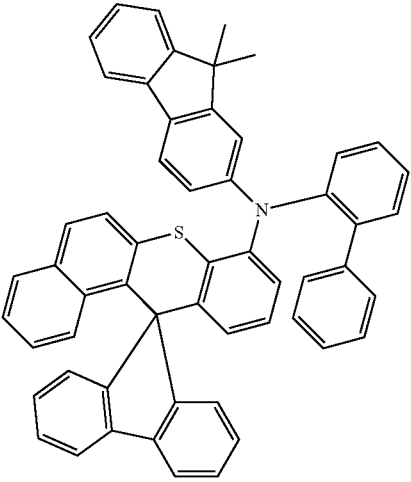
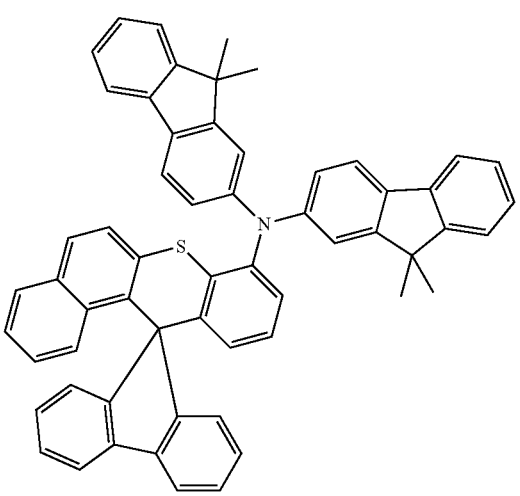
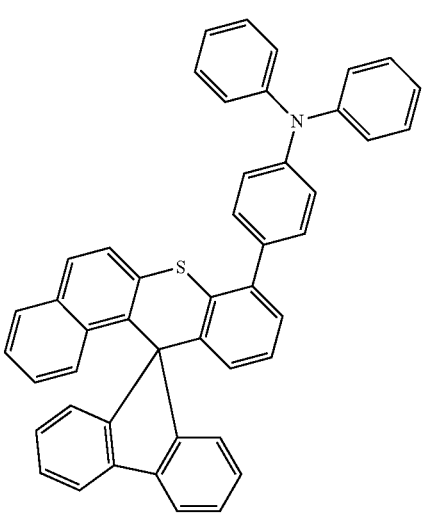

165
-continued
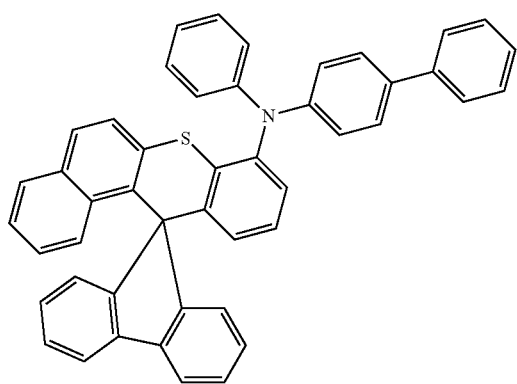
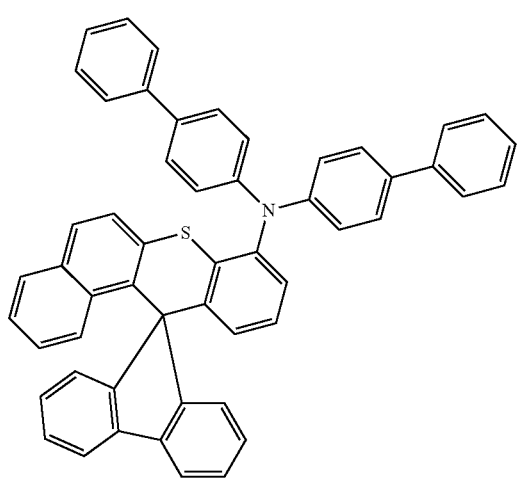
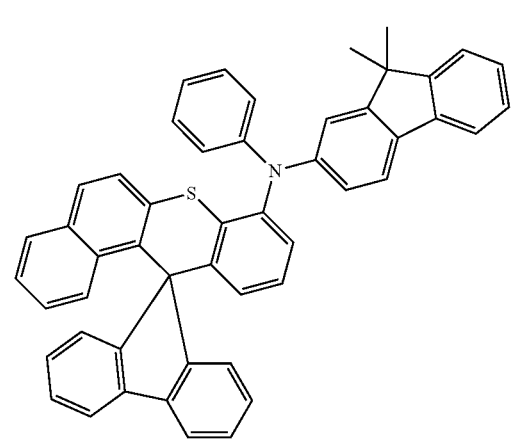
166
-continued
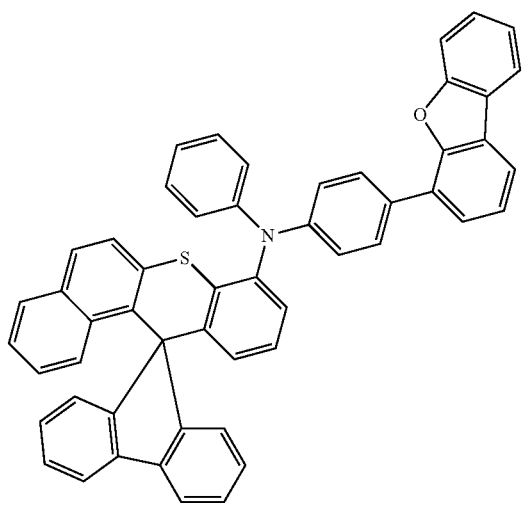
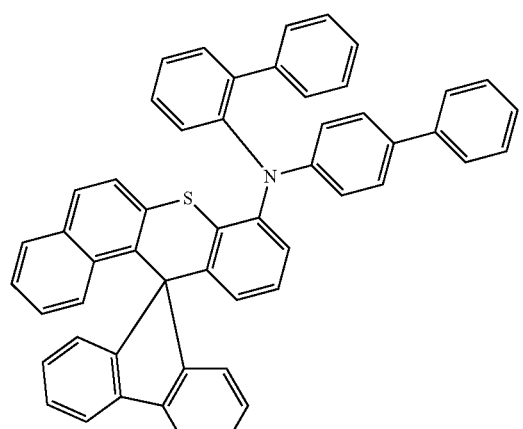
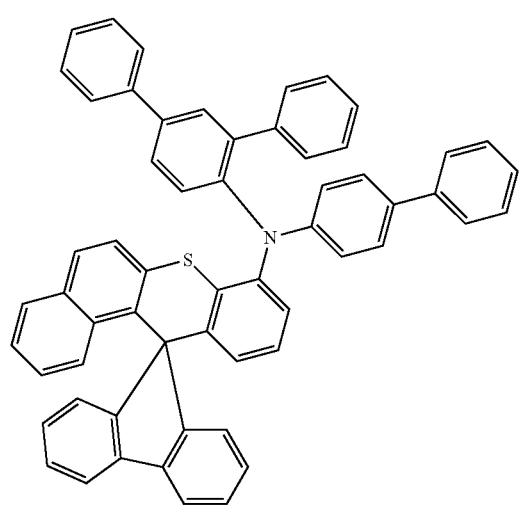

167
-continued
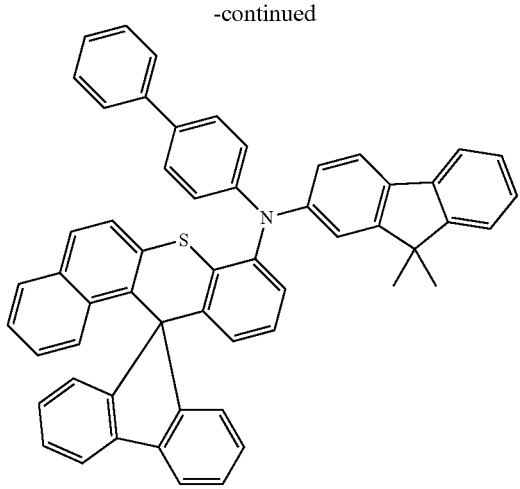
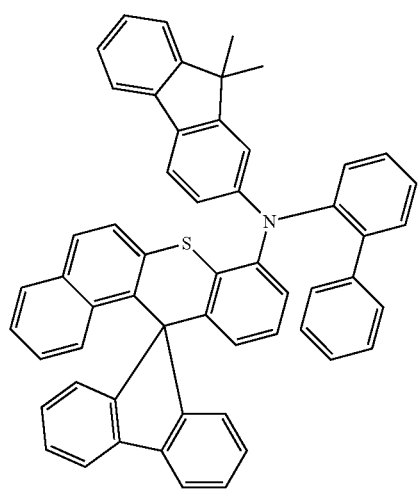
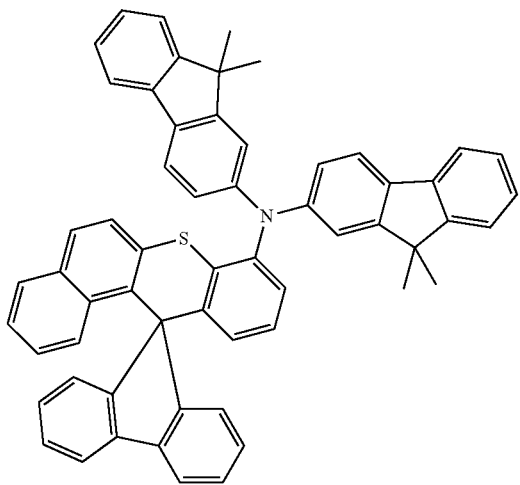
168
-continued
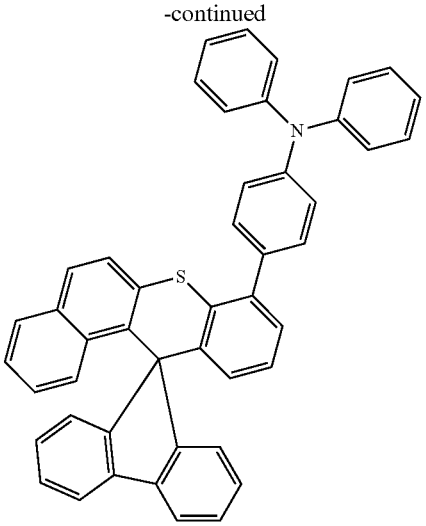
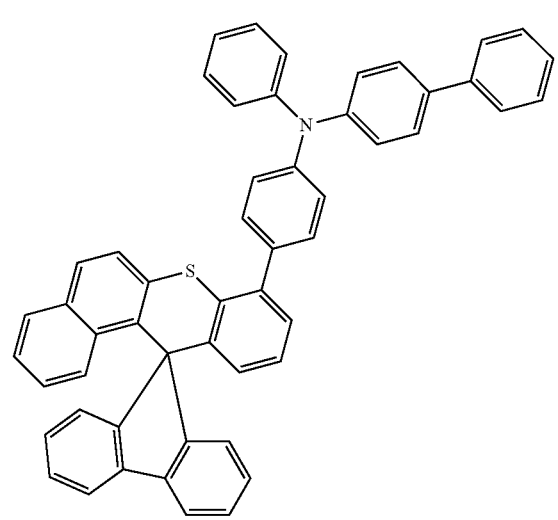
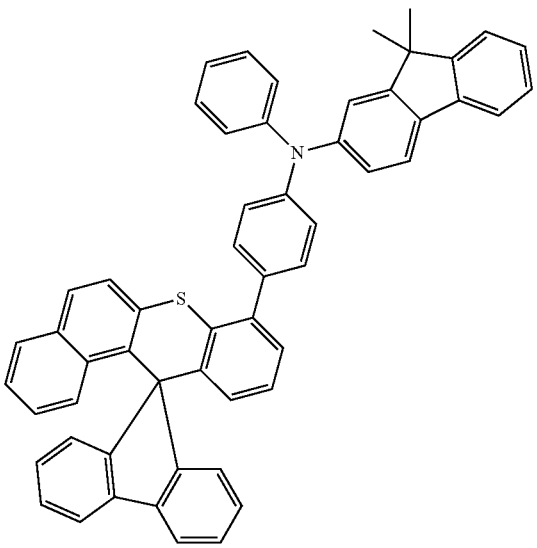

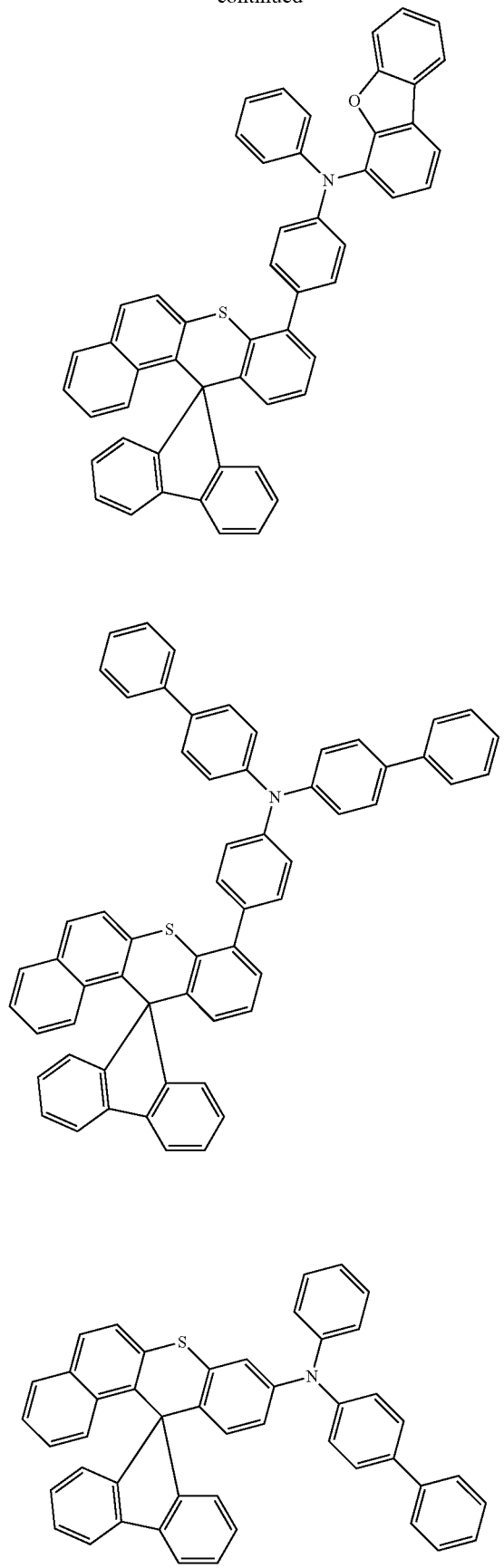
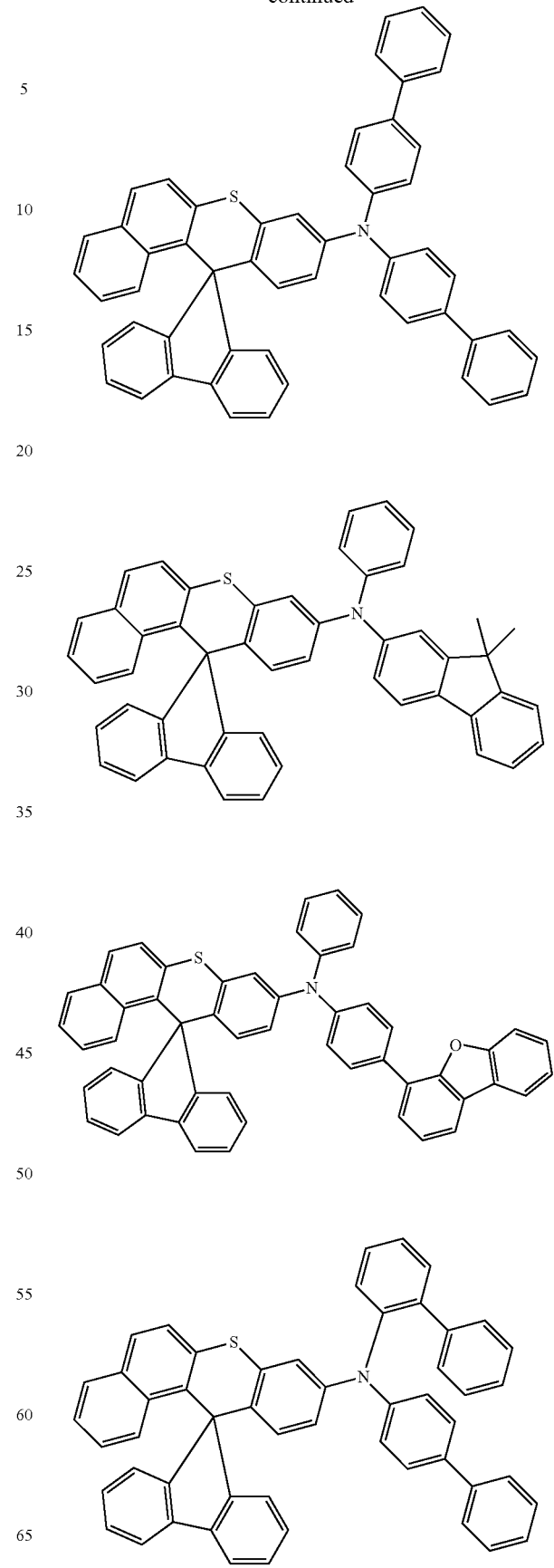

171
-continued
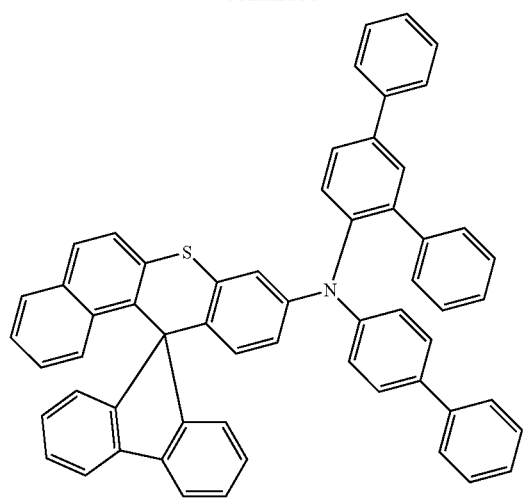
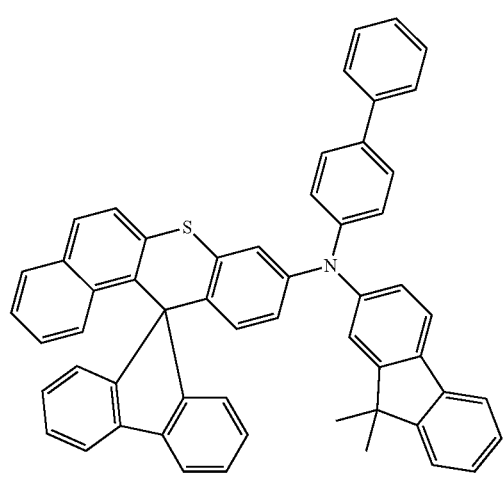
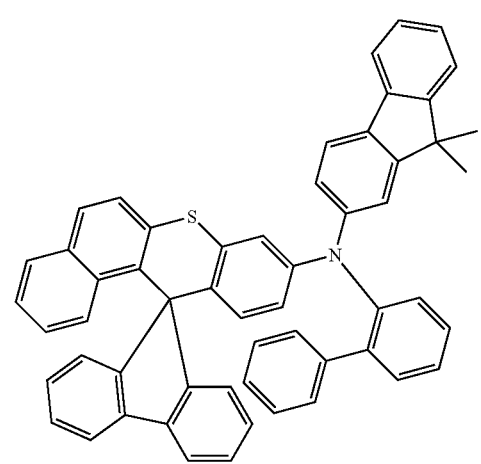
172
-continued
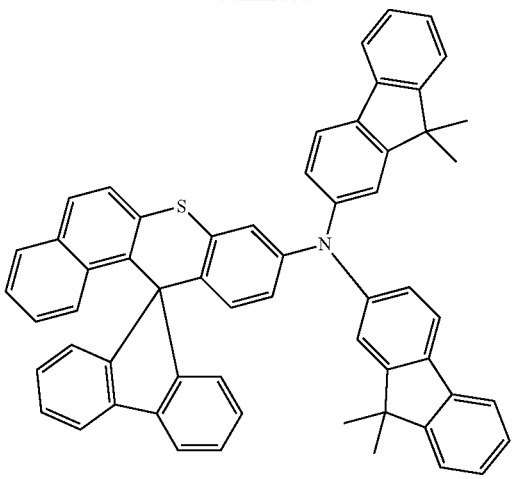
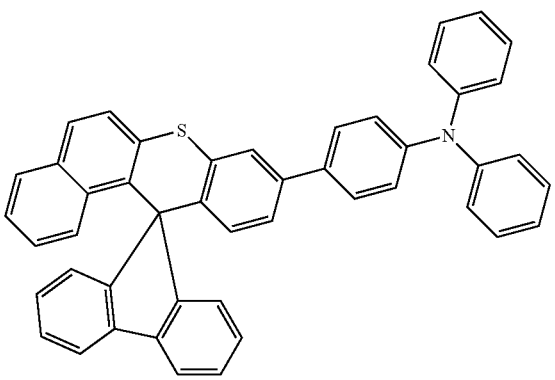
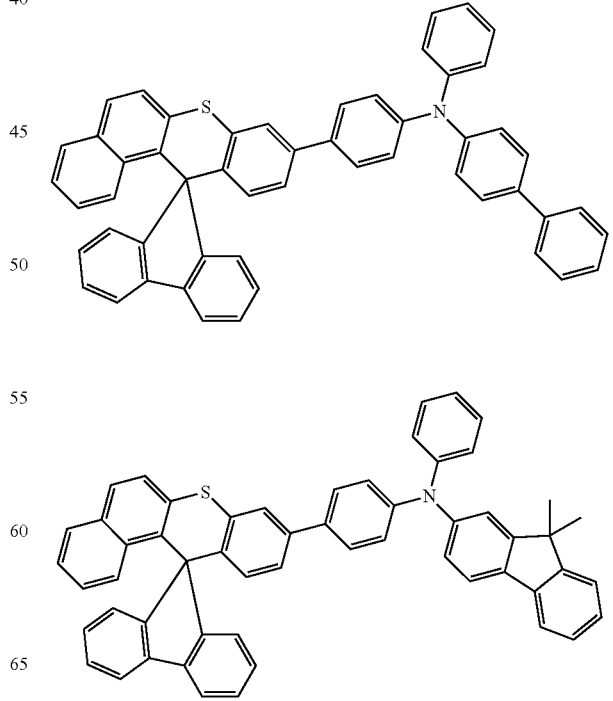

173
-continued
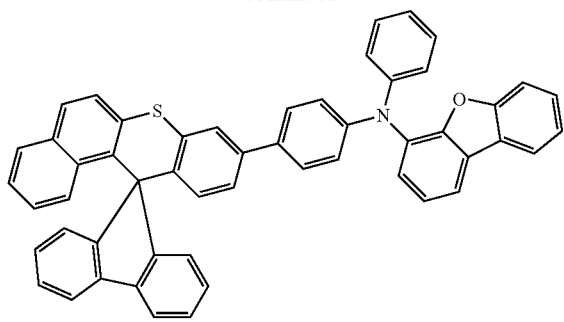
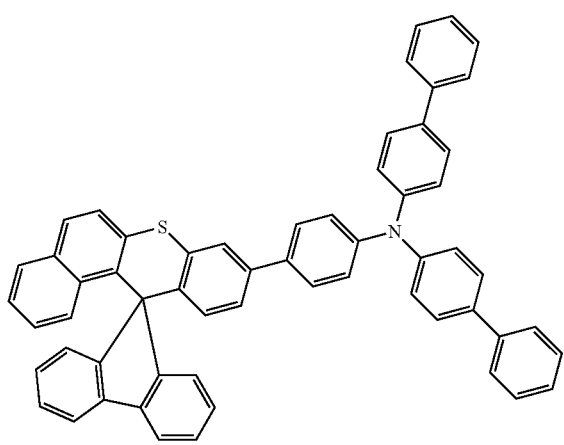
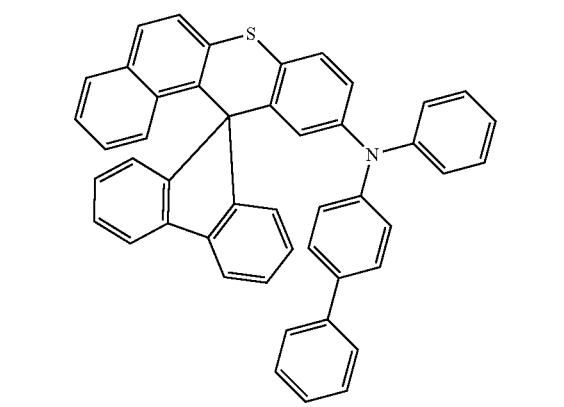
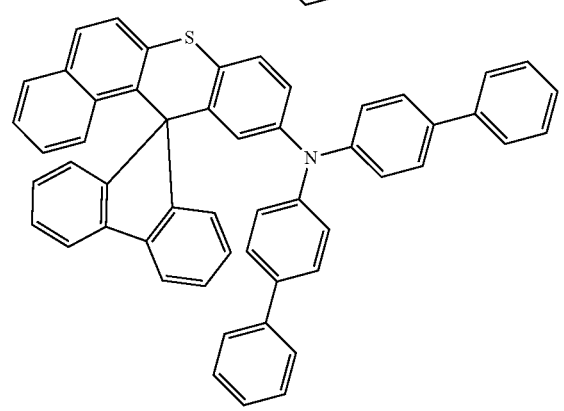
174
-continued
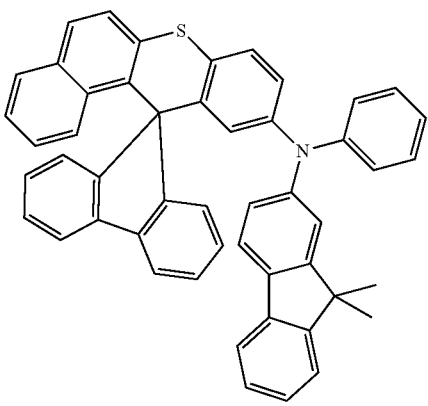
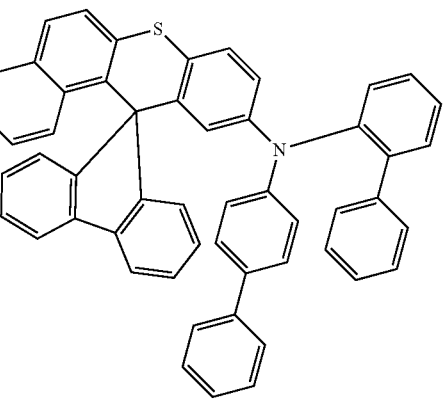
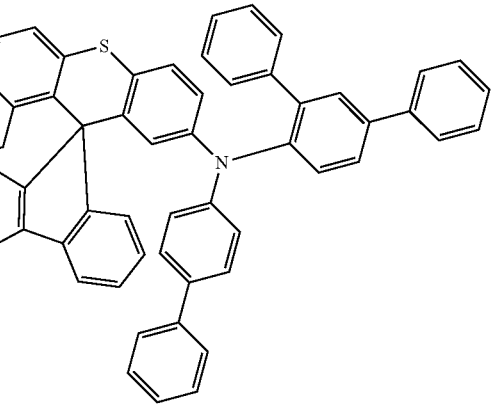
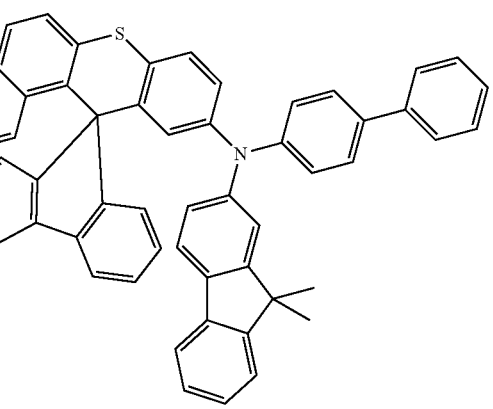

175
-continued
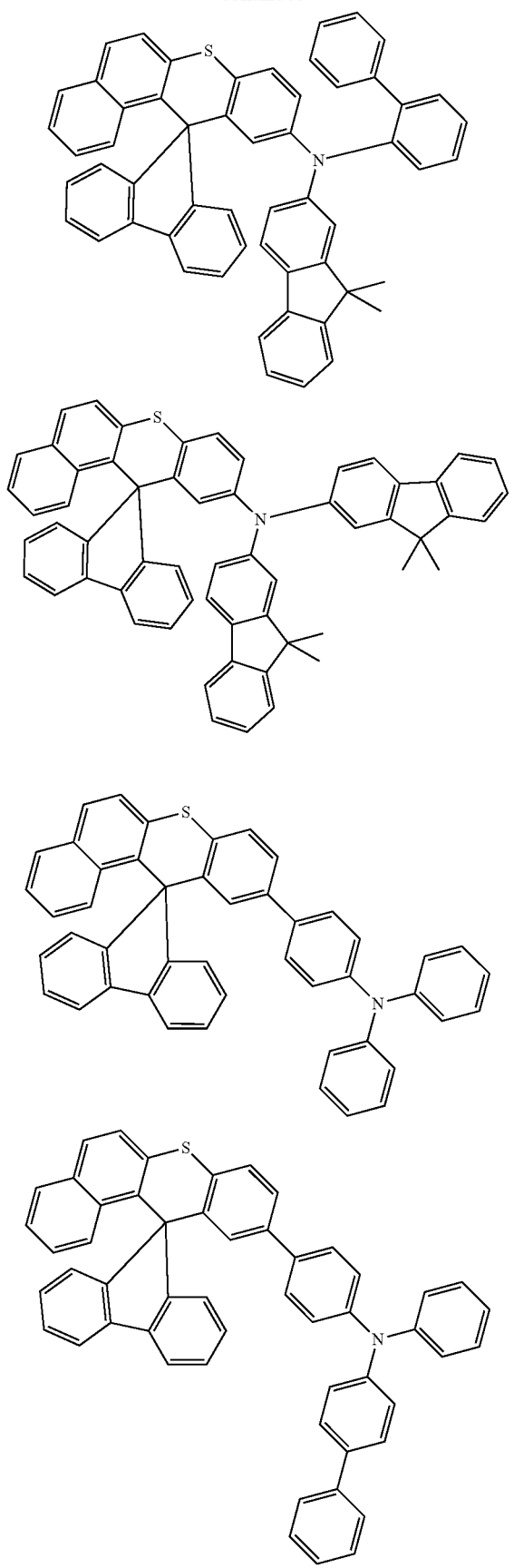
176
-continued
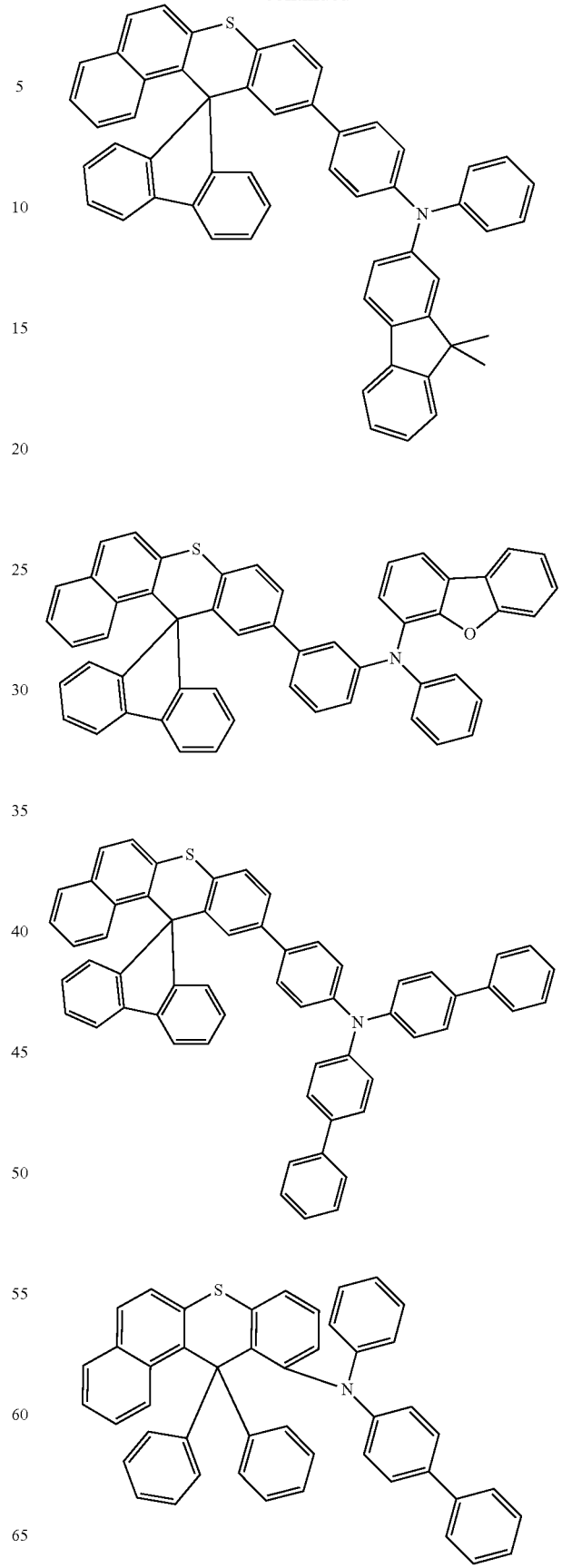

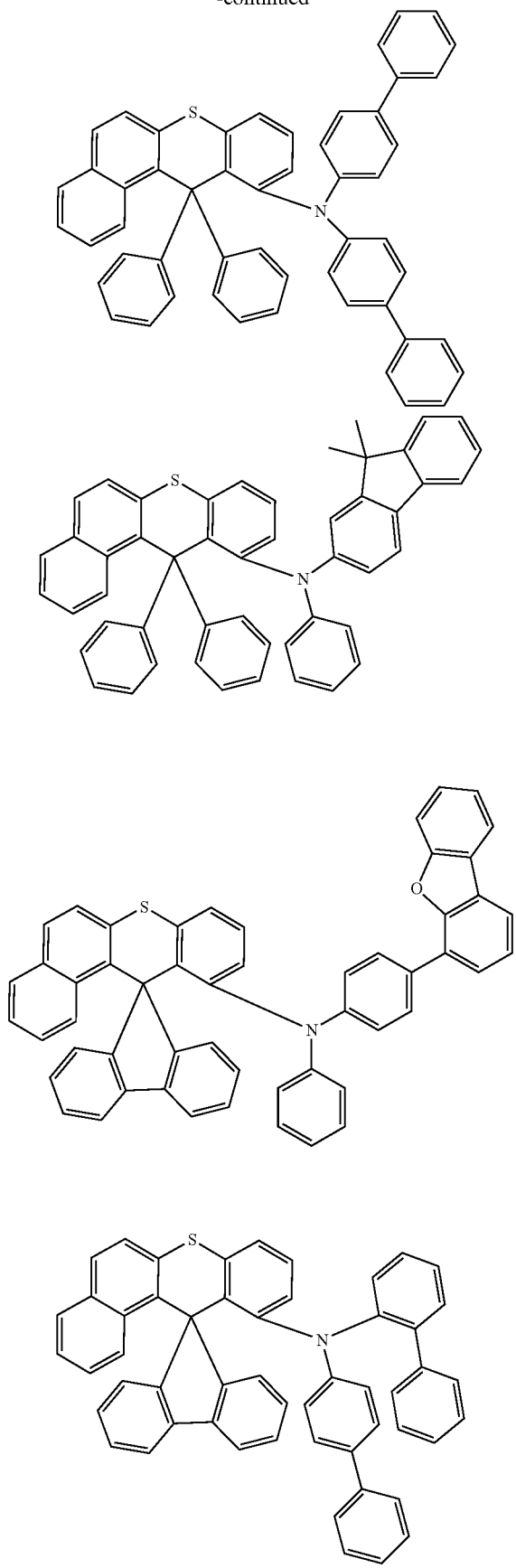
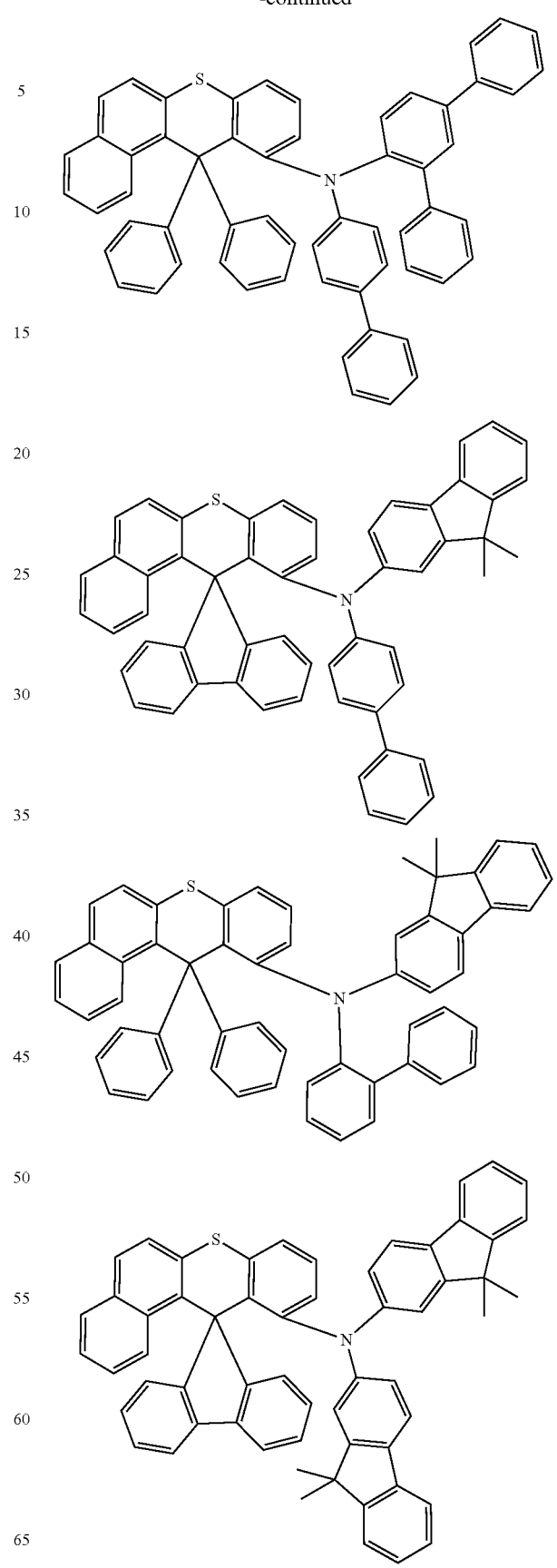

179
-continued
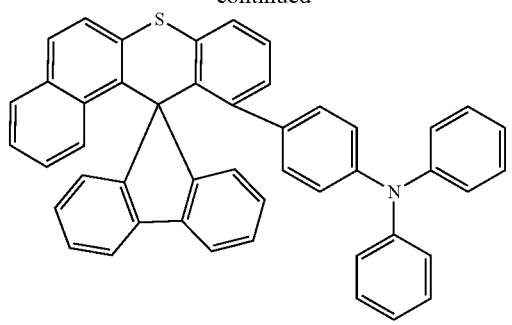
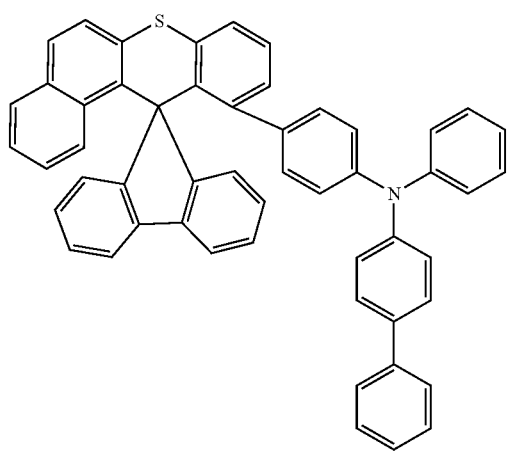
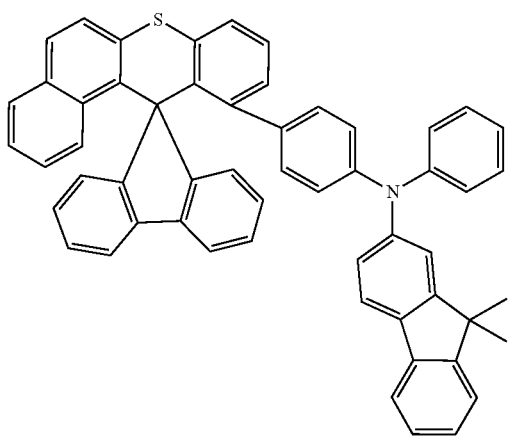
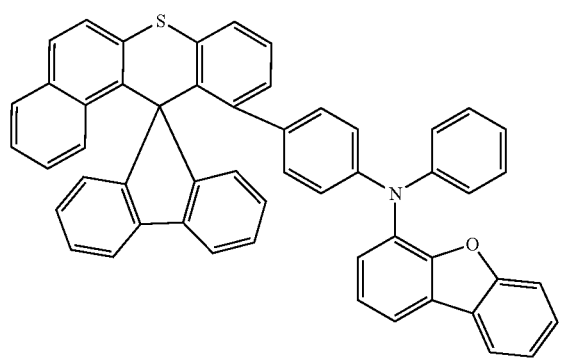
180
-continued
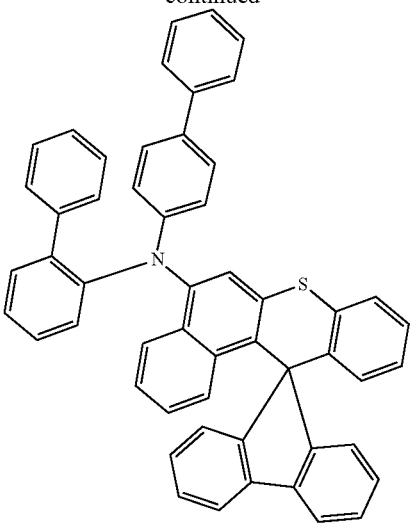
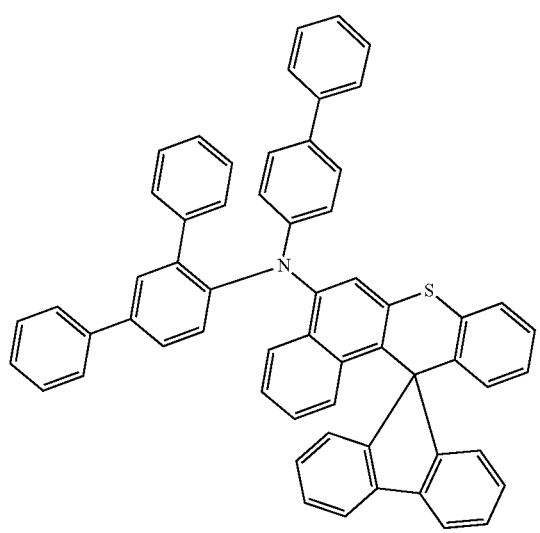
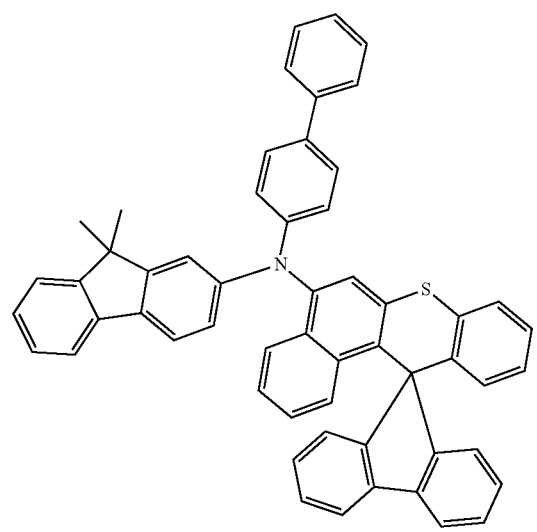

181
-continued
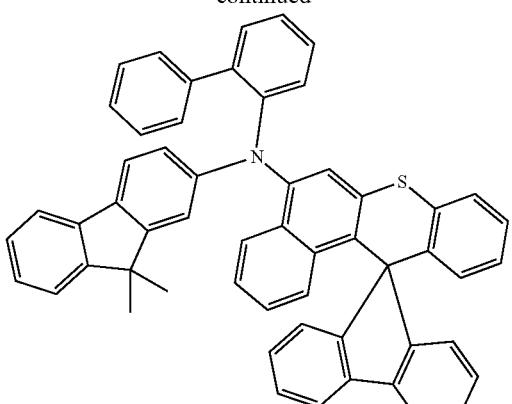
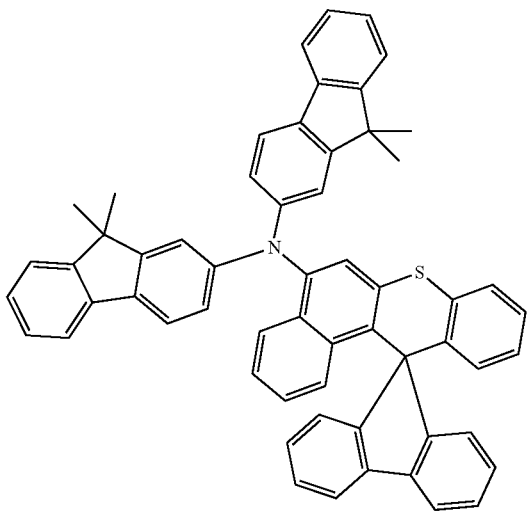
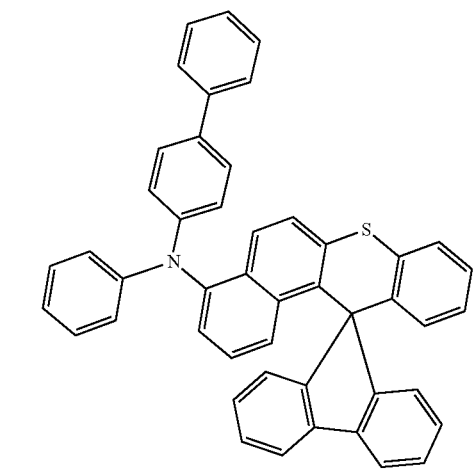
182
-continued
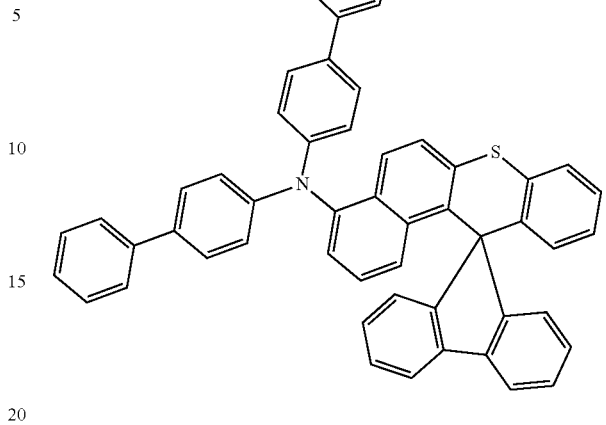
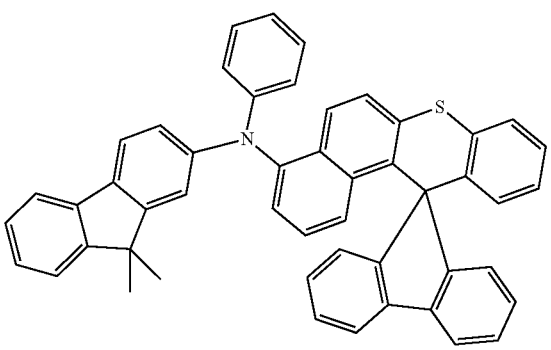
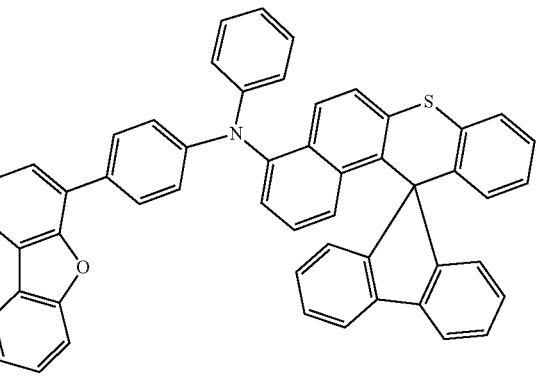
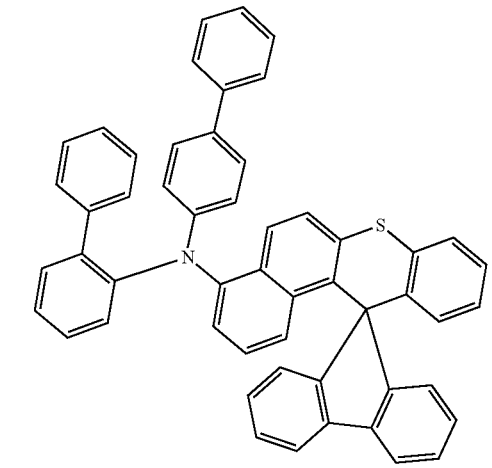

-continued
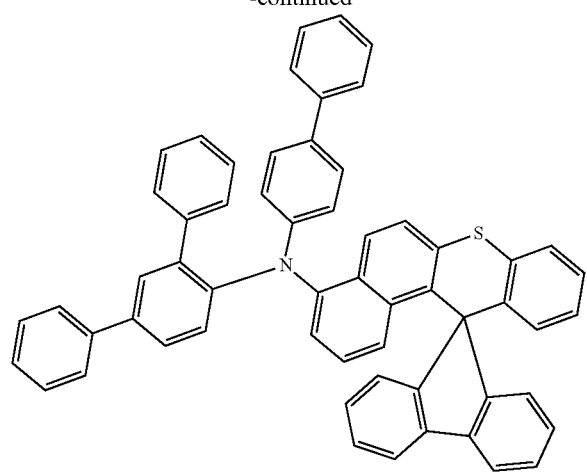
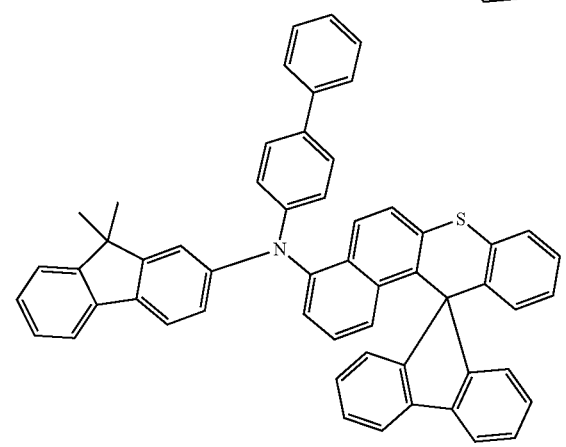
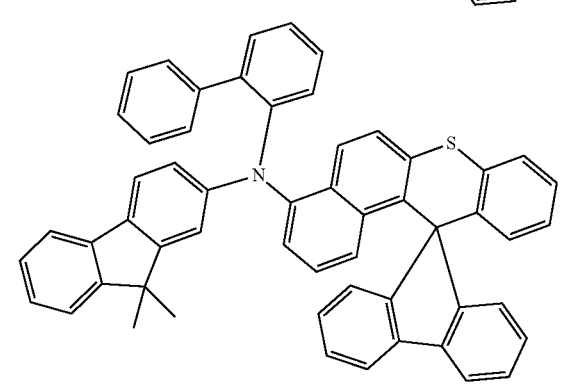
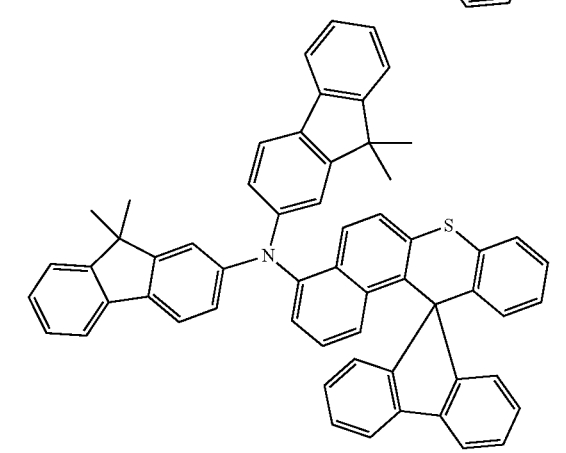
-continued
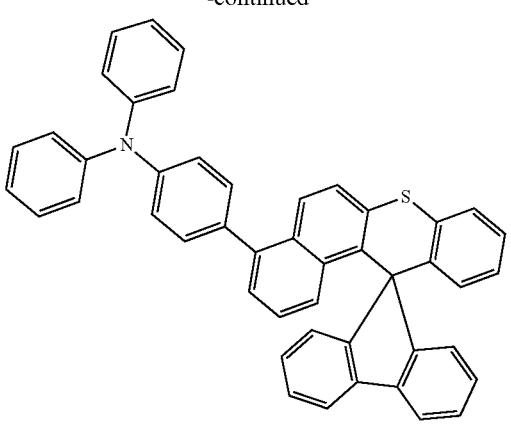
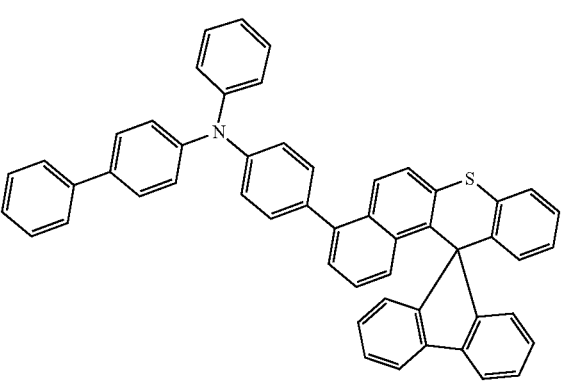
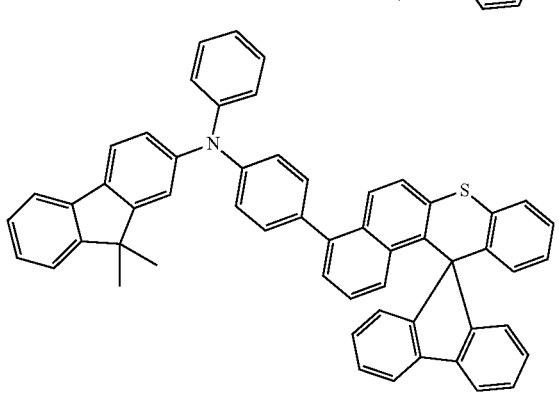
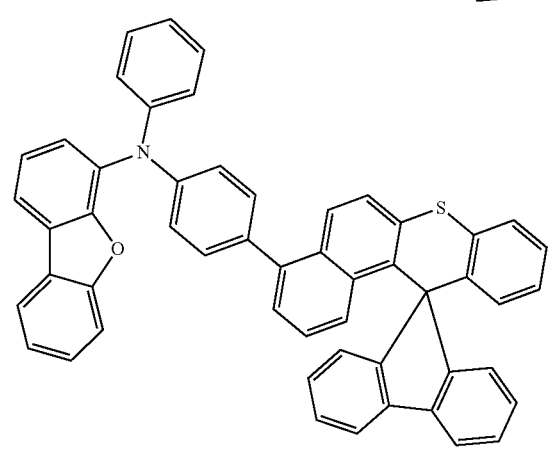

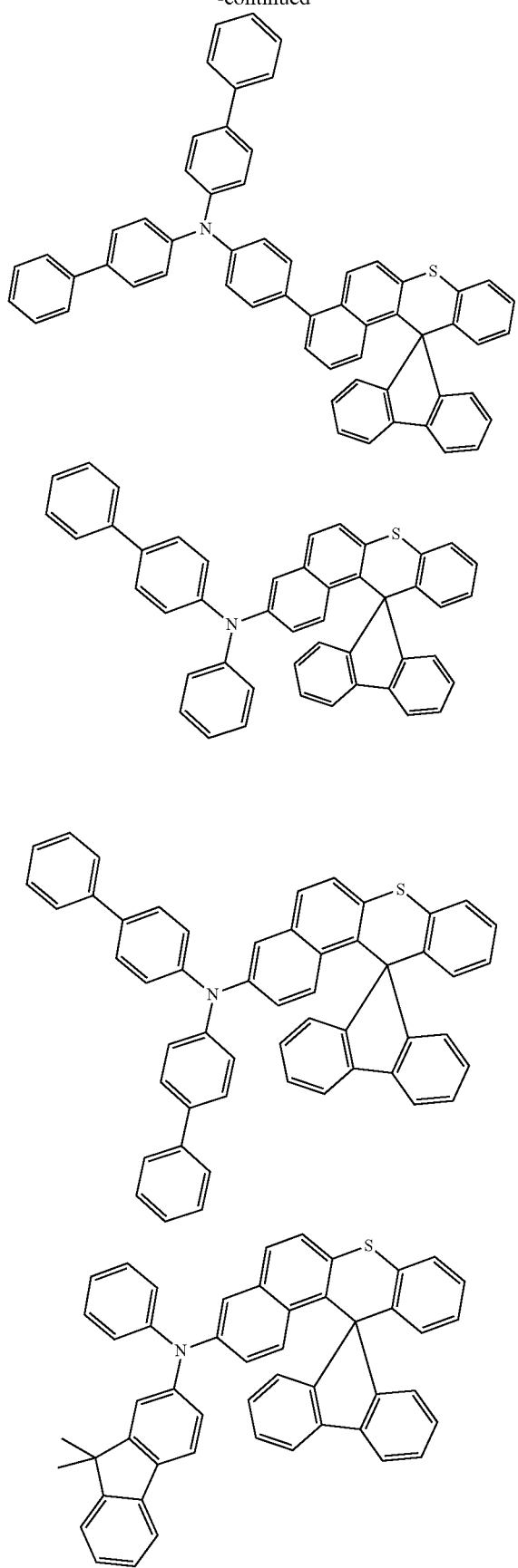
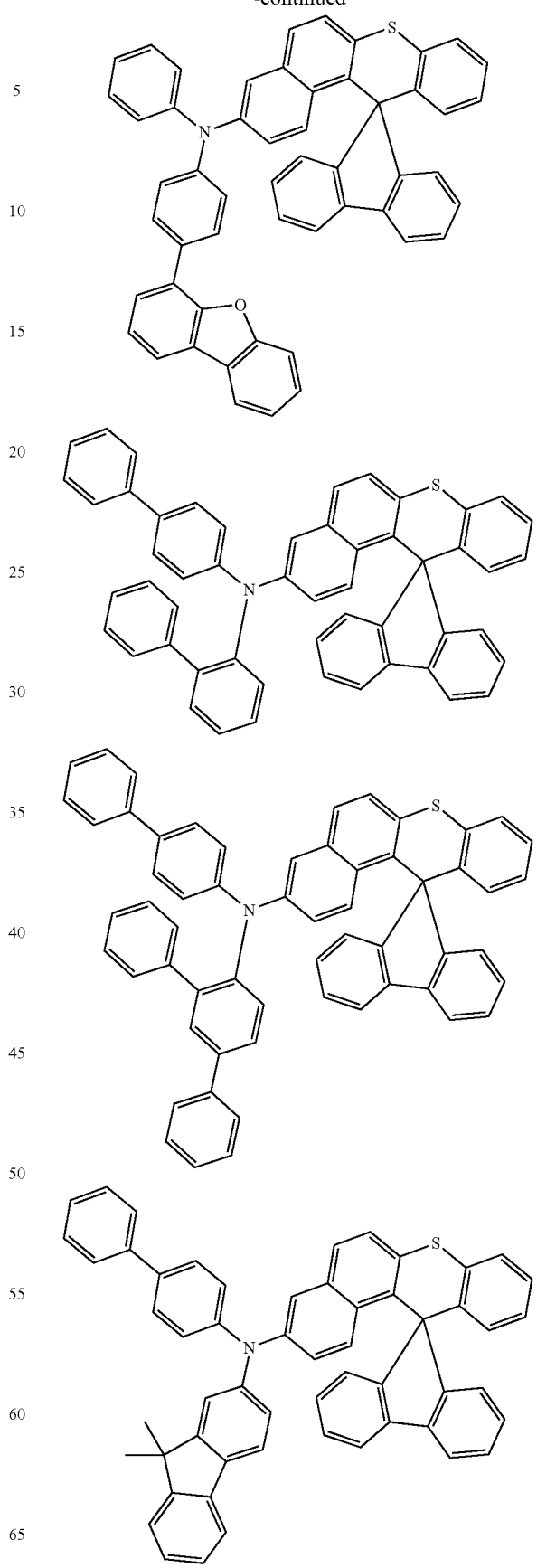

187
-continued
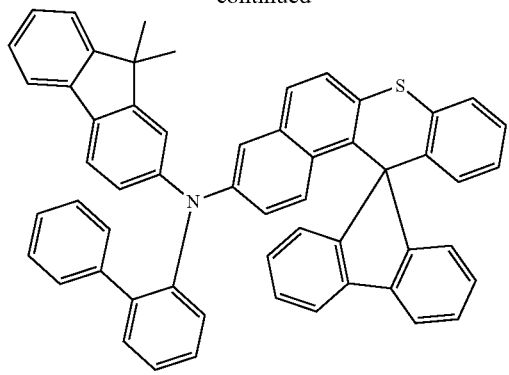
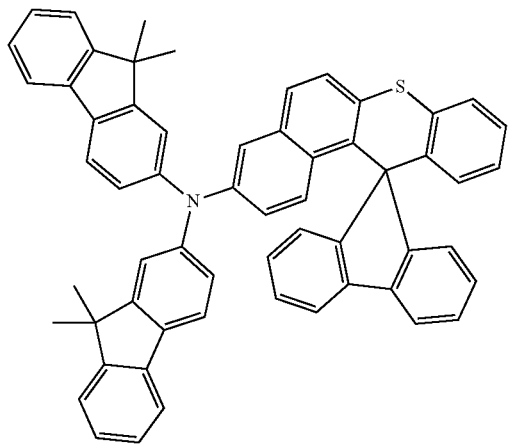
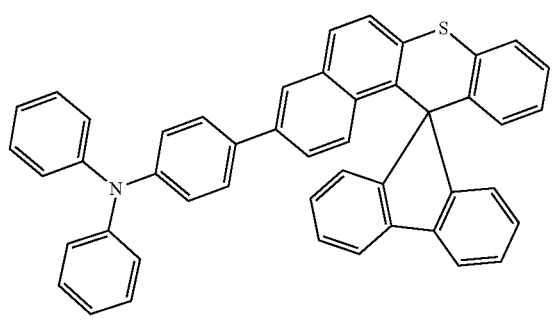
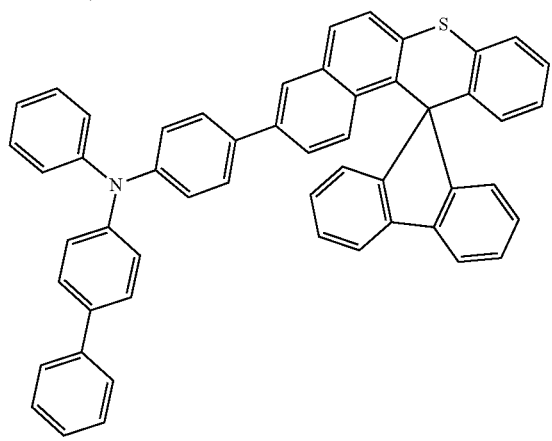
188
-continued
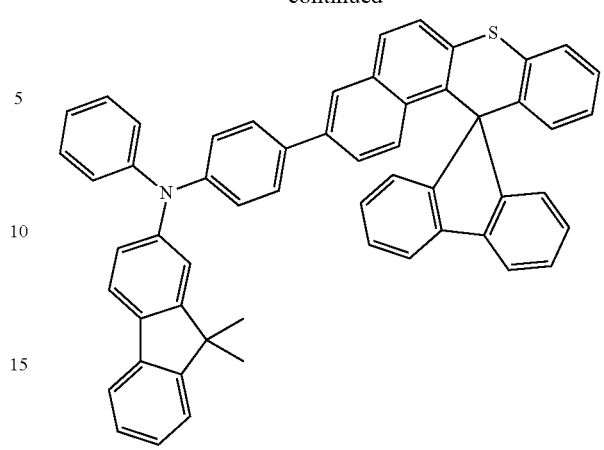
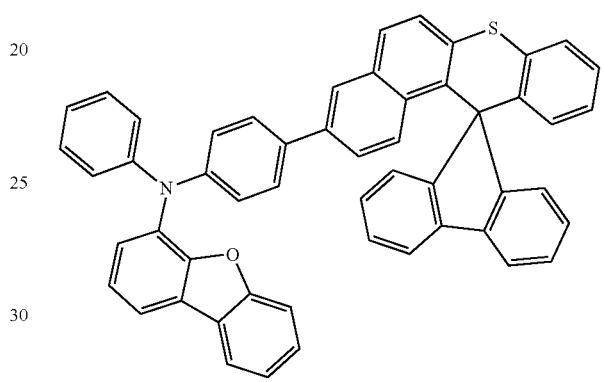
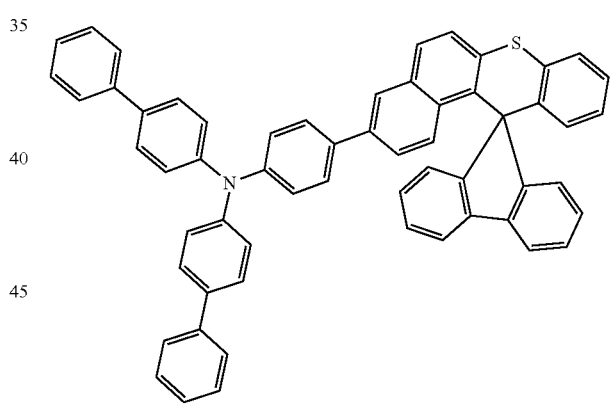
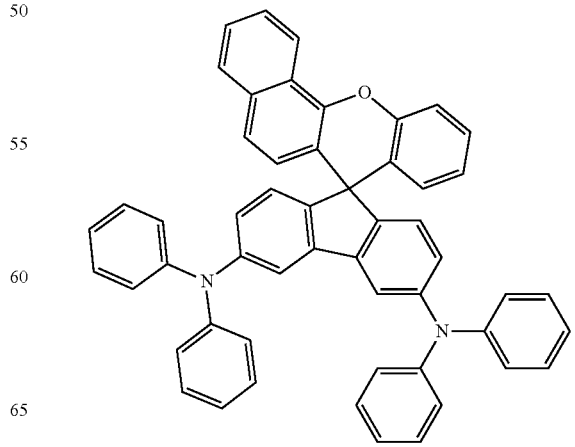

189
-continued
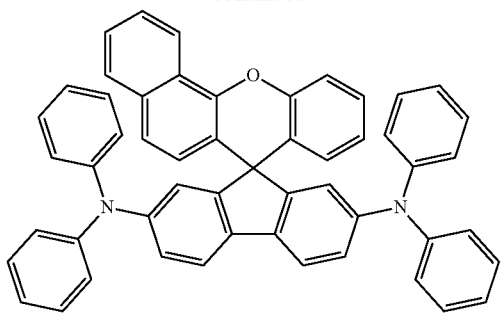
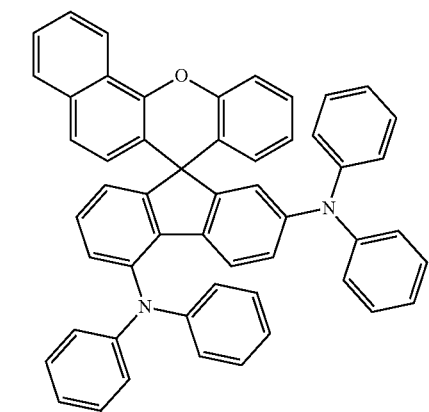
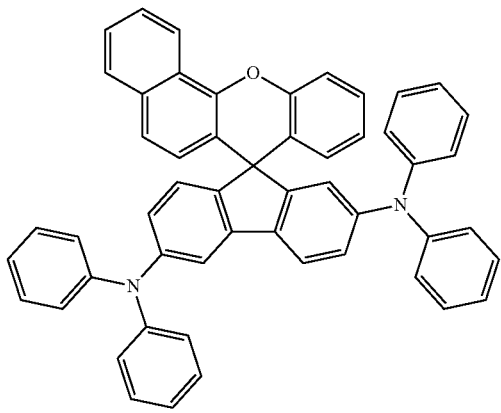
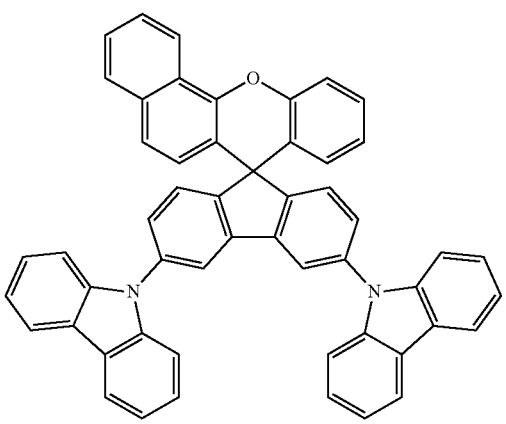
190
-continued
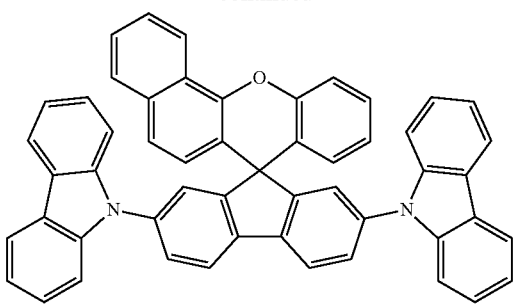
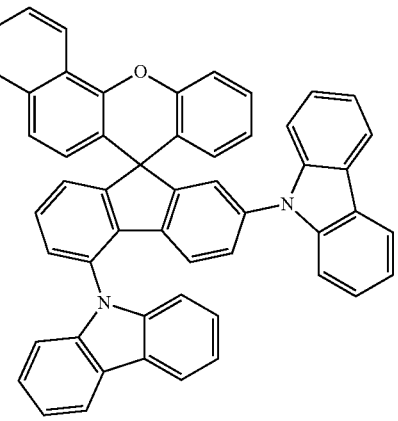
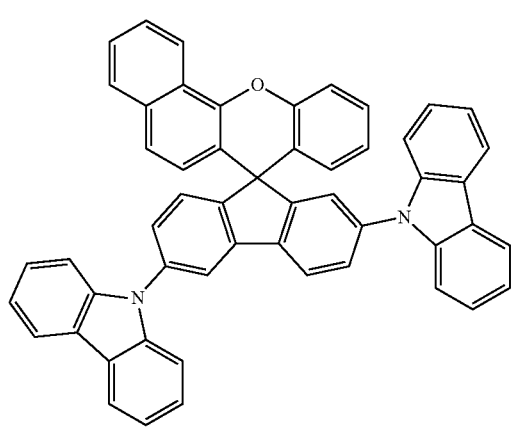
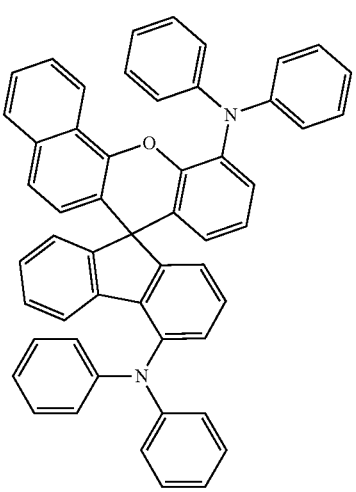

191
-continued
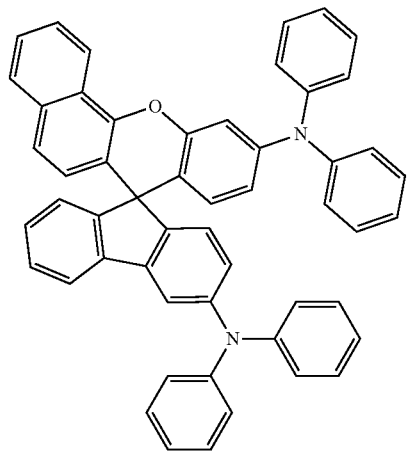
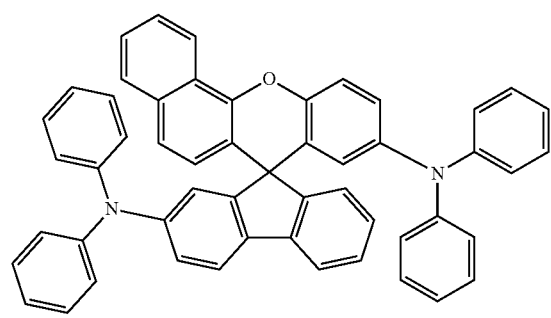
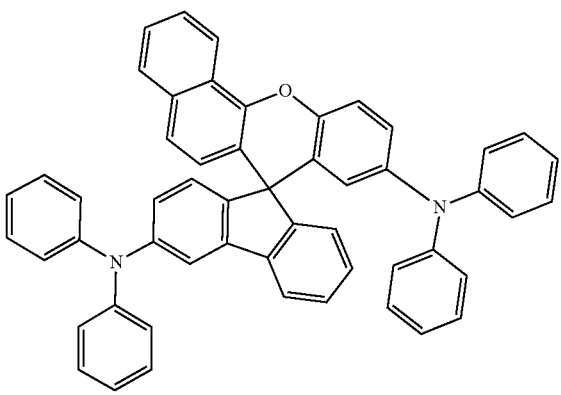
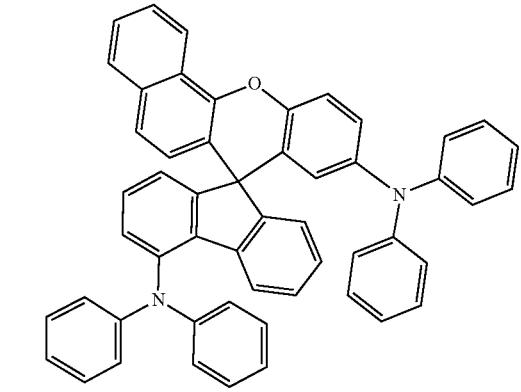
192
-continued
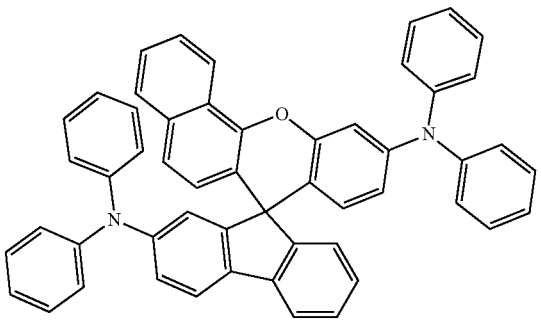
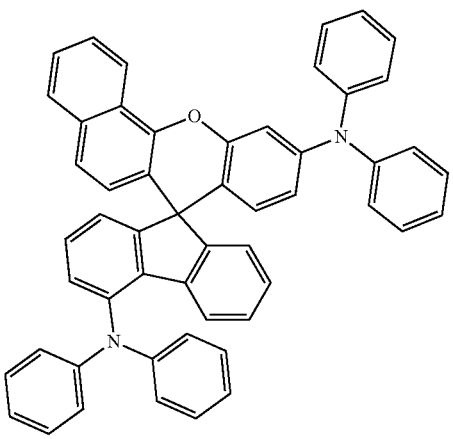
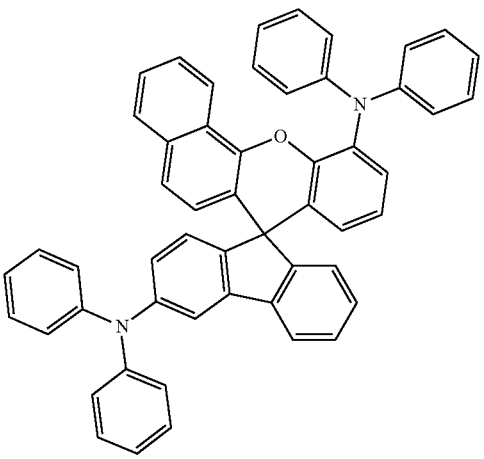
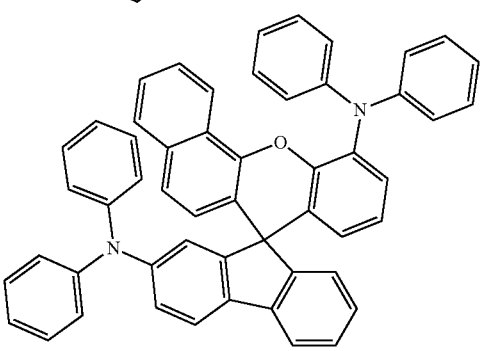

| 193 | 194 |
|---|---|
| -continued | -continued |
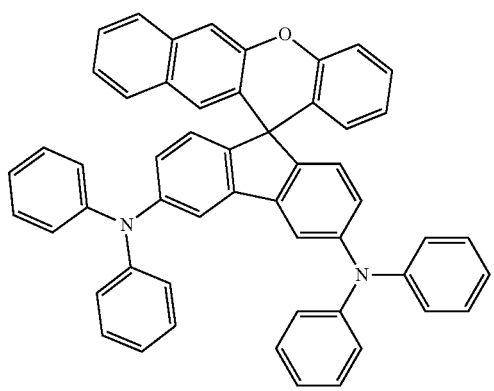
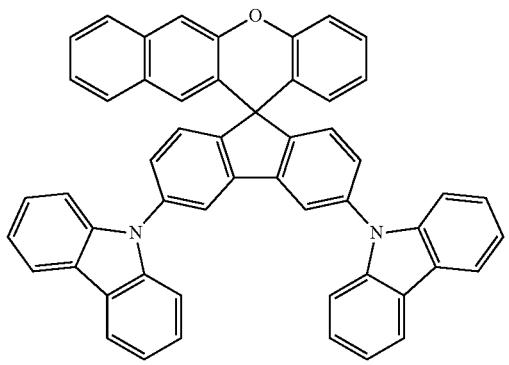
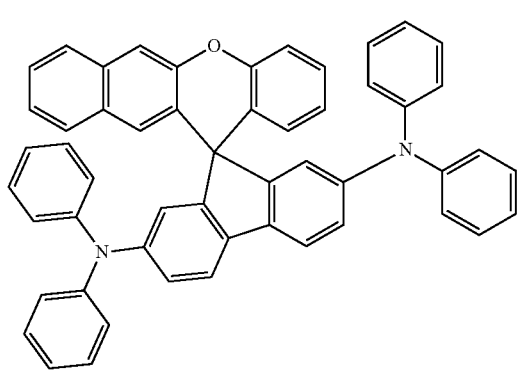
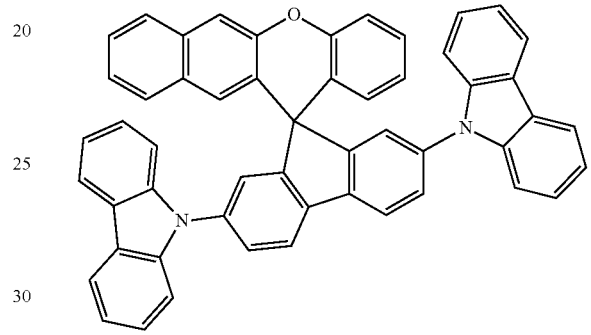
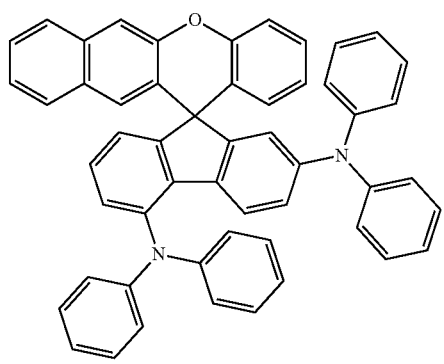
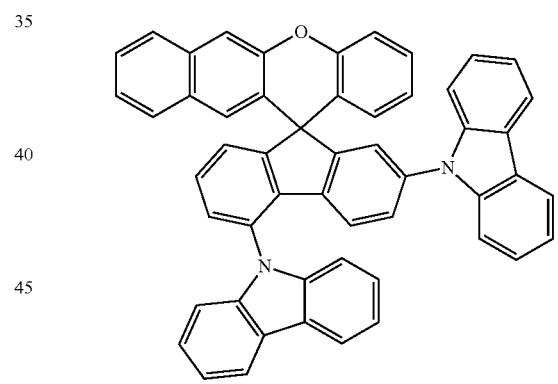
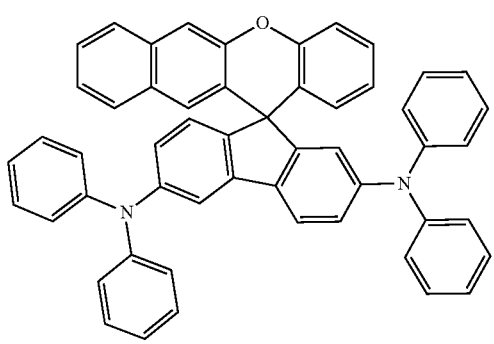
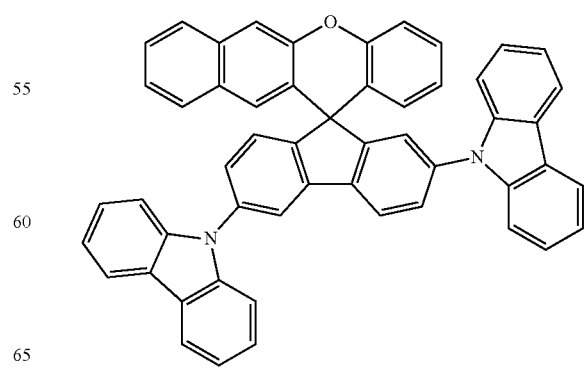

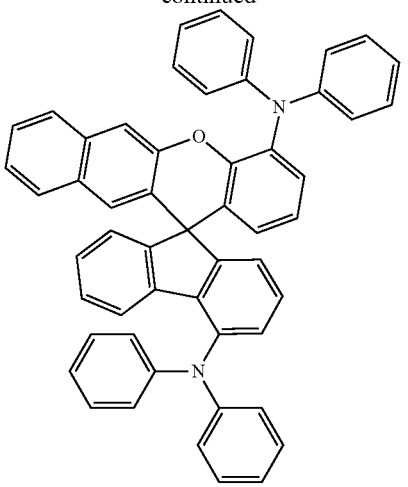
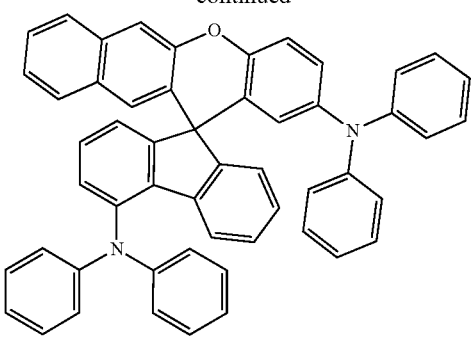

197
-continued
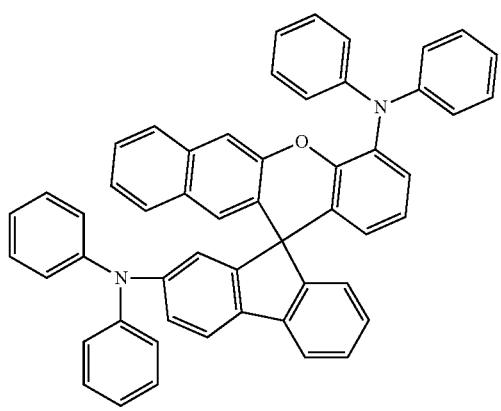
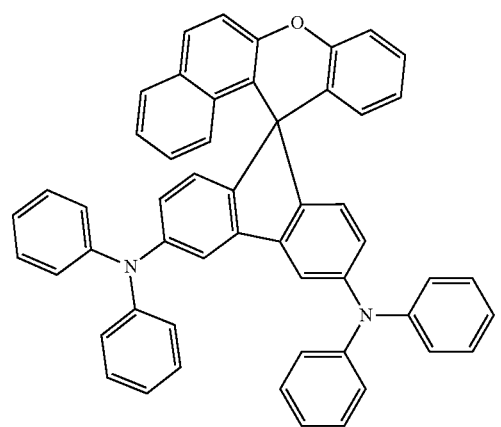
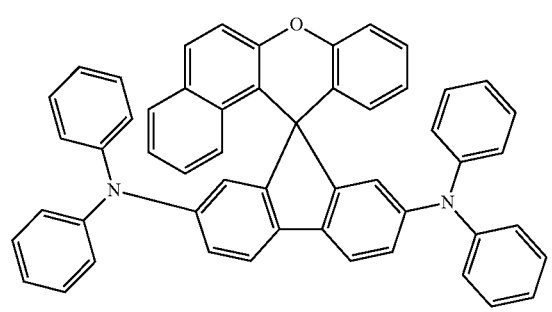
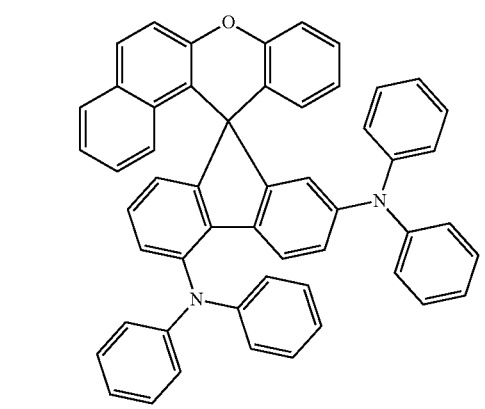
198
-continued
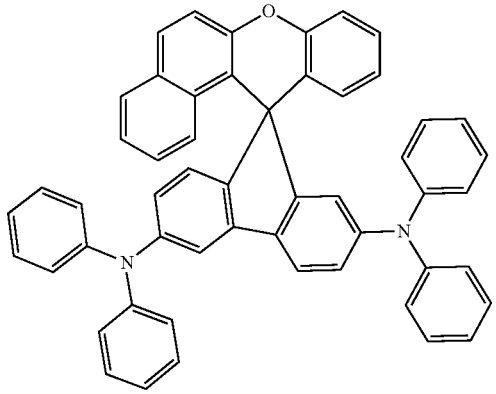
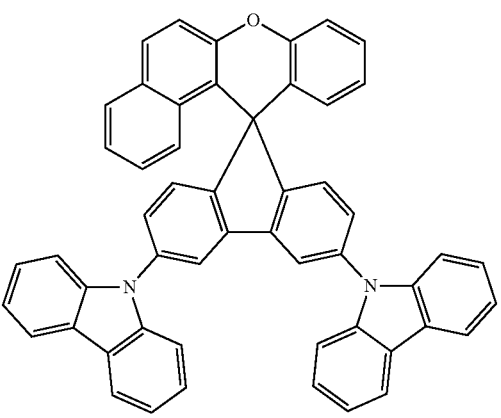
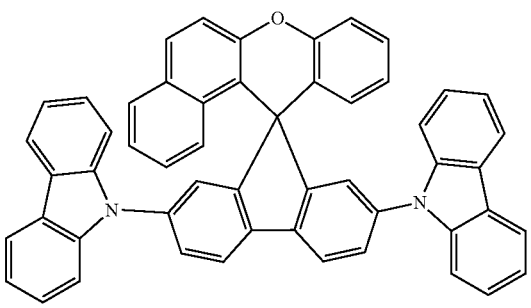
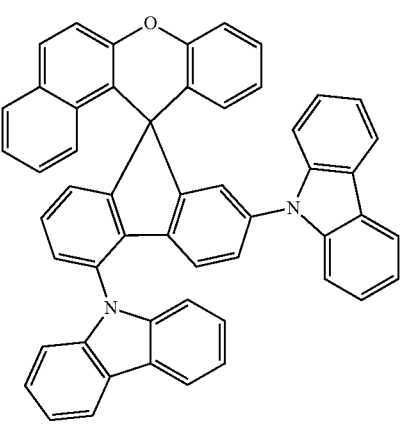

199
-continued
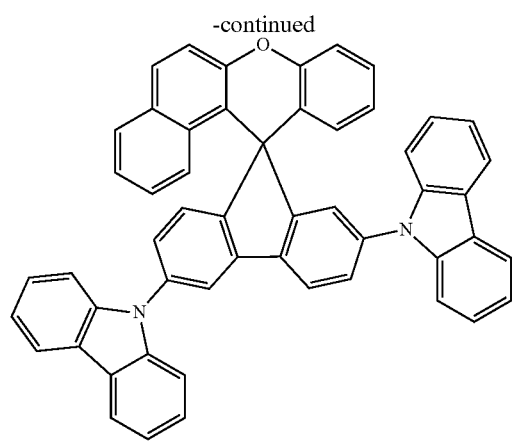
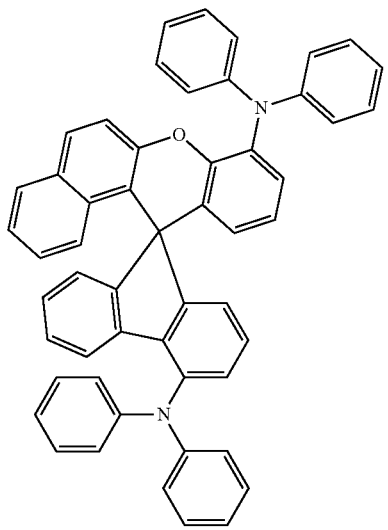
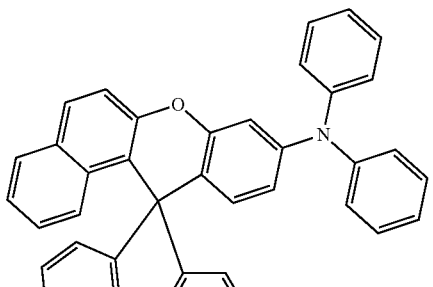
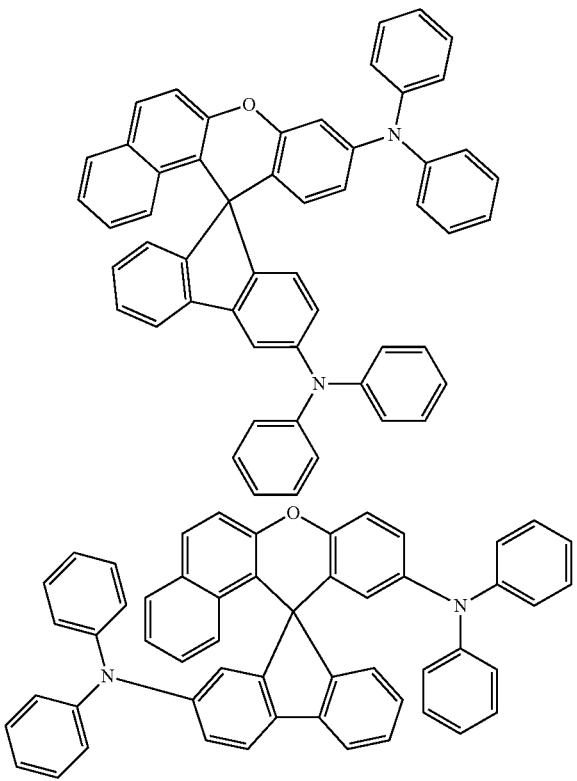
200
-continued
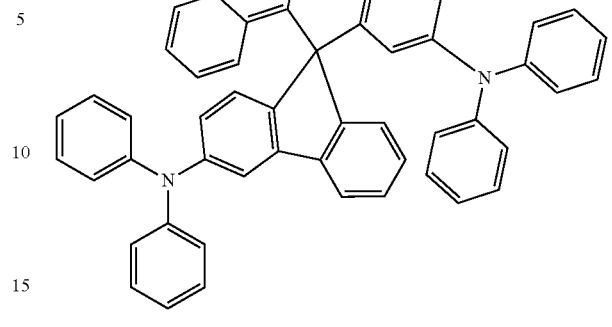
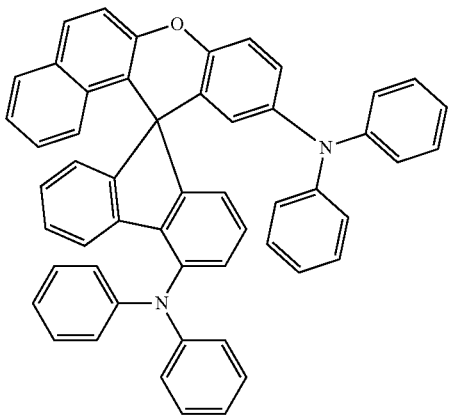
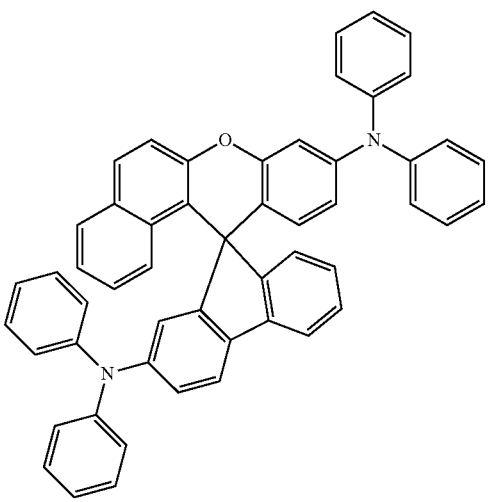

201
-continued
202
-continued
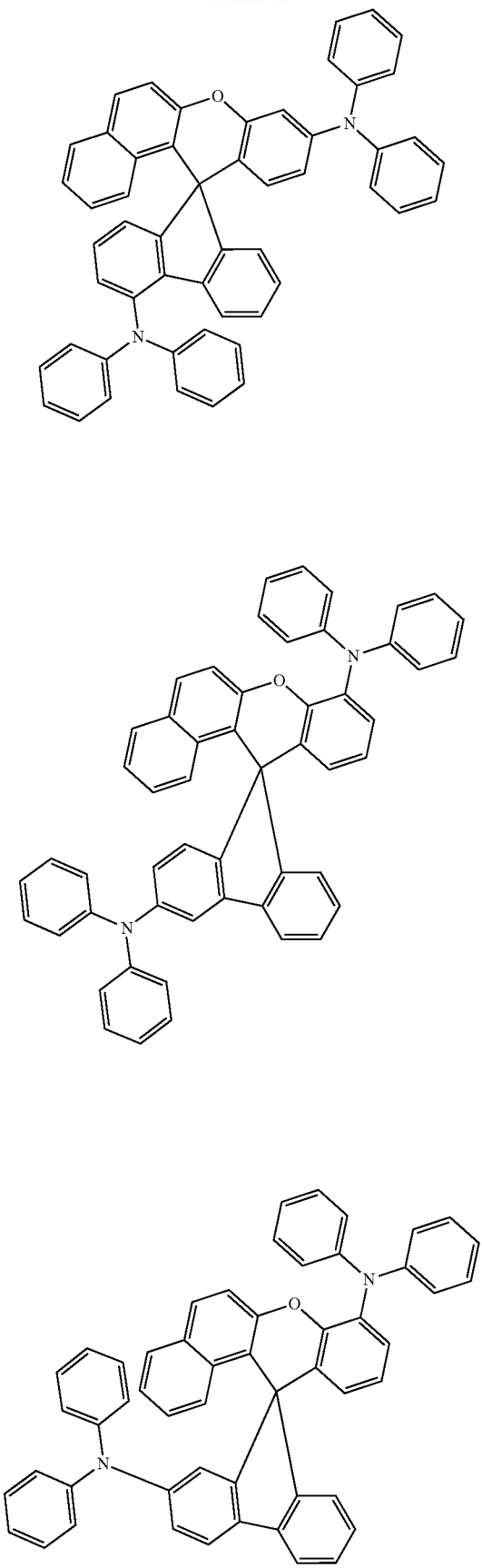
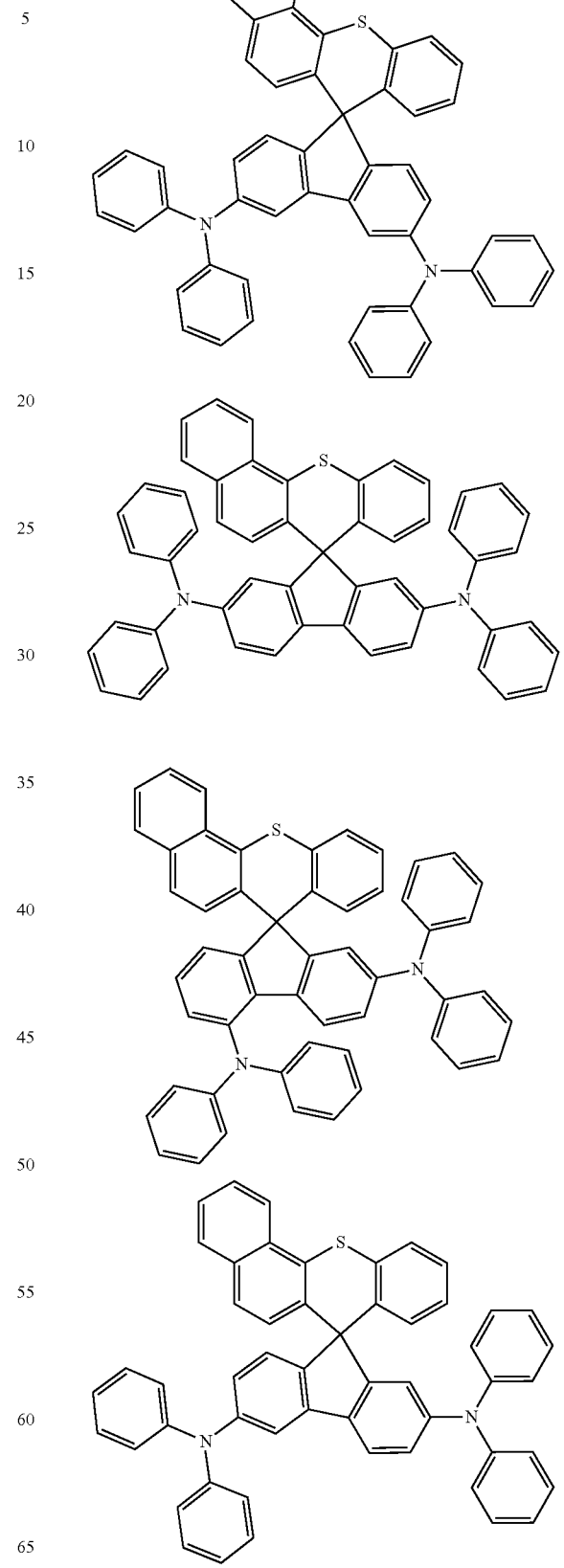

203
-continued
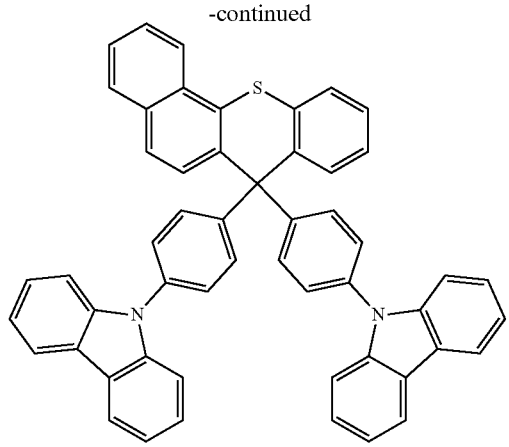
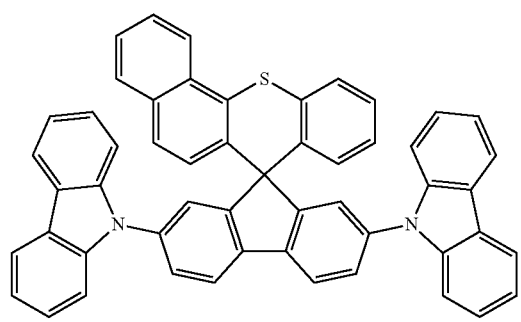
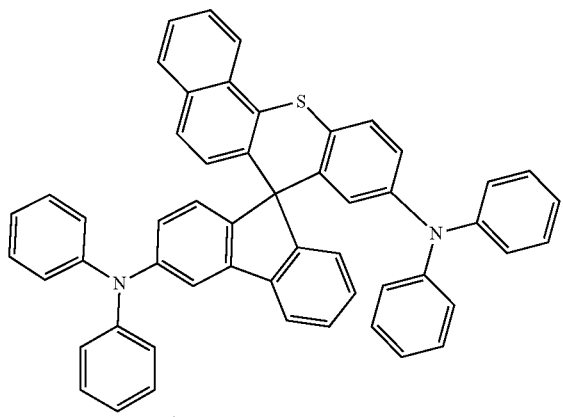
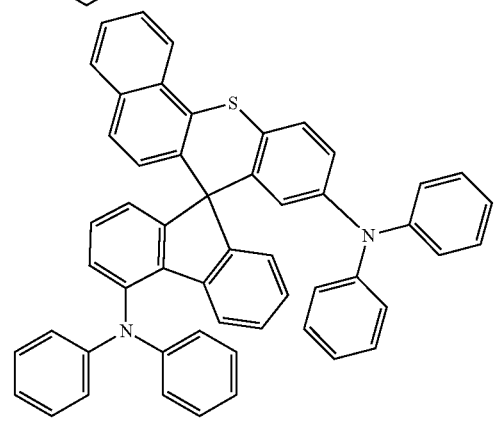
204
-continued
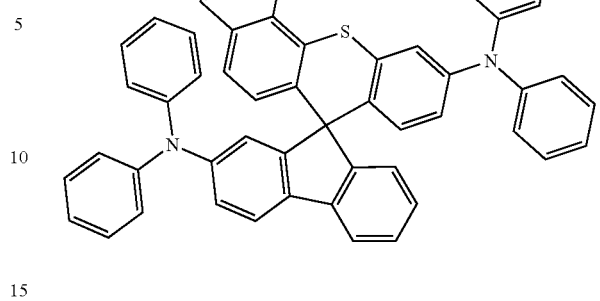
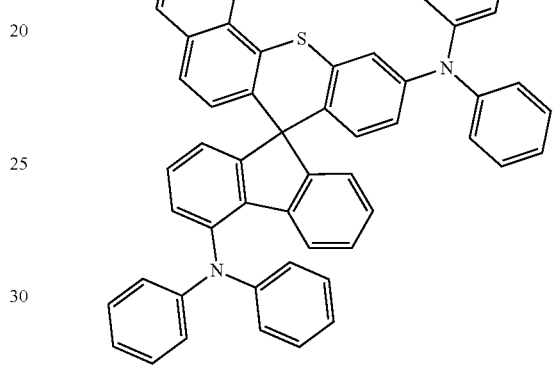
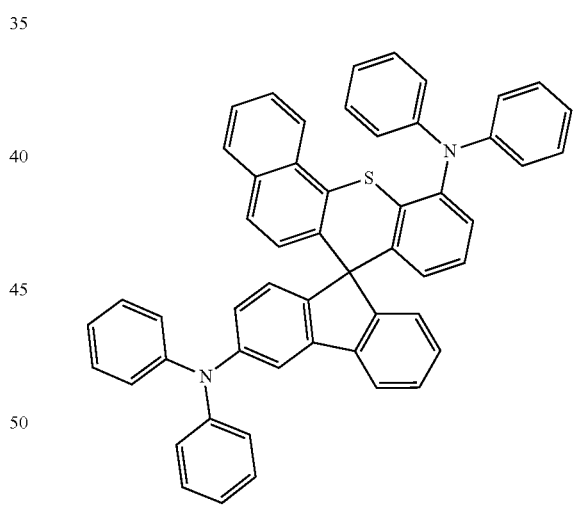
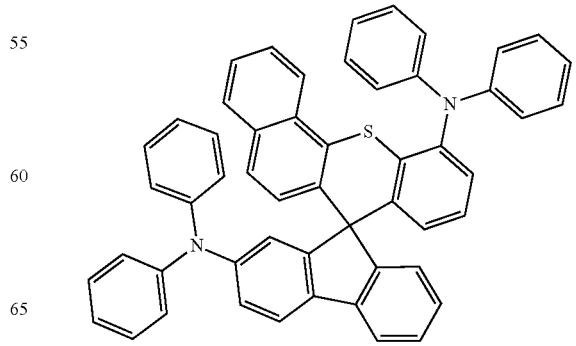

205
-continued
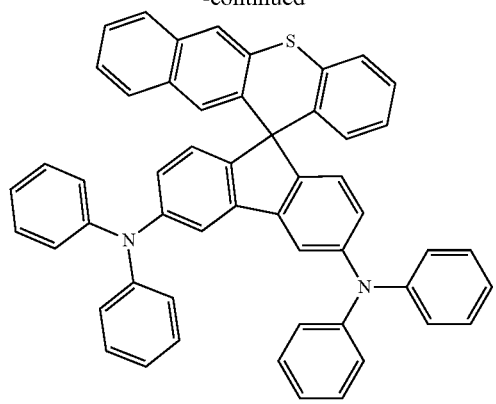
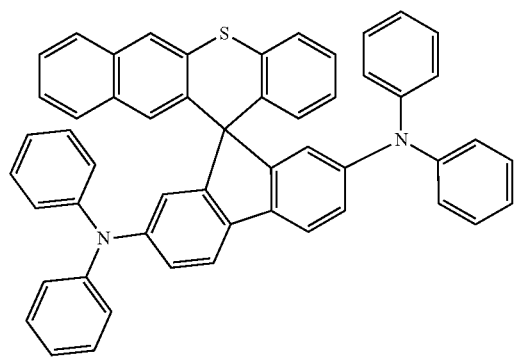
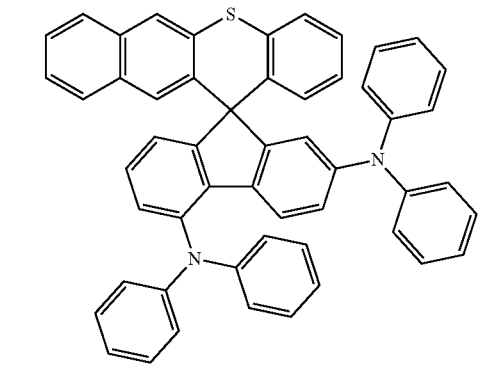
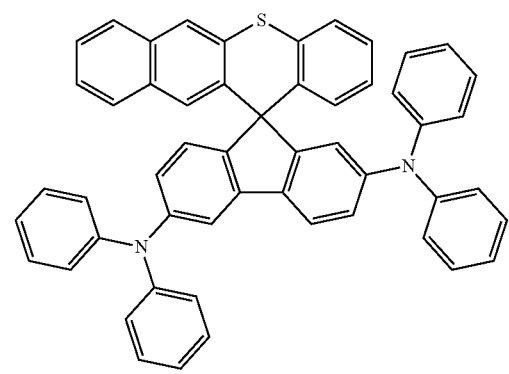
206
-continued
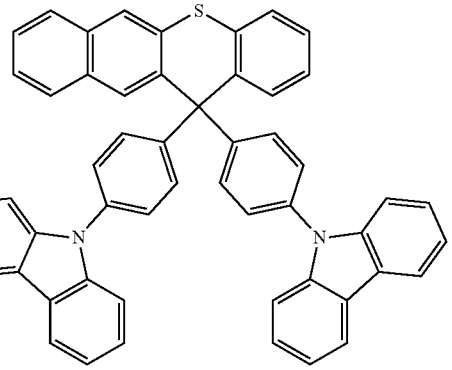
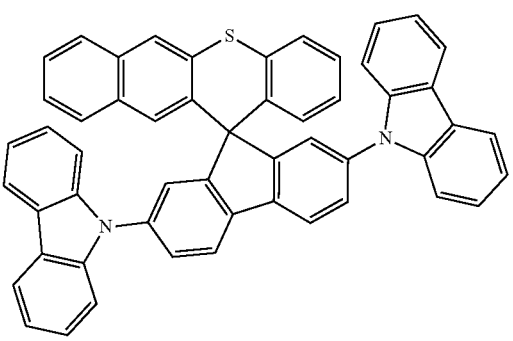
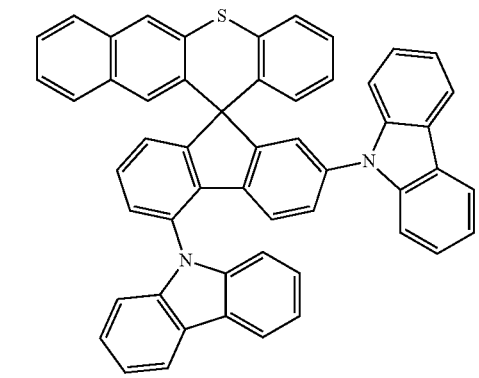
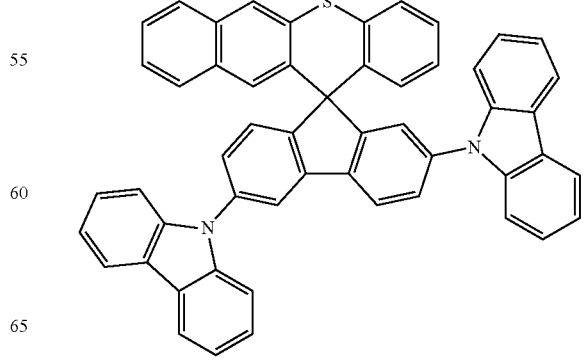

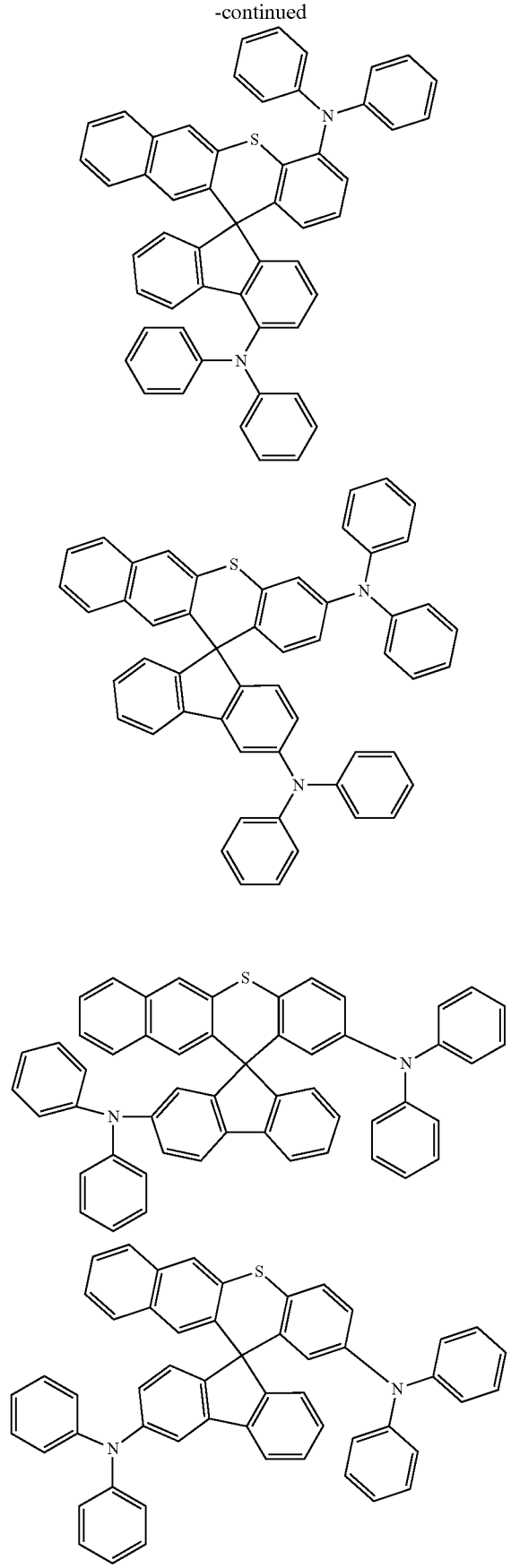
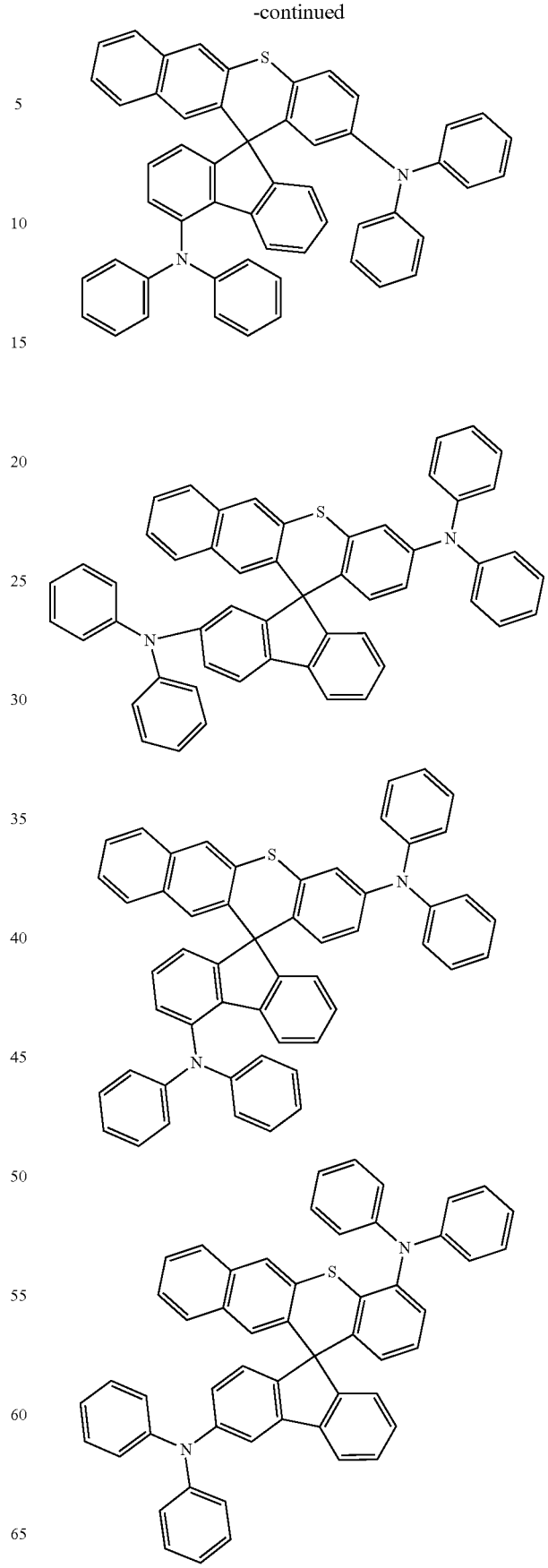

209
-continued
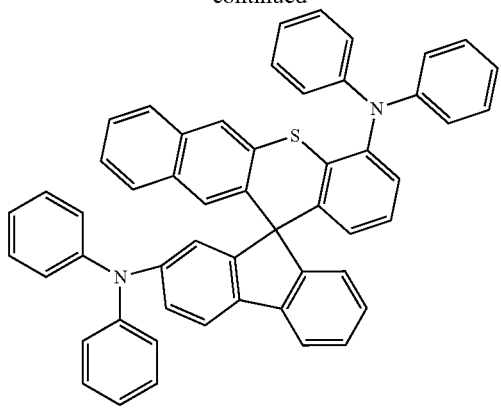
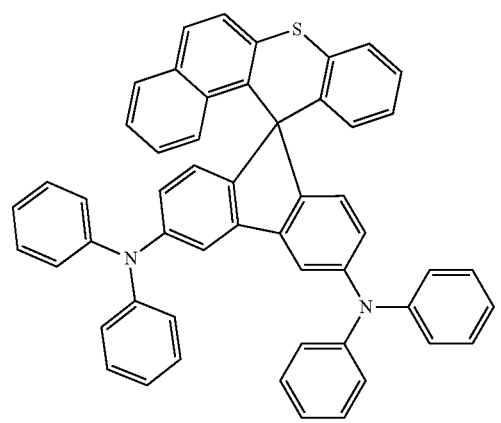
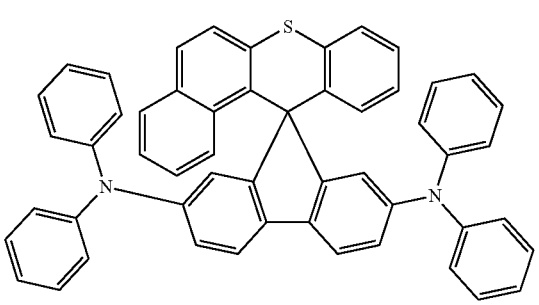
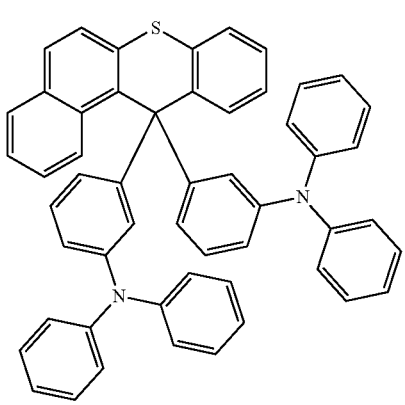
210
-continued
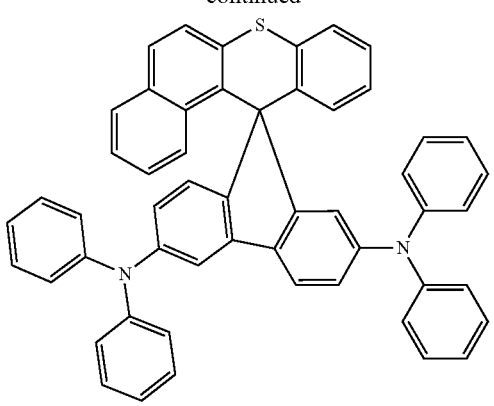
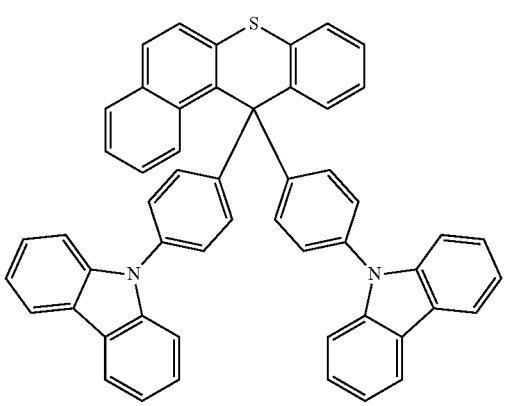
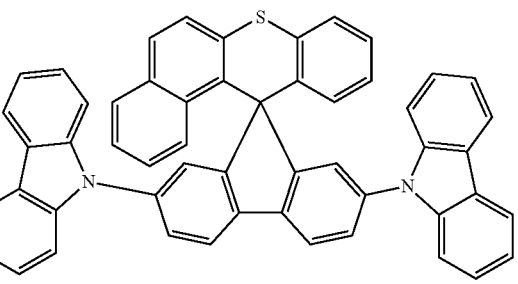
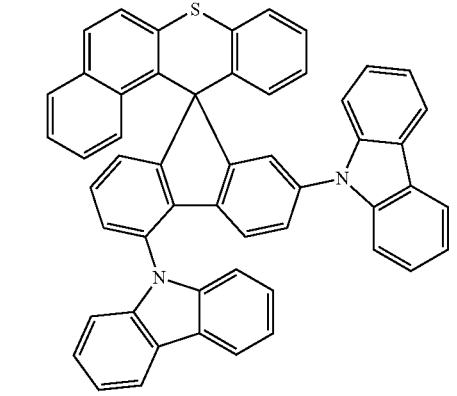

211
-continued
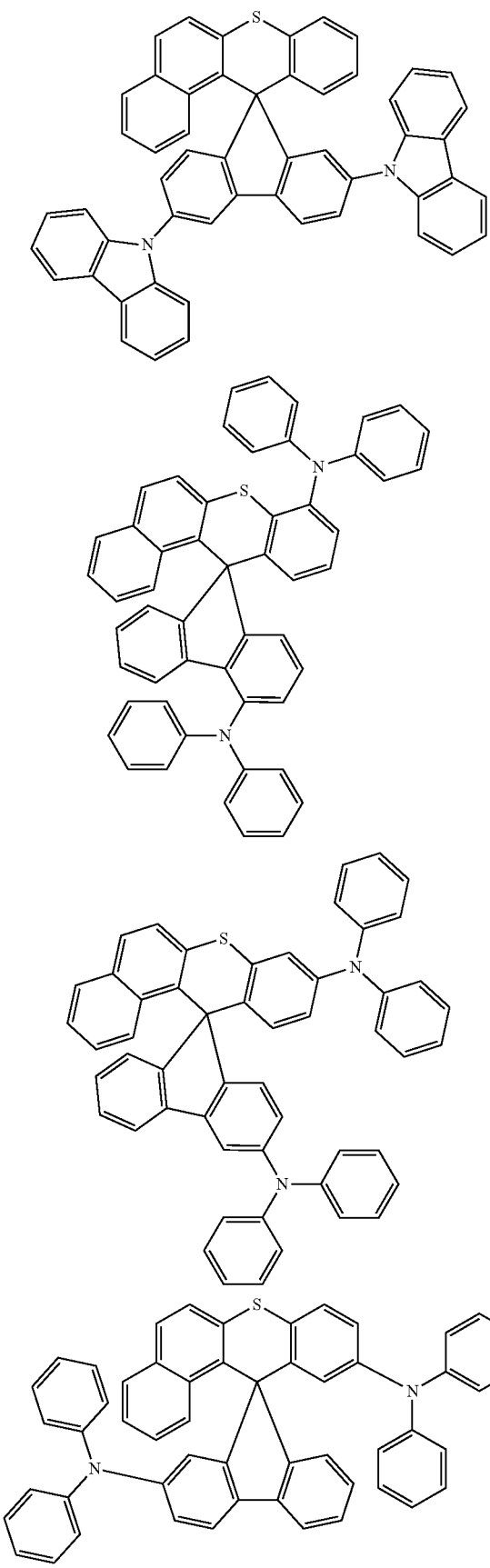
212
-continued
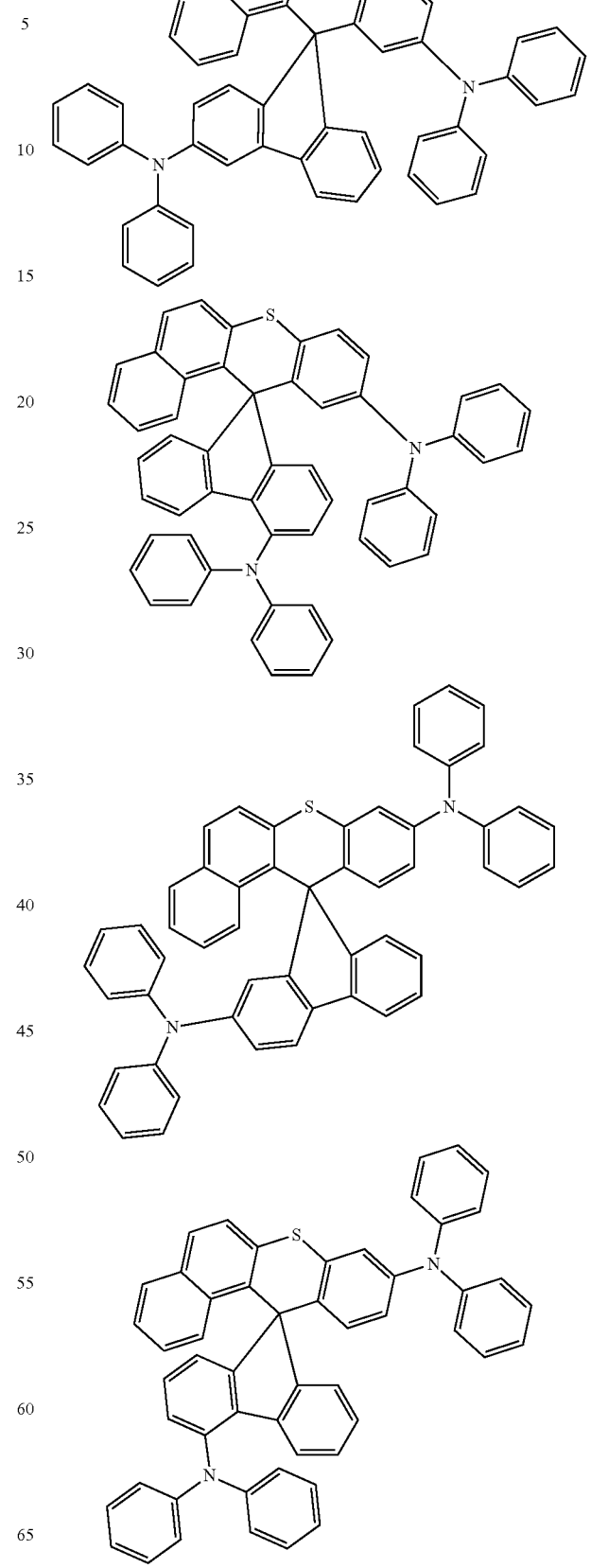

213
-continued
214
-continued
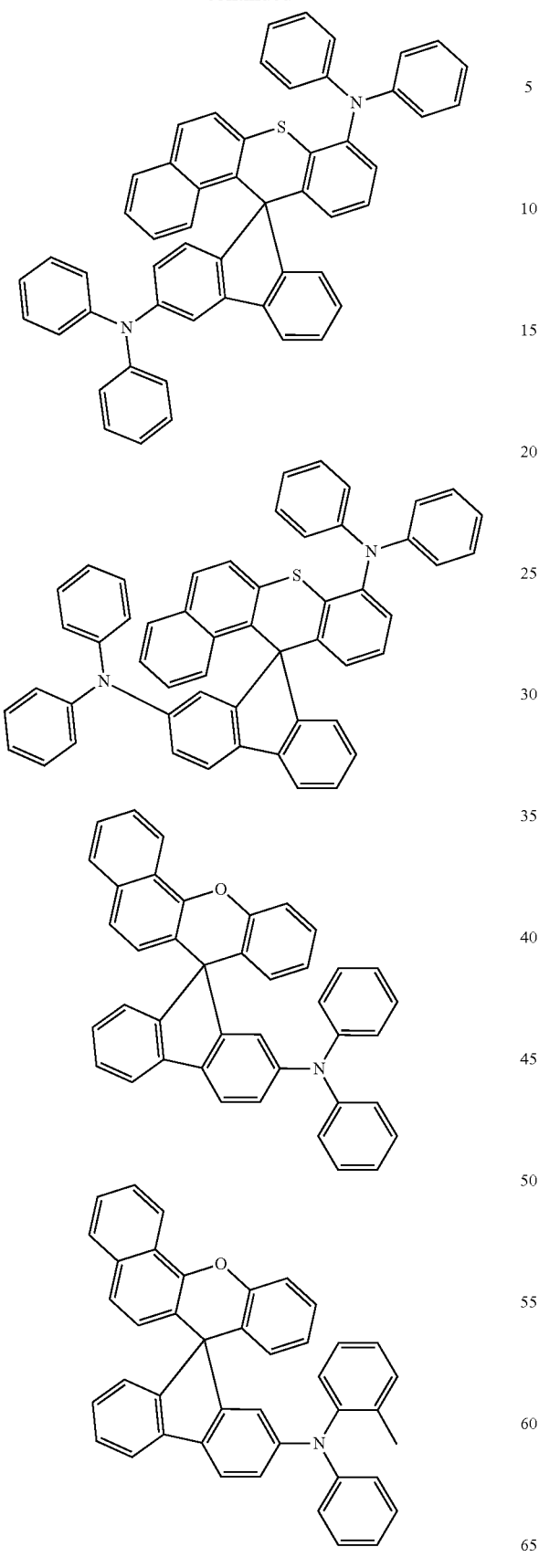
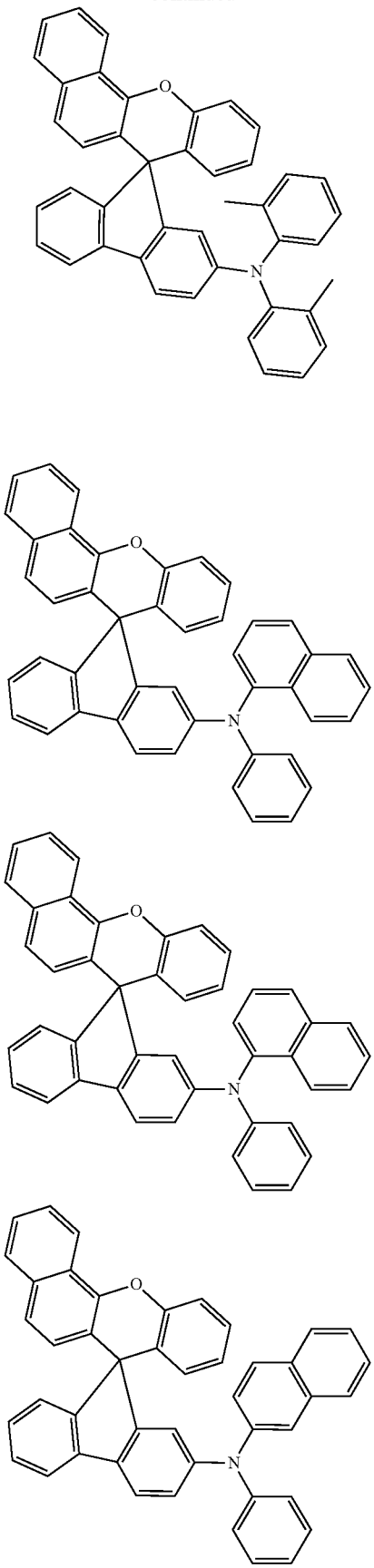

215
-continued
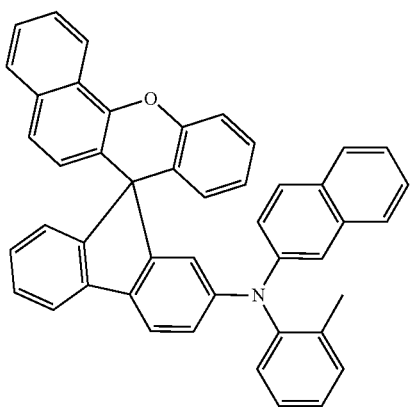
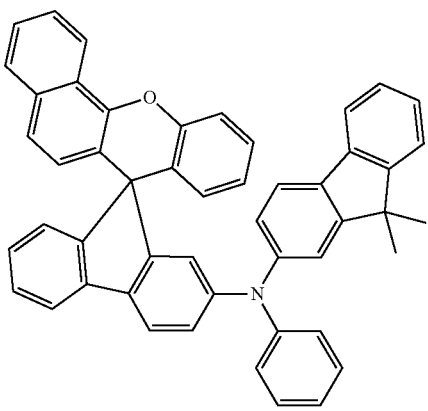
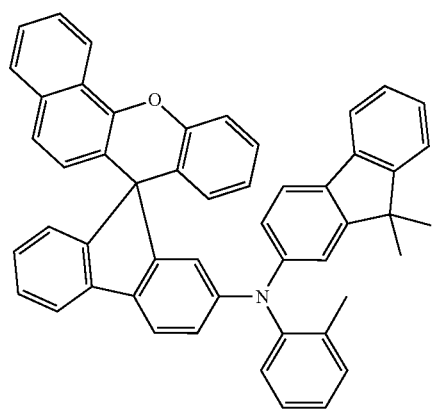
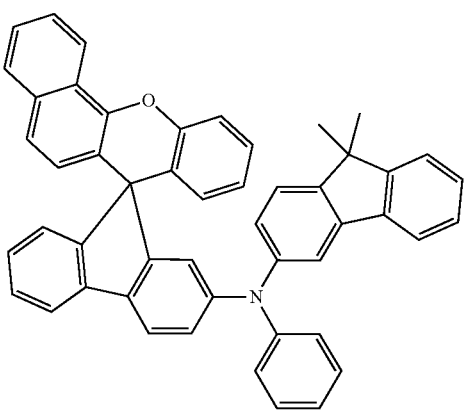
216
-continued
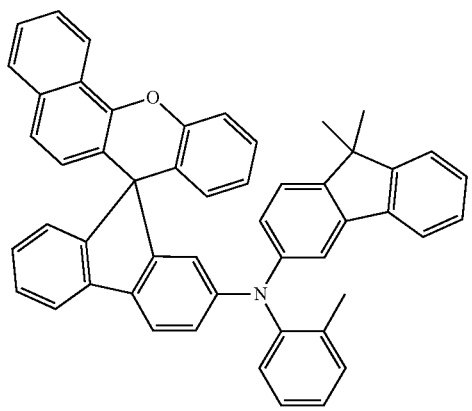
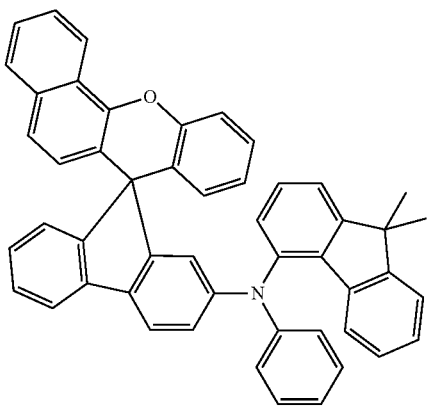
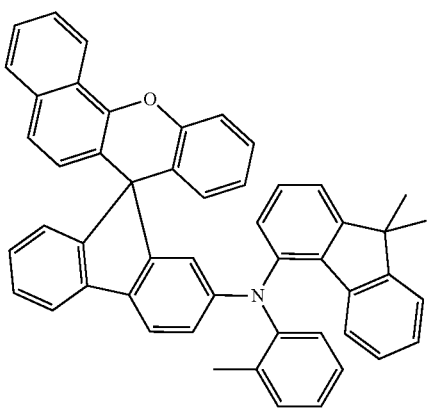
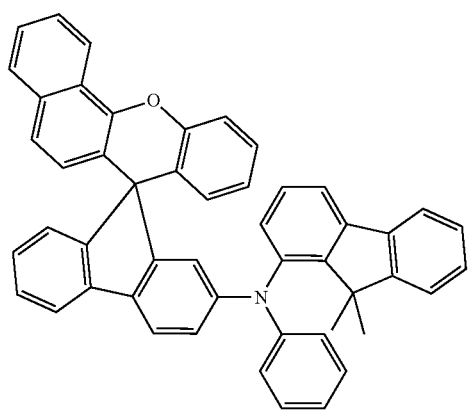

217
-continued
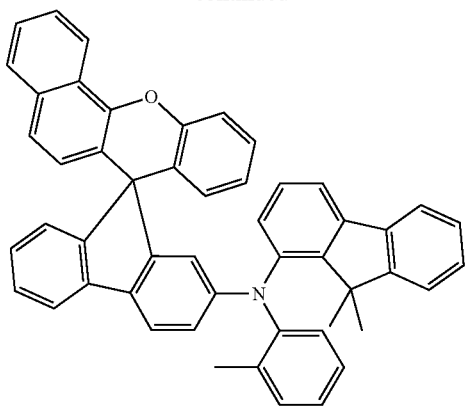
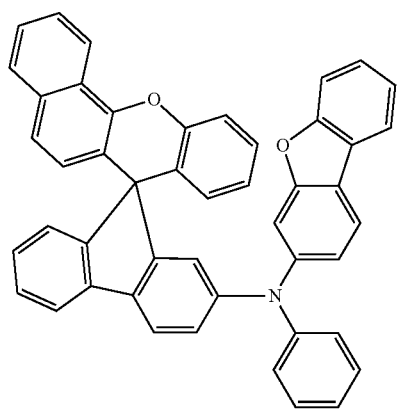
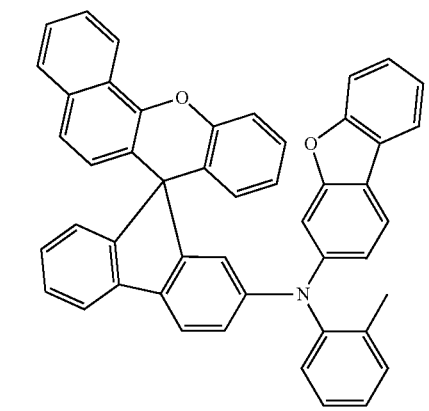
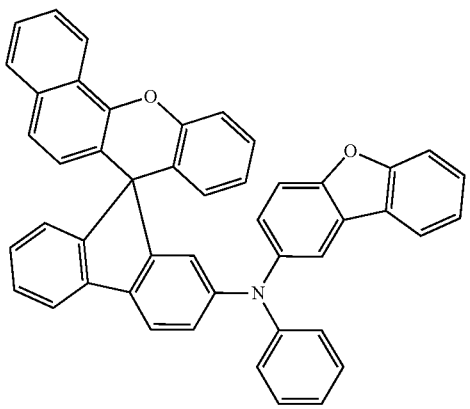
218
-continued
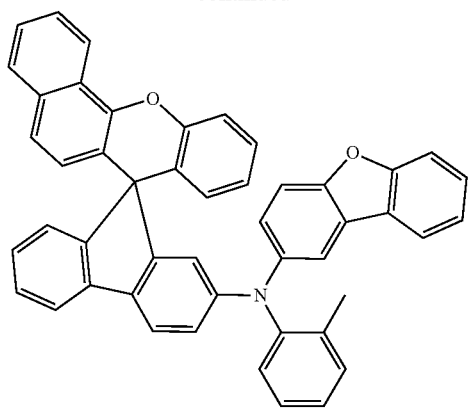
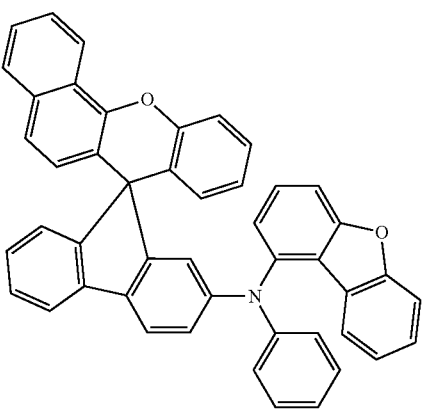
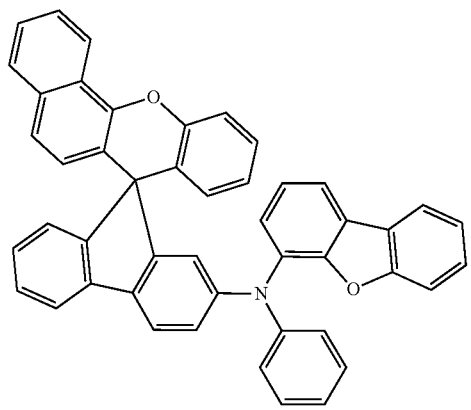
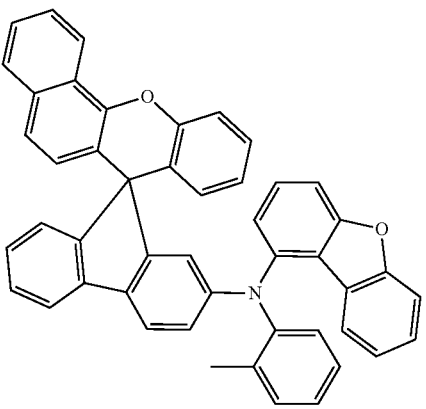

219
-continued
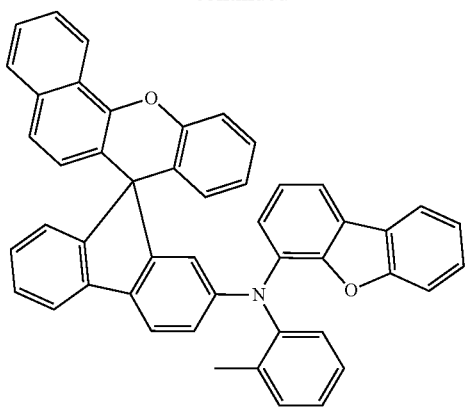
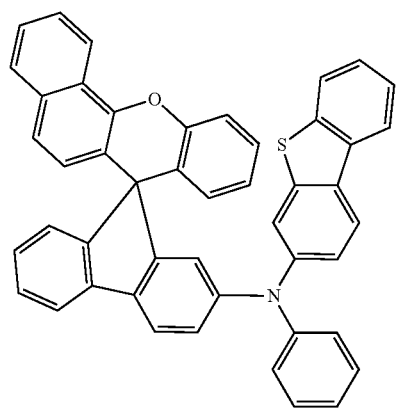
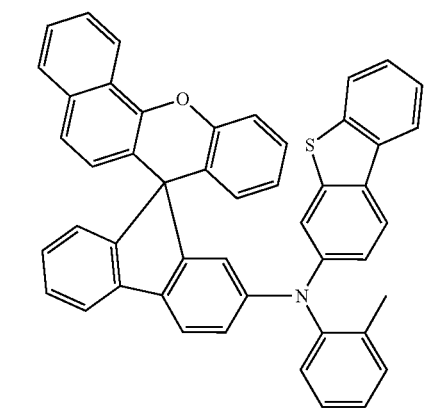
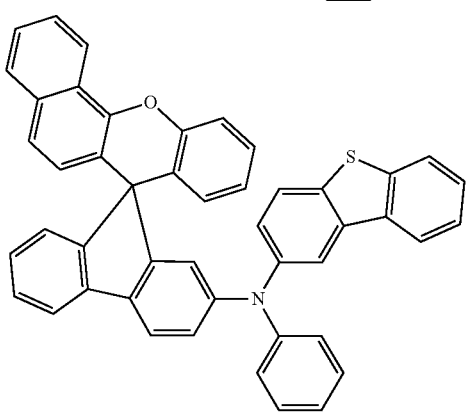
220
-continued
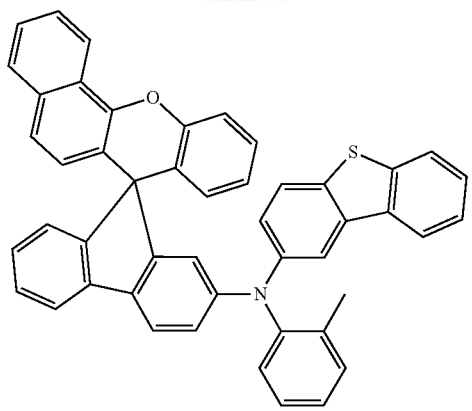
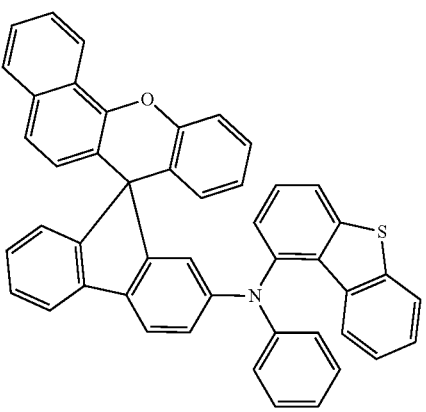
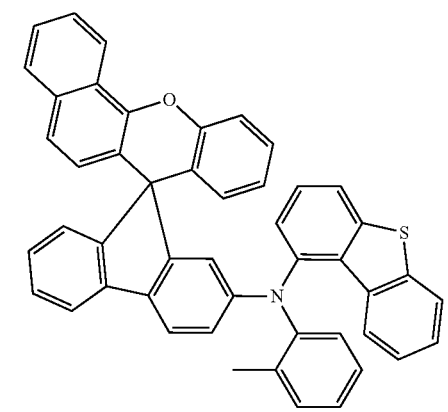
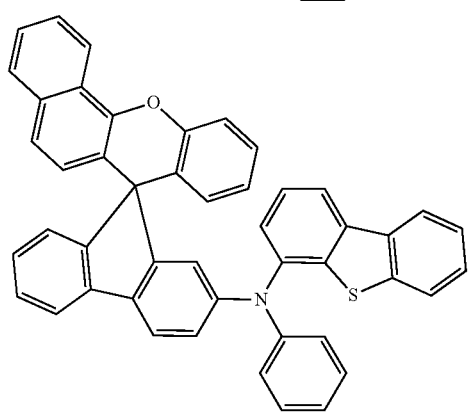

221
-continued
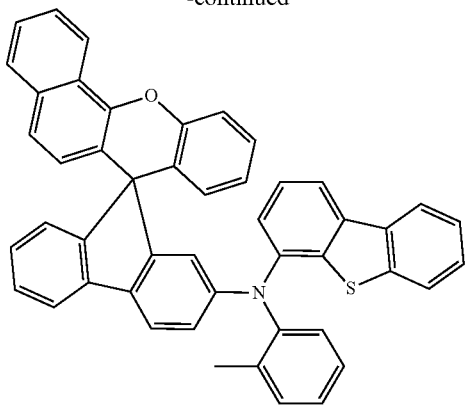
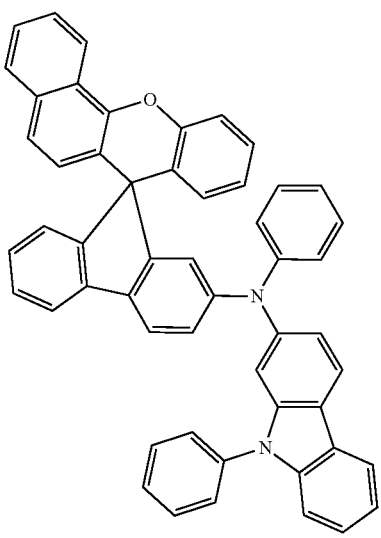
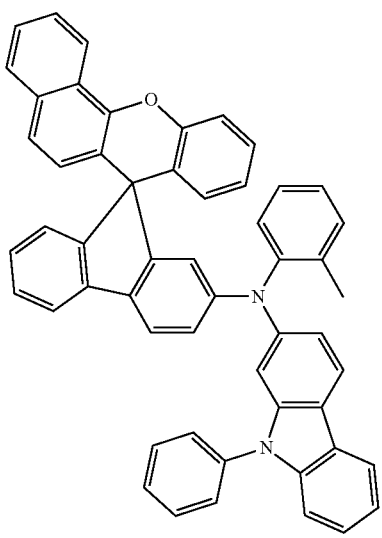
222
-continued
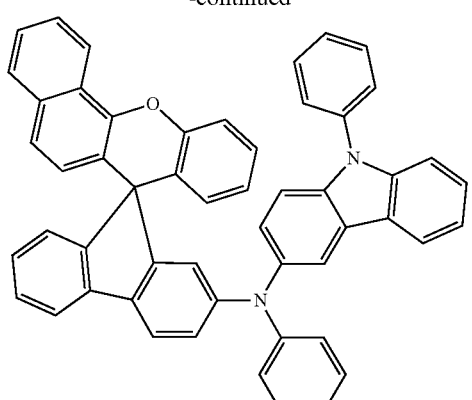
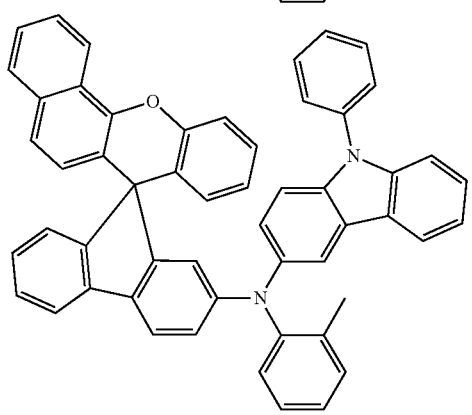
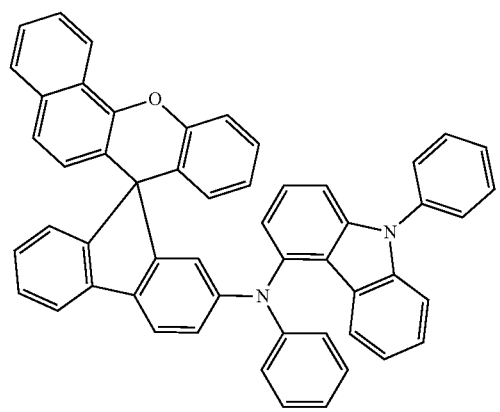
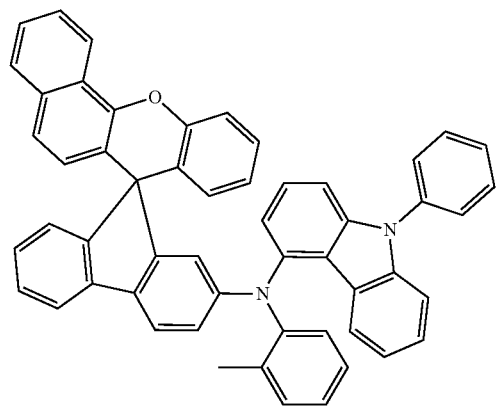

223
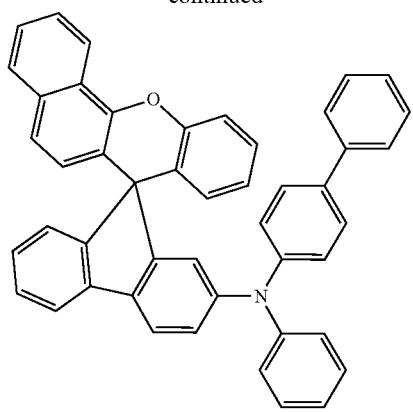
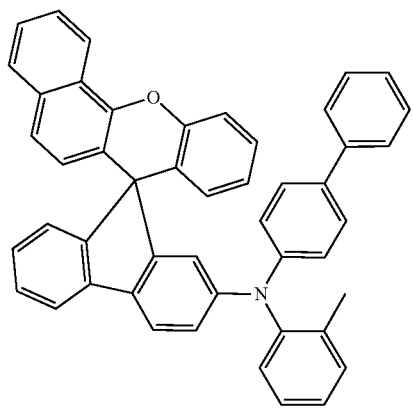
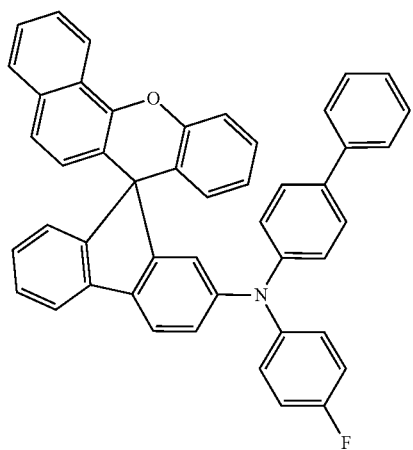
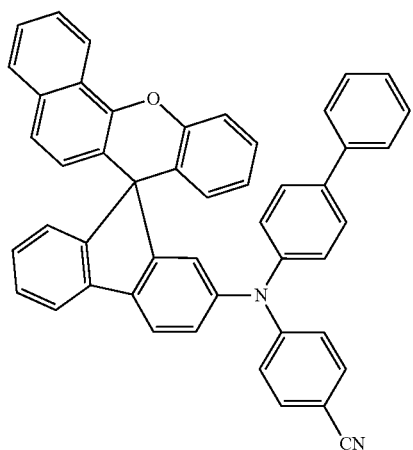
224
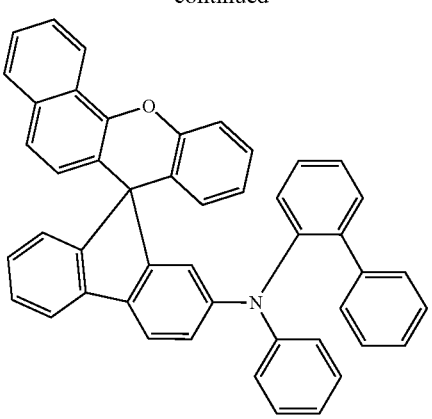
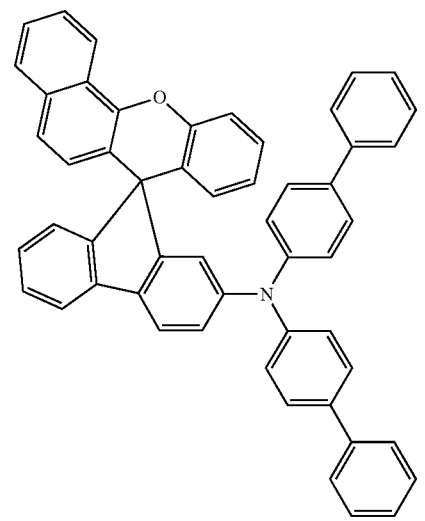
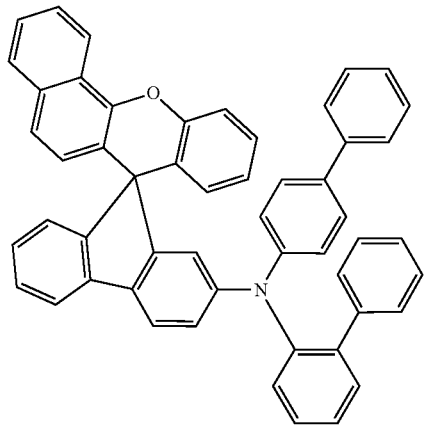

225
-continued
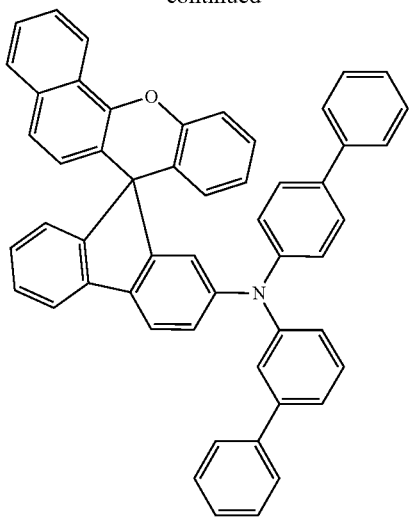
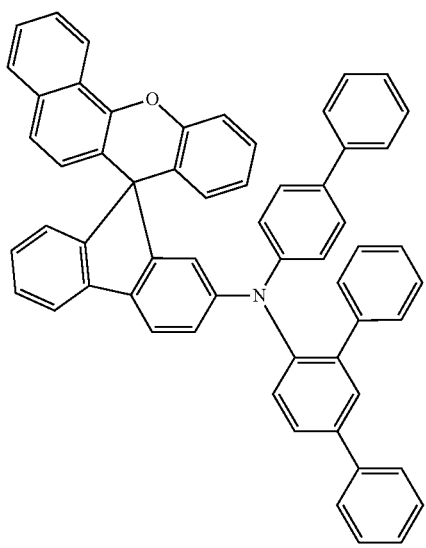
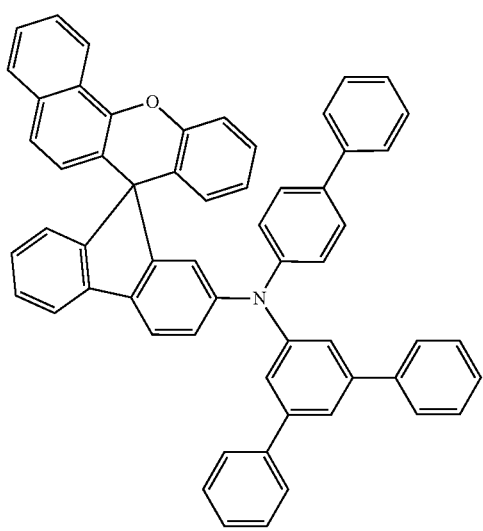
226
-continued
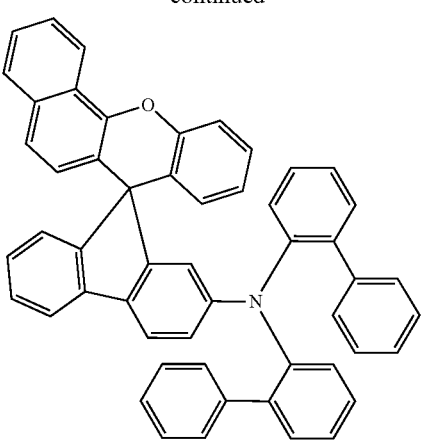
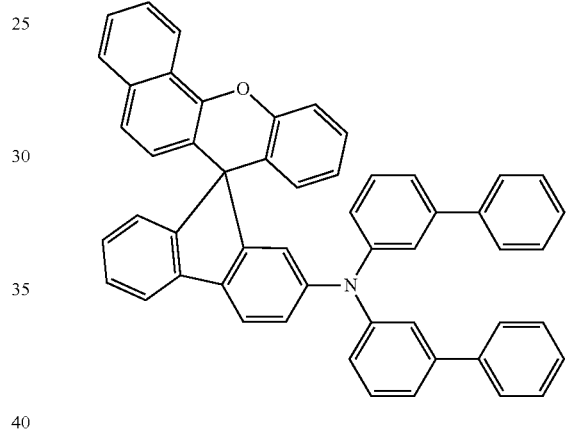

227
-continued
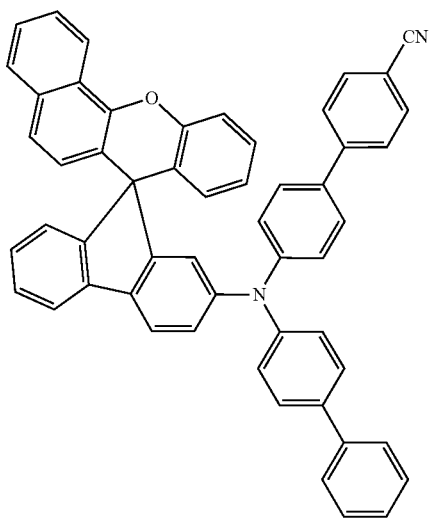
228
-continued
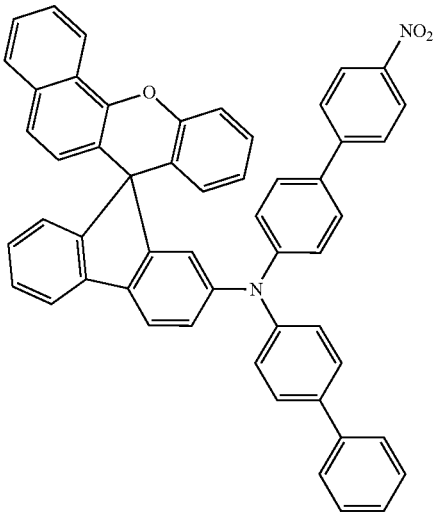
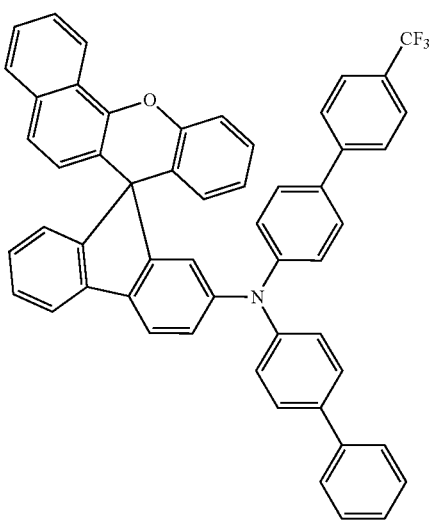
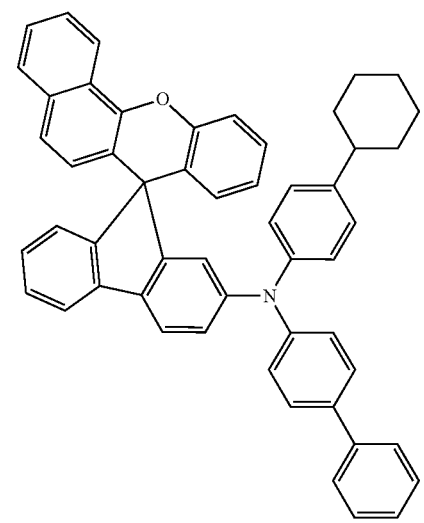
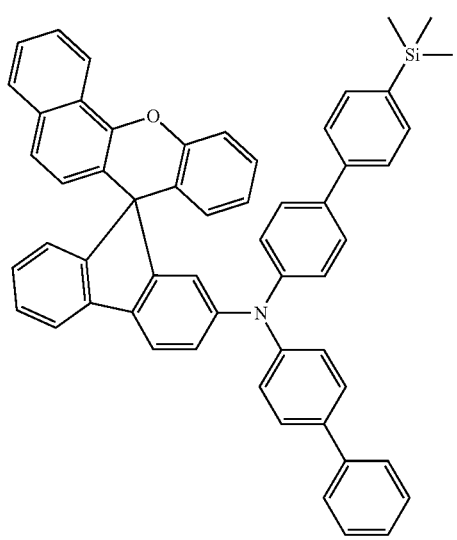
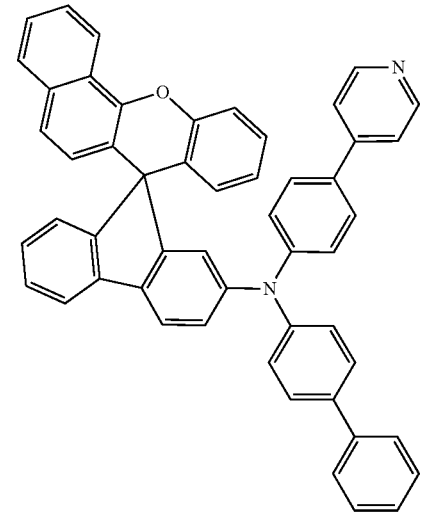

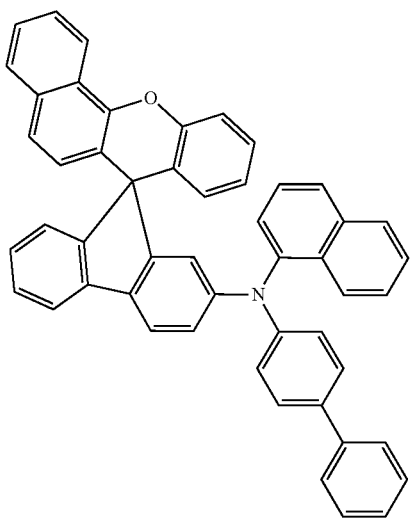
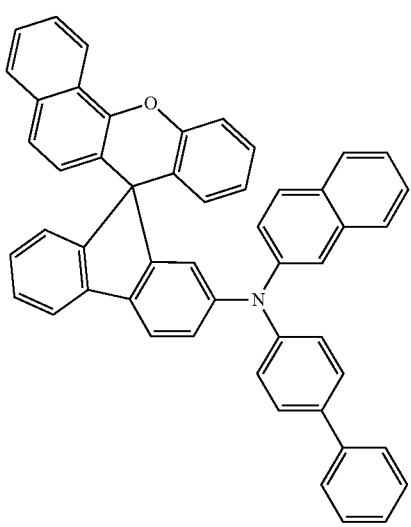
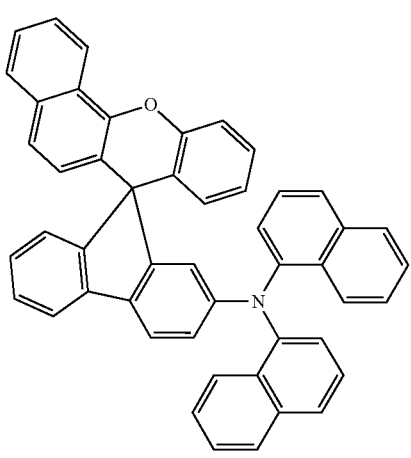
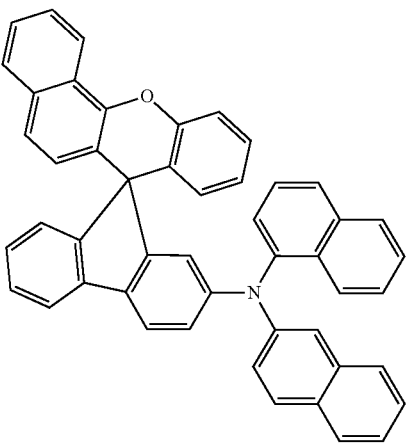
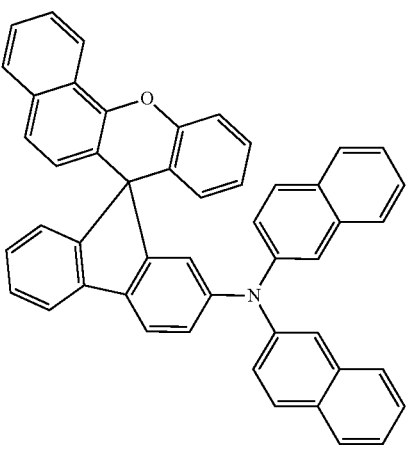
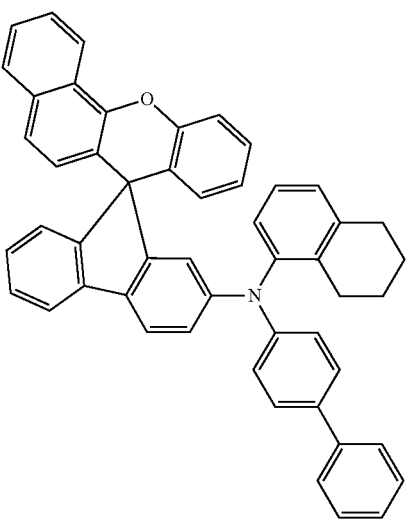

231
-continued
232
-continued
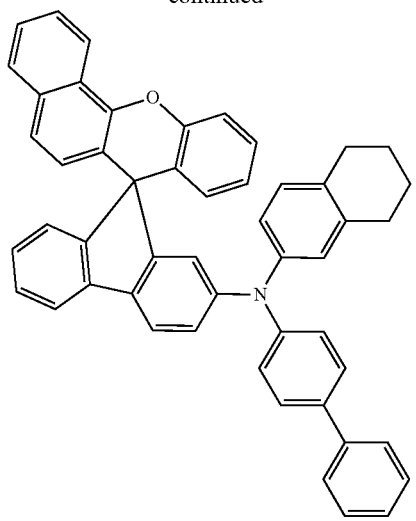
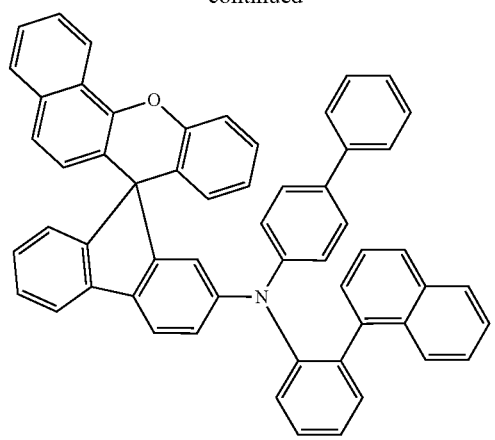
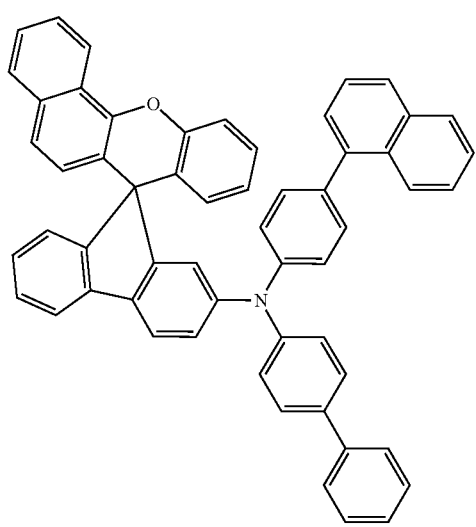
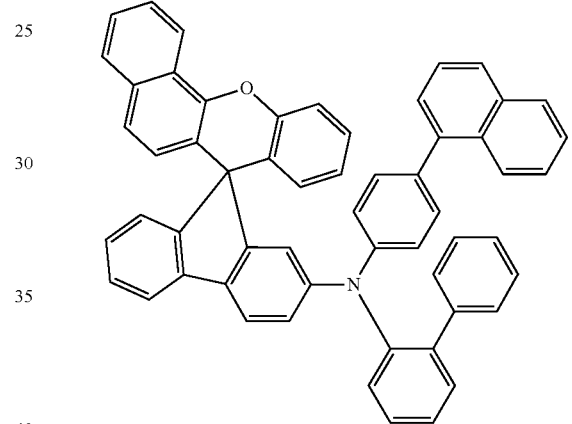
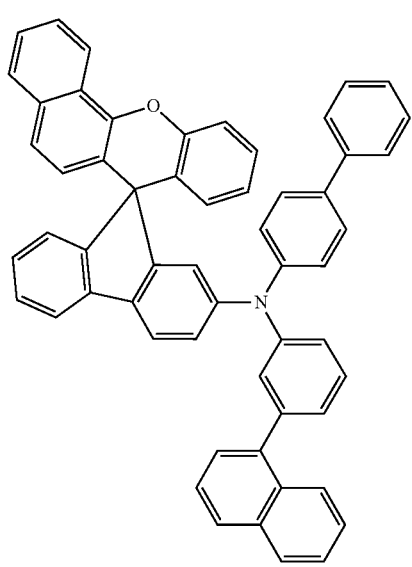
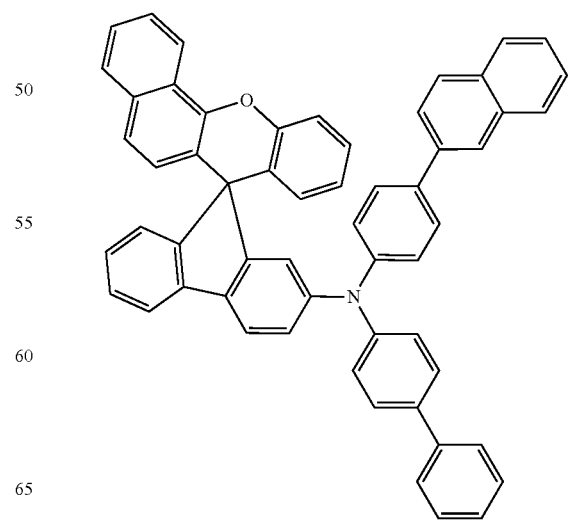

233
-continued
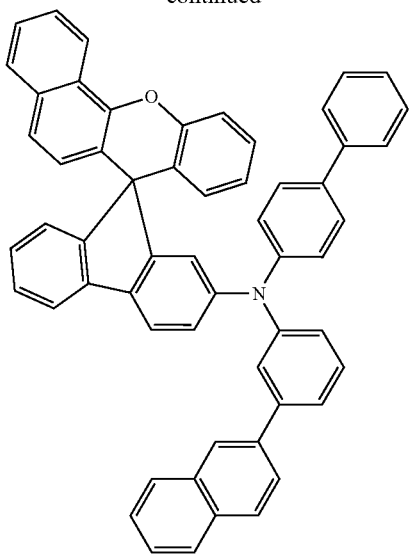
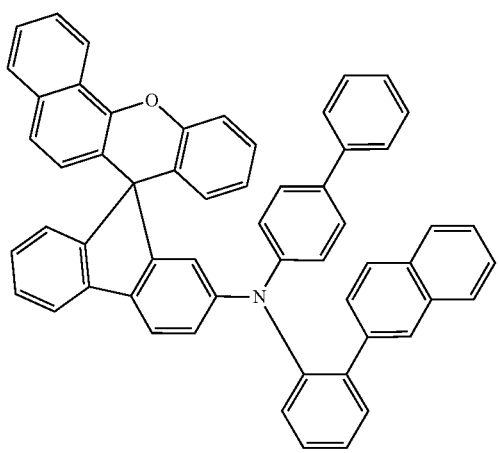
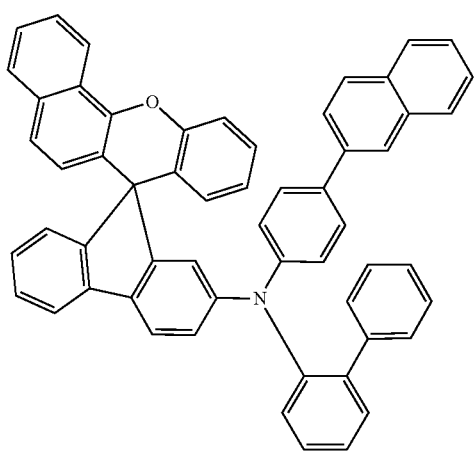
234
-continued
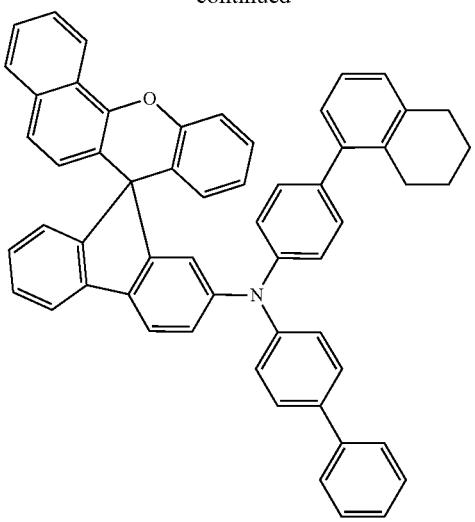
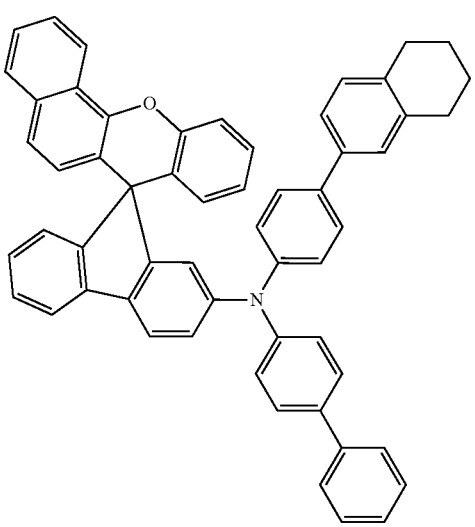
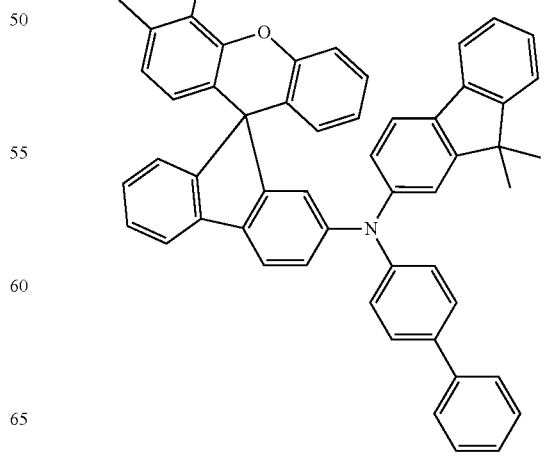

235
-continued
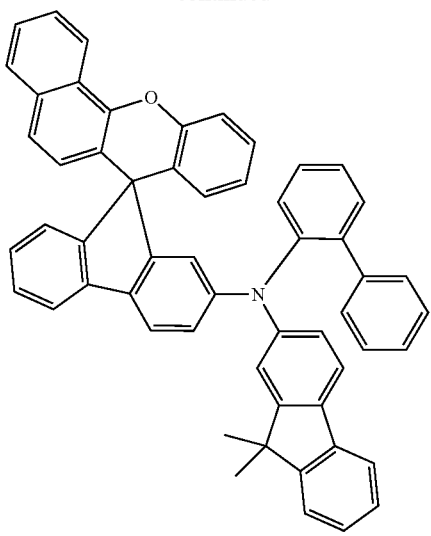
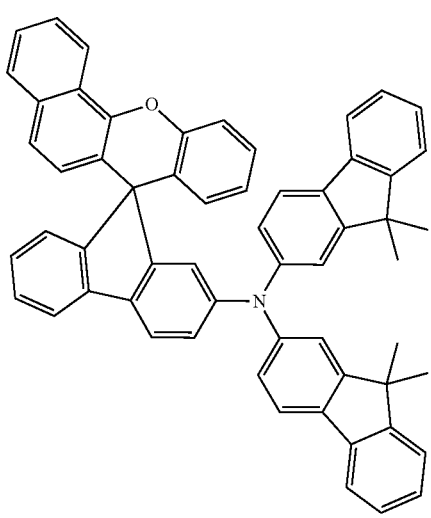
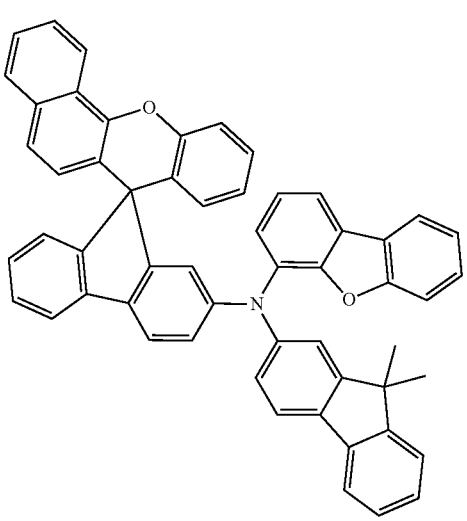
236
-continued
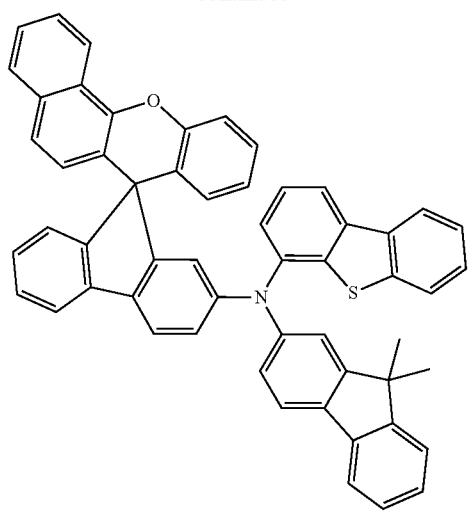
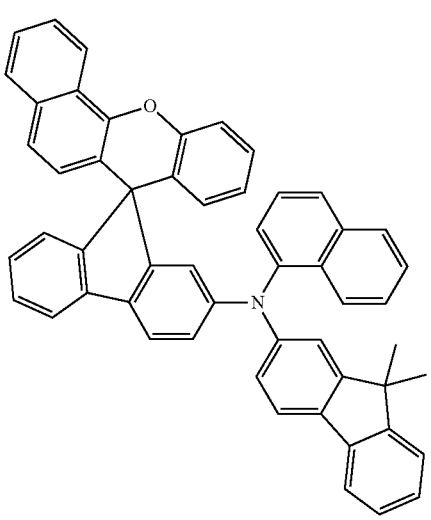
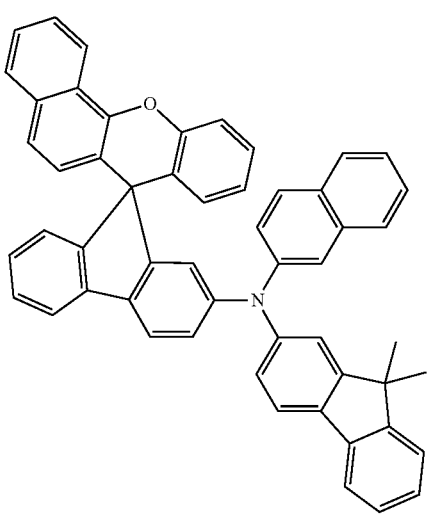

237
-continued
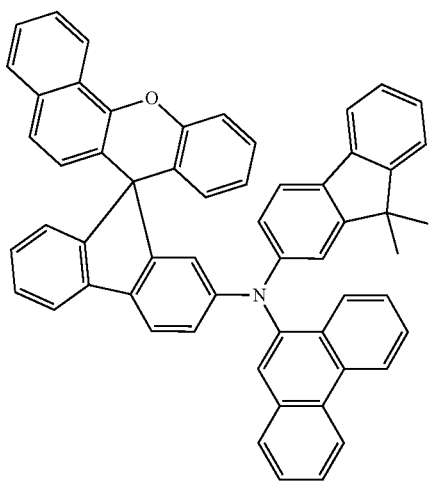
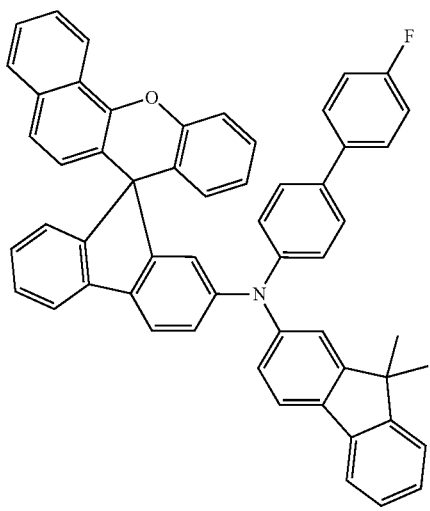
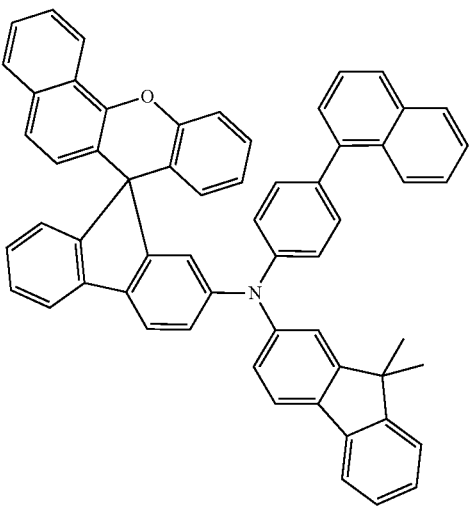
238
-continued
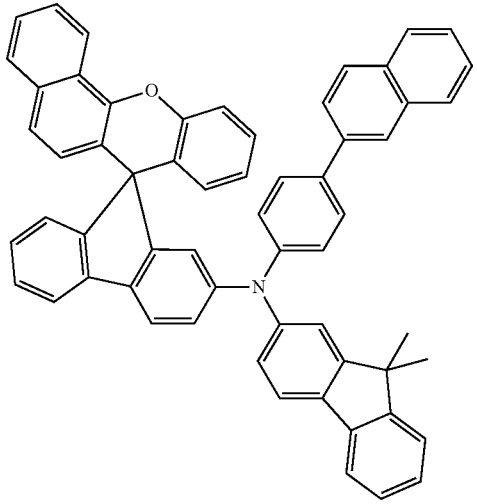
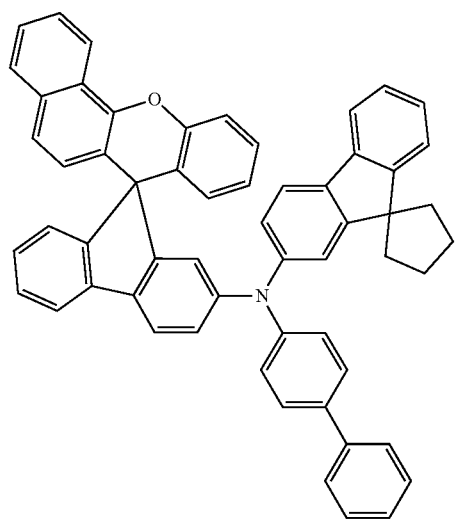
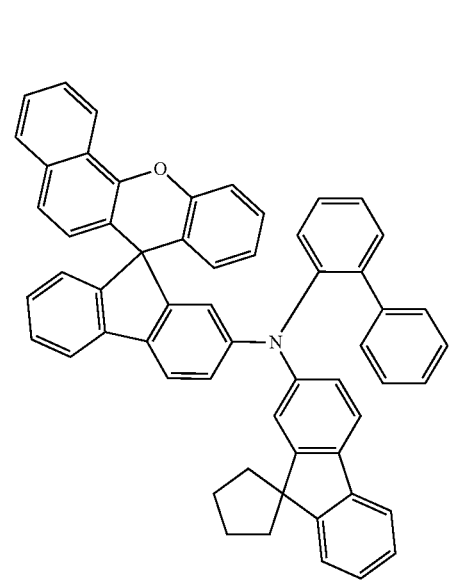

239
-continued
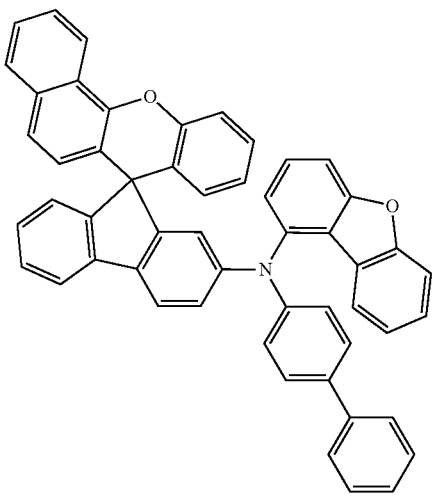
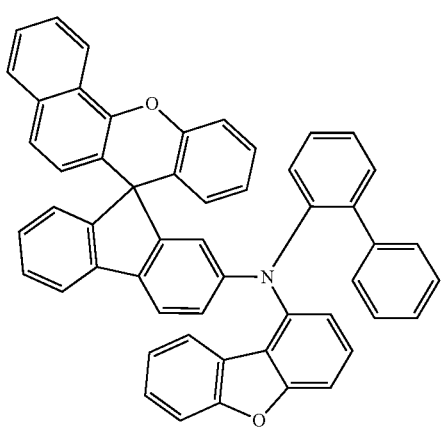
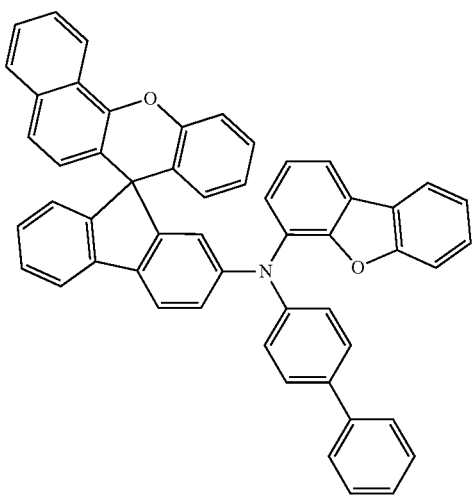
240
-continued
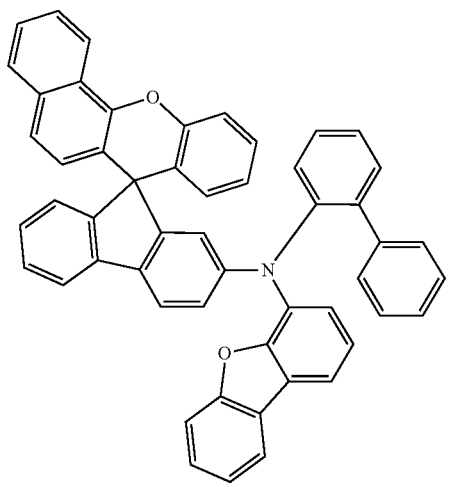
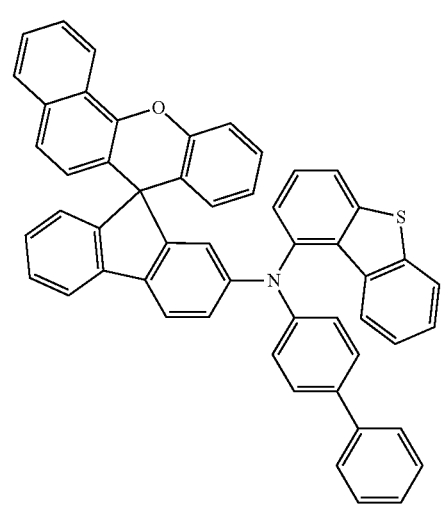
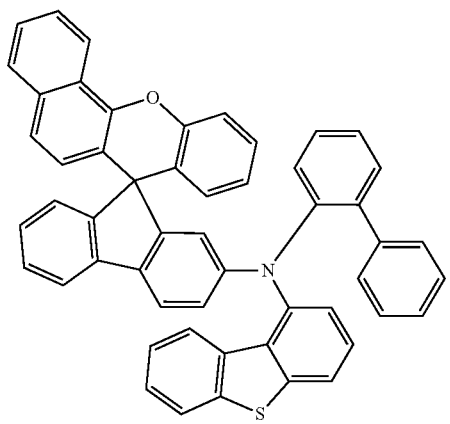

241
-continued
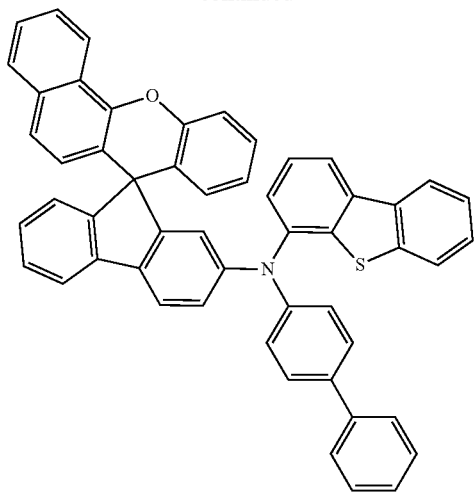
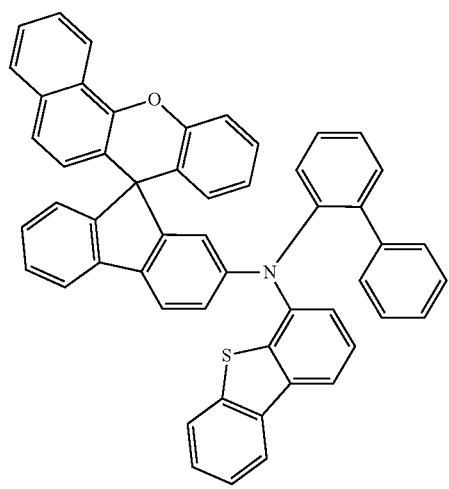
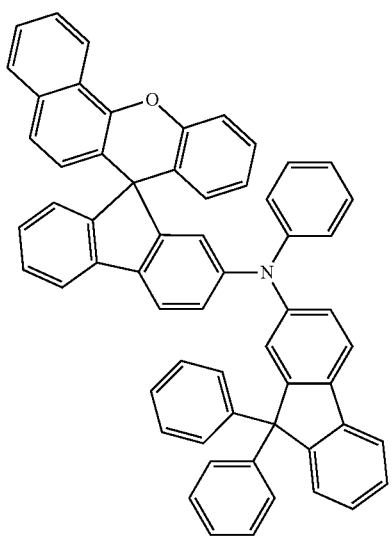
242
-continued
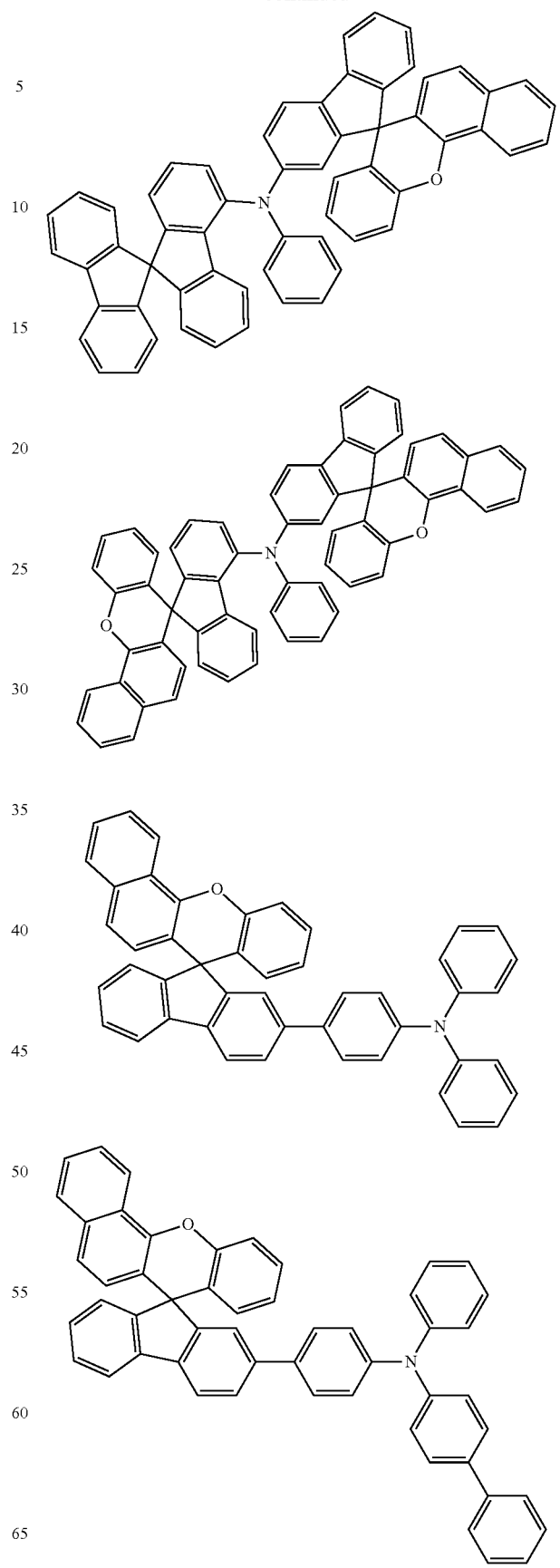

243
-continued
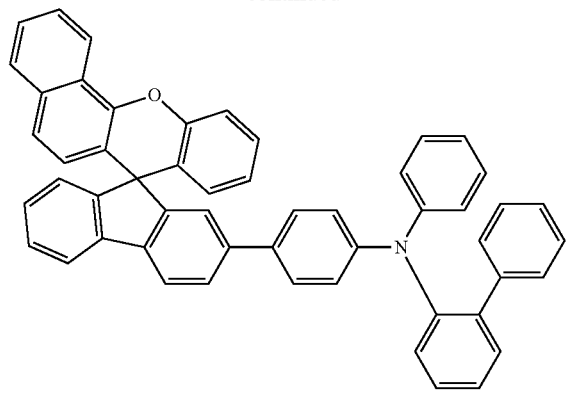
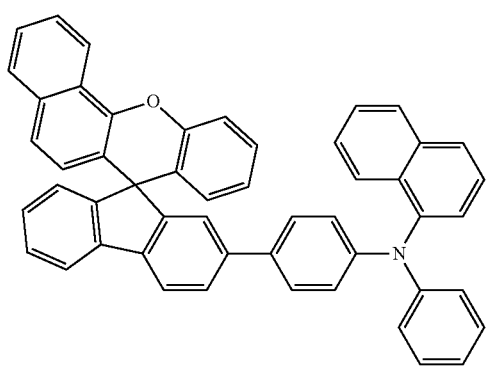
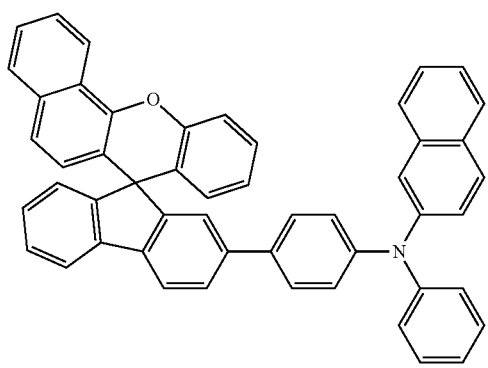
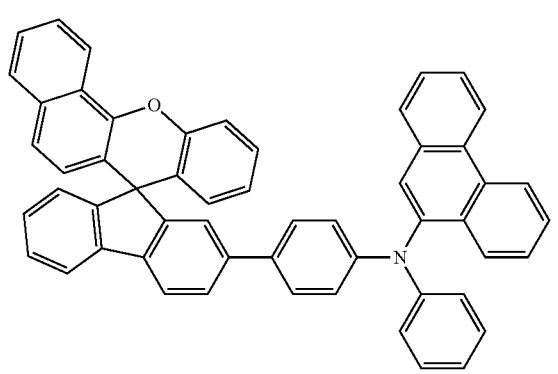
244
-continued
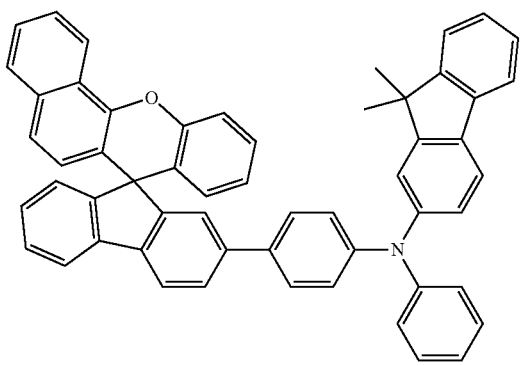
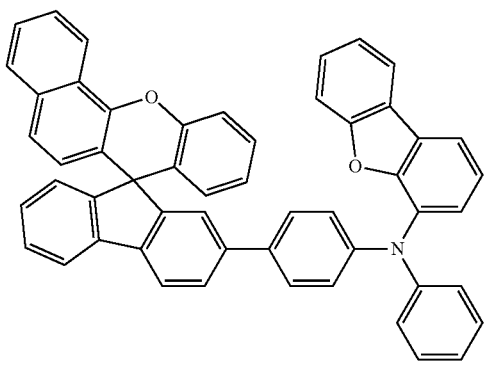
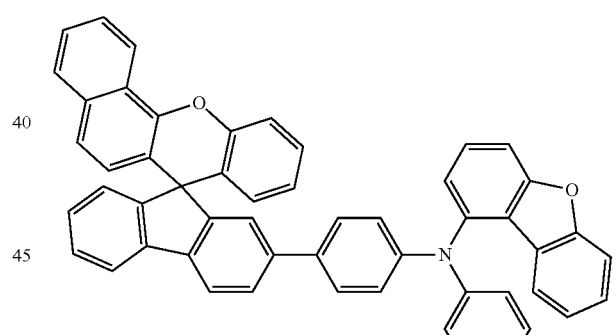
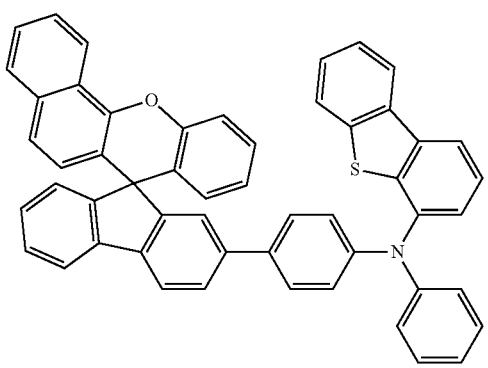

245
-continued
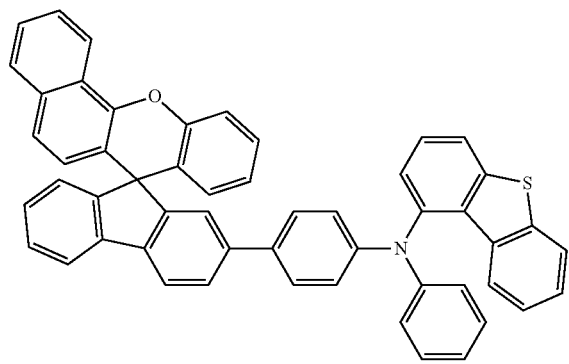
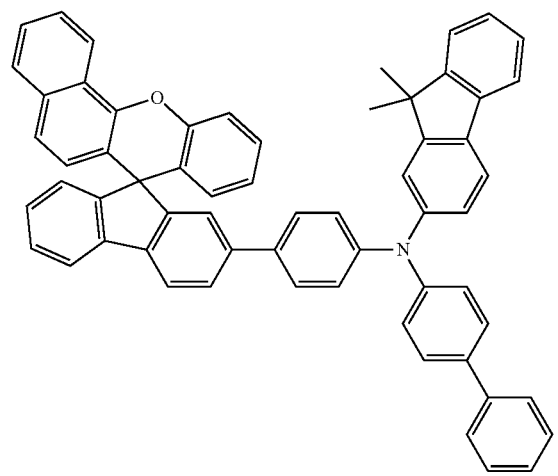
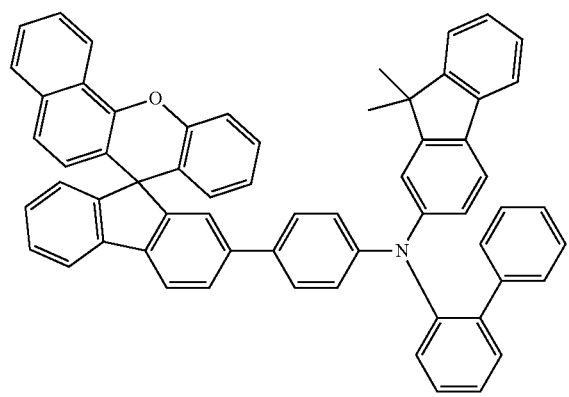
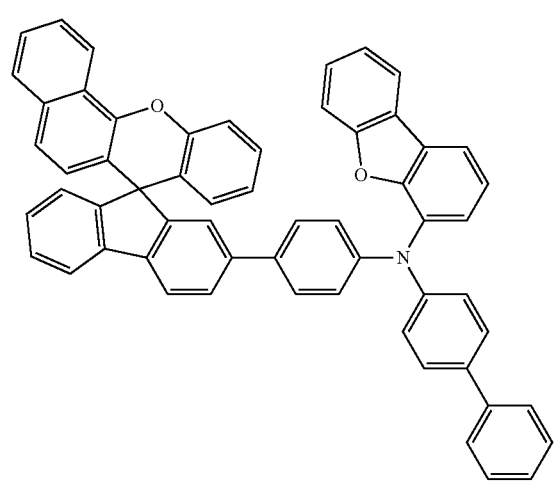
246
-continued
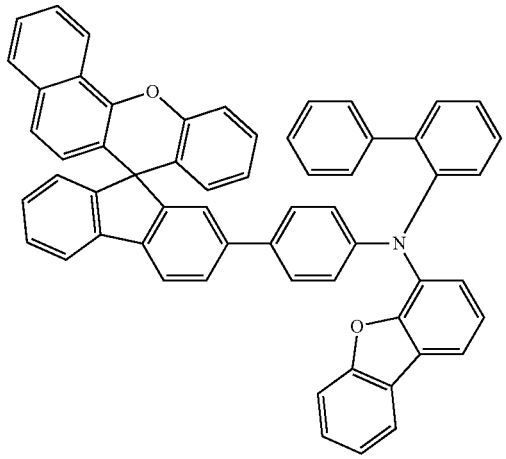
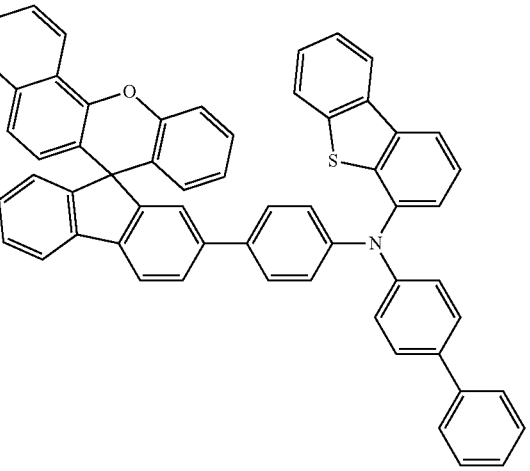
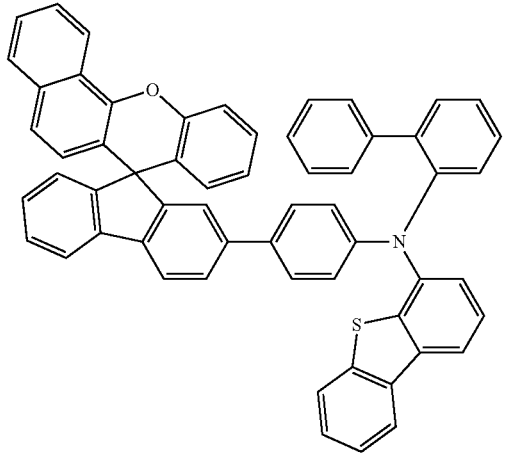

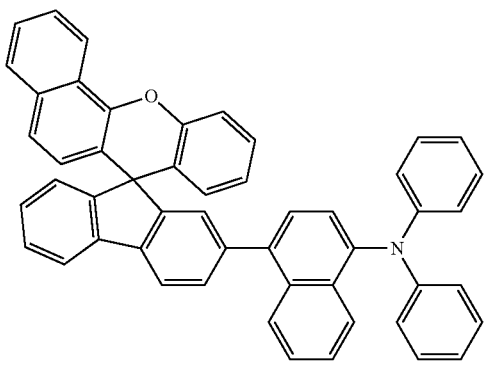
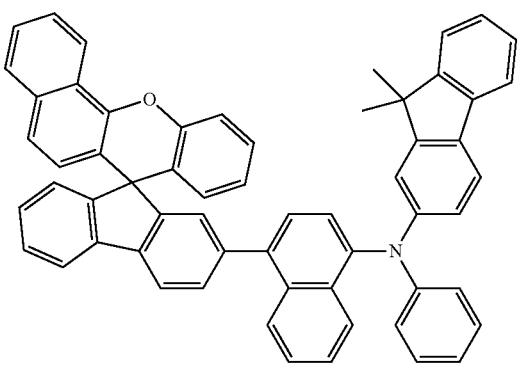
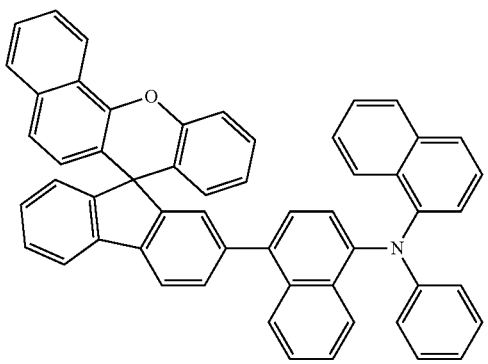
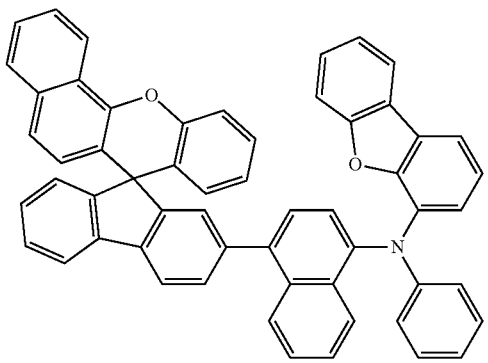
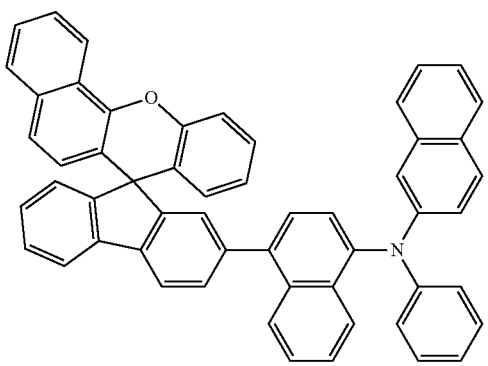
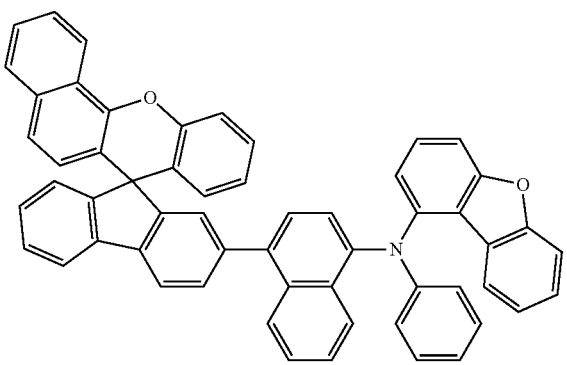
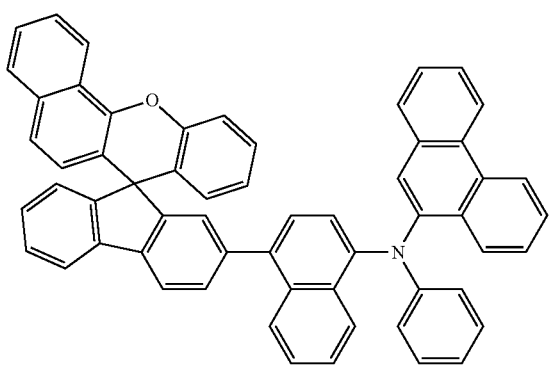
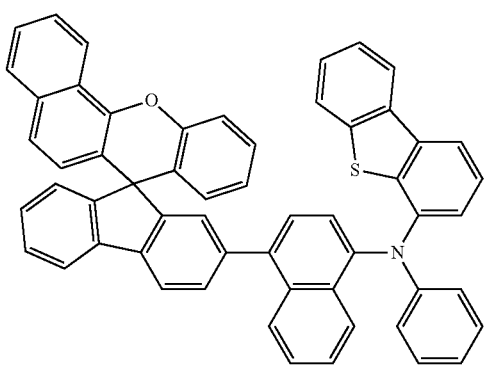

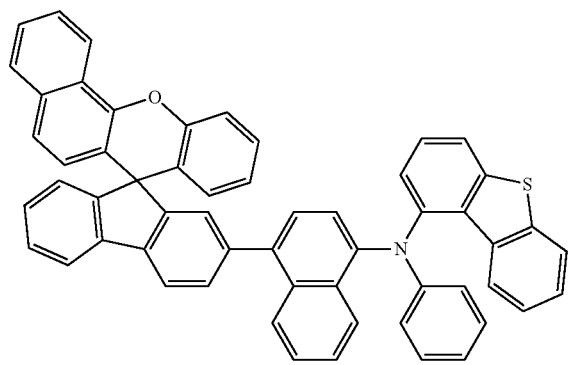
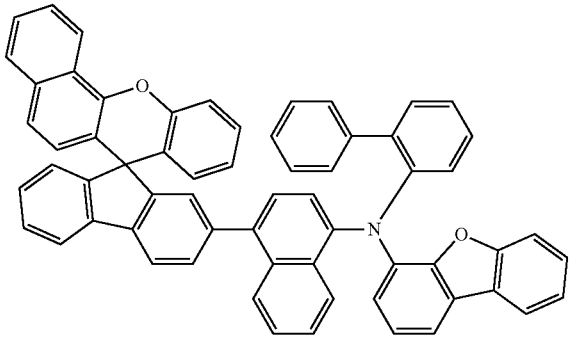
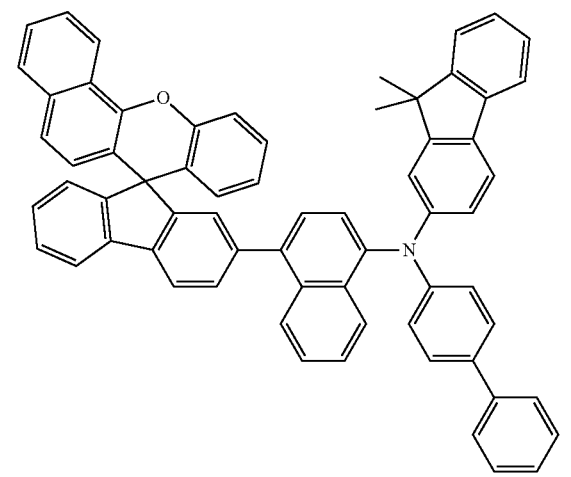
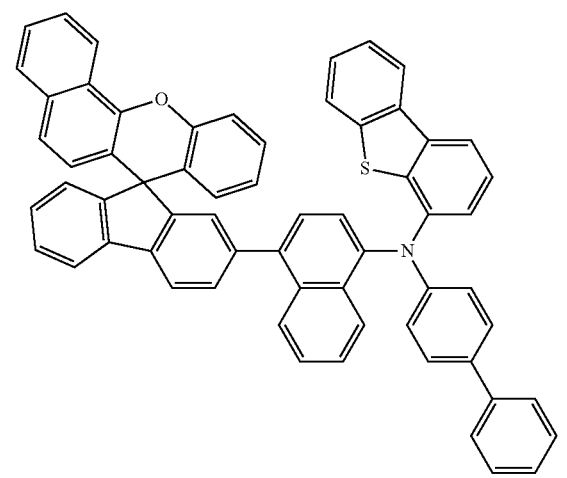
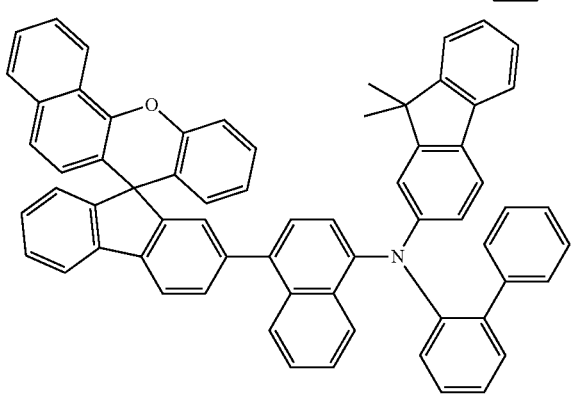
For another example, in Chemical Formula 1, $X_1$ may be a single bond and $X_2$ may be O or S, and such an organic compound may be selected from the following group.
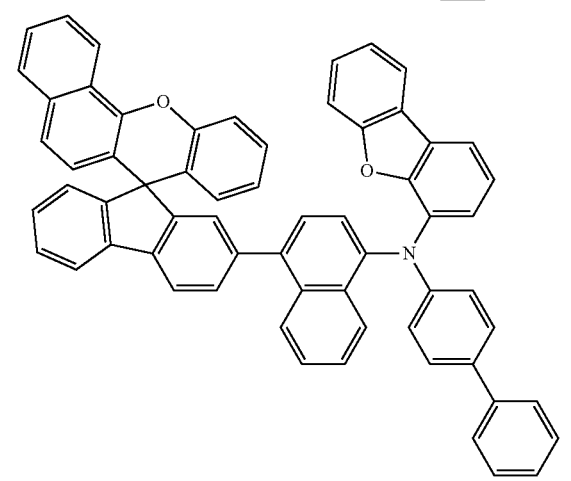
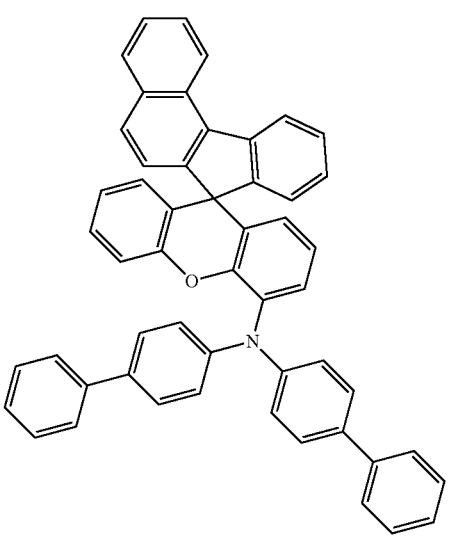

251
-continued
252
-continued
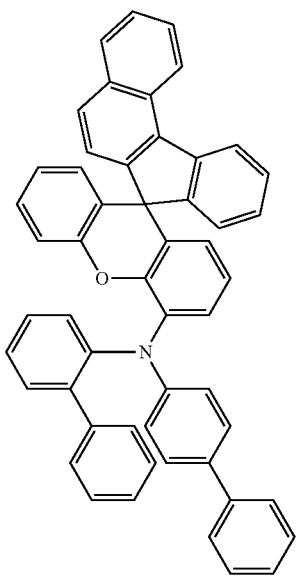
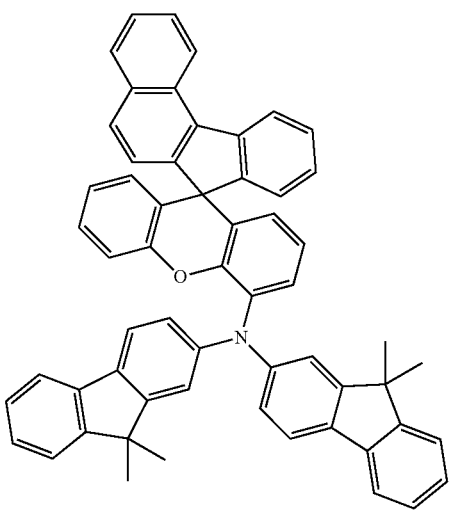
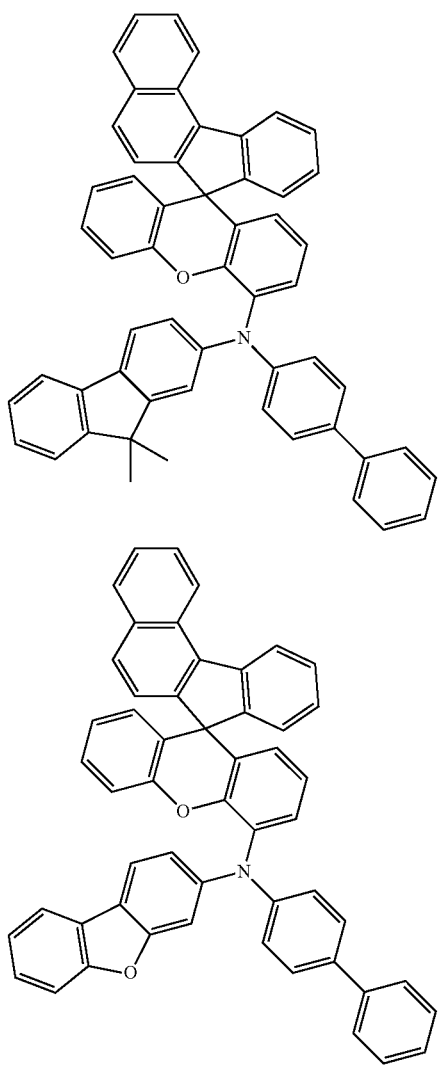
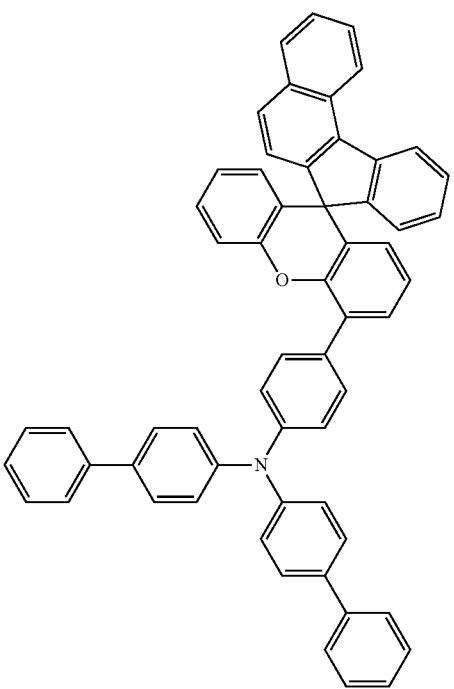

253
-continued
254
-continued
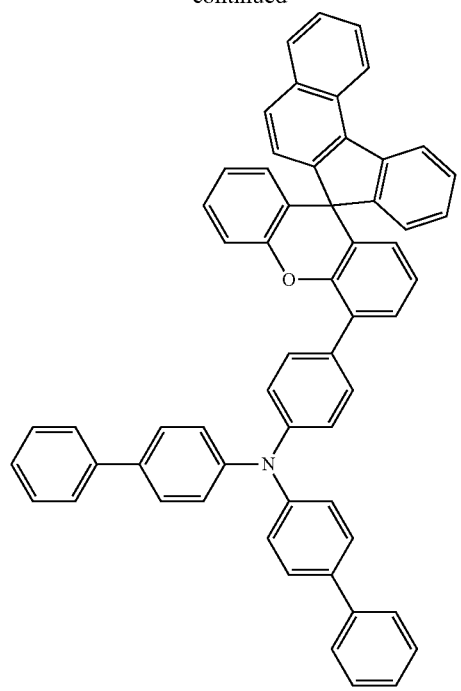
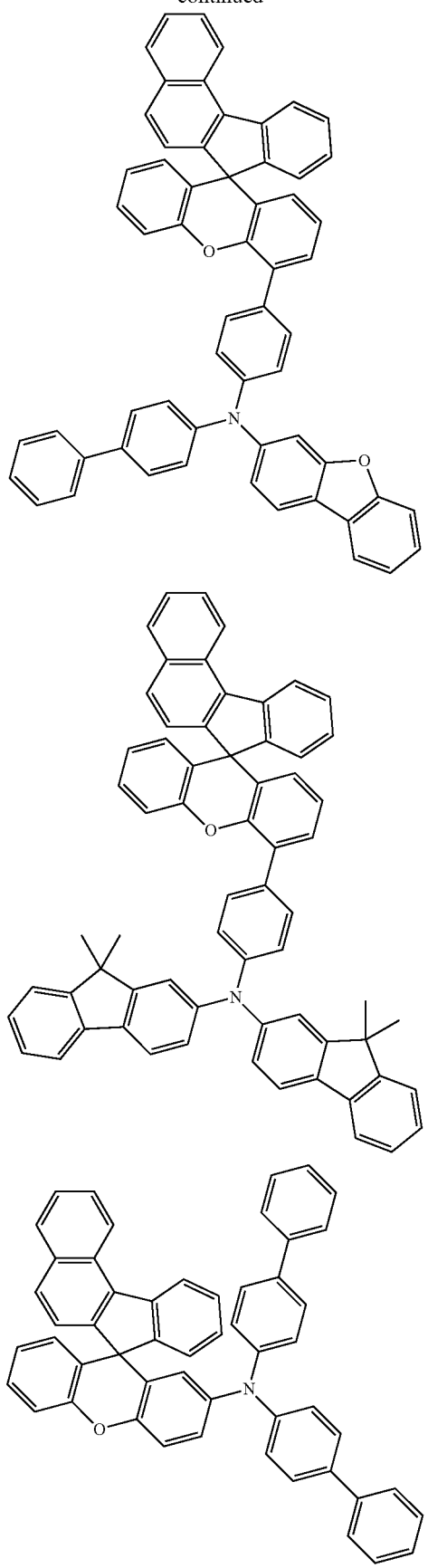
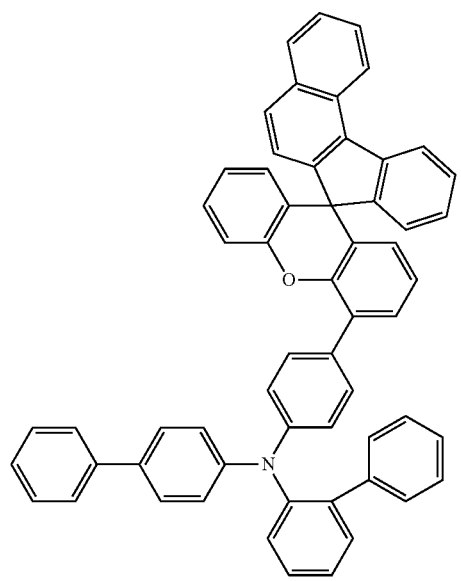

255
-continued
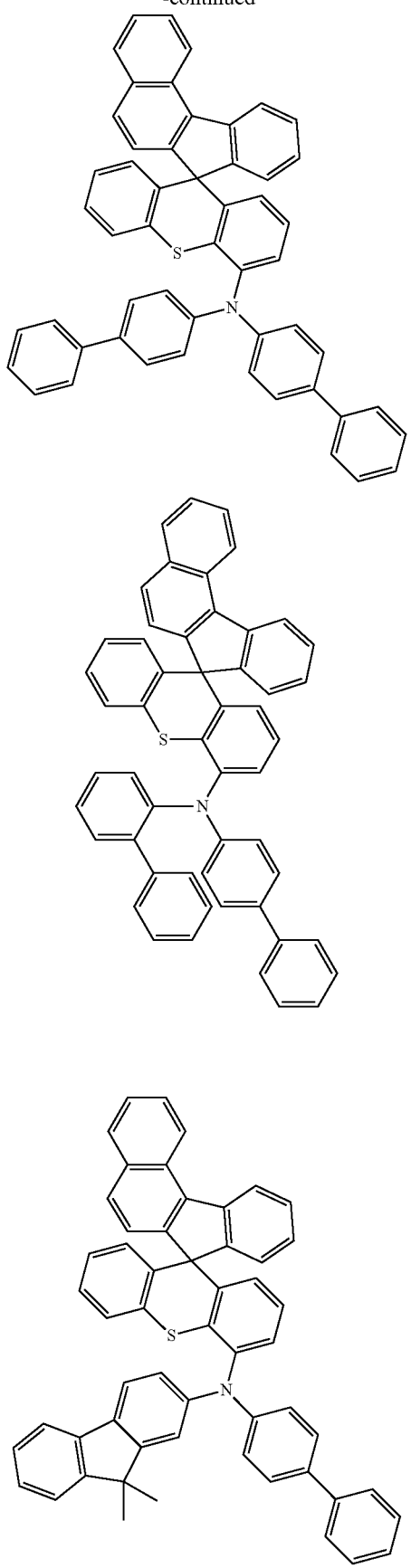
256
-continued
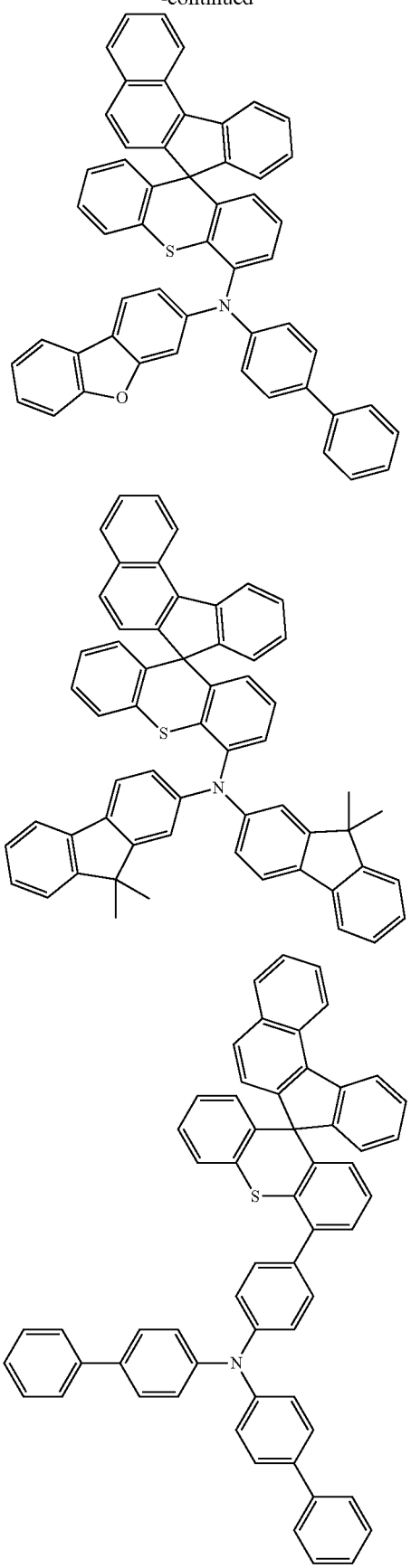

257
-continued
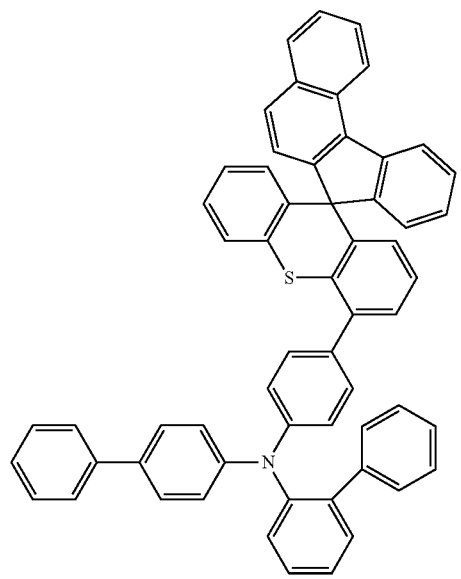
258
-continued
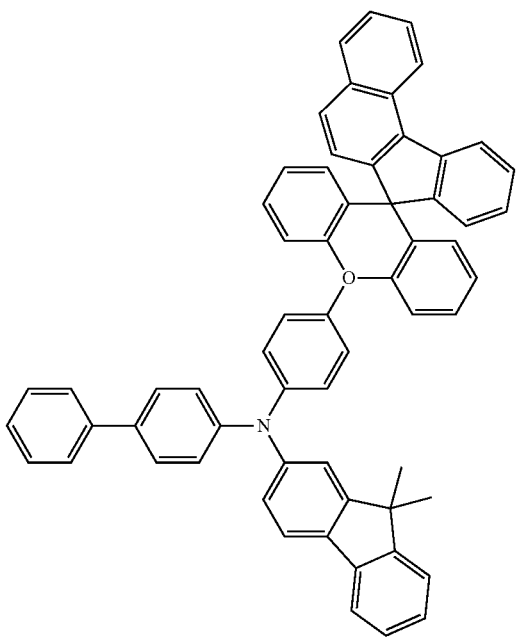
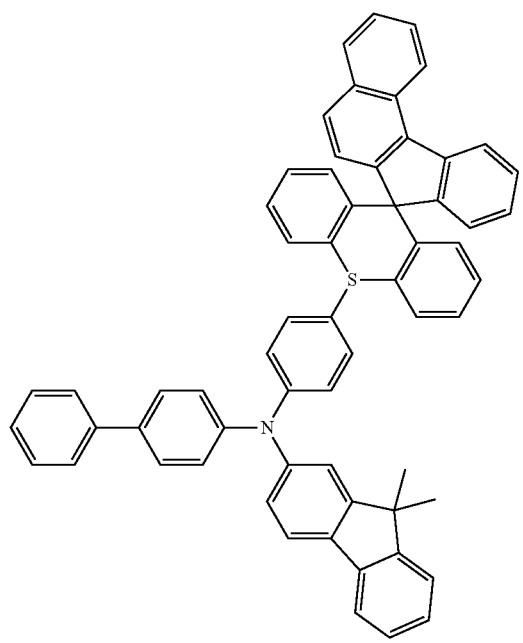
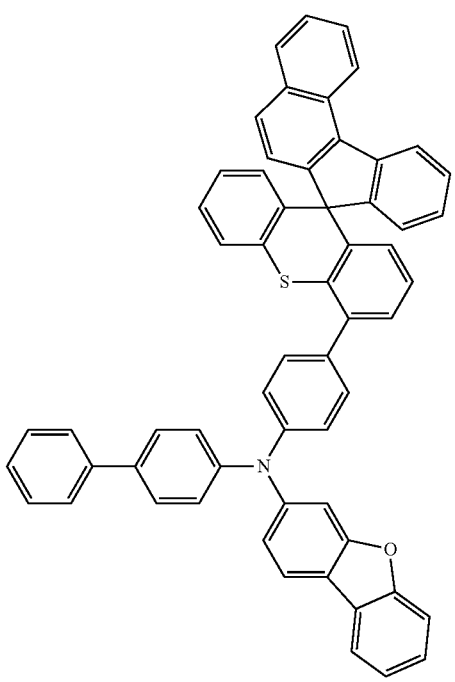 [SMILES: c1ccc(-c2ccc(N(c3ccc(-c4cccc5c4Sc4ccccc4C54c5ccccc5-c5c4ccc4ccccc54)cc3)c3ccc4c(c3)oc3ccccc34)cc2)cc1]

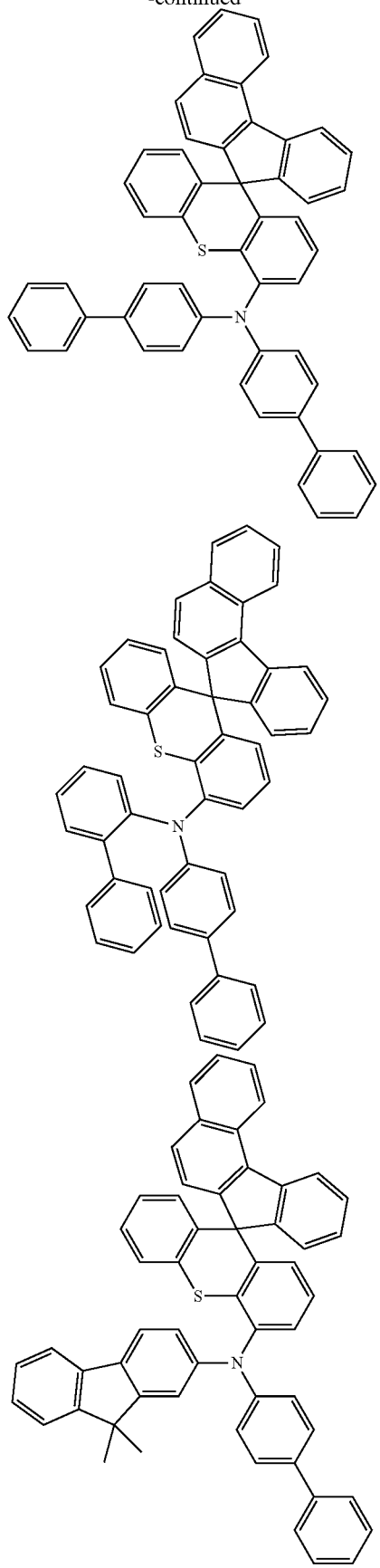
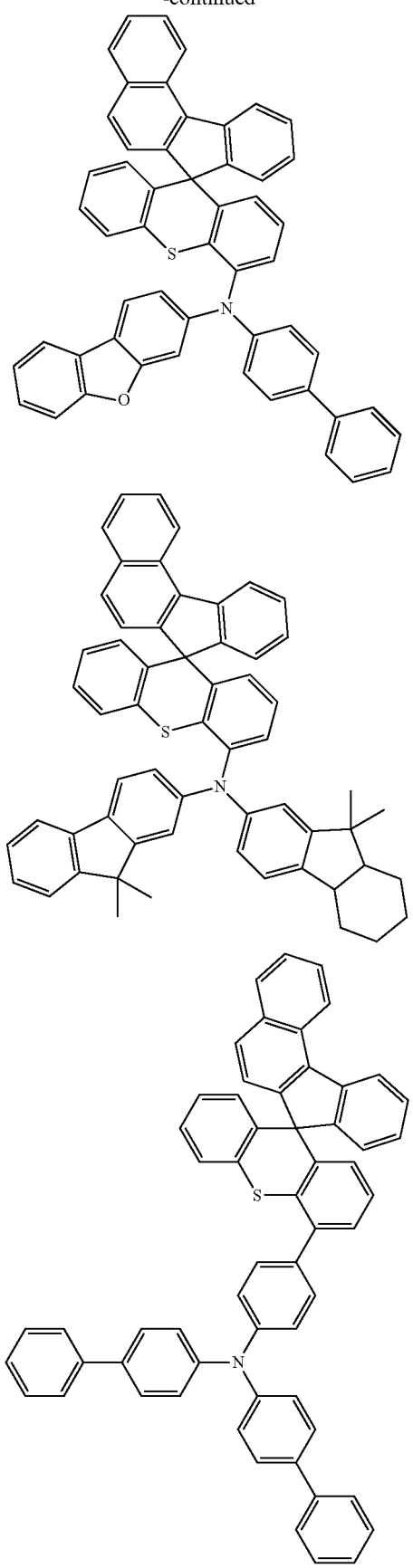

261
-continued
262
-continued
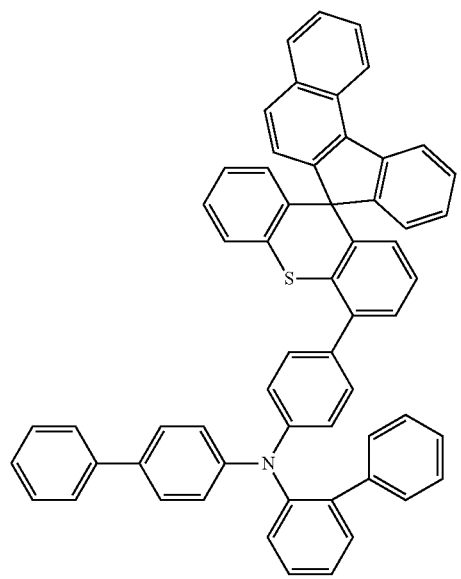
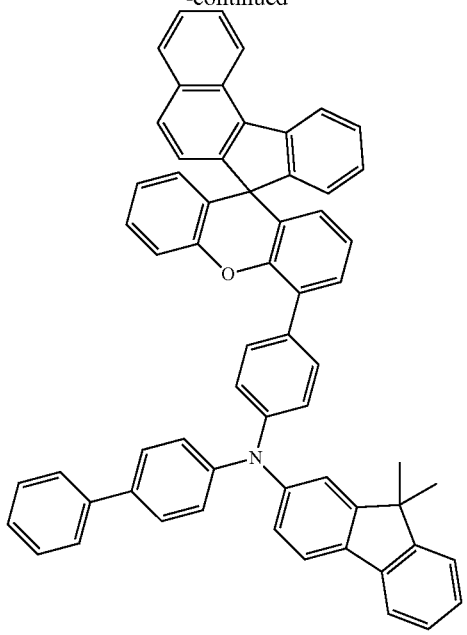
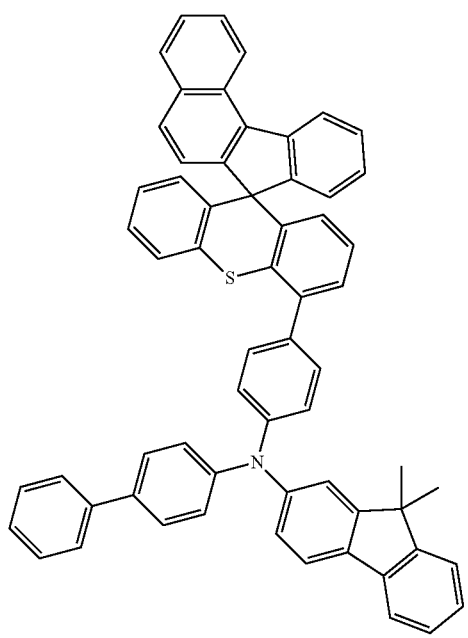
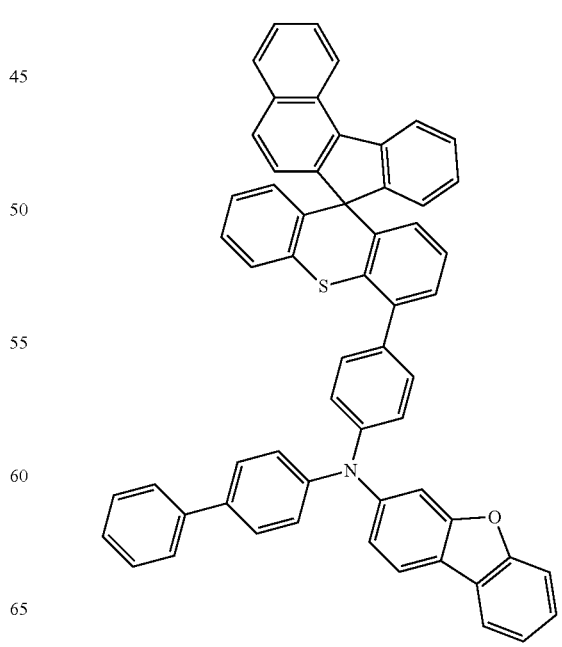

263
-continued
264
-continued
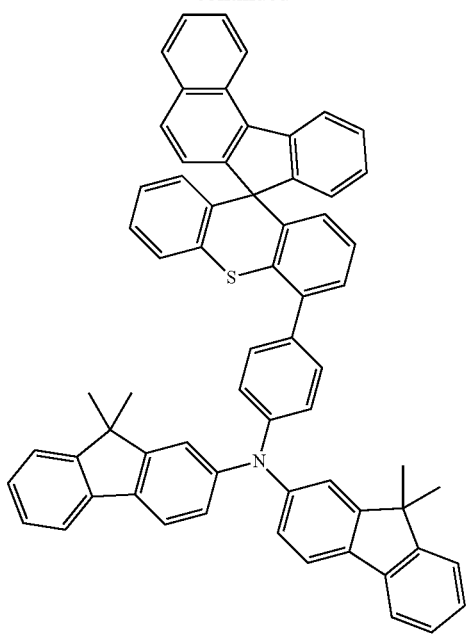
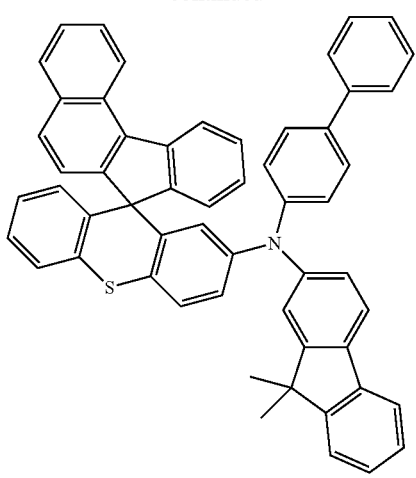
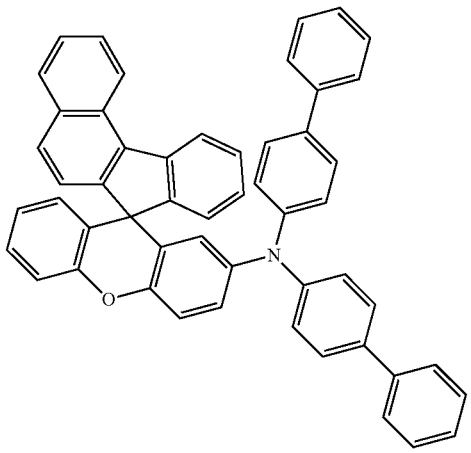
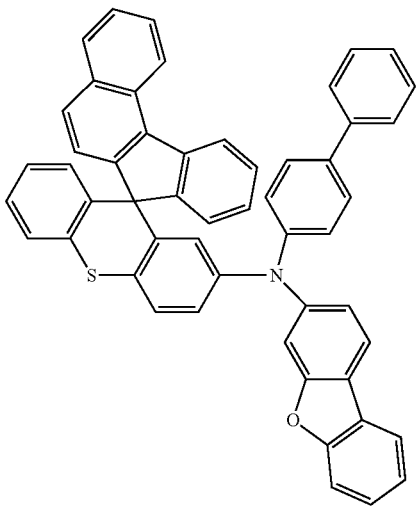
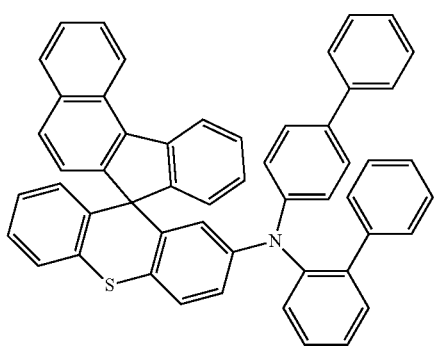
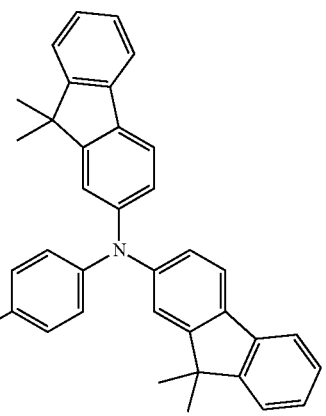

265
-continued
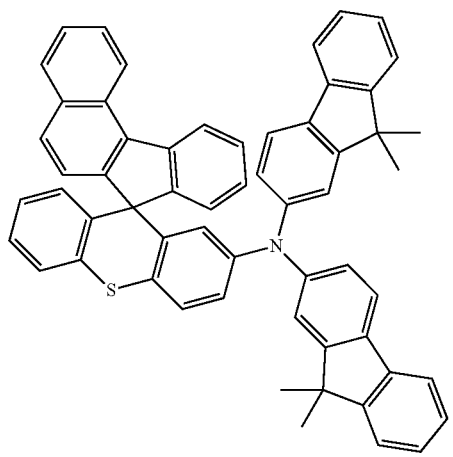
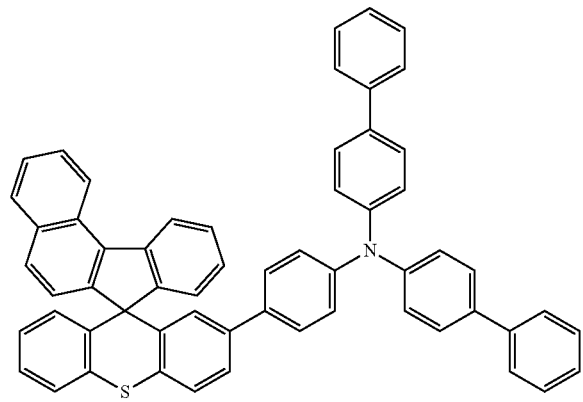
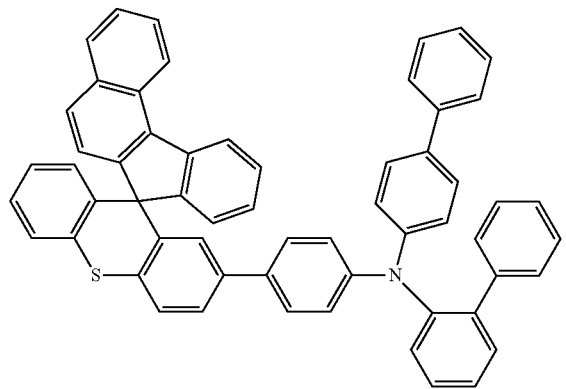
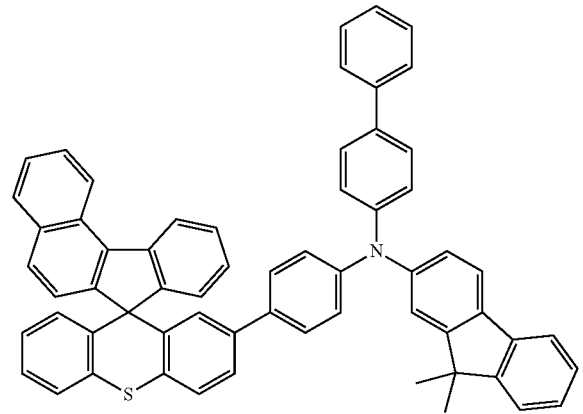
266
-continued
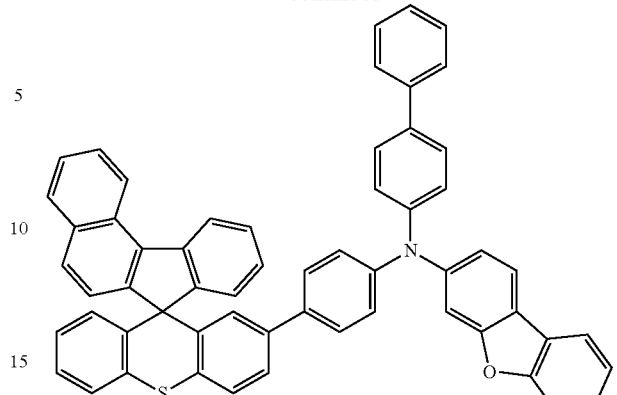
For yet another example, in Chemical Formula 1, $X_1$ may be O or S and $X_2$ may be $C(CH_3)_2$. Such an organic compound may be selected from the following group.
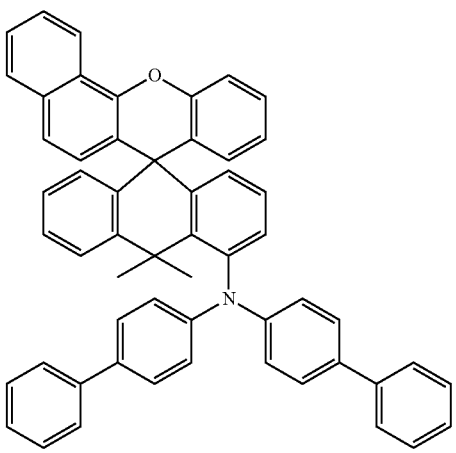
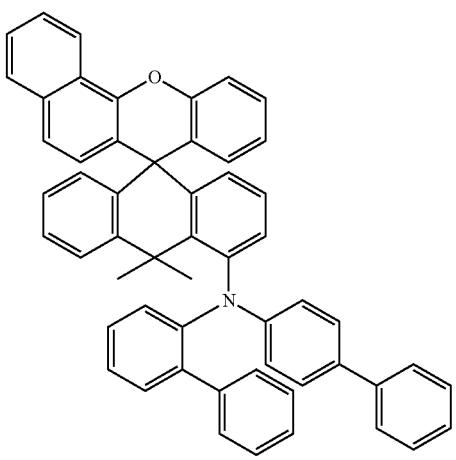

267
-continued
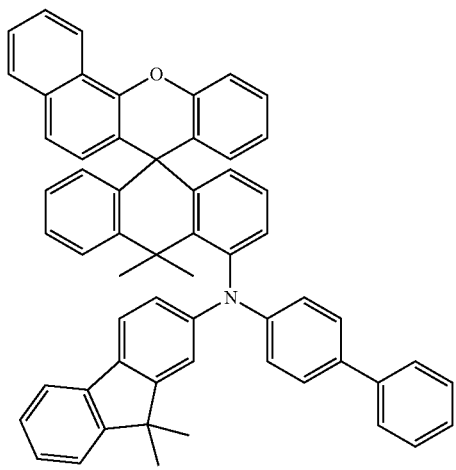
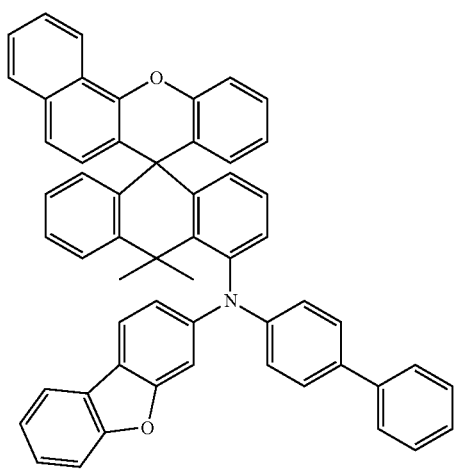
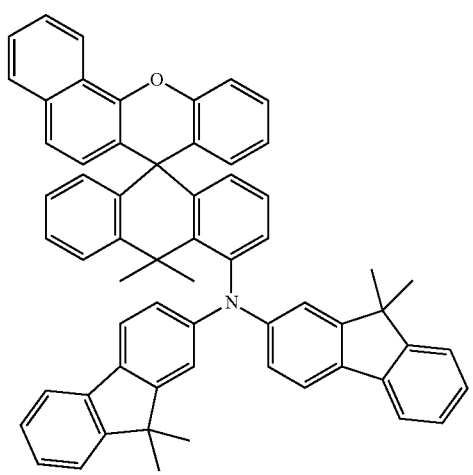
268
-continued
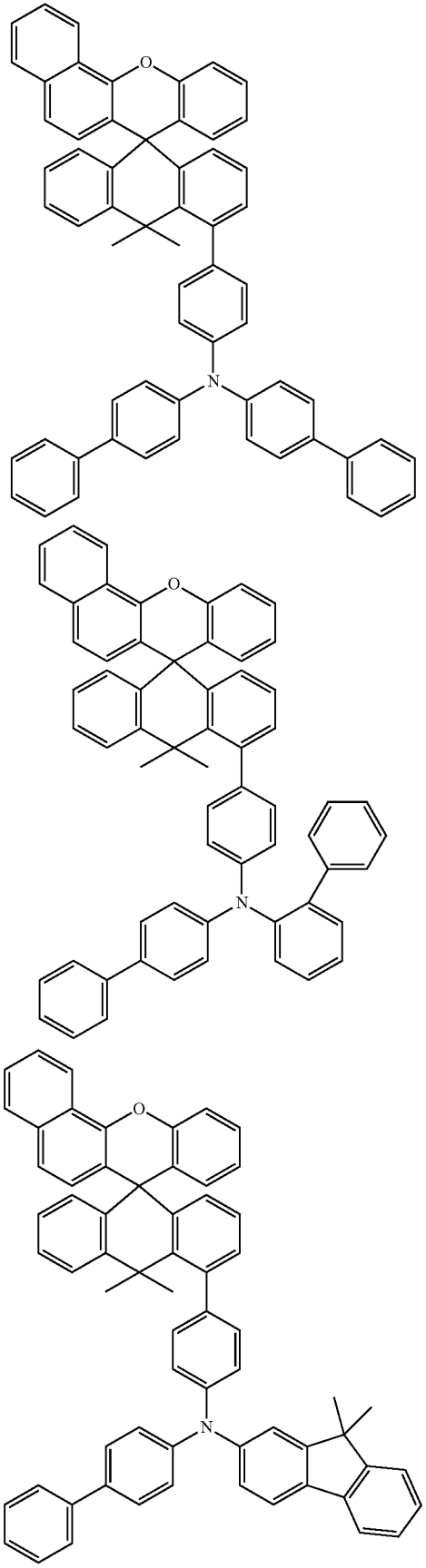

269
-continued
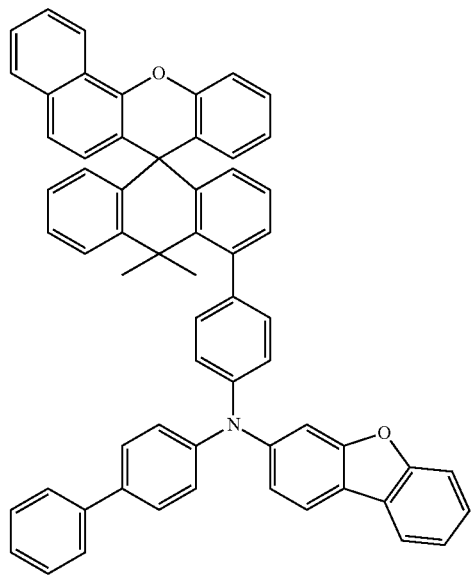
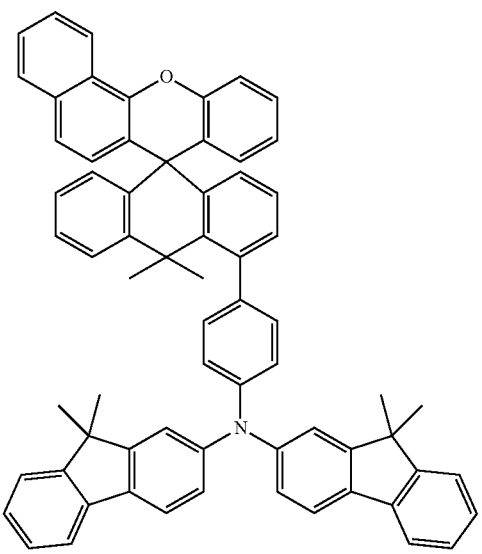
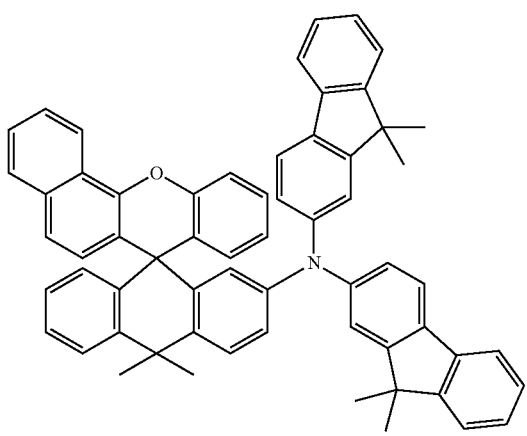
270
-continued
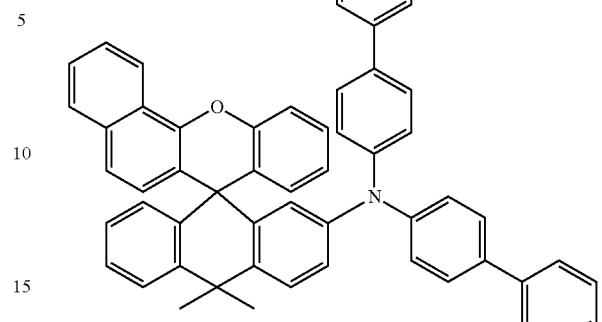
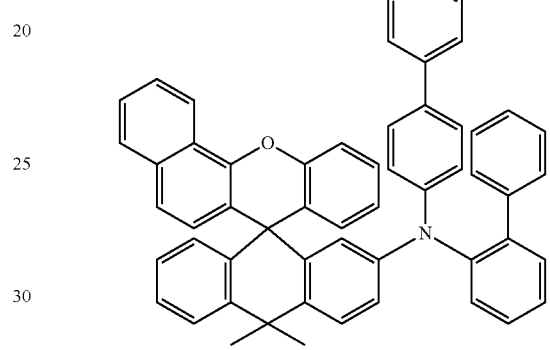
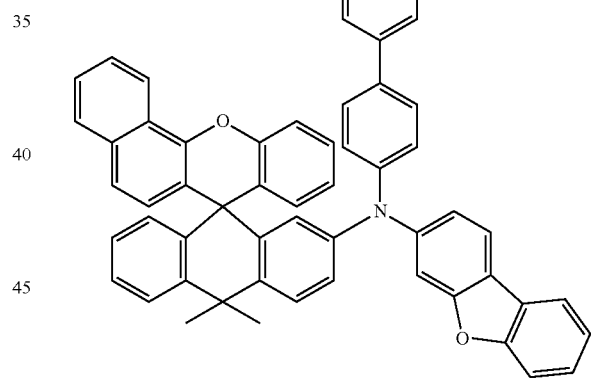
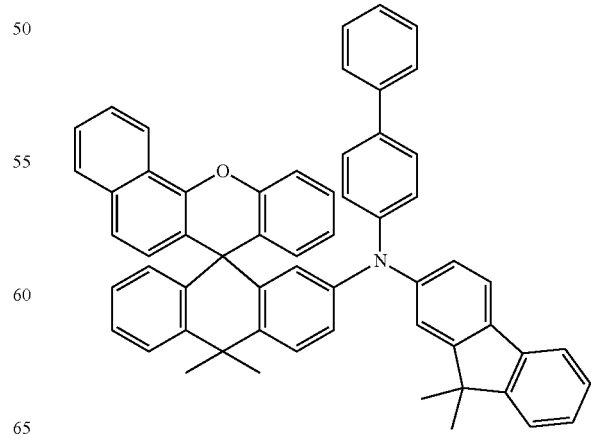

271
-continued
272
-continued
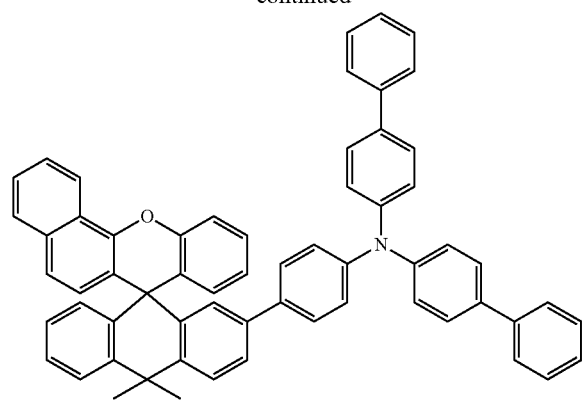
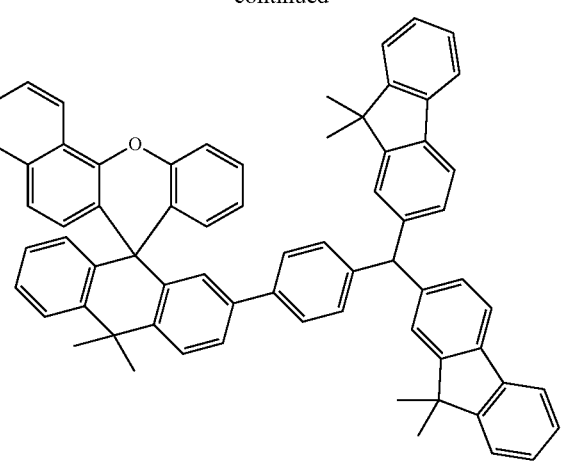
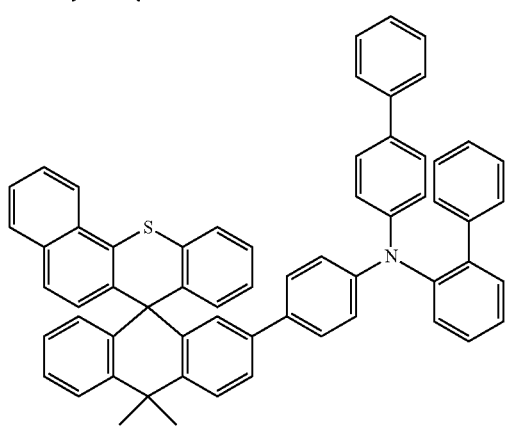
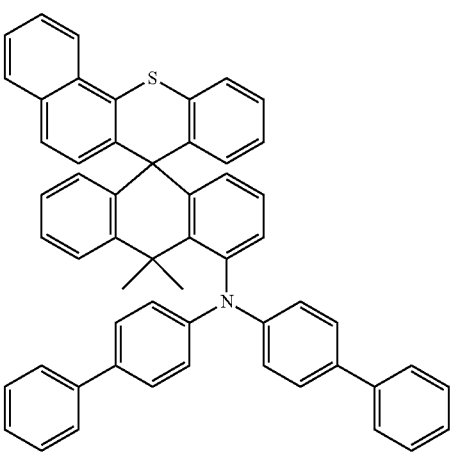
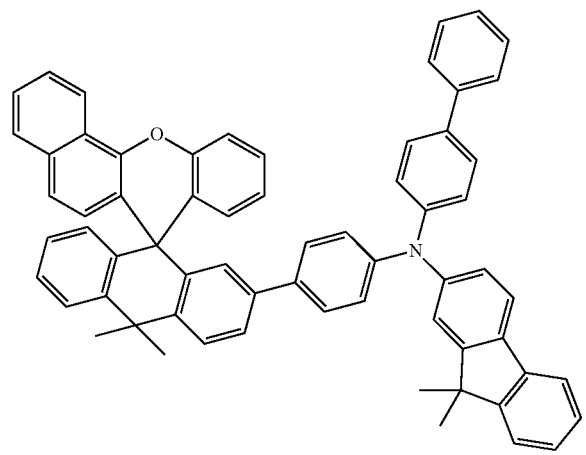
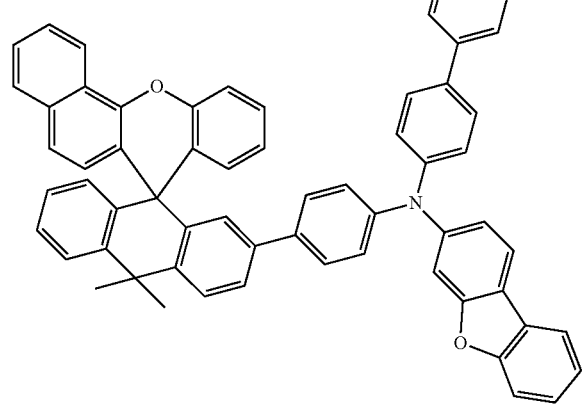
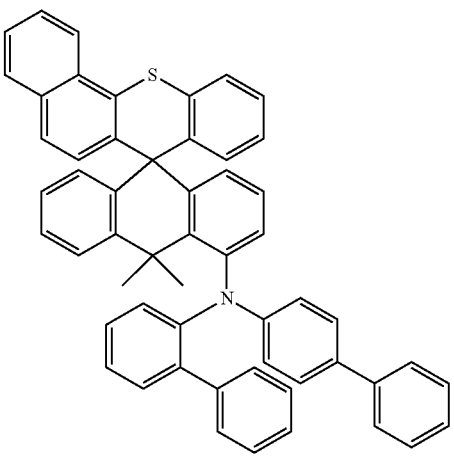

273
-continued
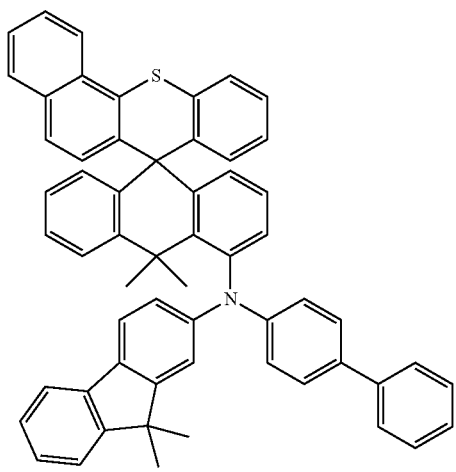
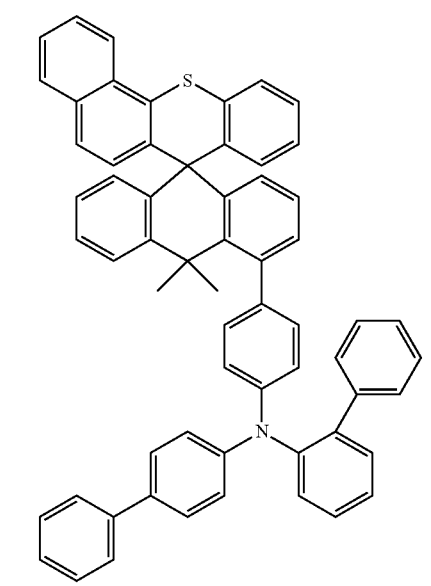
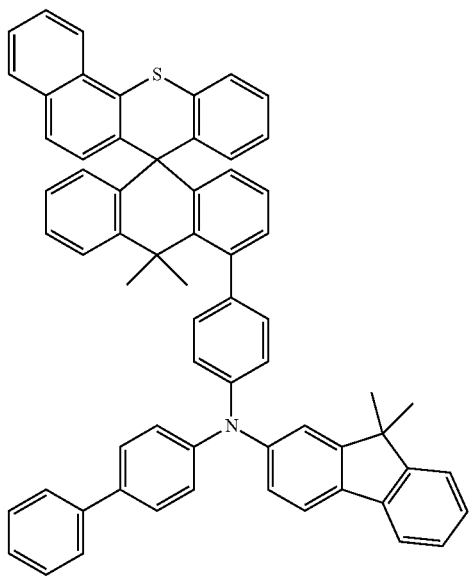 [SMILES: CC1(C)c2ccccc2-c2ccc(N(c3ccc(-c4ccccc4)cc3)c3ccc(-c4cccc5c4C(C)(C)c4ccccc4C54c5ccccc5Oc5c4ccc4ccccc54)cc3)cc21]
274
-continued
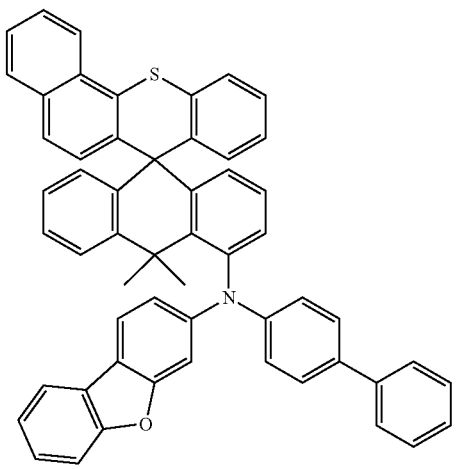
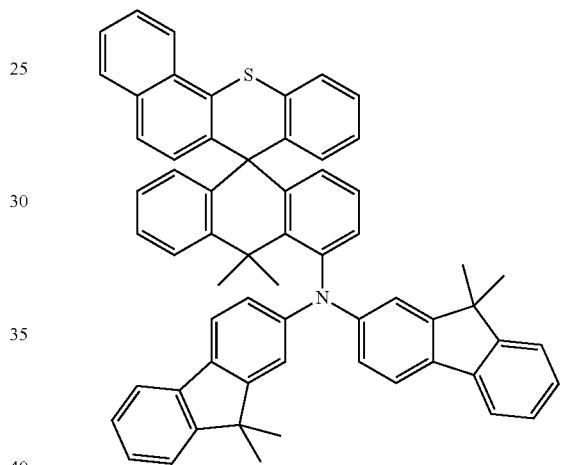
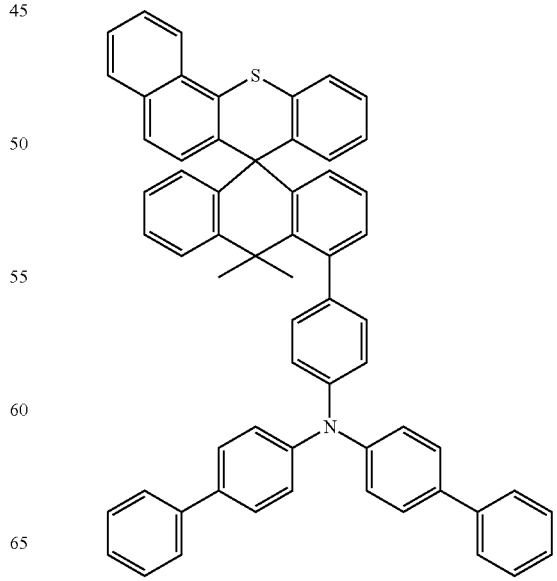

275
-continued
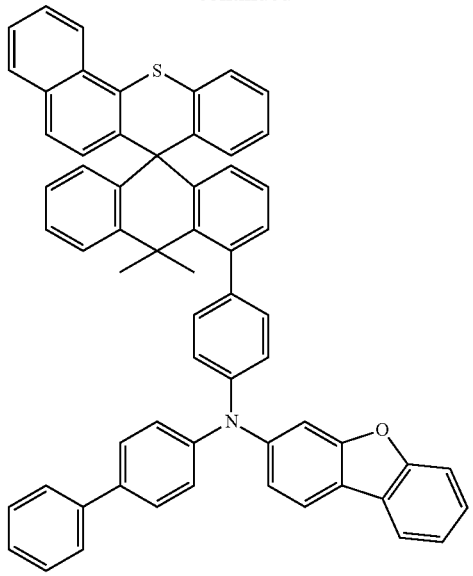
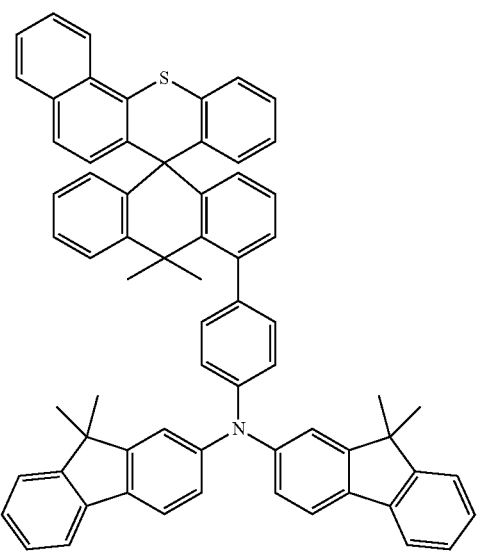
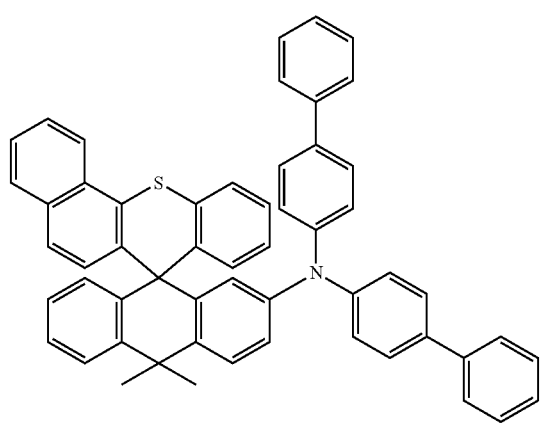
276
-continued
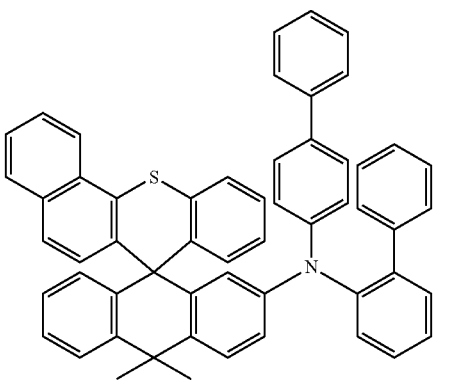
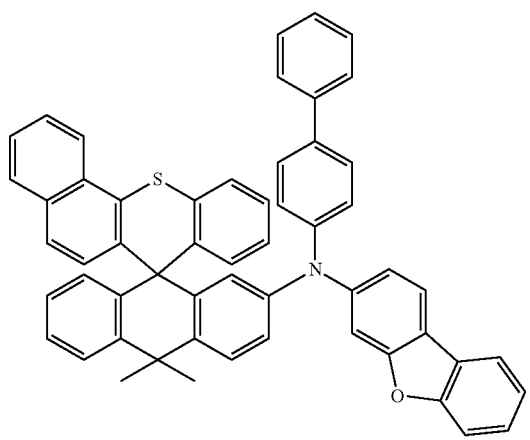
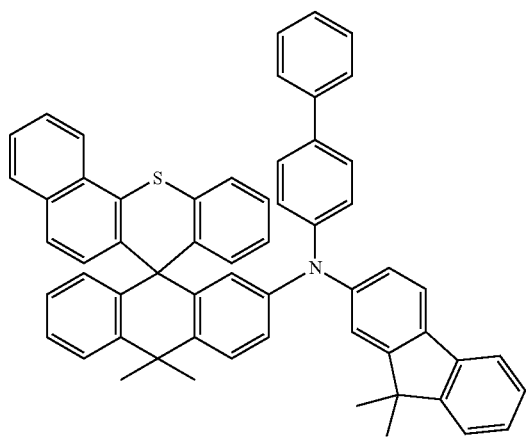
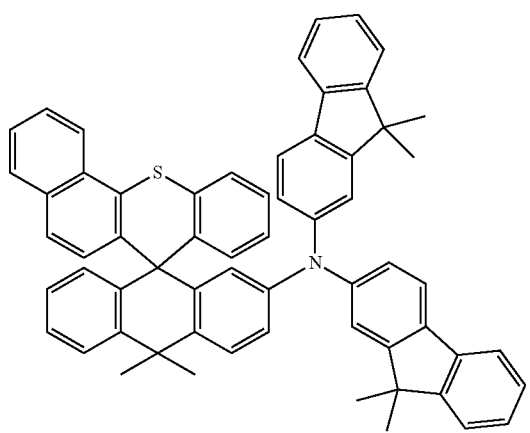

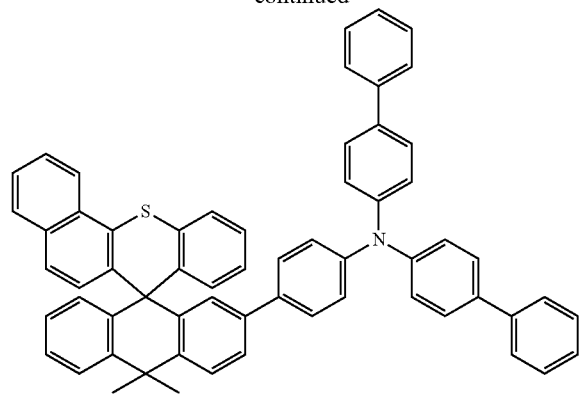
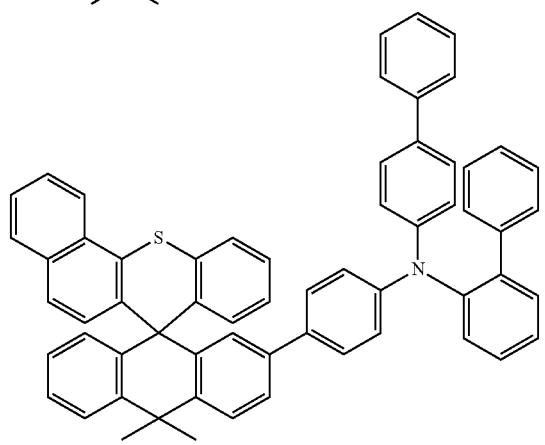
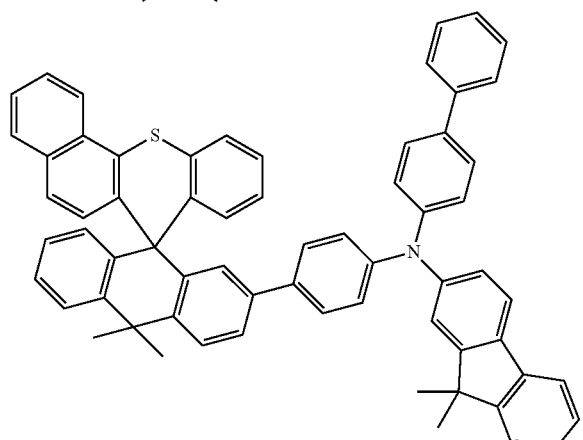
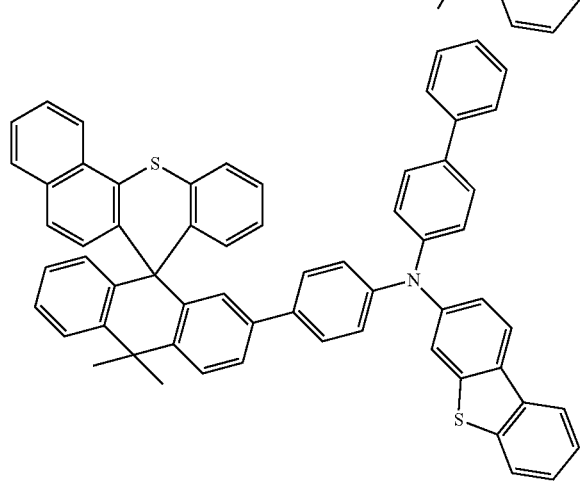
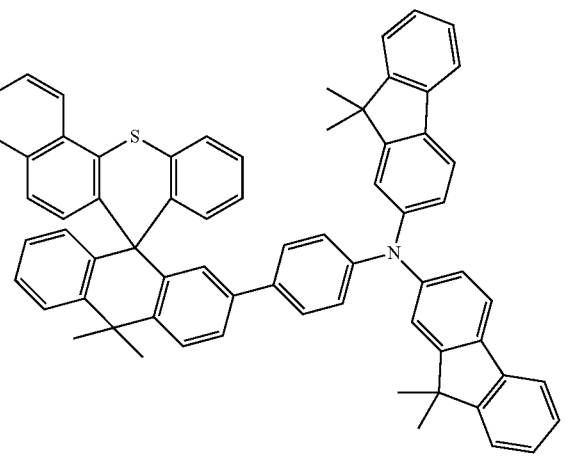
For still another example, in Chemical Formula 1, $X_1$ may be $C(CH_3)_2$ and $X_2$ may be O or S. Such an organic compound may be selected from the following group.
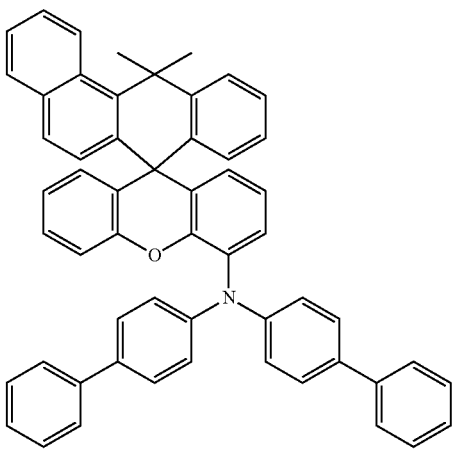
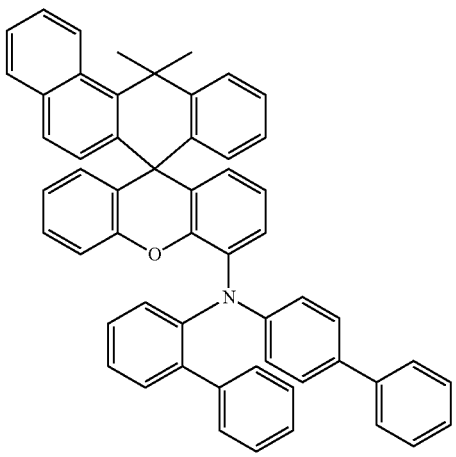

279
-continued
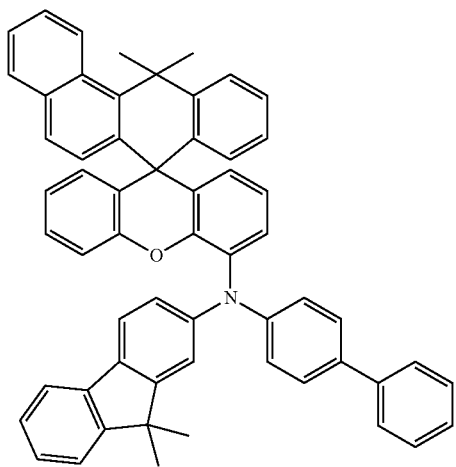
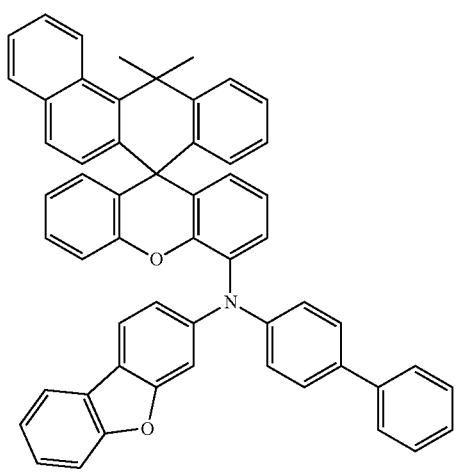
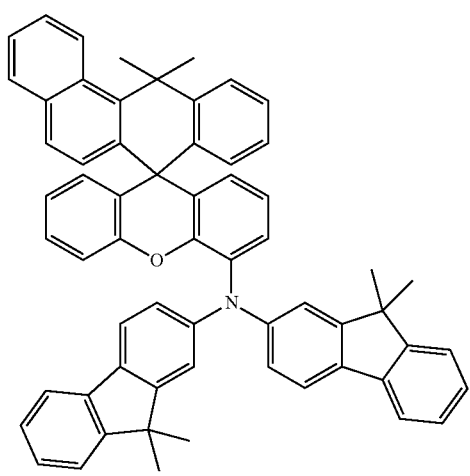
280
-continued
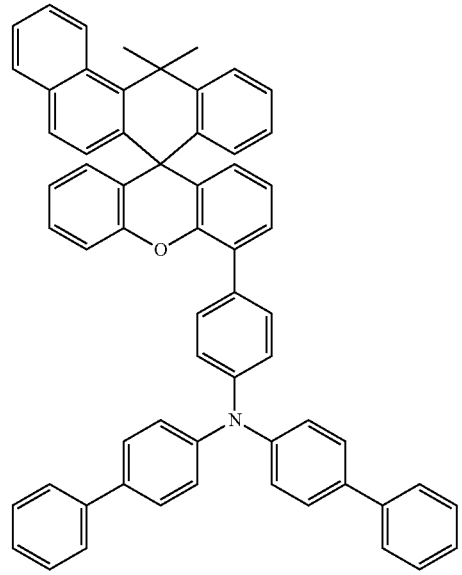
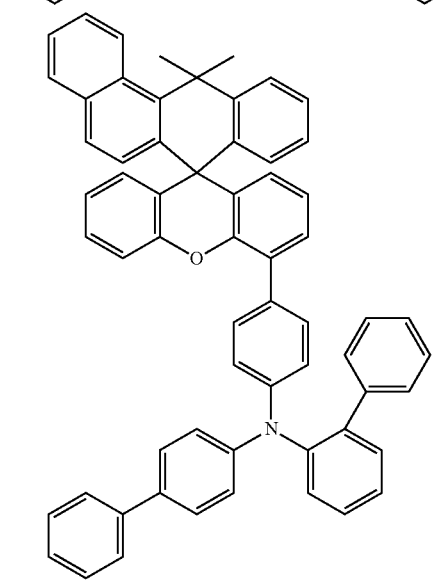

281
-continued
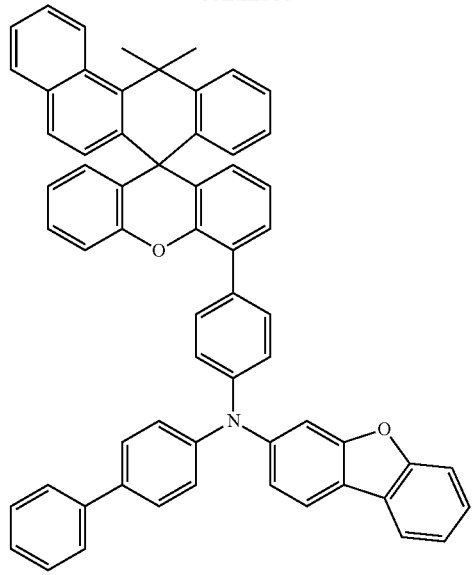
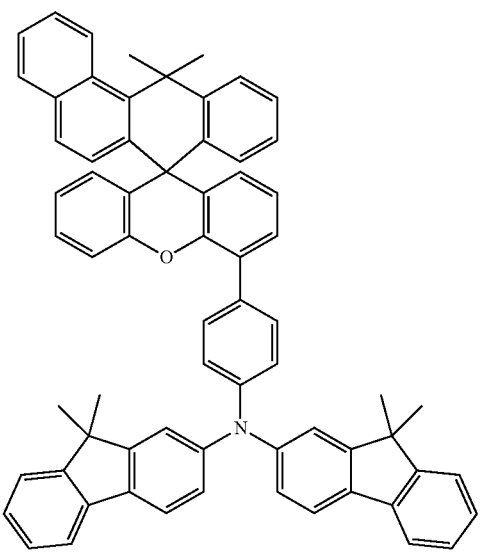
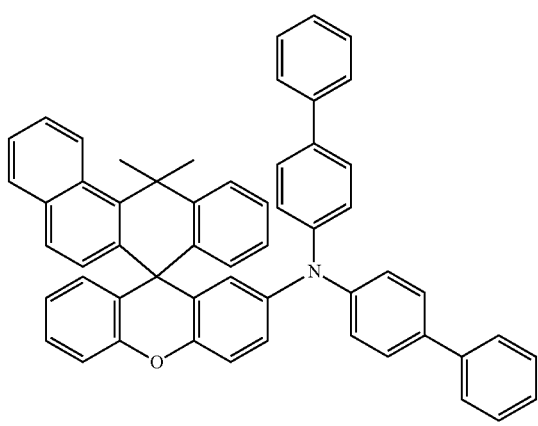 [SMILES: CC1(C)c2ccccc2C2(c3ccccc3Oc3c2ccc2ccccc32)c2cc(N(c3ccc(-c4ccccc4)cc3)c3ccc(-c4ccccc4)cc3)ccc21]
282
-continued
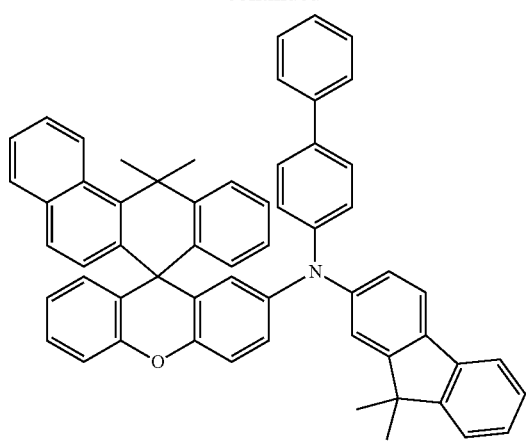
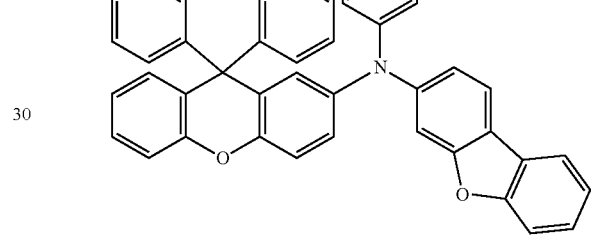
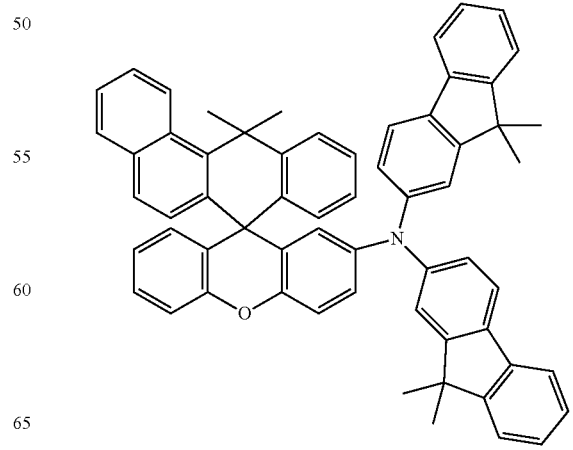

283
-continued
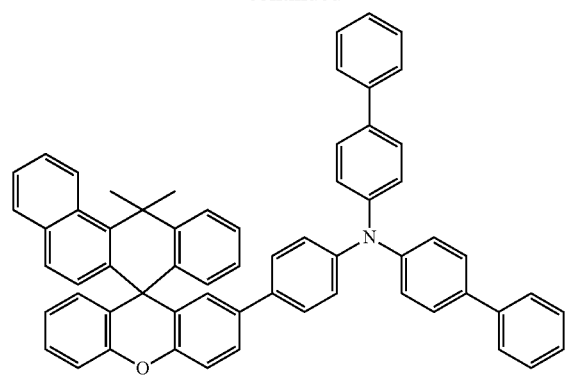
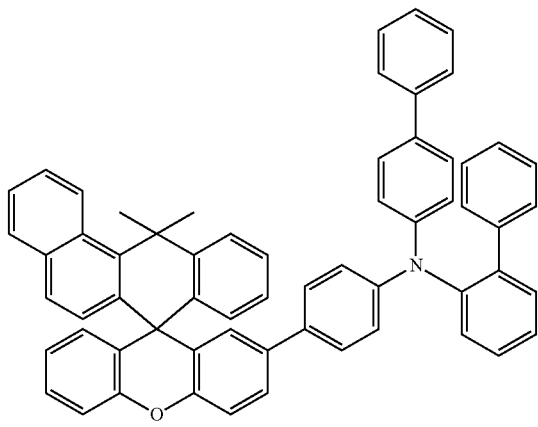
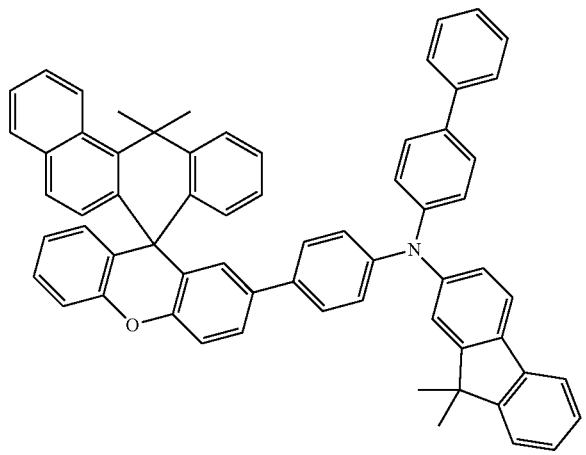 [SMILES: CC1(C)c2ccccc2-c2ccc(N(c3ccc(-c4ccccc4)cc3)c3ccc(-c4ccc5c(c4)C4(c6ccccc6S5)c5ccccc5C(C)(C)c5c4ccc4ccccc54)cc3)cc21]
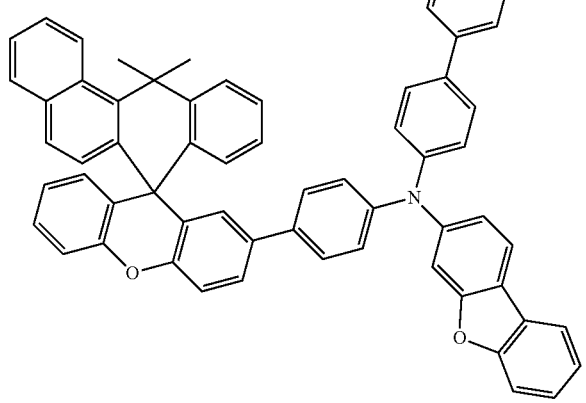
284
-continued
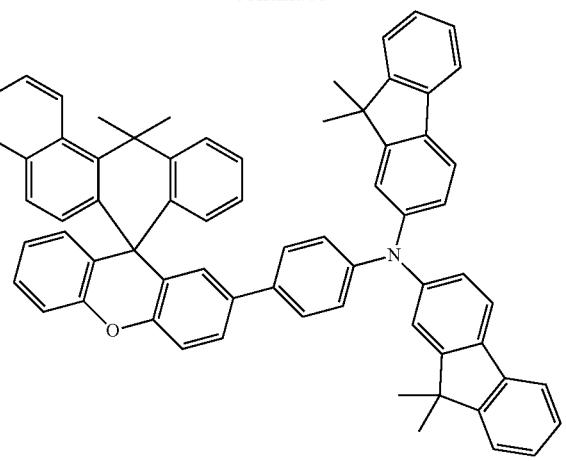
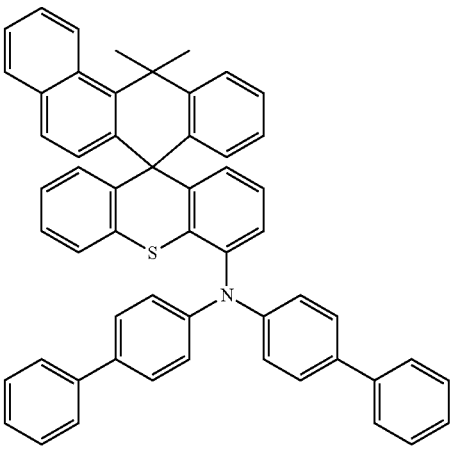
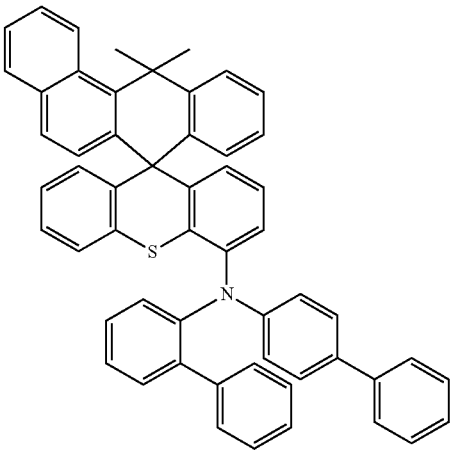

285
-continued
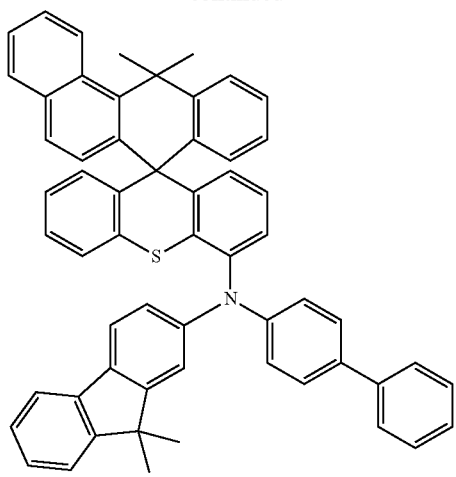
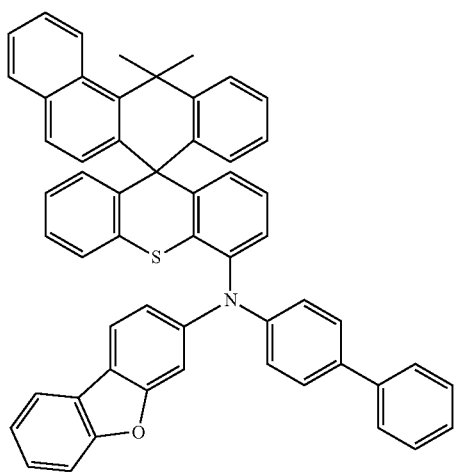
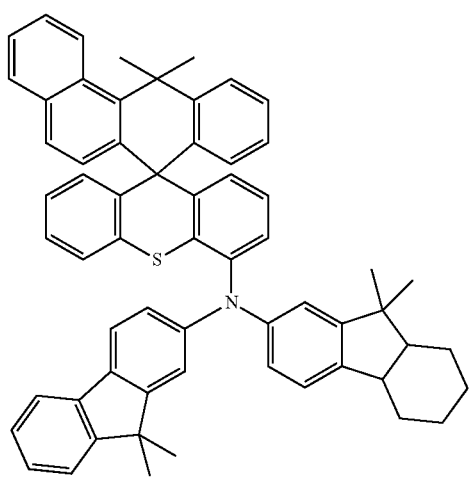
286
-continued
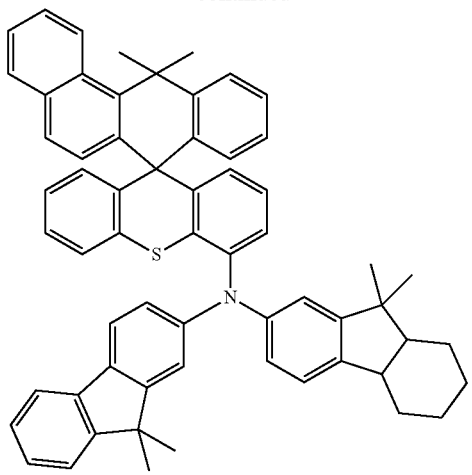
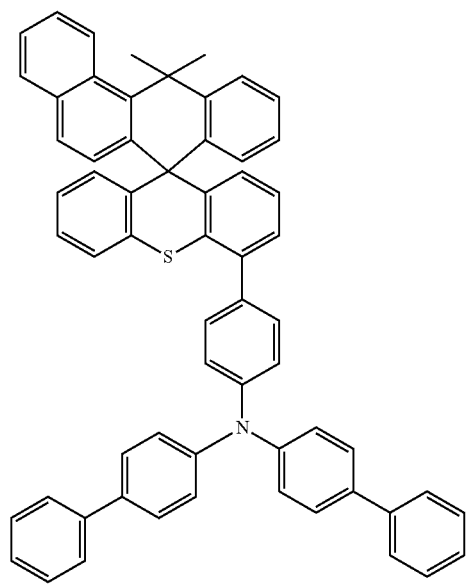
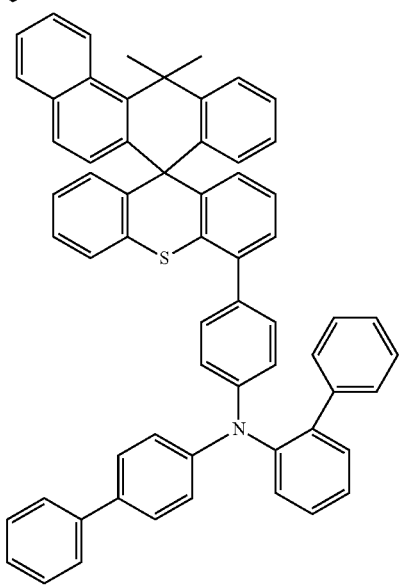

287
-continued
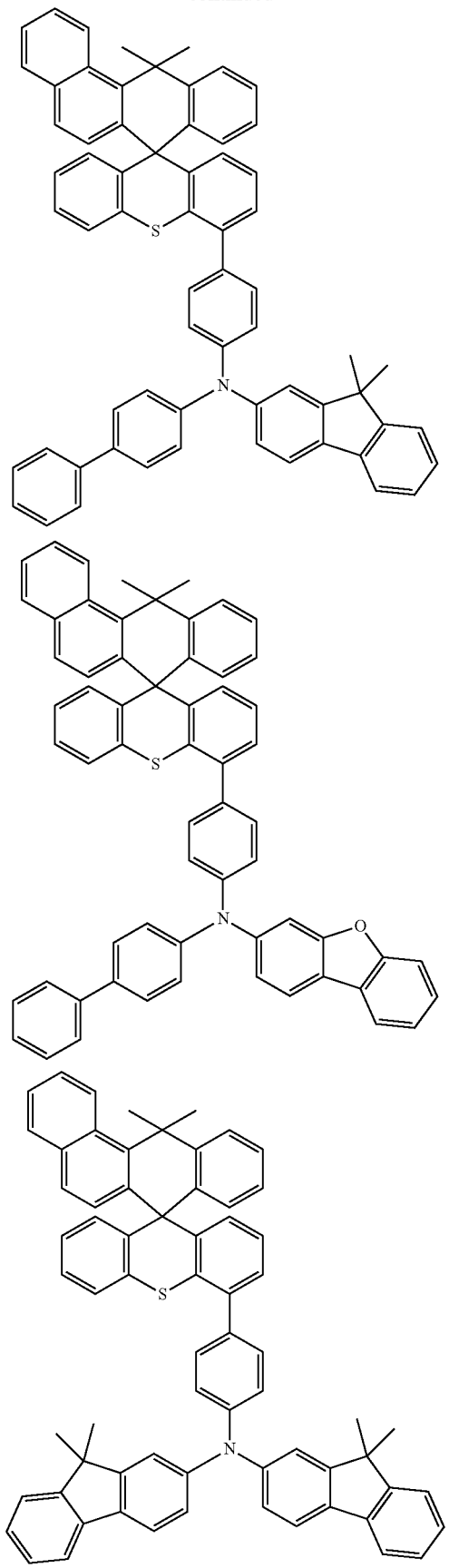
288
-continued
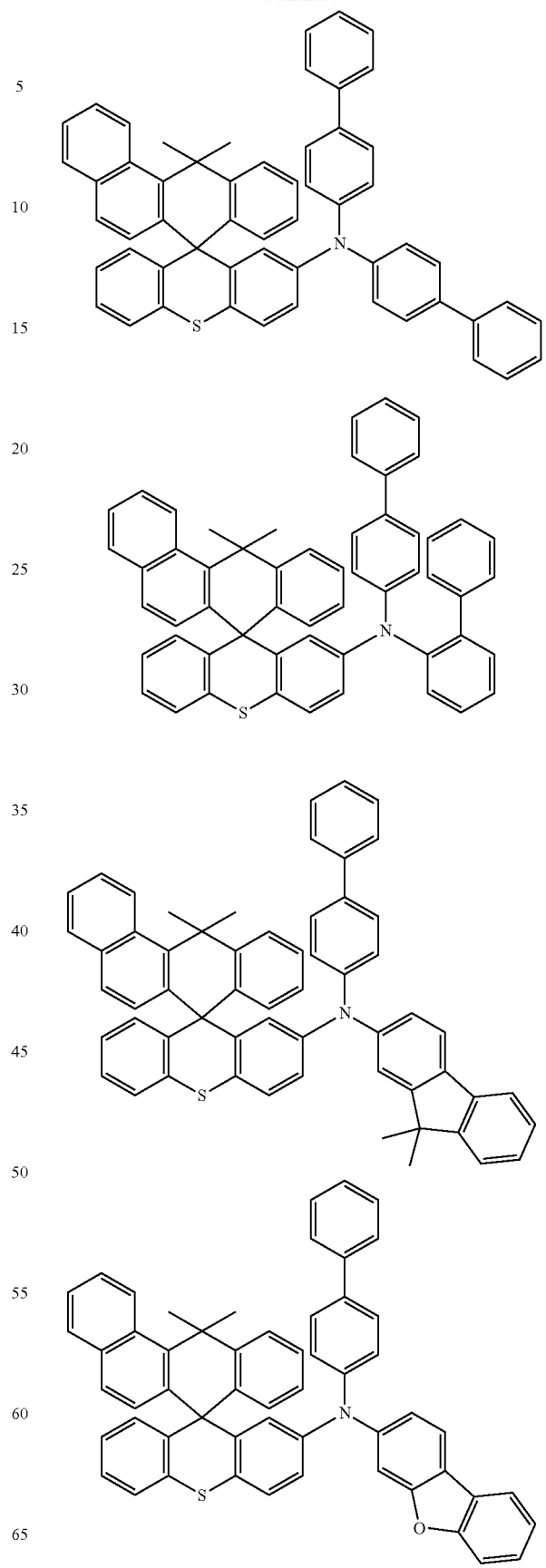

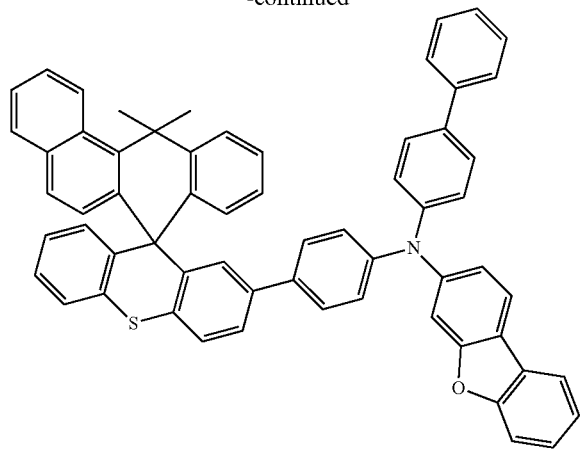
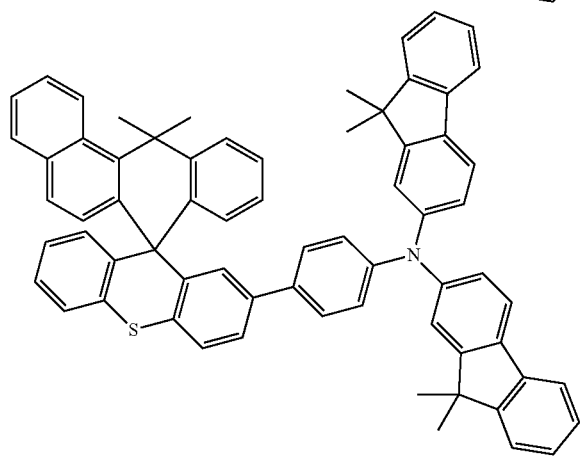
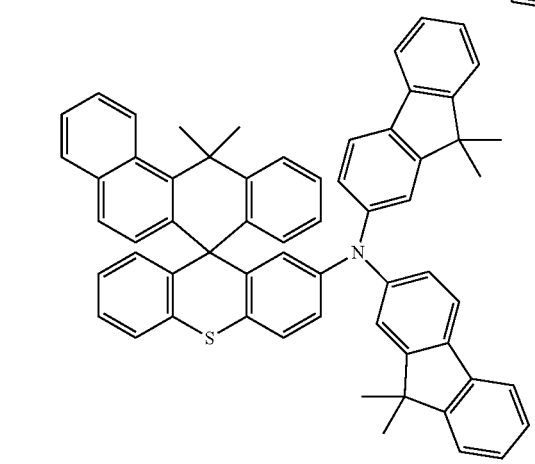
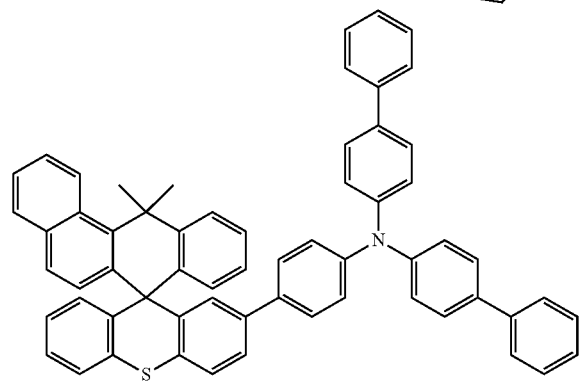
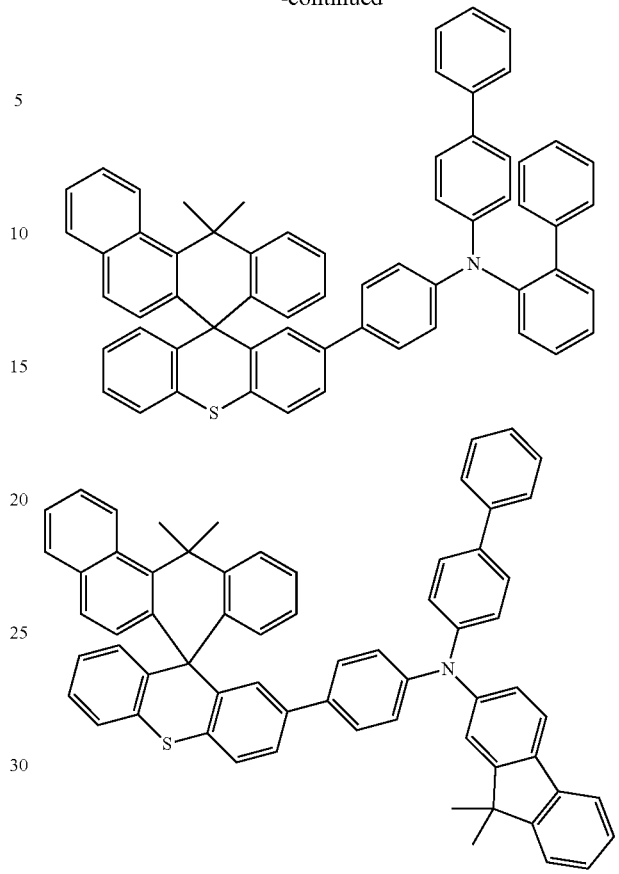

The organic compound represented by Chemical Formula 1 according to an exemplary embodiment of the present disclosure has hole transport properties and electron blocking properties. Therefore, the organic compound represented by Chemical Formula 1 may be included in a hole transport layer or an electron blocking layer among a plurality of organic layers disposed between an anode and a cathode of an organic light emitting display device, thereby providing high luminous efficiency and long lifetime. This will be described later.

Hereinafter, an organic light emitting display device according to an exemplary embodiment of the present disclosure will be described with reference to the accompanying drawings.

Figure 2:
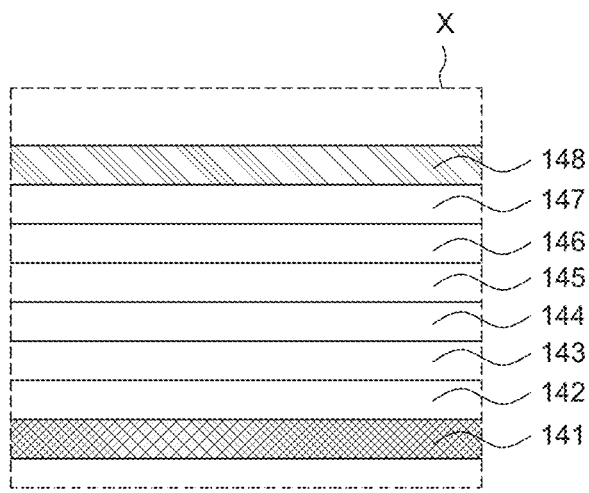
FIG. 2 is an enlarged view provided to explain the organic light emitting display device according to an exemplary embodiment of the present disclosure.

FIG. 1 is a schematic cross-sectional view of an organic light emitting display device according to an exemplary embodiment of the present disclosure, and FIG. 2 is an enlarged view of a portion "X" in FIG. 1.

Referring to FIG. 1 and FIG. 2, an organic light emitting display device 100 includes a substrate 110, a thin film transistor 120 and an organic light emitting element 140. The organic light emitting element 140 includes a red organic light emitting element 140R formed in a red sub-pixel R, a green organic light emitting element 140G formed in a green sub-pixel G and a blue organic light emitting element 140B formed in a blue sub-pixel B. Each of the organic light emitting elements 140R, 140G and 140B includes an anode 141, a plurality of organic layers and a cathode 148. For example, the plurality of organic layers may have a structure in which a hole injection layer 142, a hole transport layer 143, an electron blocking layer 144, a light emitting layer 145, an electron transport layer 146 and an electron injection layer 147 are laminated.

FIG. 1 illustrates only a red sub-pixel R, a green sub-pixel G and a blue sub-pixel B among a plurality of sub-pixels for convenience in explanation. Also, FIG. 1 illustrates that the organic light emitting display device 100 according to an exemplary embodiment of the present disclosure is driven in a top emission type. However, the present disclosure is not limited to the top emission type.

Hereinafter, the elements of the organic light emitting display device 100 according to an exemplary embodiment of the present disclosure will be described in detail with reference to FIG. 1 and FIG. 2.

The substrate 110 is configured to support various elements of the organic light emitting display device 100 and may be formed of an insulating material. For example, the substrate may be a glass substrate or a plastic substrate. For example, the plastic substrate may be made of one selected from polyethylene polyimide, polyether sulfone, naphthalate, polyethylene terephthalate and polycarbonate, but may not be limited thereto.

A buffer layer 131 for protecting various elements of the organic light emitting display device 100 against the permeation of oxygen or moisture from the outside is disposed on the substrate 110. Although FIG. 1 illustrates the buffer layer 131 as a single layer, the buffer layer 131 may be selectively formed as a multi-layered structure when necessary.

The thin film transistor 120 including a gate electrode 121, an active layer 122, a source electrode 123 and a drain electrode 124 is disposed on the buffer layer 131. Specifically, the active layer 122 is disposed on the substrate 110 and a gate insulating layer 132 for insulating the active layer 122 and the gate electrode 121 is disposed on the active layer 122. Also, an interlayer insulating layer 133 for insulating the gate electrode 121 from the source electrode 123 and the drain electrode 124 is disposed on the buffer layer 131. The source electrode 123 and the drain electrode 124 each in contact with the active layer 122 are formed on the interlayer insulating layer 133.

The thin film transistor 120 is formed in each of the red sub-pixel R, the green sub-pixel G and the blue sub-pixel B regions. FIG. 1 illustrates only a driving thin film transistor among various thin film transistors which may be included in the organic light emitting display device 100 for convenience in explanation. Also, FIG. 1 illustrates that the thin film transistor 120 has a coplanar structure, but may not be limited thereto. The thin film transistor 120 may have an inverted-staggered structure.

An overcoating layer 134 may be disposed on the thin film transistor 120. The overcoating layer 134 planarizes an upper part of the substrate 110.

The organic light emitting element 140 including the red organic light emitting element 140R, the green organic light emitting element 140G and the blue organic light emitting element 140B is disposed on the overcoating layer 134.

Although not illustrated in FIG. 1, the overcoating layer 134 includes a contact hole (not illustrated) for electrically connecting the thin film transistor 120 with the anode 141 of the organic light emitting element 140. The anode 141 of the organic light emitting element 140 is disposed on the overcoating layer 134. A bank 135 is disposed on the anode 141 and the overcoating layer 134 to divide the adjacent sub-pixel regions. Also, the bank 135 may divide pixel regions each including a plurality of sub-pixel regions.

Hereinafter, the blue organic light emitting element 140B among the red organic light emitting element 140R, the green organic light emitting element 140G and the blue organic light emitting element 140B will be described in detail with reference to FIG. 1 and FIG. 2. The blue organic light emitting element 140B is described as an example for convenience in explanation, but the application of the organic compound represented by Chemical Formula 1 of the present disclosure is not limited to the blue organic light emitting element 140B.

Referring to FIG. 2, the blue organic light emitting element 140B includes the anode 141, a plurality of organic layers and the cathode 148. For example, the plurality of organic layers includes the hole injection layer 142, the hole transport layer 143, the electron blocking layer 144, the light emitting layer 145, the electron transport layer 146 and the electron injection layer 147.

The anode 141 is disposed on the overcoating layer 134. The anode 141 is formed of a conductive material having a high work function for supplying holes to the light emitting layer 145. The anode 141 may be a transparent conductive layer formed of transparent conductive oxide (TCO). For example, the anode 141 may be formed of one or more transparent conductive oxides selected from indium-tin-oxide (ITO), indium-zinc-oxide (IZO), indium-tin-zinc oxide (ITZO), tin oxide ($SnO_2$), zinc oxide (Zno), indium-copper-oxide (ICO) and aluminum:zinc oxide (Al:ZnO (AZO)), but may not be limited thereto.

Referring to FIG. 1, the anode 141 may be separately formed for each of the red sub-pixel R, the green sub-pixel G and the blue sub-pixel B regions. Also, sub-pixel regions may be divided by the bank 135 disposed on the anode 141 and the overcoating layer 134.

In the organic light emitting display device 100 driven in the top emission type, if the anode 141 is formed as a transparent conductive layer, a reflective layer (not illustrated) may be formed under the anode. The reflective layer may be formed as a conductive layer having excellent reflectivity. Thus, the reflective layer may reflect light emitted from the light emitting layer 145 of the organic light emitting element 140 to an upper part of the organic light emitting display device 100. For example, the reflective layer may be formed of aluminum-palladium-copper alloy. The reflective layer may be electrically connected with the source electrode 123 of the thin film transistor 120 through the contact hole in the overcoating layer 134.

The hole injection layer 142 for injecting holes supplied from the anode 141 to the light emitting layer 145 is disposed on the anode 141. The hole injection layer 142 is formed of a material for improving the interface characteristics between the anode 141 and the hole transport layer 143 and enabling holes to be smoothly injected to the light emitting layer 145.

For example, the hole injection layer 142 may be formed of one or more compounds selected from the group consisting of HAT-CN (dipyrazino[2,3-f:2',3'-h]quinoxaline-2,3,6, 7,10,11-hexacarbonitrile), CuPc (phthalocyanine), PEDOT: PSS, NPD (N,N'-bis(naphthalene-1-yl)-N,N'-bis(phenyl)-2, 2'-dimethylbenzidine), and the like, but may not be limited thereto.

The hole transport layer 143 for smoothly transferring holes from the hole injection layer 142 to the light emitting layer 145 is disposed on the hole injection layer 142.

For example, the hole transport layer 143 may be formed of one or more compounds selected from the group consisting of NPD, TPD (N,N'-bis-(3-methylphenyl)-N,N'-bis-(phenyl)-benzidine), S-TAD (2,2',7,7'-tetrakis(N,N-dimethylamino)-9,9-spirofluorene), PVK (poly(9-vinylcarbazole)), PPV (Poly(p-phenylenevinylene), CBP (4,4'-N,N'-dicarbazole-biphenyl), mCP (1,3-Bis(N-carbazolyl)benzene), MTDATA (4,4',4''-Tris(N-3-methylphenyl-N-phenyl-amino)-triphenylamine), and the like, but may not be limited thereto.

The electron blocking layer 144 containing the organic compound represented by Chemical Formula 1 is disposed on the hole transport layer 143.

[Chemical Formula 1]

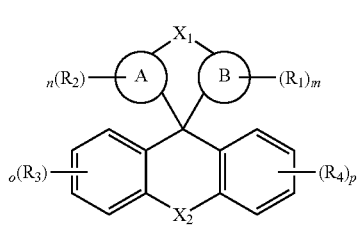

In Chemical Formula 1, the ring A, the ring B, $X_1$, $X_2$, $R_1$, $R_2$, $R_3$, $R_4$, m, n, o and p are identical to those defined above. The other features of the organic compound represented by Chemical Formula 1 are the same as described above, and, thus, redundant explanation thereof will be omitted.

The organic compound represented by Chemical Formula 1 has a relatively low electron affinity. Thus, it may effectively block the flow of electrons to suppress the leakage of electrons from the light emitting layer 145 to the hole transport layer 143. Also, it may maximize the retention time of electrons in the light emitting layer 145. That is, since the electron blocking layer 144 is formed of the organic compound represented by Chemical Formula 1, the recombination efficiency of holes and electrons in the light emitting layer 145 may be improved. As a result, the luminous efficiency and lifetime of the organic light emitting display device 100 may be greatly improved.

The light emitting layer 145 is disposed on the electron blocking layer 144. The light emitting layer 145 emits light by recombining electrons and holes therein. For example, the light emitting layer 145 of the blue organic light emitting element 140B emits blue light by recombining electrons and holes therein. The light emitting layer 145 is formed of a host and a dopant. The host of the light emitting layer 145 serves to transmit energy to the dopant in order to improve the luminous efficiency and color purity. The dopant is a dye organic material which is added in a small amount to the host.

For example, a host of the light emitting layer 145 for emitting blue light may be a beryllium-based complex but may not be limited thereto. For example, a dopant of the light emitting layer 145 for emitting blue light may be selected from perylene compounds, coumarin compounds, anthracene compounds, pyrene compounds and iridium phosphorescent dopant materials, but may not be limited thereto.

The electron transport layer 146 is disposed on the light emitting layer 145. The electron transport layer 146 accelerates the transport of electrons to the light emitting layer 145. The electron transport layer 146 enables electrons supplied from the cathode 148 to be readily transferred to the light emitting layer 145.

For example, the electron transport layer 146 may be imidazole, oxadiazole, triazole, phenanthroline, benzoxazole, benzothiazole, benzimidazole, triazine, and derivatives thereof, but may not be limited thereto.

For example, the electron transport layer 146 may be selected from Liq(8-hydroxyquinolinolato-lithium), PBD (2-(4-biphenyl)-5-(4-tert-butylphenyl)-1,3,4-oxadiazole), TAZ (3-(4-biphenyl)4-phenyl-5-tert-butylphenyl-1,2,4-triazole), spiro-PBD, BCP (2,9-Dimethyl-4,7-diphenyl-1,10-phenanthroline) and BAlq (bis(2-methyl-8-quinolinolate)-4-(phenylphenolato)aluminium), but may not be limited thereto.

Although not illustrated in FIG. 2, a hole blocking layer may be disposed between the light emitting layer 145 and the electron transport layer 146. The hole blocking layer may block the leakage of holes from the light emitting layer 145 to the electron transport layer 146, resulting in excellent recombination efficiency of holes and electrons in the light emitting layer 145. As such, the electron blocking layer 144 may be disposed on one surface of the light emitting layer 145 and the hole blocking layer may be disposed on the other surface. In this case, holes injected from the anode 141 and electrons injected from the cathode 148 are trapped in the light emitting layer. Therefore, the recombination efficiency of electrons and holes may be further improved. Accordingly, it is possible to lower a driving voltage of the organic light emitting display device 100 and improve the luminous efficiency and luminance. Also, it is possible to improve the luminescence lifetime of the organic light emitting display device 100.

The electron injection layer 147 is disposed on the electron transport layer 146. The electron injection layer 147 enables electrons supplied from the cathode 148 to be smoothly injected into the electron transport layer 146. For example, the electron injection layer 147 may be formed containing one or more members of $BaF_2$, LiF, CsF, NaF, $BaF_2$, $Li_2O$, Bao, Liq (lithium quinolate) and lithium benzoate, but may not be limited thereto.

The cathode 148 is disposed on the electron injection layer 147. The cathode 148 may be formed of a metal material having a low work function for smoothly supplying electrons to the light emitting layer 145. For example, the cathode 148 may be formed of a metal material selected from Ca, Ba, Al, Ag and alloys containing one or more thereof, but may not be limited thereto.

Referring to FIG. 1, the cathode 148 is not patterned and formed as a single layer on the anode 141. That is, the cathode 148 is formed as a single layer in the red sub-pixel R, the green sub-pixel G and the blue sub-pixel B regions. If the organic light emitting display device 100 is driven in the top emission type, the cathode 148 may be formed to a very small thickness and thus may be substantially transparent.

Although not illustrated in FIG. 1 and FIG. 2, a protection layer is formed on the cathode 148 to suppress the permeation of moisture or oxygen from the outside into the organic light emitting element. For example, the protection layer may have a structure in which an inorganic layer of an inorganic insulating material and an organic layer of an organic material are laminated but may not be limited thereto. For another example, the protection layer may be formed by depositing a compound such as N4,N4'-bis[4-[bis(3-methylphenyl)amino]phenyl]-N4,N4'-diphenyl-[1,1'-biphenyl]-4,4'-diamine (DNTPD) or N4,N4'-diphenyl-N4, N4'-bis(4-(9-phenyl-9H-carbazol-3-yl)phenyl)-[1,1'-biphenyl]-4,4'-diamine to form a capping layer and then bonding a seal cap containing a moisture absorbent thereon using an adhesive member.

The organic light emitting display device 100 according to an exemplary embodiment of the present disclosure includes the organic compound represented by Chemical Formula 1 as the electron blocking layer 144. Thus, it is possible to effectively block electrons leaking from the light emitting layer 145 to the hole transport layer 143 or the hole injection layer 142. By blocking the leakage of electrons from the light emitting layer 145, the recombination efficiency of electrons and holes in the light emitting layer 145 may be improved. Thus, all the luminous efficiency, luminance and lifetime of the organic light emitting display device 100 may be improved. Therefore, according to an exemplary embodiment of the present disclosure, it is possible to provide the organic light emitting display device 100 which has high luminous efficiency and long lifetime.

As described above, the compound represented by Chemical Formula 1 has hole transport properties and electron blocking properties. Therefore, the compound represented by Chemical Formula 1 may be applied to a hole transport layer and/or electron blocking layer among organic layers of an organic light emitting display device.

Figure 3:
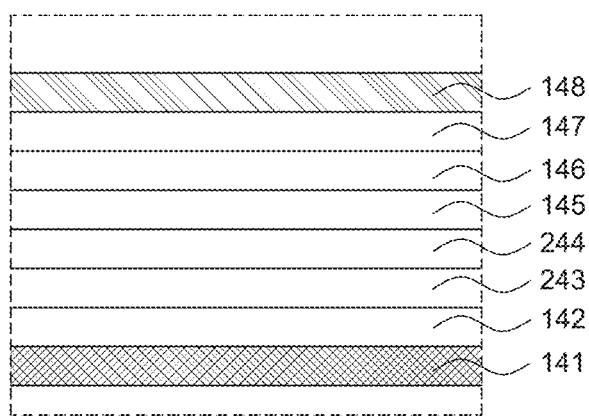
FIG. 3 is a cross-sectional view of a blue organic light emitting element of an organic light emitting display device according to another exemplary embodiment of the present disclosure.

FIG. 3 is a cross-sectional view of a blue organic light emitting element of an organic light emitting display device according to another exemplary embodiment of the present disclosure. The organic light emitting display device according to another exemplary embodiment of the present disclosure is substantially the same as the exemplary embodiment illustrated in FIG. 1 and FIG. 2 except the compound represented by Chemical Formula 1 is used in a hole transport layer instead of an electron blocking layer of the blue organic light emitting element. Therefore, redundant explanation thereof will be omitted.

Referring to FIG. 3, the blue organic light emitting element 240B includes the anode 141, the hole injection layer 142, a hole transport layer 243, an electron blocking layer 244, the light emitting layer 145, the electron transport layer 146, the electron injection layer 147 and the cathode 148.

The hole transport layer 243 contains the compound represented by Chemical Formula 1. The compound represented by Chemical Formula 1 has excellent hole transport properties and thus may easily transport holes injected from the anode 141 to the light emitting layer 145. Therefore, the recombination efficiency of holes and electrons in the light emitting layer 145 may be improved.

Also, the compound represented by Chemical Formula 1 has electron blocking properties as well as the hole transport properties. Therefore, the hole transport layer 243 containing the compound represented by Chemical Formula 1 may easily transport holes injected from the anode 141 to the light emitting layer 145. Also, the hole transport layer 243 containing the compound represented by Chemical Formula 1 may suppress the leakage of electrons, which have been injected from the cathode 148 into the light emitting layer 145, to the hole transport layer 243.

Therefore, it is possible to control and balance flows of electrons and holes.

For example, the electron blocking layer 244 may contain a known electron blocking compound such as N-phenyl-N-(4-(spiro[benzo[de]anthracene-7,9'-fluoren]-2'-yl)phenyl) dibenzo[b,d]furan-4-amine, N-phenylcarbazole, polyvinylcarbazole, N,N'-bis(3-methylphenyl)-N,N'-diphenyl-[1,1-biphenyl]-4,4'-diamine or 4,4'-cyclohexylidene bis[N,N-bis (4-methylphenyl)benzenamine].

Since the compound represented by Chemical Formula 1 contained in the hole transport layer has electron blocking properties, the electron blocking layer 244 may be omitted as necessary.

Hereinafter, the above-described effects of the present disclosure will be described in more detail with reference to Exemplary Embodiments and Comparative Embodiments. However, the following Exemplary Embodiments are provided for the purpose of illustration, but do not limit the scope of the present disclosure.

Synthesis Embodiment 1: Synthesis of Compound 1

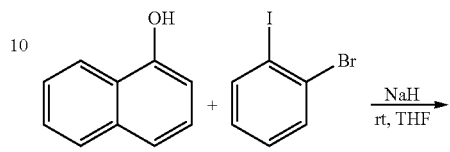

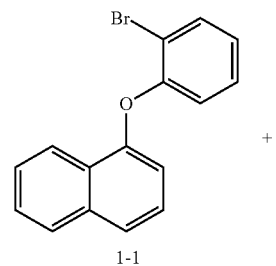

1-1

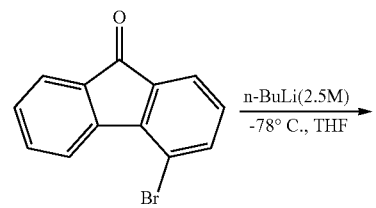

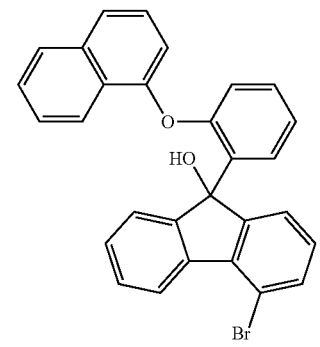

1-2

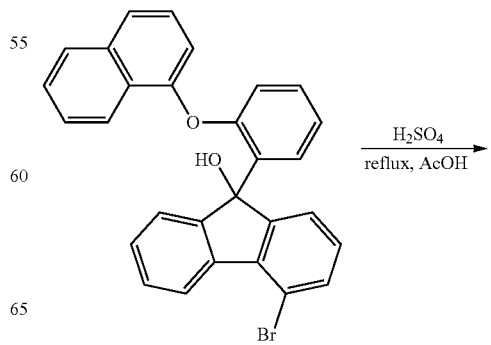

-continued

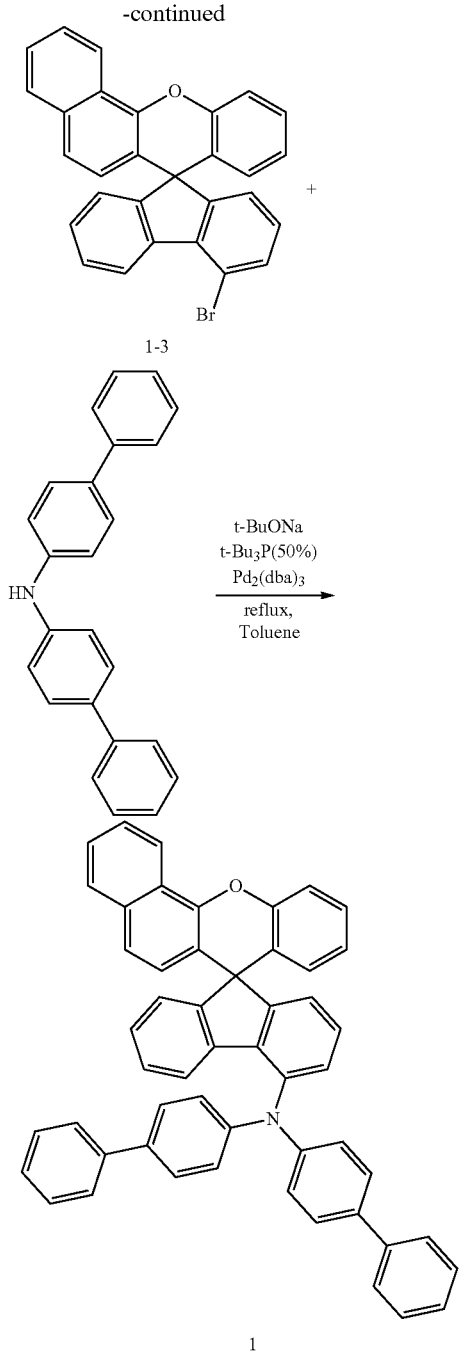

(1) Synthesis of Intermediate 1-1

6.2 g of 1-naphthol (42 mmol) was dissolved in 60 ml of anhydrous tetrahydrofuran in a nitrogen atmosphere. Then, after 4 g of sodium hydride (168 mmol) was very slowly added thereto, 11.8 g of 1-bromo-2-iodobenzene (42 mmol) was added thereto. Then, the reaction solution was reacted at room temperature for 16 hours with stirring. After completion of the reaction, an organic layer was worked up with 100 ml of water and 100 ml of dichloromethane. The organic layer was dried with MgSO$_4$ and then, the filtrate was distilled. Then, the reaction product was purified by column chromatography to obtain 8.2 g of intermediate 1-1 (1-(2-bromophenoxy) naphthalene)(yield: 65.2%).

(2) Synthesis of Intermediate 1-2

12 g of 1-(2-bromophenoxy) naphthalene (40 mmol) was dissolved in 60 ml of anhydrous tetrahydrofuran in a nitrogen atmosphere and maintained at −78° C. for 30 minutes. Then, 20 g of 2.5 M n-butyllithium (48 mmol) was slowly added thereto and stirred at −78° C. for 3 hours. Then, 10.4 g of 4-bromo-9H-fluoren-9-one (40 mmol) was dissolved in 100 ml of anhydrous tetrahydrofuran and then added dropwise thereto. After dropwise, addition was completed, the reaction product was reacted for 12 hours with stirring. After completion of the reaction, an organic layer was worked up with 300 ml of ethyl acetate and 500 ml of water. The organic layer was dried with MgSO$_4$ and then the filtrate was distilled. Then, the reaction product was purified by column chromatography and recrystallized with heptane/dichloromethane to obtain 13 g of intermediate 1-2 (4-bromo-9-(2-(naphthalene-1-yloxy)phenyl)-9H-fluoren-9-ol) (yield: 67%).

(3) Synthesis of Intermediate 1-3

12 g of 4-bromo-9-(2-(naphthalene-1-yloxy)phenyl)-9H-fluoren-9-ol (25 mmol) was dissolved in 120 ml of acetic acid at 90° C. in a nitrogen atmosphere. Then, 0.24 g of sulfuric acid (2.5 mmol) was added thereto and reacted at 120° C. for 3 hours with stirring. After completion of the reaction, the reaction product was cooled to room temperature and an organic layer was worked up with 300 ml of ethyl acetate and 300 ml of water. The organic layer was dried with MgSO$_4$ and then the filtrate was distilled. Then, the reaction product was purified by column chromatography and recrystallized with methanol/dichloromethane to obtain 11 g of intermediate 1-3 (4'-bromospiro(benzo[c]xanthene-7,9'-fluoren))(yield: 95%).

(4) Synthesis of Compound 1

5.0 g of 4'-bromospiro(benzo[c]xanthene-7,9'-fluoren) (11 mmol), 3.37 g of di(1,1'-biphenyl-4-yl)amine (10.5 mmol) and 2.02 g of sodium tert-butoxide (21 mmol) were dissolved in 100 ml of toluene and maintained at 60° C. for 30 minutes in a nitrogen atmosphere. Then, 0.20 g of tris(dibenzylideneacetone)dipalladium(0) (0.20 mmol) and 0.20 ml of tri-tert-butylphosphine (50 wt % in toluene) (solute: 0.80 mmol) were added thereto. Then, the reaction product was reacted at from 100° C. to 110° C. for 5 hours under reflux. After completion of the reaction, the reaction product was cooled to room temperature and an organic layer was worked up with 300 ml of water and 200 ml of dichloromethane. The organic layer was dried with MgSO$_4$ and then the filtrate was distilled. Then, the reaction product was purified by column chromatography and recrystallized with methanol/dichloromethane to obtain 3.6 g of compound 1 (yield: 48.8%).

MALDI-TOF MS: m/z=701.27 (C$_{53}$H$_{35}$NO=701.87)

Synthesis Embodiment 2: Synthesis of Compound 2

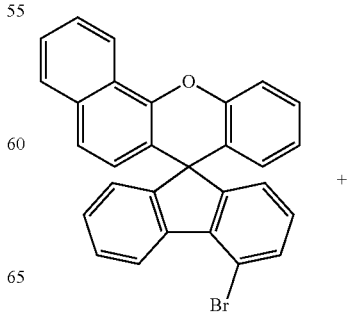

-continued

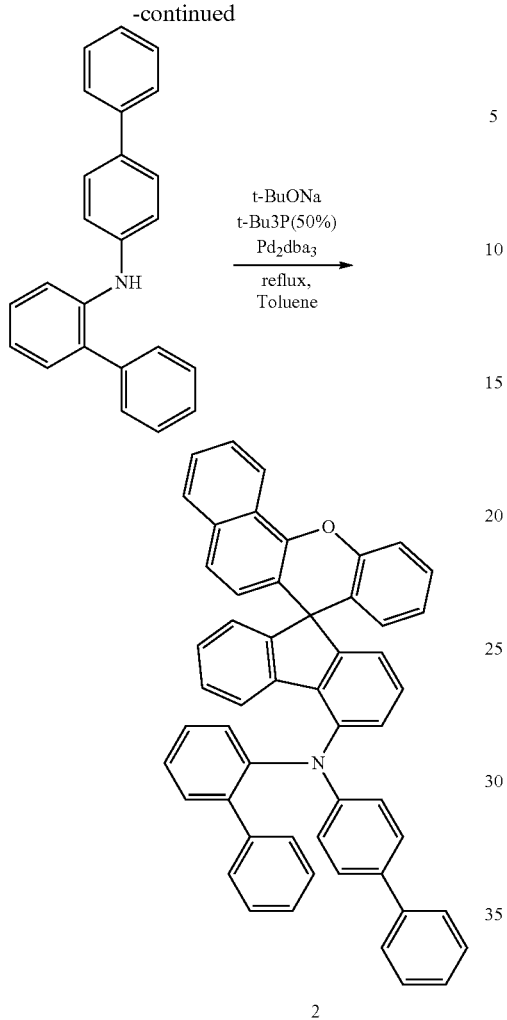

2

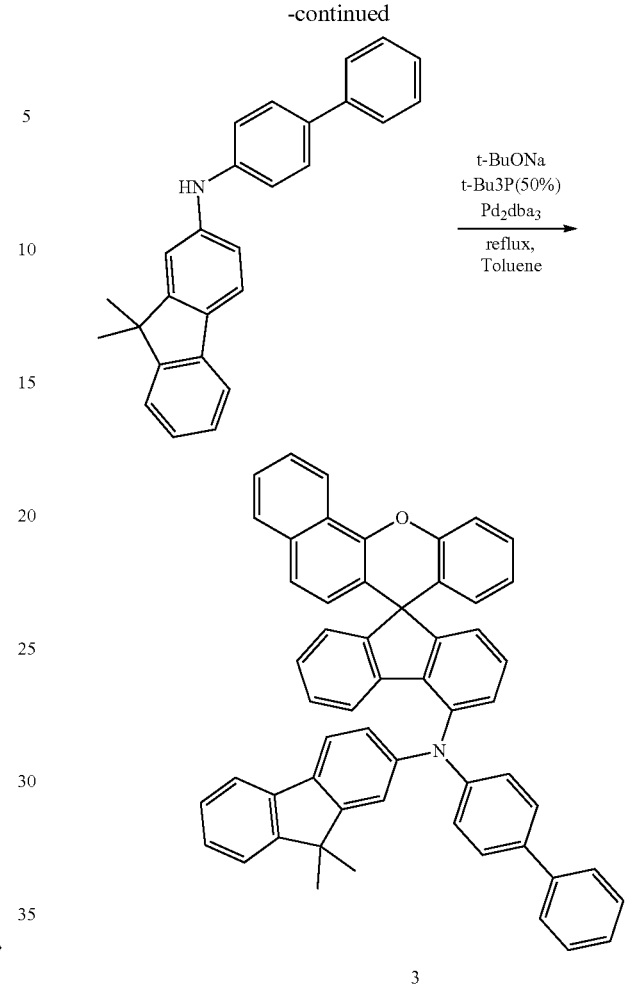

3

3.5 g of compound 2 (yield: 47.5%) was obtained in the same manner as in Process (4) of Synthesis Embodiment 1 except that 3.37 g of N-([1,1'-biphenyl]-4-yl)-[1,1'-biphenyl]-2-amine (10.5 mmol) was used instead of 3.37 g of di(1,1'-biphenyl-4-yl)amine (10.5 mmol) in Process (4) of Synthesis Embodiment 1.

MALDI-TOF MS: m/z=701.27 ($C_{53}H_{35}NO$=701.87)

Synthesis Embodiment 3: Synthesis of Compound 3

3.41 g of compound 3 (yield: 52.6%) was obtained in the same manner as in Process (4) of Synthesis Embodiment 1 except that 3.79 g of N-([1,1'-biphenyl]-4-yl)-9,9-dimethyl-9H-fluoren-2-amine (10.5 mmol) was used instead of 3.37 g of di(1,1'-biphenyl-4-yl)amine (10.5 mmol) in Process (4) of Synthesis Embodiment 1.

MALDI-TOF MS: m/z=741.30 ($C_{56}H_{39}NO$=741.93)

Synthesis Embodiment 4: Synthesis of Compound 4

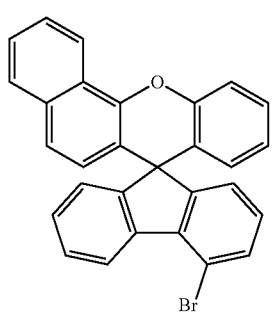 +

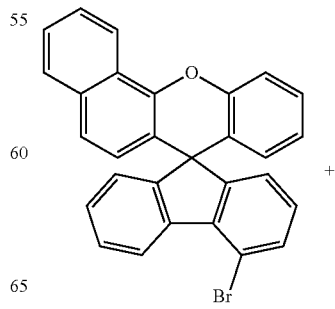 +

301
-continued

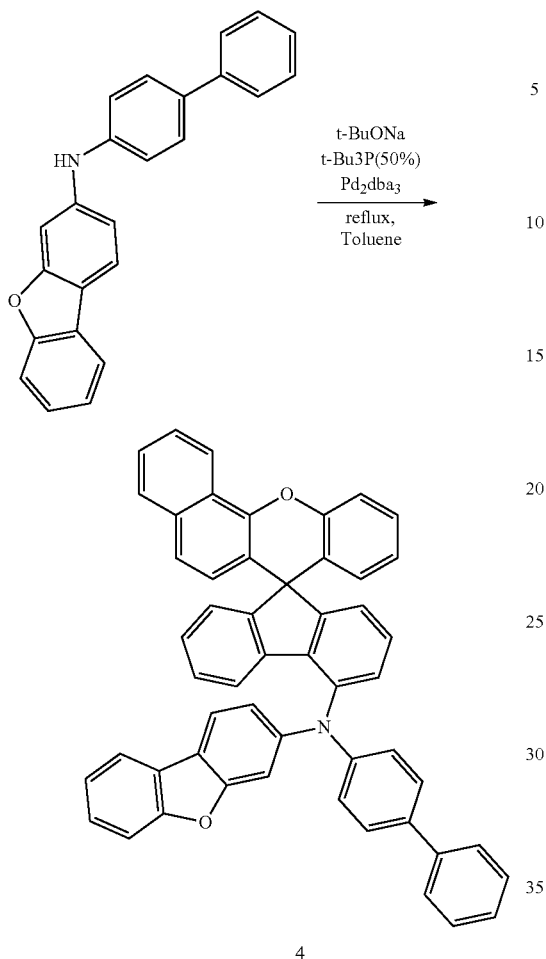

4

4.3 g of compound 4 (yield: 57.2%) was obtained in the same manner as in Process (4) of Synthesis Embodiment 1 except that 3.52 g of N-([1,1'-biphenyl]-4-yl)dibenzo[b,d]furan-3-amine (10.5 mmol) was used instead of 3.37 g of di(1,1'-biphenyl-4-yl)amine (10.5 mmol) in Process (4) of Synthesis Embodiment 1.

MALDI-TOF MS: m/z=715.25 ($C_{53}H_{33}NO_2$=715.85)

Synthesis Embodiment 5: Synthesis of Compound 5

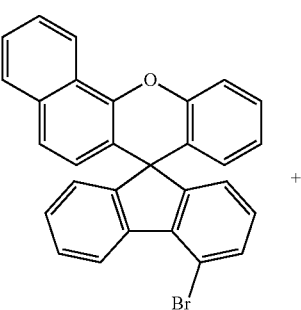

+

302
-continued

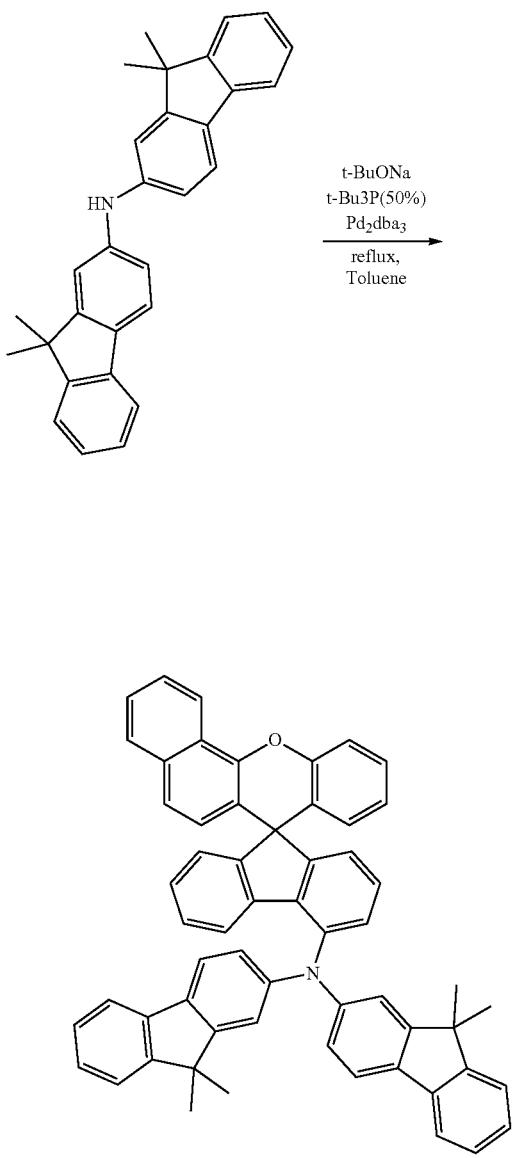

5

4.6 g of compound 5 (yield: 56.0%) was obtained in the same manner as in Process (4) of Synthesis Embodiment 1 except that 4.21 g of bis(9,9-dimethyl-9H-fluoren-2-yl)amine (10.5 mmol) was used instead of 3.37 g of di(1,1'-biphenyl-4-yl)amine (10.5 mmol) in Process (4) of Synthesis Embodiment 1.

MALDI-TOF m/z=781.33 ($C_{59}H_{43}NO$=782.00)

Synthesis Embodiment 6: Synthesis of Compound 6

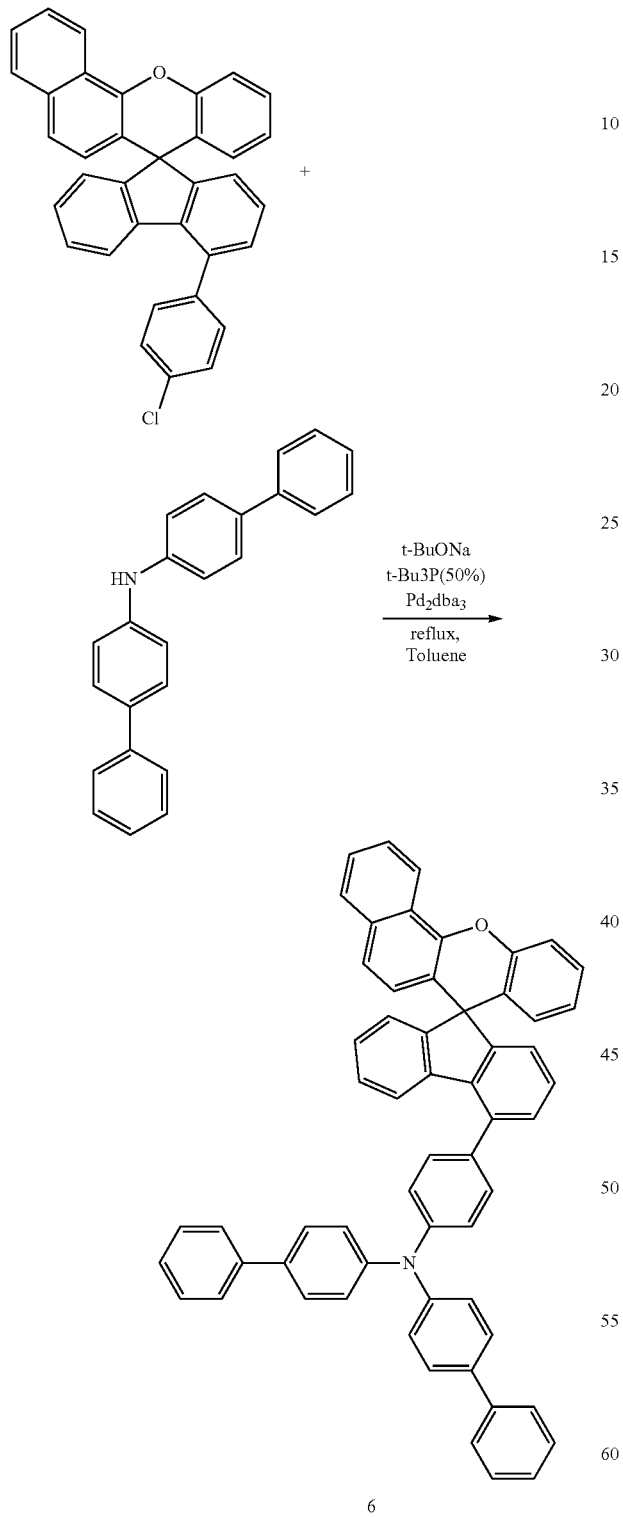

Synthesis Embodiment 7: Synthesis of Compound 7

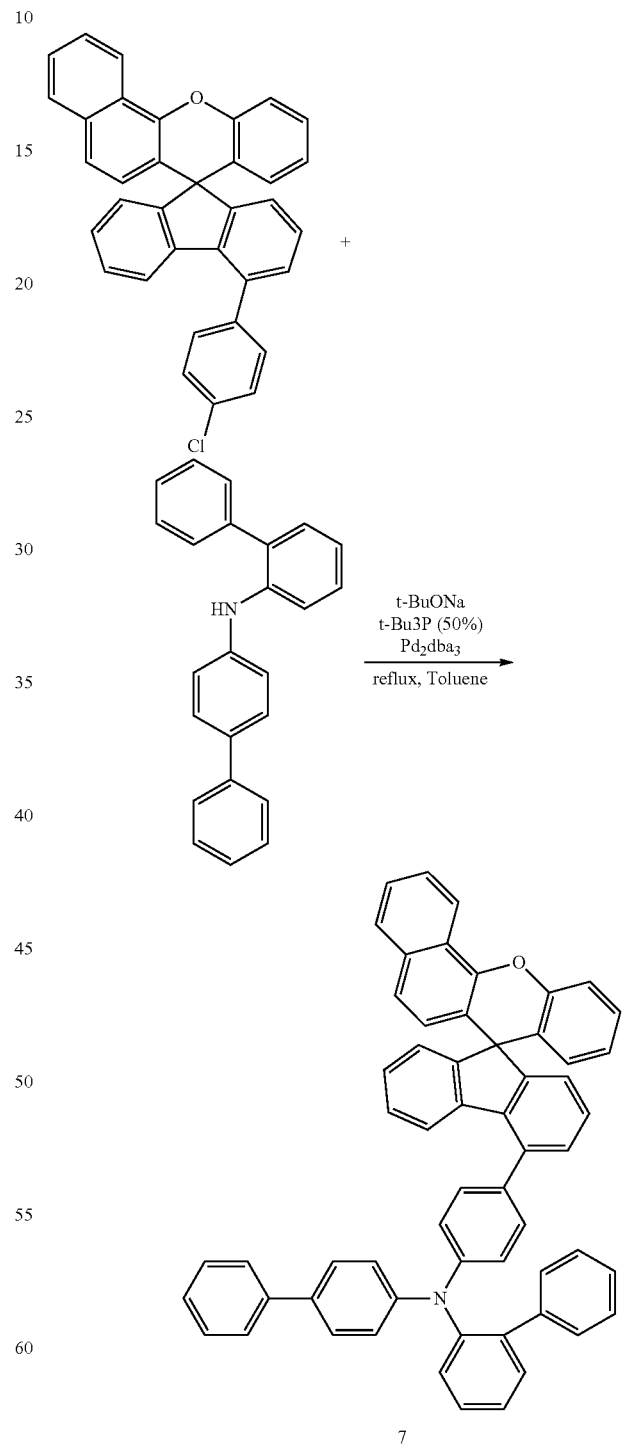

4.1 g of compound 6 (yield: 50.2%) was obtained in the same manner as in Process (4) of Synthesis Embodiment 1 except that 5.7 g of 4'-(4-chlorophenyl)spiro(benzo[c]xanthene-7,9'-fluoren) (11 mmol) was used instead of 5.0 g of 41-bromospiro(benzo[c]xanthene-7,9'-fluoren) (11 mmol) in Process (4) of Synthesis Embodiment 1.

MALDI-TOF m/z=777.30 ($C_{59}H_{39}NO$=777.97)

4.4 g of compound 7 (yield: 53.8%) was obtained in the same manner as in Process (4) of Synthesis Embodiment 1 except that 5.7 g of 4'-(4-chlorophenyl)spiro(benzo[c]xanthene-7,9'-fluoren) (11 mmol) was used instead of 5.0 g of 4'-bromospiro(benzo[c]xanthene-7,9'-fluoren) (11 mmol) and 3.37 g of N-([1,1'-biphenyl]-4-yl)-[1,1'-biphenyl]-2-amine (10.5 mmol) was used instead of 3.37 g of di(1,1'-biphenyl-4-yl)amine (10.5 mmol) in Process (4) of Synthesis Embodiment 1.

MALDI-TOF MS: m/z=777.30 ($C_{59}H_{39}NO$=777.97)

Synthesis Embodiment 8: Synthesis of Compound 8

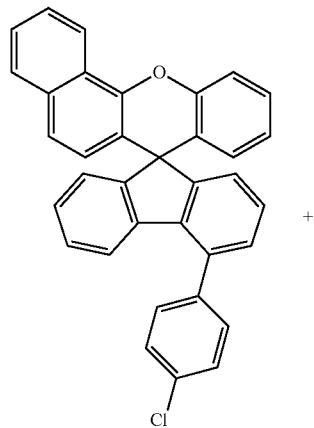
+

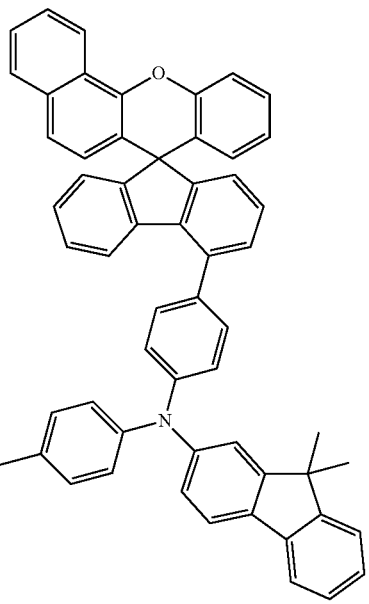

8

4.6 g of compound 8 (yield: 53.5%) was obtained in the same manner as in Process (4) of Synthesis Embodiment 1 except that 5.7 g of 4'-(4-chlorophenyl)spiro(benzo[c]xanthene-7,9'-fluoren) (11 mmol) was used instead of 5.0 g of 4'-bromospiro(benzo[c]xanthene-7,9'-fluoren) (11 mmol) and 3.79 g of N-([1,1'-biphenyl]-4-yl)-9,9-dimethyl-9H-fluoren-2-amine (10.5 mmol) was used instead of 3.37 g of di(1,1'-biphenyl-4-yl)amine (10.5 mmol) in Process (4) of Synthesis Embodiment 1.

MALDI-TOF MS: m/z=817.33 ($C_{62}H_{43}NO$=818.03)

Synthesis Embodiment 9: Synthesis of Compound 9

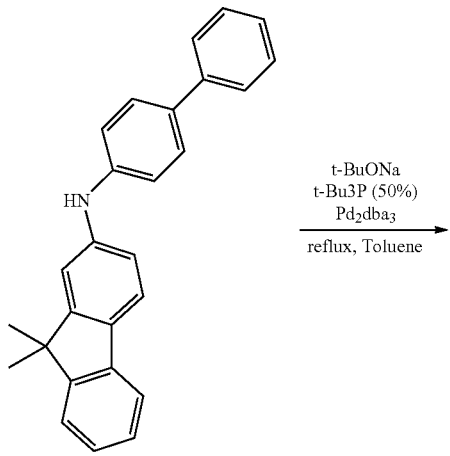 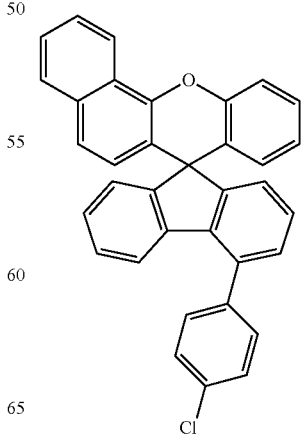
+

Synthesis Embodiment 10: Synthesis of Compound 10

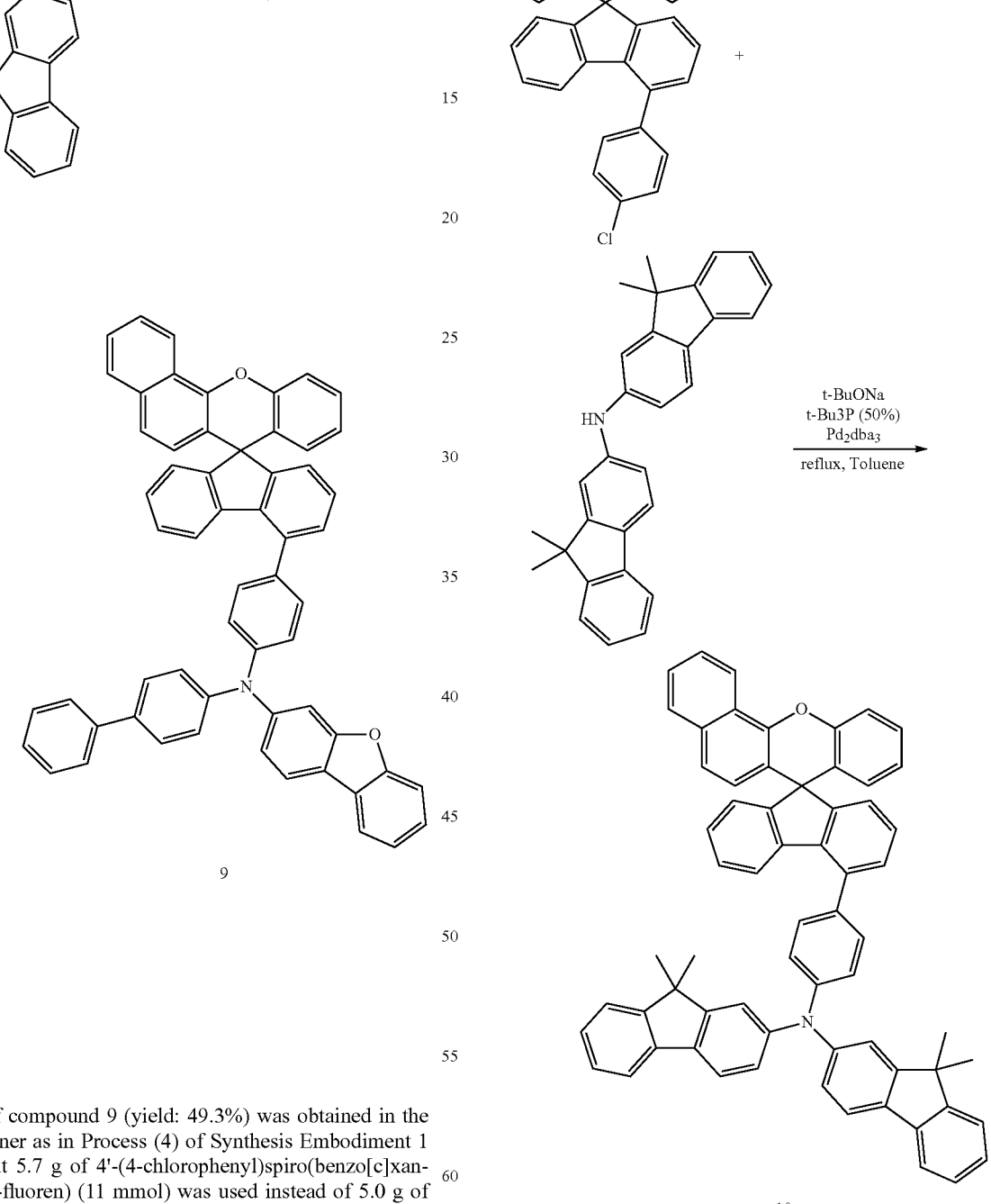

4.1 g of compound 9 (yield: 49.3%) was obtained in the same manner as in Process (4) of Synthesis Embodiment 1 except that 5.7 g of 4'-(4-chlorophenyl)spiro(benzo[c]xanthene-7,9'-fluoren) (11 mmol) was used instead of 5.0 g of 4'-bromospiro(benzo[c]xanthene-7,9'-fluoren) (11 mmol) and 3.52 g of N-([1,1'-biphenyl]-4-yl)dibenzo[b,d]furan-3-amine (10.5 mmol) was used instead of 3.37 g of di(1,1'-biphenyl-4-yl)amine (10.5 mmol) in Process (4) of Synthesis Embodiment 1.

MALDI-TOF MS: m/z=791.28 ($C_{59}H_{37}NO_2$=791.95)

4.3 g of compound 10 (yield: 47.7%) was obtained in the same manner as in Process (4) of Synthesis Embodiment 1 except that 5.7 g of 4'-(4-chlorophenyl)spiro(benzo[c]xanthene-7,9'-fluoren) (11 mmol) was used instead of 5.0 g of 4'-bromospiro(benzo[c]xanthene-7,9'-fluoren) (11 mmol) and 4.21 g of bis(9,9-dimethyl-9H-fluoren-2-yl)amine (10.5 mmol) was used instead of 3.37 g of di(1,1'-biphenyl-4-yl) amine (10.5 mmol) in Process (4) of Synthesis Embodiment 1.

MALDI-TOF MS: m/z=857.37 ($C_{65}H_{47}NO$=858.10)

Synthesis Embodiment 11: Synthesis of Compound 11

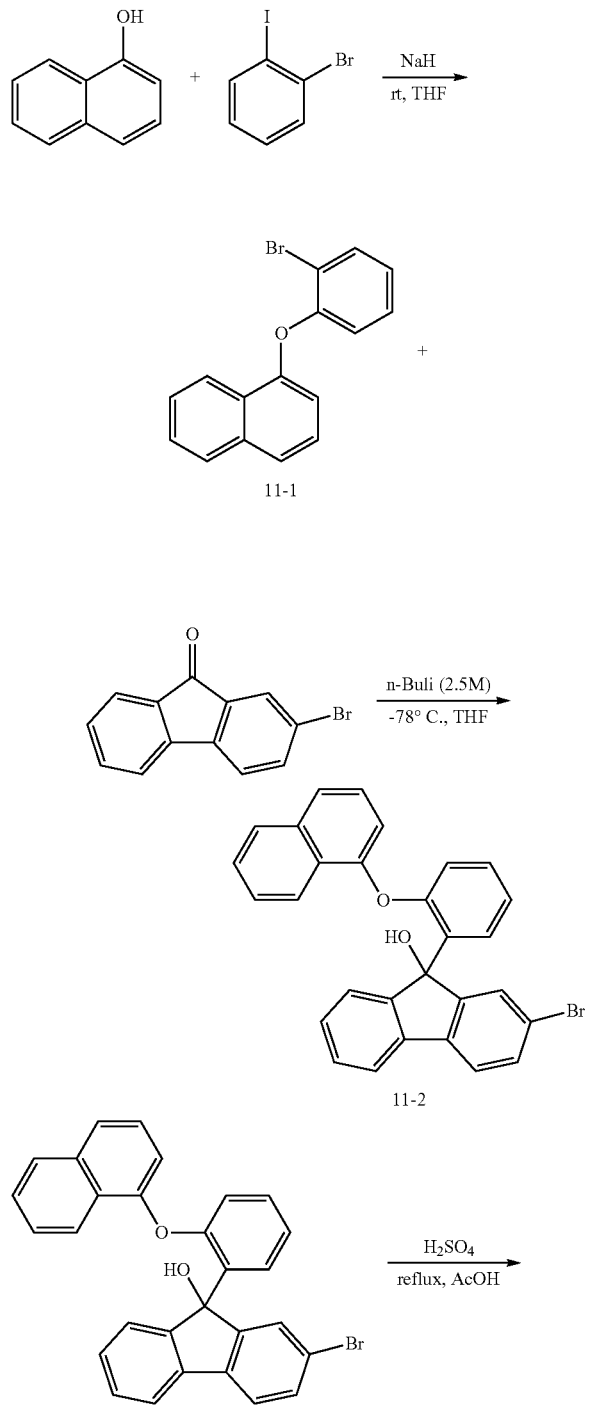

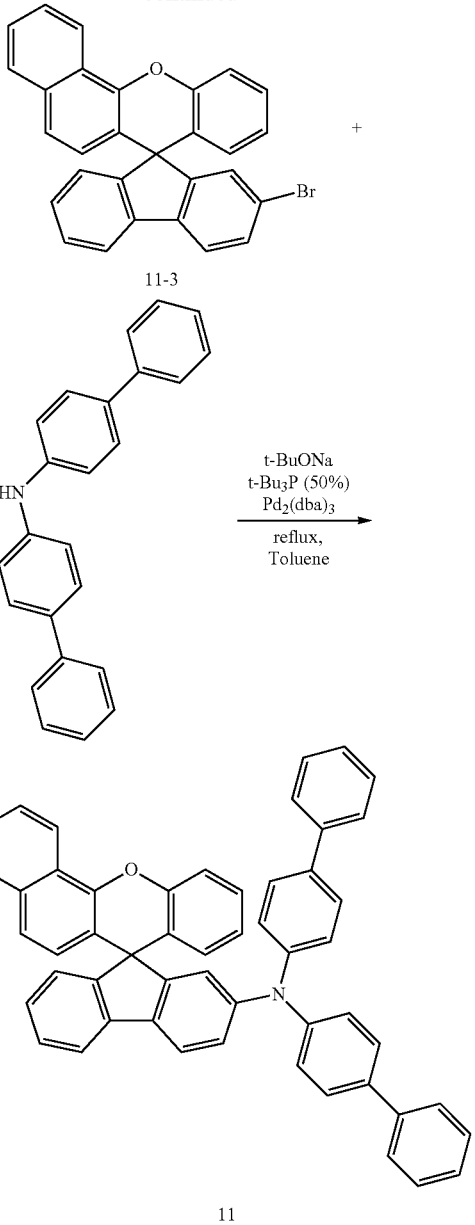

(1) Synthesis of Intermediate 11-1

6.2 g of 1-naphthol (42 mmol) was dissolved in 60 ml of anhydrous tetrahydrofuran in a nitrogen atmosphere. Then, after 4 g of sodium hydride (168 mmol) was very slowly added thereto, 11.8 g of 1-bromo-2-iodobenzene (42 mmol) was added thereto. Then, the reaction solution was reacted at room temperature for 16 hours with stirring. After completion of the reaction, an organic layer was worked up with 100 ml of water and 100 ml of dichloromethane. The organic layer was dried with $MgSO_4$ and then, the filtrate was distilled. Then, the reaction product was purified by column chromatography to obtain 8.2 g of intermediate 11-1 (1-(2-bromophenoxy) naphthalene)(yield: 65.2%).

(2) Synthesis of Intermediate 11-2 was 12 g of 1-(2-bromophenoxy) naphthalene (40 mmol) was dissolved in 60 ml of tetrahydrofuran in a nitrogen atmosphere and maintained at −78° C. for 30 minutes. Then, 20 g of 2.5 M n-butyllithium (48 mmol) was slowly added thereto and stirred at −78° C. for 3 hours. Then, 10.4 g of 2-bromo-9H-fluoren-9-one (40 mmol) was dissolved in 100 ml of tetrahydrofuran and then added dropwise thereto. Then, the reaction product was reacted for 12 hours with stirring. After completion of the reaction, an organic layer was worked up with 300 ml of ethyl acetate and 500 ml of water. The organic layer was dried with MgSO$_4$ and then the filtrate was distilled. Then, the reaction product was purified by column chromatography and recrystallized with heptane/dichloromethane to obtain 11 g of intermediate 11-2 (2-bromo-9-(2-(naphthalene-1-yloxy)phenyl)-9H-fluoren-9-ol) (yield: 57.4%).

(3) Synthesis of Intermediate 11-3

11 g of 2-bromo-9-(2-(naphthalene-1-yloxy)phenyl)-9H-fluoren-9-ol (23 mmol) was dissolved in 120 ml of acetic acid at 90° C. in a nitrogen atmosphere. Then, 0.23 g of sulfuric acid (2.3 mmol) was added thereto and reacted at 120° C. for 3 hours with stirring. After completion of the reaction, the reaction product was cooled to room temperature and an organic layer was worked up with 300 ml of ethyl acetate and 300 ml of water. The organic layer was dried with MgSO$_4$ and then the filtrate was distilled. Then, the reaction product was purified by column chromatography and recrystallized with methanol/dichloromethane to obtain 9.8 g of intermediate 11-3 (2'-bromospiro(benzo[c]xanthene-7,9'-fluoren))(yield: 92.4%).

(4) Synthesis of Compound 11

9.0 g of 2'-bromospiro(benzo[c]xanthene-7,9'-fluoren) (20 mmol), 6.43 g of di(1,1'-biphenyl-4-yl)amine (19.05 mmol) and 3.66 g of sodium tert-butoxide (38.10 mmol) were dissolved in 100 ml of toluene and maintained at 60° C. for 30 minutes in a nitrogen atmosphere. Then, 0.35 of g tris(dibenzylideneacetone)dipalladium(0) (0.38 mmol) and 0.36 ml of tri-tert-butylphosphine (50 wt % in toluene) (solute: 1.52 mmol) were added thereto. Then, the reaction product was reacted at from 100° C. to 110° C. for 5 hours under reflux. After completion of the reaction, the reaction product was cooled to room temperature and an organic layer was worked up with 300 ml of water and 200 ml of dichloromethane. The organic layer was dried with MgSO$_4$ and then the filtrate was distilled. Then, the reaction product was purified by column chromatography and recrystallized with methanol/dichloromethane to obtain 6.8 g of compound 11 (yield: 50.9%).

MALDI-TOF MS: m/z=701.27 (C$_{53}$H$_{35}$NO=701.87)

Synthesis Embodiment 12: Synthesis of Compound 12

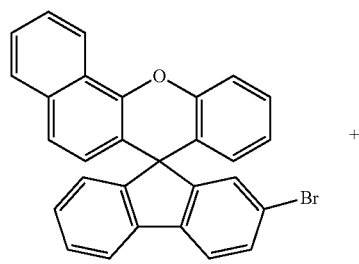

+

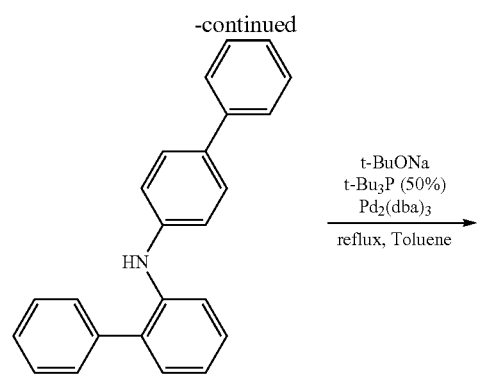

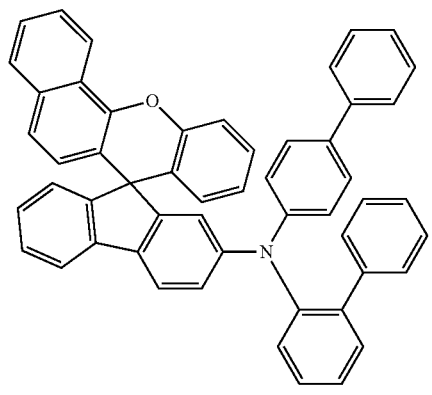

6.2 g of compound 12 (yield: 46.4%) was obtained in the same manner as in Process (4) of Synthesis Embodiment 11 except that 6.43 g of N-([1,1'-biphenyl]-4-yl)-[1,1'-biphenyl]-2-amine (19.05 mmol) was used instead of 6.43 g of di(1,1'-biphenyl-4-yl)amine (19.05 mmol) in Process (4) of Synthesis Embodiment 11.

MALDI-TOF MS: m/z=701.27 (C$_{53}$H$_{35}$NO=701.87)

Synthesis Embodiment 13: Synthesis of Compound 13

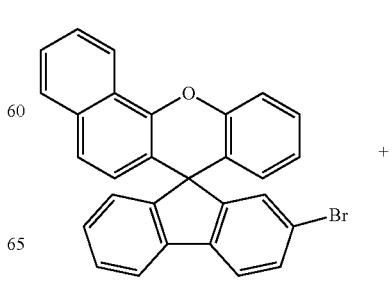

+

313
-continued

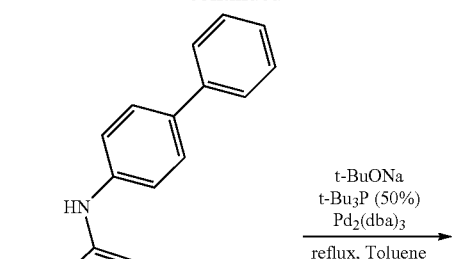

314
-continued

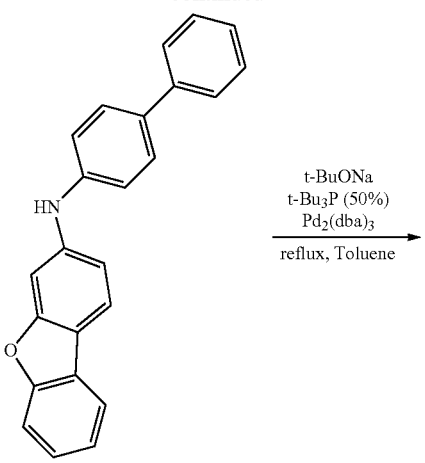

6.6 g of compound 13 (yield: 46.7%) was obtained in the same manner as in Process (4) of Synthesis Embodiment 11 except that 6.88 g of N-([1,1'-biphenyl]-4-yl)-9,9-dimethyl-9H-fluoren-2-amine (19.05 mmol) was used instead of 6.43 g of di(1,1'-biphenyl-4-yl)amine (19.05 mmol) in Process (4) of Synthesis Embodiment 11.

MALDI-TOF MS: m/z=741.30 ($C_{56}H_{39}NO$=741.93)

Synthesis Embodiment 14: Synthesis of Compound 14

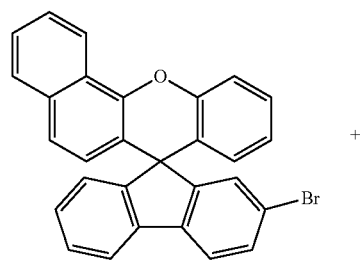

5.2 g of compound 14 (yield: 38.1%) was obtained in the same manner as in Process (4) of Synthesis Embodiment 11 except that 6.39 g of N-([1,1'-biphenyl]-4-yl)dibenzo[b,d]furan-3-amine (19.05 mmol) was used instead of 6.43 g of di(1,1'-biphenyl-4-yl)amine (19.05 mmol) in Process (4) of Synthesis Embodiment 11.

MALDI-TOF MS: m/z=715.25 ($C_{53}H_{33}NO_2$=715.85)

Synthesis Embodiment 15: Synthesis of Compound 15

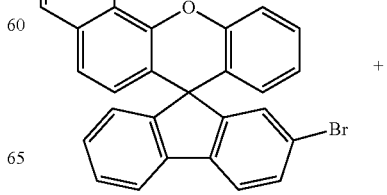

315
-continued

316
-continued

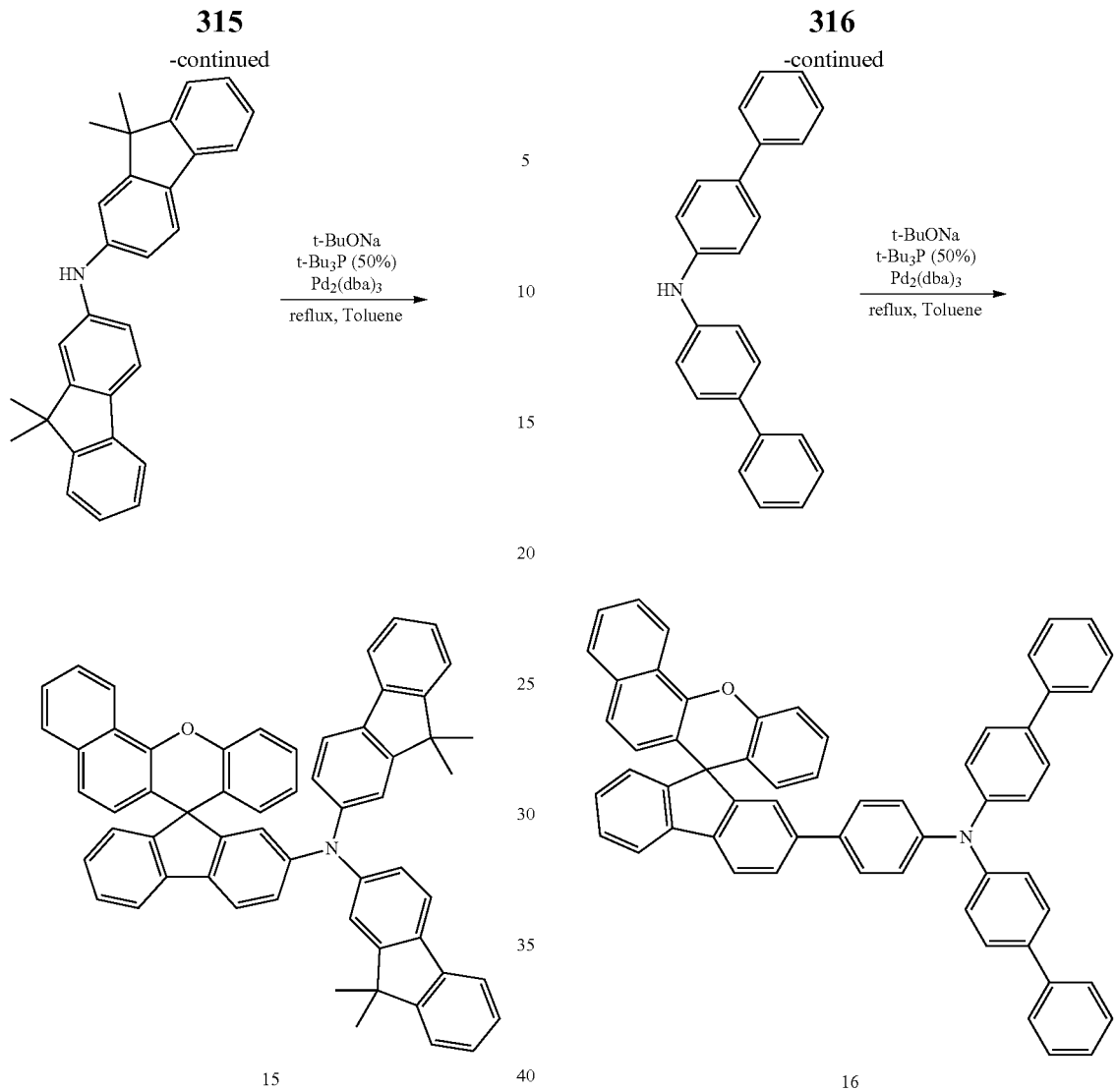

15

16

7.1 g of compound 15 (yield: 47.7%) was obtained in the same manner as in Process (4) of Synthesis Embodiment 11 except that 7.65 g of bis(9,9-dimethyl-9H-fluoren-2-yl)amine (19.05 mmol) was used instead of 6.43 g of di(1,1'-biphenyl-4-yl)amine (19.05 mmol) in Process (4) of Synthesis Embodiment 11.

MALDI-TOF MS: m/z=781.33 ($C_{59}H_{43}NO$=782.00)

Synthesis Embodiment 16: Synthesis of Compound 16

7.4 g of compound 16 (yield: 49.9%) was obtained in the same manner as in Process (4) of Synthesis Embodiment 11 except that 9.86 g of 2'-(4-chlorophenyl)spiro(benzo[c]xanthene-7,9'-fluoren) (20 mmol) was used instead of 9.0 g of 2'-bromospiro(benzo[c]xanthene-7,9'-fluoren) (20 mmol) in Process (4) of Synthesis Embodiment 11.

MALDI-TOF MS: m/z=777.30 ($C_{59}H_{39}NO$=777.97)

Synthesis Embodiment 17: Synthesis of Compound 17

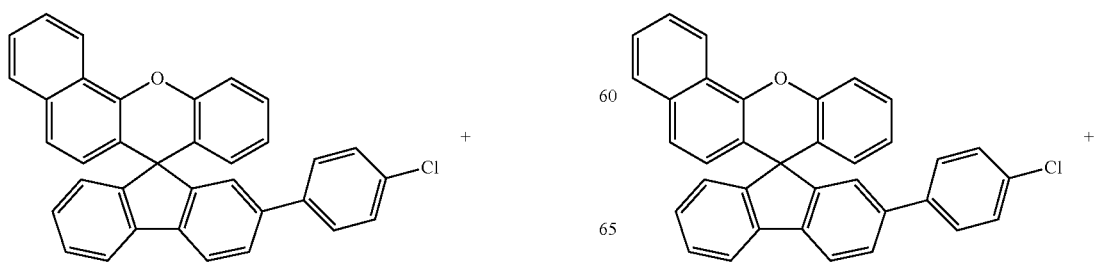

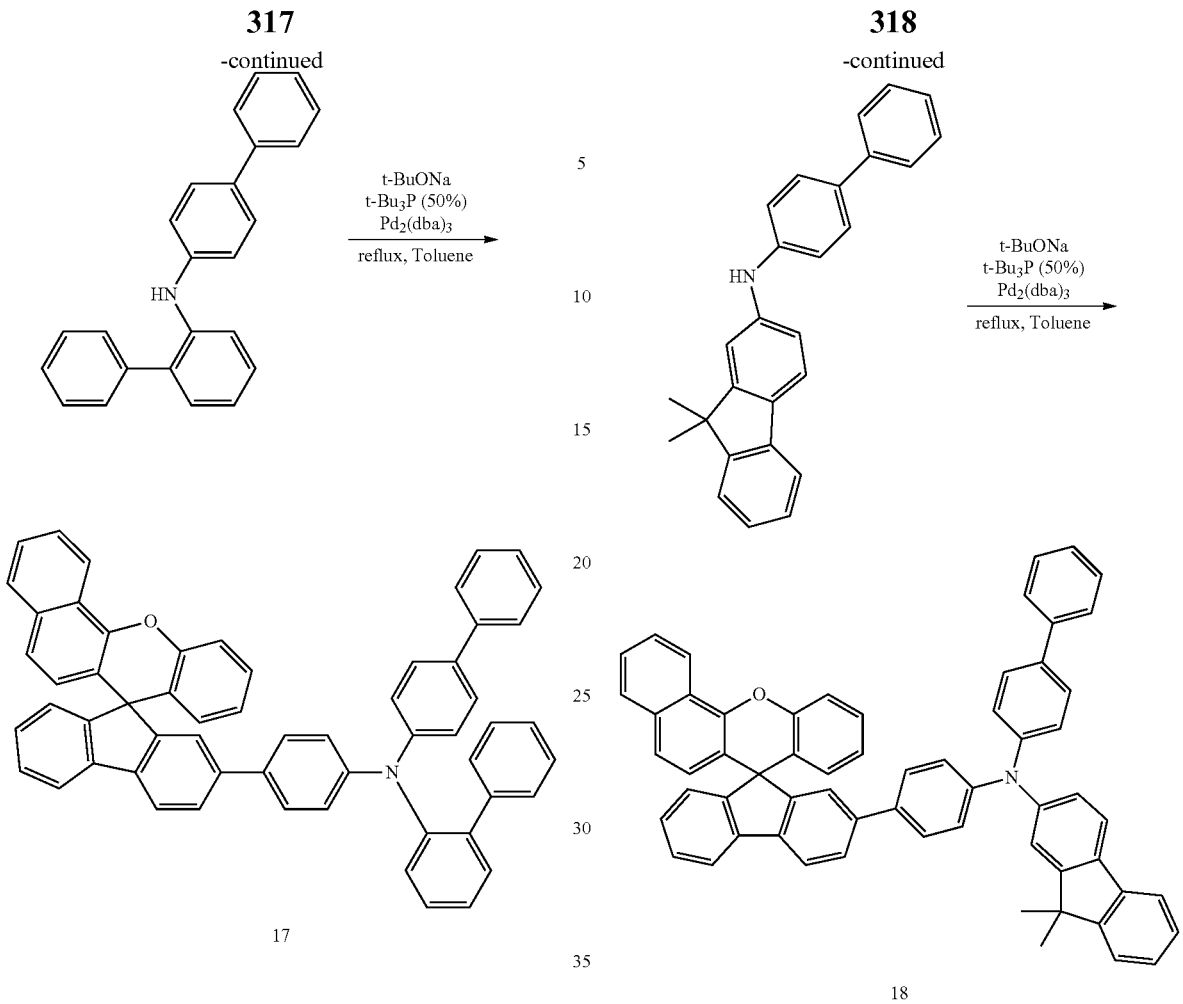

7.6 g of compound 17 (yield: 51.3%) was obtained in the same manner as in Process (4) of Synthesis Embodiment 11 except that 9.86 g of 2'-(4-chlorophenyl)spiro(benzo[c]xanthene-7,9'-fluoren) (20 mmol) was used instead of 9.0 g of 2'-bromospiro(benzo[c]xanthene-7,9'-fluoren) (20 mmol) and 6.43 g of N-([1,1'-biphenyl]-4-yl)-[1,1'-biphenyl]-2-amine (19.05 mmol) was used instead of 6.43 g of di(1,1'-biphenyl-4-yl)amine (19.05 mmol) in Process (4) of Synthesis Embodiment 11.

MALDI-TOF MS: m/z=777.30 ($C_{59}H_{39}NO$=777.97)

Synthesis Embodiment 18: Synthesis of Compound 18

7.9 g of compound 18 (yield: 50.7%) was obtained in the same manner as in Process (4) of Synthesis Embodiment 11 except that 9.86 g of 2'-(4-chlorophenyl)spiro(benzo[c]xanthene-7,9'-fluoren) (20 mmol) was used instead of 9.0 g of 2'-bromospiro(benzo[c]xanthene-7,9'-fluoren) (20 mmol) and 6.89 g of N-([1,1'-biphenyl]-4-yl)-9,9-dimethyl-9H-fluoren-2-amine (19.05 mmol) was used instead of 6.43 g of di(1,1'-biphenyl-4-yl)amine (19.05 mmol) in Process (4) of Synthesis Embodiment 11.

MALDI-TOF MS: m/z=817.33 ($C_{62}H_{43}NO$=818.03)

Synthesis Embodiment 19: Synthesis of Compound 19

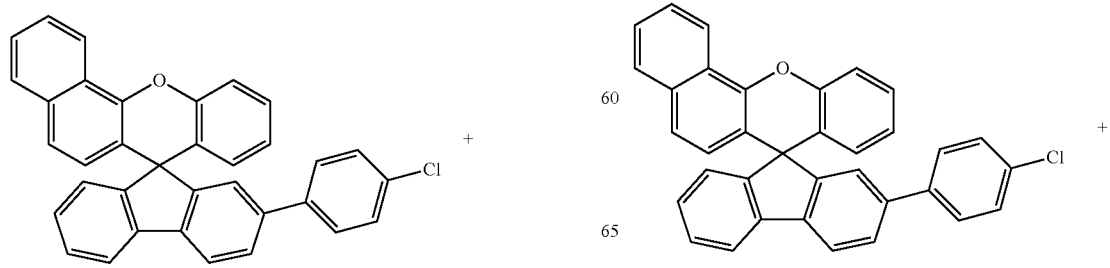

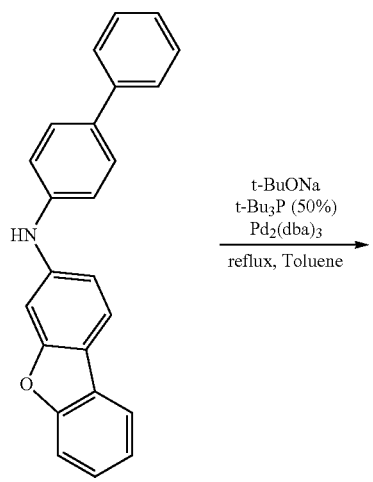

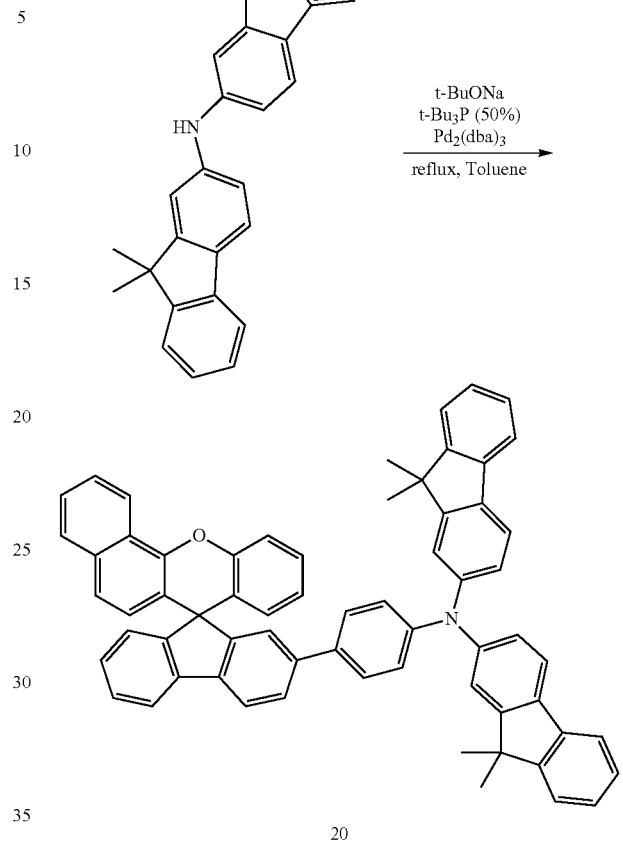

6.6 g of compound 19 (yield: 43.7%) was obtained in the same manner as in Process (4) of Synthesis Embodiment 11 except that 9.86 g of 2'-(4-chlorophenyl)spiro(benzo[c]xanthene-7,9'-fluoren) (20 mmol) was used instead of 9.0 g of 2'-bromospiro(benzo[c]xanthene-7,9'-fluoren) (20 mmol) and 6.39 g of N-([1,1'-biphenyl]-4-yl)dibenzo[b,d]furan-3-amine (19.05 mmol) was used instead of 6.43 g of di(1,1'-biphenyl-4-yl)amine (19:05 mmol) in Process (4) of Synthesis Embodiment 11.

MALDI-TOF MS: m/z=791.28 ($C_{59}H_{37}NO_2$=791.95)

Synthesis Embodiment 20: Synthesis of Compound 20

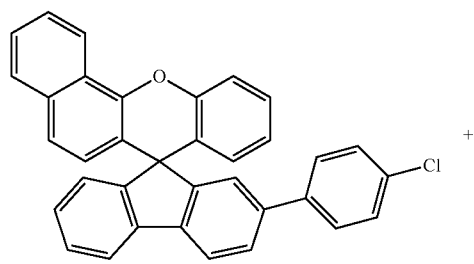

8.3 g of compound 20 (yield: 50.8%) was obtained in the same manner as in Process (4) of Synthesis Embodiment 11 except that 9.86 g of 2'-(4-chlorophenyl)spiro(benzo[c]xanthene-7,9'-fluoren) (20 mmol) was used instead of 9.0 g of 2'-bromospiro(benzo[c]xanthene-7,9'-fluoren) (20 mmol) and 7.67 g of bis(9,9-dimethyl-9H-fluoren-2-yl)amine (19.05 mmol) was used instead of 6.43 g of di(1,1'-biphenyl-4-yl)amine (19.05 mmol) in Process (4) of Synthesis Embodiment 11.

MALDI-TOF MS: m/z=857.37 ($C_{65}H_{47}NO$=858.10).

Example 1

An anode made of ITO (10 nm) was formed on a substrate including an Ag alloy layer as a light reflecting layer thereon and surface-treated by irradiating N2 plasma or UV-ozone thereto. Then, 1,4,5,8,9,11-hexaazatriphenylenehexacarbonitrile (HATCN) was deposited to a thickness of 10 nm on the ITO to form a hole injection layer. Thereafter, N4,N4,N4',N4'-tetra([1,1'-biphenyl]-4-yl)-[1,1'-biphenyl]-4,4'-diamine was deposited to a thickness of 110 nm on the hole injection layer to form a hole transport layer. Subsequently, Compound 1 prepared in Synthesis Embodiment 1 was deposited to a thickness of 10 nm on the hole transport layer to form an electron blocking layer. Then, while 9,10-bis(2-naphthyl) anthracene (ADN) was deposited on the electron blocking layer, 3 wt % of 2,5,8,11-tetra-butyl-perylene as a dopant was co-deposited to form a blue light emitting layer having a thickness of 25 nm. An anthracene derivative and Liq(8-Quinolinolato lithium) were mixed at a weight ratio of 1:1 and deposited to a thickness of 30 nm on the light emitting layer to form an electron transport layer. Then, Liq was deposited to a thickness of 1 nm on the electron transport layer to form an electron injection layer. Thereafter, magnesium and silver were mixed at a weight ratio of 9:1 and then deposited to a thickness of 15 nm on the electron injection layer to form a cathode. Subsequently, N4,N4'-bis[4-[bis(3-methylphenyl)amino]phenyl]-N4,N4'-diphenyl-[1,1'-biphenyl]-4,4'-diamine (DNTPD) was deposited to a thickness of 60 nm on the cathode to form a capping layer. A seal cap containing a moisture absorbent was bonded on the capping layer using a UV-curable adhesive, thereby manufacturing an organic light emitting element.

Examples 2 to 10

Organic light emitting elements were manufactured in the same manner as in Example 1 except for using Compounds 2 to 10 synthesized in respective Synthesis Embodiment 2 to 10 as an electron blocking layer instead of using Compound 1.

Comparative Example 1 and Comparative Example 2

Organic light emitting elements were manufactured in the same manner as in Example 1 except for using Compound A and Compound B as an electron blocking layer instead of using Compound 1.

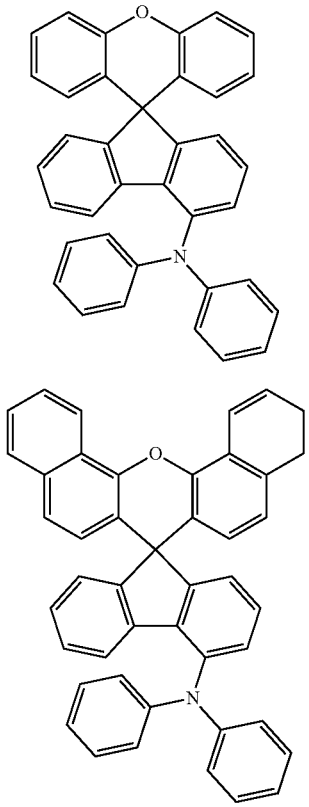

Experimental Example 1

The driving voltage, current efficiency, power efficiency and CIE color coordinates of the organic light emitting elements manufactured in Examples 1 to 10 and Comparative Examples 1 and 2 were measured. The driving voltage, current efficiency, power efficiency and CIE color coordinates 5 were measured at 10 mA/cm² using an electric-optical characteristic analyzer. The results are shown in Table 1 below.

TABLE 1

| | Electron blocking layer | Driving voltage (V) | Current efficiency (Cd/A) | Power efficiency (lm/W) | CIEx | CIEy |
|---|---|---|---|---|---|---|
| Example 1 | Compound 1 | 3.83 | 6.5 | 5.3 | 0.138 | 0.051 |
| Example 2 | Compound 2 | 3.79 | 6.3 | 5.2 | 0.138 | 0.050 |
| Example 3 | Compound 3 | 3.73 | 6.0 | 5.0 | 0.138 | 0.052 |
| Example 4 | Compound 4 | 3.71 | 5.8 | 4.9 | 0.139 | 0.048 |
| Example 5 | Compound 5 | 3.73 | 6.5 | 5.4 | 0.138 | 0.051 |
| Example 6 | Compound 6 | 3.99 | 6.3 | 5.0 | 0.138 | 0.050 |
| Example 7 | Compound 7 | 3.97 | 6.3 | 5.0 | 0.140 | 0.047 |
| Example 8 | Compound 8 | 3.92 | 6.3 | 5.0 | 0.140 | 0.046 |
| Example 9 | Compound 9 | 3.74 | 6.1 | 5.1 | 0.139 | 0.047 |
| Example 10 | Compound 10 | 3.74 | 6.3 | 5.3 | 0.139 | 0.047 |
| Comparative Example1 | Compound A | 4.05 | 4.7 | 3.7 | 0.137 | 0.048 |
| Comparative Example2 | Compound B | 4.10 | 4.0 | 3.1 | 0.138 | 0.047 |

As shown in Table 1 above, it can be seen that Examples 1 to 10 adopting Compounds 1 to 10 as an electron blocking layer according to an exemplary embodiment of the present disclosure have a lower driving voltage and higher current efficiency and power efficiency than Comparative Examples 1 and 2. Also, it can be seen that Examples 1 to 10 show blue color coordinates equivalent to those of Comparative Examples 1 and 2. Therefore, it can be seen that when Compounds 1 to 10 are used as an electron blocking layer, they do not influence the luminescent properties of an organic light emitting element.

Example 11

An anode made of ITO (10 nm) was formed on a substrate including an Ag alloy layer as a light reflecting layer thereon and surface-treated by irradiating N2 plasma or UV-ozone thereto. Then, 1,4,5,8,9,11-hexaazatriphenylenehexacarbonitrile (HATCN) was deposited to a thickness of 10 nm on the ITO to form a hole injection layer. Thereafter, Compound 11 prepared in Synthesis Embodiment 11 was deposited to a thickness of 100 nm on the hole injection layer to form a hole transport layer. Subsequently, N-phenyl-N-(4-(spiro[benzo[de]anthracene-7,9'-fluoren]-2'-yl)phenyl) dibenzo[b,d]furan-4-amine was deposited to a thickness of 10 nm on the hole transport layer to form an electron blocking layer. Then, while 9-(1-naphthyl)-10-(2-naphthyl)anthracene (α,β-ADN) was deposited on the electron blocking layer, N1,N1,N6,N6-tetrakis(4-(1-silyl)phenyl)pyrene-1,6-diamine as a dopant was co-deposited to form a blue light emitting layer having a thickness of 25 nm. Thereafter, 2-(4-(9,10-di(naphthalene-2-yl) anthracene-2-yl)phenyl)-1-phenyl-1H-benzo[d]imidazole and Liq were mixed at a weight ratio of 1:1 and deposited to a thickness of 36 nm on the light emitting layer to form an electron transport layer. Subsequently, magnesium and silver were mixed at a weight ratio of 9:1 and then deposited to a thickness of 16 nm on the electron transport layer to form a cathode. Then, N4,N4'-diphenyl-N4,N4'-bis(4-(9-phenyl-9H-carbazol-3-yl)phenyl-[1,1'-biphenyl]-4,4'-diamine was deposited to a thickness of 60 nm on the cathode to form a capping layer. A seal cap containing a moisture absorbent was bonded on the capping layer using a UV-curable adhesive, thereby manufacturing an organic light emitting element.

Examples 12 to 20

Organic light emitting elements were manufactured in the same manner as in Example 11 except for using Compounds 12 to synthesized in respective Synthesis Embodiment 12 to 20 as a hole transport layer instead of using Compound 11.

Comparative Example 3 and Comparative Example 4

Organic light emitting elements were manufactured in the same manner as in Example 11 except for using Compound C and Compound D as a hole transport layer instead of using Compound 11.

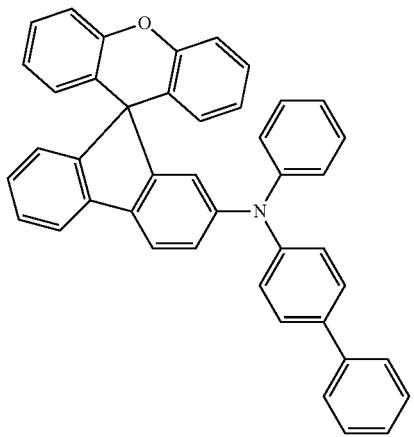

C

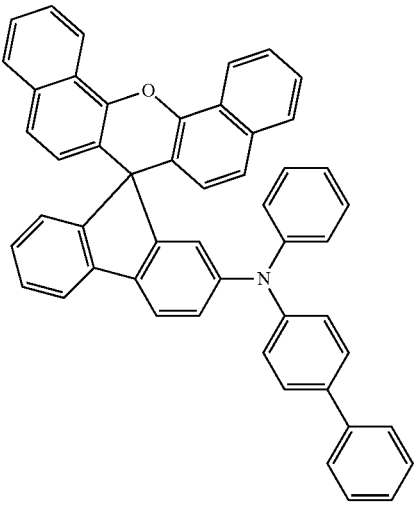

D

Experimental Example 2

The driving voltage, current efficiency, power efficiency and CIE color coordinates of the organic light emitting elements manufactured in Examples 11 to 20 and Comparative Examples 3 and 4 were measured. The driving voltage, current efficiency, power efficiency and CIE color coordinates were measured at 10 mA/cm$^2$ using an electric-optical characteristic analyzer. The results are shown in Table 2 below.

TABLE 2

| | Hole transport layer | Driving voltage (V) | Current efficiency (Cd/A) | Power efficiency (lm/W) | CIEx | CIEy |
|---|---|---|---|---|---|---|
| Example 11 | Compound 11 | 3.88 | 6.7 | 5.4 | 0.139 | 0.046 |
| Example 12 | Compound 12 | 3.82 | 6.7 | 5.5 | 0.138 | 0.047 |
| Example 13 | Compound 13 | 3.72 | 7.5 | 6.4 | 0.135 | 0.057 |
| Example 14 | Compound 14 | 3.70 | 7.1 | 6.0 | 0.137 | 0.053 |
| Example 15 | Compound 15 | 3.74 | 7.1 | 5.9 | 0.138 | 0.050 |
| Example 16 | Compound 16 | 3.73 | 7.1 | 6.0 | 0.138 | 0.051 |
| Example 17 | Compound 17 | 3.68 | 6.7 | 5.6 | 0.138 | 0.050 |
| Example 18 | Compound 18 | 3.76 | 7.0 | 5.9 | 0.137 | 0.052 |
| Example 19 | Compound 19 | 3.71 | 6.9 | 549 | 0.137 | 0.052 |
| Example 20 | Compound 20 | 3.73 | 7.0 | 5.9 | 0.138 | 0.051 |
| Comparative Example3 | Compound C | 3.98 | 6.3 | 5.0 | 0.137 | 0.053 |
| Comparative Example4 | Compound D | 3.96 | 6.5 | 4.9 | 0.137 | 0.052 |

As shown in Table 2 above, it can be seen that Examples 11 to 20 adopting Compounds 11 to 20 as a hole transport layer according to an exemplary embodiment of the present disclosure have a lower driving voltage and higher current efficiency and power efficiency than Comparative Examples 3 and 4. Also, it can be seen that Examples 11 to 20 show blue color coordinates equivalent to those of Comparative Examples 3 and 4. Therefore, it can be seen that when Compounds 11 to 20 are used as a hole transport layer, they do not influence the luminescent properties of an organic light emitting element.

As shown in the results of Experimental Examples 1 and 2, if the organic compound represented by Chemical Formula 1 of the present disclosure is used in an hole transport layer or an electron blocking layer among organic layers of an organic light emitting element, it may lower driving voltage and improve current efficiency and power efficiency without influencing the luminescent properties of the organic light emitting element. Accordingly, it is possible to provide an organic light emitting element with high luminous efficiency and long lifetime.

The exemplary embodiments of the present disclosure can also be described as follows:

According to an aspect of the present disclosure, an organic compound represented by the following Chemical Formula 1:

[Chemical Formula 1]

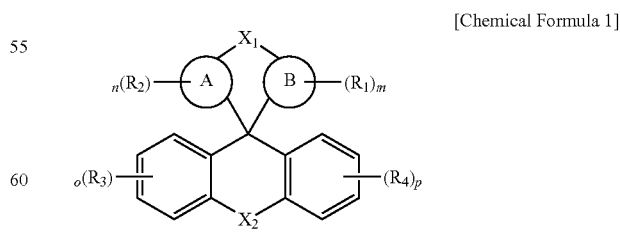

wherein in the above Chemical Formula 1,
a ring A and a ring B are different from each other and each independently substituted or unsubstituted $C_6$-$C_{10}$ arylene groups, $X_1$ and $X_2$ are the same as or different from each other, and each independently selected from the group consisting of a single bond, $C(R_5)(R_6)$, O and S, and at least one of $X_1$ and $X_2$ is O or S, $R_1$, $R_2$, $R_3$ and $R_4$ are the same as or different from each other, and each independently selected from the group consisting of a functional group represented by the following Chemical Formula 2, hydrogen, deuterium, substituted or unsubstituted $C_1$-$C_{20}$ alkyl groups, substituted or unsubstituted $C_2$-$C_{20}$ alkenyl groups, substituted or unsubstituted $C_2$-$C_{24}$ alkynyl groups, substituted or unsubstituted $C_1$-$C_{20}$ alkoxy groups, substituted or unsubstituted $C_1$-$C_{20}$ alkyl amine groups, substituted or unsubstituted $C_1$-$C_{20}$ alkyl silyl groups, substituted or unsubstituted $C_1$-$C_{20}$ alkoxy silyl groups, substituted or unsubstituted $C_3$-$C_{30}$ cycloalkyl silyl groups, substituted or unsubstituted $C_5$-$C_{30}$ aryl silyl groups, substituted or unsubstituted $C_5$-$C_{30}$ aryl groups, substituted or unsubstituted $C_5$-$C_{30}$ aryl amine groups, substituted or unsubstituted $C_3$-$C_{30}$ heteroaryl groups, a halogen group, a cyano group, a carboxyl group, a carbonyl group, an amine group, a nitro group, and combinations thereof, one or two of $R_1$, $R_2$, $R_3$ and $R_4$ are the functional group represented by the following Chemical Formula 2, $R_5$ and $R_6$ are the same as or different from each other, and each independently selected from the group consisting of hydrogen, deuterium, substituted or unsubstituted $C_1$-$C_{20}$ alkyl groups, substituted or unsubstituted $C_2$-$C_{20}$ alkenyl groups, substituted or unsubstituted $C_2$-$C_{24}$ alkynyl groups, substituted or unsubstituted $C_1$-$C_{20}$ alkoxy groups, substituted or unsubstituted $C_1$-$C_{20}$ alkyl amine groups, substituted or unsubstituted $C_1$-$C_{20}$ alkyl silyl groups, substituted or unsubstituted $C_1$-$C_{20}$ alkoxy silyl groups, substituted or unsubstituted $C_3$-$C_{30}$ cycloalkyl silyl groups, substituted or unsubstituted $C_5$-$C_{30}$ aryl silyl groups, substituted or unsubstituted $C_5$-$C_{30}$ aryl groups, substituted or unsubstituted $C_5$-$C_{30}$ aryl amine groups, substituted or unsubstituted $C_3$-$C_{30}$ heteroaryl groups, a halogen group, a cyano group, a carboxyl group, a carbonyl group, an amine group, a nitro group, and combinations thereof, m and n are each independently an integer of 0 to 6, and p are each independently an integer of 0 to 4, a sum of m, n, o and p is equal to or more than 1,

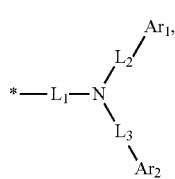

[Chemical Formula 2]

and in the above Chemical Formula 2, $L_1$, $L_2$ and $L_3$ are the same as or different from each other, and each independently selected from the group consisting of a single bond, substituted or unsubstituted $C_5$-$C_{30}$ arylene groups, substituted or unsubstituted $C_3$-$C_{30}$ heteroarylene groups, substituted or unsubstituted $C_1$-$C_{20}$ alkylene groups, substituted or unsubstituted $C_3$-$C_{20}$ cycloalkylene groups, substituted or unsubstituted $C_2$-$C_{20}$ alkenylene groups, substituted or unsubstituted $C_3$-$C_{20}$ cycloalkenylene groups, substituted or unsubstituted $C_1$-$C_{20}$ heteroalkylene groups, substituted or unsubstituted $C_3$-$C_{20}$ heterocycloalkylene groups, substituted or unsubstituted $C_2$-$C_{20}$ heteroalkenylene groups and substituted or unsubstituted $C_3$-$C_{20}$ heterocycloalkenylene groups, and $Ar_1$ and $Ar_2$ are the same as or different from each other, and each independently selected from the group consisting of substituted or unsubstituted $C_5$-$C_{30}$ aryl groups, substituted or unsubstituted $C_3$-$C_{30}$ heteroaryl groups, substituted or unsubstituted $C_3$-$C_{20}$ cycloalkyl groups, substituted or unsubstituted $C_6$-$C_{30}$ aralkyl groups, substituted or unsubstituted $C_6$-$C_{30}$ heteroaralkyl groups and substituted or unsubstituted $C_5$-$C_{30}$ arylamino groups.

In the above Chemical Formula 2, $L_1$, $L_2$ and $L_3$ may be the same as or different from each other, and each independently may be selected from a single bond, substituted or unsubstituted $C_6$-$C_{18}$ arylene groups and substituted or unsubstituted $C_3$-$C_{12}$ heteroarylene groups.

In the above Chemical Formula 2, $L_1$, $L_2$ and $L_3$ may be the same as or different from each other, and each independently may be selected from a single bond, phenylene, biphenylene, terphenylene, naphthylene, phenanthrenylene, anthracenylene and carbazolylene.

In the above Chemical Formula 2, $L_1$, $L_2$ and $L_3$ may be single bonds, and $Ar_1$ and $Ar_2$ may be connected to each other to form a hetero fused ring.

The functional group represented by the above Chemical Formula 2 may be represented by the following Chemical Formula 4:

[Chemical Formula 4]

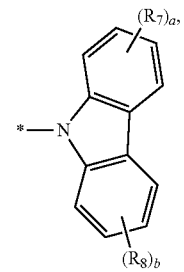

and in the above Chemical Formula 4, Ry and Re may be the same as or different from each other, and each independently may be selected from the group consisting of hydrogen, deuterium, substituted or unsubstituted $C_1$-$C_{20}$ alkyl groups, substituted or unsubstituted $C_2$-$C_{20}$ alkenyl groups, substituted or unsubstituted $C_2$-$C_{24}$ alkynyl groups, substituted or unsubstituted $C_1$-$C_{20}$ alkoxy groups, substituted or unsubstituted $C_1$-$C_{20}$ alkyl amine groups, substituted or unsubstituted $C_1$-$C_{20}$ alkyl silyl groups, substituted or unsubstituted $C_1$-$C_{20}$ alkoxy silyl groups, substituted or unsubstituted $C_3$-$C_{30}$ cycloalkyl silyl groups, substituted or unsubstituted $C_5$-$C_{30}$ aryl silyl groups, substituted or unsubstituted $C_5$-$C_{30}$ aryl groups, substituted or unsubstituted $C_5$-$C_{30}$ aryl amine groups, substituted or unsubstituted $C_3$-$C_{30}$ heteroaryl groups, a halogen group, a cyano group, a carboxyl group, a carbonyl group, an amine group, a nitro group, and combinations thereof, a and b may be each independently an integer of 0 to 4.

In the above Chemical Formula 2, Ar and $Ar_2$ may be the same as or different from each other, and each independently may be selected from substituted or unsubstituted $C_6$-$C_{30}$ aryl groups, substituted or unsubstituted $C_5$-$C_{30}$ heteroaryl groups and substituted or unsubstituted $C_3$-$C_{20}$ cycloalkyl groups.

The above Chemical Formula 2, $Ar_1$ and $Ar_2$ may be the same as or different from each other, and each independently may be selected from the group represented by the following Chemical Formulas:

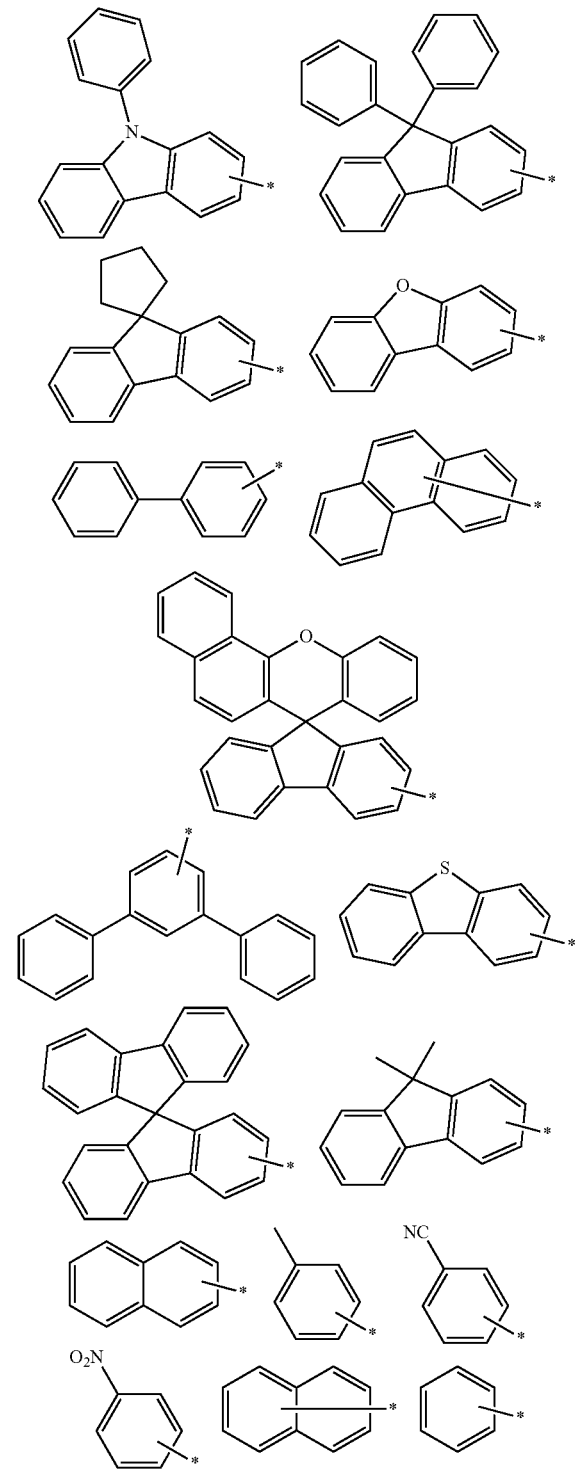

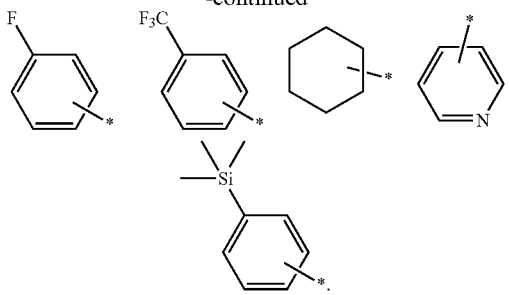

In the above Chemical Formula 1, one of $X_1$ and $X_2$ may be O or S and the other one may be a single bond.

The organic compound represented by Chemical Formula 1 may be selected from compounds represented by the following Chemical Formulas 3-1, 3-2 and 3-3:

[Chemical Formula 3-1]

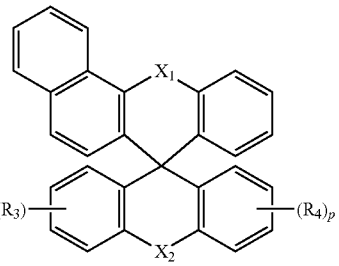

[Chemical Formula 3-2]

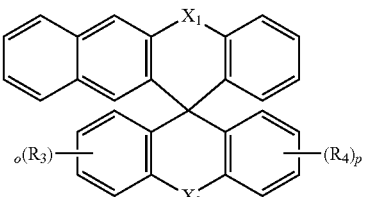

[Chemical Formula 3-3]

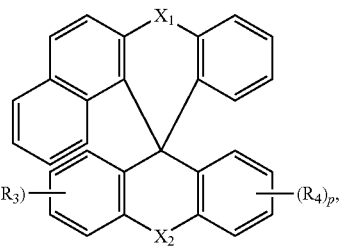

and in the above Chemical Formulas 3-1, 3-2 and 3-3, one of $X_1$ and $X_2$ may be O or s, and the other one may be selected from the group consisting of a single bond, $C(R_5)(R_6)$, O and S, at least one of $R_3$ and $R_4$ may be the functional group represented by Chemical Formula 2, and $R_3$, $R_4$, $R_5$, $R_6$, o and p may be identical to those defined in the above Chemical Formula 1.

According to an another aspect of the present disclosure, an organic light emitting display device, comprising:

a plurality of sub-pixels, wherein at least one of the plurality of sub-pixels includes an organic light emitting element including:
an anode;
a plurality of organic layers disposed on the anode; and
a cathode disposed on the organic layer, and
at least one of the plurality of organic layers contains an organic compound represented by Chemical Formula 1,

[Chemical Formula 1]

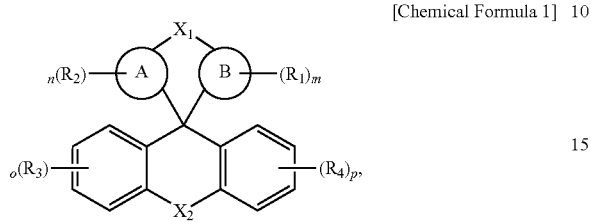

and
wherein in the above Chemical Formula 1,
a ring A and a ring B are different from each other and each independently substituted or unsubstituted $C_6$-$C_{10}$ arylene groups,
$X_1$ and $X_2$ are the same as or different from each other, and each independently selected from the group consisting of a single bond, $C(R_5)(R_6)$, O and S, and at least one of $X_1$ and $X_2$ is O or S,
$R_1$, $R_2$, $R_3$ and $R_4$ are the same as or different from each other, and each independently selected from the group consisting of a functional group represented by the following Chemical Formula 2, hydrogen, deuterium, substituted or unsubstituted $C_1$-$C_{20}$ alkyl groups, substituted or unsubstituted $C_2$-$C_{20}$ alkenyl groups, substituted or unsubstituted $C_2$-$C_{24}$ alkynyl groups, substituted or unsubstituted $C_1$-$C_{20}$ alkoxy groups, substituted or unsubstituted $C_1$-$C_{20}$ alkyl amine groups, substituted or unsubstituted $C_1$-$C_{20}$ alkyl silyl groups, substituted or unsubstituted $C_1$-$C_{20}$ alkoxy silyl groups, substituted or unsubstituted $C_3$-$C_{30}$ cycloalkyl silyl groups, substituted or unsubstituted $C_5$-$C_{30}$ aryl silyl groups, substituted or unsubstituted. $C_5$-$C_{30}$ aryl groups, substituted or unsubstituted $C_5$-$C_{30}$ aryl amine groups, substituted or unsubstituted $C_3$-$C_{30}$ heteroaryl groups, a halogen group, a cyano group, a carboxyl group, a carbonyl group, an amine group, a nitro group, and combinations thereof,
one or two of $R_1$, $R_2$, $R_3$ and $R_4$ are the functional group represented by the following Chemical Formula 2,
$R_5$ and $R_6$ are the same as or different from each other, and each independently selected from the group consisting of hydrogen, deuterium, substituted or unsubstituted $C_1$-$C_{20}$ alkyl groups, substituted or unsubstituted $C_2$-$C_{20}$ alkenyl groups, substituted or unsubstituted $C_2$-$C_{24}$ alkynyl groups, substituted or unsubstituted $C_1$-$C_{20}$ alkoxy groups, substituted or unsubstituted $C_1$-$C_{20}$ alkyl amine groups, substituted or unsubstituted $C_1$-$C_{20}$ alkyl silyl groups, substituted or unsubstituted $C_1$-$C_{20}$ alkoxy silyl groups, substituted or unsubstituted $C_3$-$C_{30}$ cycloalkyl silyl groups, substituted or unsubstituted $C_5$-$C_{30}$ aryl silyl groups, substituted or unsubstituted $C_5$-$C_{30}$ aryl groups, substituted or unsubstituted $C_5$-$C_{30}$ aryl amine groups, substituted or unsubstituted $C_3$-$C_{30}$ heteroaryl groups, a halogen group, a cyano group, a carboxyl group, a carbonyl group, an amine group, a nitro group, and combinations thereof,
m and n are each independently an integer of 0 to 6,
and p are each independently an integer of 0 to 4,
a sum of m, n, o and p is equal to or more than 1,

[Chemical Formula 2]

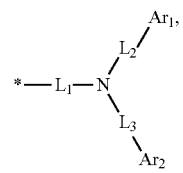

and
in the above Chemical Formula 2,
$L_1$, $L_2$ and La are the same as or different from each other, and each independently selected from the group consisting of a single bond, substituted or unsubstituted $C_5$-$C_{30}$ arylene groups, substituted or unsubstituted $C_3$-$C_{30}$ heteroarylene groups, substituted or unsubstituted $C_1$-$C_{20}$ alkylene groups, substituted or unsubstituted $C_3$-$C_{20}$ cycloalkylene groups, substituted or unsubstituted $C_2$-$C_{20}$ alkenylene groups, substituted or unsubstituted $C_3$-$C_{20}$ cycloalkenylene groups, substituted or unsubstituted $C_1$-$C_{20}$ heteroalkylene groups, substituted or unsubstituted $C_3$-$C_{20}$ heterocycloalkylene groups, substituted or unsubstituted $C_2$-$C_{20}$ heteroalkenylene groups and substituted or unsubstituted $C_3$-$C_{20}$ heterocycloalkenylene groups, and
$Ar_1$ and $Ar_2$ are the same as or different from each other, and each independently selected from the group consisting of substituted or unsubstituted $C_5$-$C_{30}$ aryl groups, substituted or unsubstituted $C_3$-$C_{30}$ heteroaryl groups, substituted or unsubstituted $C_3$-$C_{20}$ cycloalkyl groups, substituted or unsubstituted $C_6$-$C_{30}$ aralkyl groups, substituted or unsubstituted $C_6$-$C_{30}$ heteroaralkyl groups and substituted or unsubstituted $C_5$-$C_{30}$ arylamino groups.

The plurality of organic layers may include a hole transport layer disposed on the anode and a light emitting layer disposed on the hole transport layer, and the hole transport layer may contain the organic compound represented by Chemical Formula 1.

The plurality of organic layers may include a hole transport layer disposed on the anode, an electron blocking layer disposed on the hole transport layer, and a light emitting layer disposed on the electron blocking layer, and the electron blocking layer may contain the organic compound represented by Chemical Formula 1.

It will be apparent to those skilled in the art that various modifications and variations can be made in the present disclosure without departing from the technical idea or scope of the disclosure. Thus, it is intended that the present disclosure cover the modifications and variations of this disclosure provided they come within the scope of the appended claims and their equivalents.

What is claimed is:

1. An organic compound selected from compounds represented by the following Chemical Formulas 3-1, 3-2 and 3-3:

[Chemical Formula 3-1]

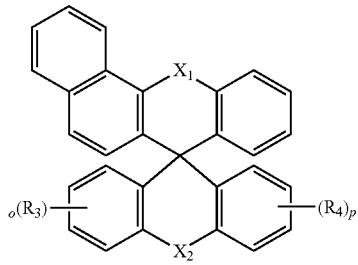

[Chemical Formula 3-2]

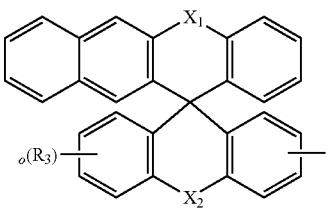

[Chemical Formula 3-3]

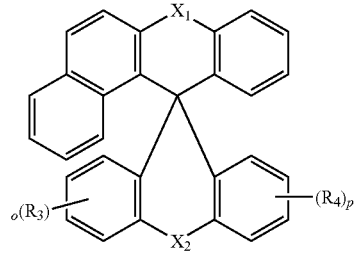

wherein in the above Chemical Formulas 3-1, 3-2 and 3-3, $X_1$ and $X_2$ are the same as or different from each other, and each independently selected from the group consisting of a single bond, $C(R_5)(R_6)$, O and S, and one of $X_1$ and $X_2$ is O or S, and another of $X_1$ and $X_2$ is a single bond or $C(R_5)(R_6)$, $R_3$ and $R_4$ are the same as or different from each other, and each independently selected from the group consisting of a functional group represented by the following Chemical Formula 2, hydrogen, deuterium, substituted or unsubstituted $C_1$-$C_{20}$ alkyl groups, substituted or unsubstituted $C_2$-$C_{20}$ alkenyl groups, substituted or unsubstituted $C_2$-$C_{24}$ alkynyl groups, substituted or unsubstituted $C_1$-$C_{20}$ alkoxy groups, substituted or unsubstituted $C_1$-$C_{20}$ alkyl amine groups, substituted or unsubstituted $C_1$-$C_{20}$ alkyl silyl groups, substituted or unsubstituted $C_1$-$C_{20}$ alkoxy silyl groups, substituted or unsubstituted $C_3$-$C_{30}$ cycloalkyl silyl groups, substituted or unsubstituted $C_5$-$C_{30}$ aryl silyl groups, substituted or unsubstituted $C_5$-$C_{30}$ aryl groups, substituted or unsubstituted $C_5$-$C_{30}$ aryl amine groups, substituted or unsubstituted $C_3$-$C_{30}$ heteroaryl groups, a halogen group, a cyano group, a carboxyl group, a carbonyl group, an amine group, and a nitro group, one or two of $R_3$ and $R_4$ are the functional group represented by the following Chemical Formula 2, $R_5$ and $R_6$ are the same as or different from each other, and each independently selected from the group consisting of hydrogen, deuterium, substituted or unsubstituted $C_1$-$C_{20}$ alkyl groups, substituted or unsubstituted $C_2$-$C_{20}$ alkenyl groups, substituted or unsubstituted $C_2$-$C_{24}$ alkynyl groups, substituted or unsubstituted $C_1$-$C_{20}$ alkoxy groups, substituted or unsubstituted $C_1$-$C_{20}$ alkyl amine groups, substituted or unsubstituted $C_1$-$C_{20}$ alkyl silyl groups, substituted or unsubstituted $C_1$-$C_{20}$ alkoxy silyl groups, substituted or unsubstituted $C_3$-$C_{30}$ cycloalkyl silyl groups, substituted or unsubstituted $C_5$-$C_{30}$ aryl silyl groups, substituted or unsubstituted $C_5$-$C_{30}$ aryl groups, substituted or unsubstituted $C_5$-$C_{30}$ aryl amine groups, substituted or unsubstituted $C_3$-$C_{30}$ heteroaryl groups, a halogen group, a cyano group, a carboxyl group, a carbonyl group, an amine group, and a nitro group, o and p are each independently an integer of 0 to 4, a sum of o and p is equal to or more than 1,

[Chemical Formula 2]

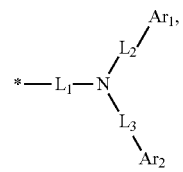

and in the above Chemical Formula 2, $L_1$, $L_2$ and $L_3$ are the same as or different from each other, and each independently selected from the group consisting of a single bond, substituted or unsubstituted $C_5$-$C_{30}$ arylene groups, substituted or unsubstituted $C_3$-$C_{30}$ heteroarylene groups, substituted or unsubstituted $C_1$-$C_{20}$ alkylene groups, substituted or unsubstituted $C_3$-$C_{20}$ cycloalkylene groups, substituted or unsubstituted $C_2$-$C_{20}$ alkenylene groups, substituted or unsubstituted $C_3$-$C_{20}$ cycloalkenylene groups, substituted or unsubstituted $C_1$-$C_{20}$ heteroalkylene groups, substituted or unsubstituted $C_3$-$C_{20}$ heterocycloalkylene groups, substituted or unsubstituted $C_2$-$C_{20}$ heteroalkenylene groups and substituted or unsubstituted $C_3$-$C_{20}$ heterocycloalkenylene groups, and $Ar_1$ and $Ar_2$ are the same as or different from each other, and each independently selected from the group represented by the following Chemical Formulas:

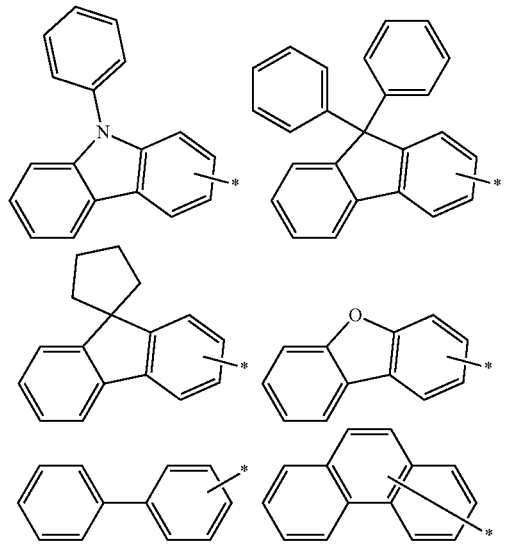

-continued

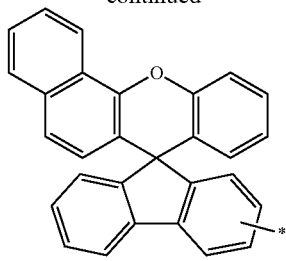

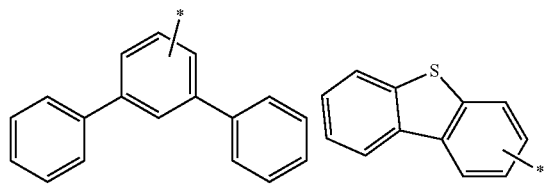

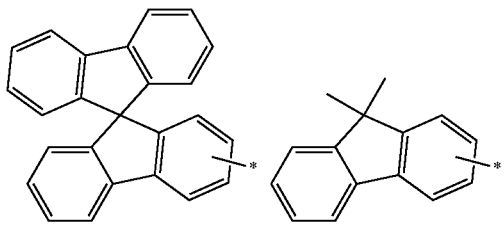

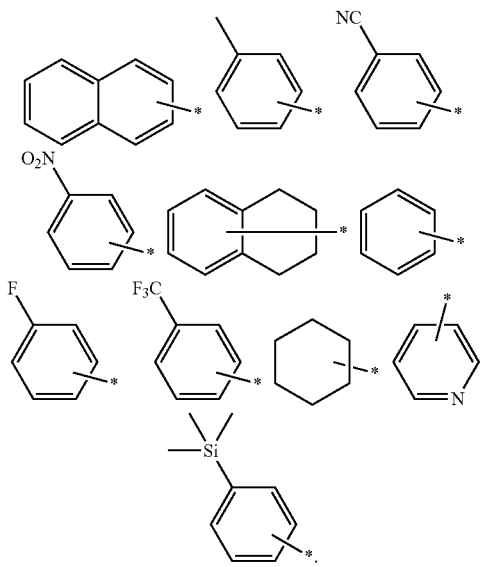

2. The organic compound according to claim 1, wherein in the above Chemical Formula 2, $L_1$, $L_2$ and $L_3$ are the same as or different from each other, and each independently selected from a single bond, substituted or unsubstituted $C_6$-$C_{18}$ arylene groups and substituted or unsubstituted $C_3$-$C_{12}$ heteroarylene groups.

3. The organic compound according to claim 1, wherein in the above Chemical Formula 2, $L_1$, $L_2$ and $L_3$ are the same as or different from each other, and each independently selected from a single bond, phenylene, biphenylene, terphenylene, naphthylene, phenanthrenylene, anthracenylene and carbazolylene.

4. An organic compound represented by the following Chemical Formula 1:

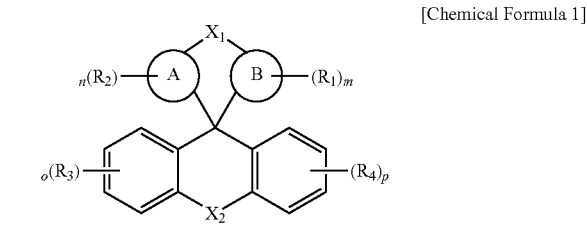

[Chemical Formula 1]

wherein in the above Chemical Formula 1, a ring A and a ring B are different from each other and each independently substituted or unsubstituted $C_6$-$C_{10}$ arylene groups, $X_1$ and $X_2$ are the same as or different from each other, and each independently selected from the group consisting of a single bond, $C(R_5)(R_6)$, O and S, and at least one of $X_1$ and $X_2$ is O or S, and another of $X_1$ and $X_2$ is a single bond or $C(R_5)(R_6)$, $R_1$, $R_2$, $R_3$ and $R_4$ are the same as or different from each other, and each independently selected from the group consisting of a functional group represented by the following Chemical Formula 2, hydrogen, deuterium, substituted or unsubstituted $C_1$-$C_{20}$ alkyl groups, substituted or unsubstituted $C_2$-$C_{20}$ alkenyl groups, substituted or unsubstituted $C_2$-$C_{24}$ alkynyl groups, substituted or unsubstituted $C_1$-$C_{20}$ alkoxy groups, substituted or unsubstituted $C_1$-$C_{20}$ alkyl amine groups, substituted or unsubstituted $C_1$-$C_{20}$ alkyl silyl groups, substituted or unsubstituted $C_1$-$C_{20}$ alkoxy silyl groups, substituted or unsubstituted $C_3$-$C_{30}$ cycloalkyl silyl groups, substituted or unsubstituted $C_5$-$C_{30}$ aryl silyl groups, substituted or unsubstituted $C_5$-$C_{30}$ aryl groups, substituted or unsubstituted $C_5$-$C_{30}$ aryl amine groups, substituted or unsubstituted $C_3$-$C_{30}$ heteroaryl groups, a halogen group, a cyano group, a carboxyl group, a carbonyl group, an amine group, and a nitro group, one or two of $R_1$, $R_2$, $R_3$ and $R_4$ are the functional group represented by the following Chemical Formula 2, $R_5$ and $R_6$ are the same as or different from each other, and each independently selected from the group consisting of hydrogen, deuterium, substituted or unsubstituted $C_1$-$C_{20}$ alkyl groups, substituted or unsubstituted $C_2$-$C_{20}$ alkenyl groups, substituted or unsubstituted $C_2$-$C_{24}$ alkynyl groups, substituted or unsubstituted $C_1$-$C_{20}$ alkoxy groups, substituted or unsubstituted $C_1$-$C_{20}$ alkyl amine groups, substituted or unsubstituted $C_1$-$C_{20}$ alkyl silyl groups, substituted or unsubstituted $C_1$-$C_{20}$ alkoxy silyl groups, substituted or unsubstituted $C_3$-$C_{30}$ cycloalkyl silyl groups, substituted or unsubstituted $C_5$-$C_{30}$ aryl silyl groups, substituted or unsubstituted $C_5$-$C_{30}$ aryl groups, substituted or unsubstituted $C_5$-$C_{30}$ aryl amine groups, substituted or unsubstituted $C_3$-$C_{30}$ heteroaryl groups, a halogen group, a cyano group, a carboxyl group, a carbonyl group, an amine group, and a nitro group, m and n are each independently an integer of 0 to 6, o and p are each independently an integer of 0 to 4, a sum of m, n, o and p is equal to or more than 1,

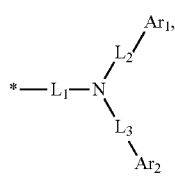

and in the above Chemical Formula 2,

Ar$_1$ and Ar$_2$ are the same as or different from each other, and each independently selected from the group consisting of substituted or unsubstituted C$_5$-C$_{30}$ aryl groups, substituted or unsubstituted C$_3$-C$_{30}$ heteroaryl groups, substituted or unsubstituted C$_3$-C$_{20}$ cycloalkyl groups, substituted or unsubstituted C$_6$-C$_{30}$ aralkyl groups, substituted or unsubstituted C$_6$-C$_{30}$ heteroaralkyl groups and substituted or unsubstituted C$_5$-C$_{30}$ arylamino groups, and L$_1$, L$_2$ and L$_3$ are single bonds, and Ar$_1$ and Ar$_2$ are connected to each other to form a hetero fused ring.

5. The organic compound according to claim 4, wherein the functional group represented by the above Chemical Formula 2 is represented by the following Chemical Formula 4:

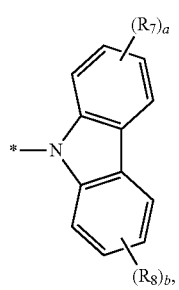

and in the above Chemical Formula 4, R$_7$ and R$_8$ are the same as or different from each other, and each independently selected from the group consisting of hydrogen, deuterium, substituted or unsubstituted C$_1$-C$_{20}$ alkyl groups, substituted or unsubstituted C$_2$-C$_{20}$ alkenyl groups, substituted or unsubstituted C$_2$-C$_{24}$ alkynyl groups, substituted or unsubstituted C$_1$-C$_{20}$ alkoxy groups, substituted or unsubstituted C$_1$-C$_{20}$ alkyl amine groups, substituted or unsubstituted C$_1$-C$_{20}$ alkyl silyl groups, substituted or unsubstituted C$_1$-C$_{20}$ alkoxy silyl groups, substituted or unsubstituted C$_3$-C$_{30}$ cycloalkyl silyl groups, substituted or unsubstituted C$_5$-C$_{30}$ aryl silyl groups, substituted or unsubstituted C$_5$-C$_{30}$ aryl groups, substituted or unsubstituted C$_5$-C$_{30}$ aryl amine groups, substituted or unsubstituted C$_3$-C$_{30}$ heteroaryl groups, a halogen group, a cyano group, a carboxyl group, a carbonyl group, an amine group, and a nitro group, and a and b are each independently an integer of 0 to 4.

6. The organic compound according to claim 4, wherein in the above Chemical Formula 2, Ar$_1$ and Ar$_2$ are the same as or different from each other, and each independently selected from substituted or unsubstituted C$_6$-C$_{30}$ aryl groups, substituted or unsubstituted C$_5$-C$_{30}$ heteroaryl groups and substituted or unsubstituted C$_3$-C$_{20}$ cycloalkyl groups.

7. The organic compound according to claim 4, wherein in the above Chemical Formula 1, one of X$_1$ and X$_2$ is O or S and the other one is a single bond.

8. The organic compound according to claim 4, wherein the organic compound represented by Chemical Formula 1 is selected from compounds represented by the following Chemical Formulas 3-1, 3-2 and 3-3:

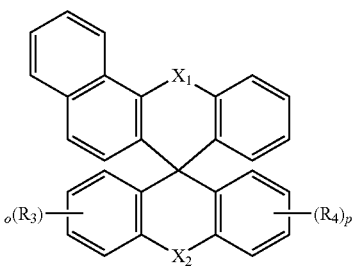

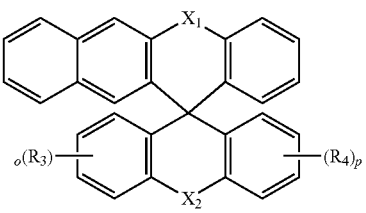

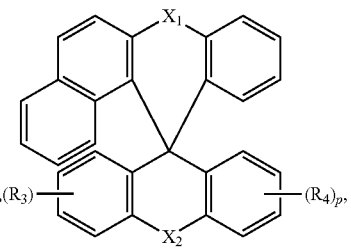

and in the above Chemical Formulas 3-1, 3-2 and 3-3, at least one of R$_3$ and R$_4$ is the functional group represented by Chemical Formula 2, and X$_1$, X$_2$, R$_3$, R$_4$, R$_5$, R$_6$, o and p are identical to those defined in the above Chemical Formula 1.

9. An organic light emitting display device, comprising:

a plurality of sub-pixels, wherein at least one of the plurality of sub-pixels includes an organic light emitting element including:

an anode;

a plurality of organic layers disposed on the anode; and a cathode disposed on the plurality of organic layers, wherein at least one of the plurality of organic layers contains the organic compound according to claim 1.

10. The organic light emitting display device according to claim 9, wherein the plurality of organic layers includes a hole transport layer disposed over the anode and a light emitting layer disposed over the hole transport layer, and the hole transport layer contains the organic compound.

11. The organic light emitting display device according to claim 9, wherein the plurality of organic layers includes a hole transport layer disposed over the anode, an electron blocking layer disposed on the hole transport layer, and a light emitting layer disposed on the electron blocking layer, and the electron blocking layer contains the organic compound.

12. An organic light emitting display device, comprising:
a plurality of sub-pixels,
wherein at least one of the plurality of sub-pixels includes an organic light emitting element including:
an anode;
a plurality of organic layers disposed on the anode; and
a cathode disposed on the plurality of organic layers, wherein
at least one of the plurality of organic layers contains an organic compound according to claim 4.

13. The organic light emitting display device according to claim 12, wherein the plurality of organic layers includes a hole transport layer disposed over the anode and a light emitting layer disposed over the hole transport layer, and
the hole transport layer contains the organic compound.

14. The organic light emitting display device according to claim 12, wherein the plurality of organic layers includes a hole transport layer disposed over the anode, an electron blocking layer disposed on the hole transport layer, and a light emitting layer disposed on the electron blocking layer, and
the electron blocking layer contains the organic compound.

15. An organic compound selected from compounds represented by the following Chemical Formulas 3-1, 3-2, and 3-3:

[Chemical Formula 3-1]

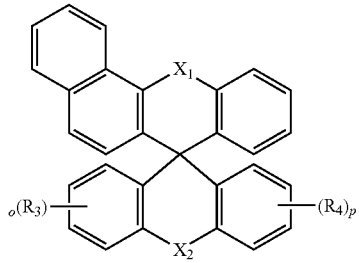

[Chemical Formula 3-2]

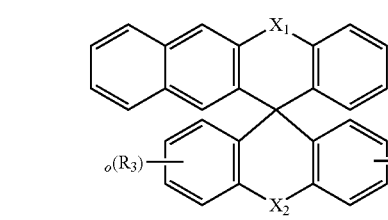

[Chemical Formula 3-3]

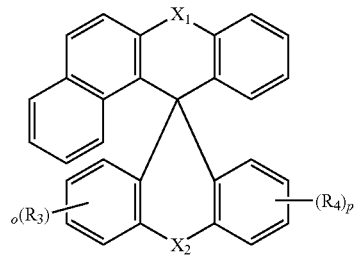

wherein in the above Chemical Formulas 3-1, 3-2, and 3-3,
$X_1$ and $X_2$ are the same as or different from each other, and each independently selected from the group consisting of a single bond, $C(R_5)(R_6)$, O, and S, and one of $X_1$ and $X_2$ is a single bond,
$R_3$ and $R_4$ are the same as or different from each other, and each independently selected from the group consisting of a functional group represented by the following Chemical Formula 2, hydrogen, deuterium, substituted or unsubstituted $C_1$-$C_{20}$ alkyl groups, substituted or unsubstituted $C_2$-$C_{20}$ alkenyl groups, substituted or unsubstituted $C_2$-$C_{24}$ alkynyl groups, substituted or unsubstituted $C_1$-$C_{20}$ alkoxy groups, substituted or unsubstituted $C_1$-$C_{20}$ alkyl amine groups, substituted or unsubstituted $C_1$-$C_{20}$ alkyl silyl groups, substituted or unsubstituted $C_1$-$C_{20}$ alkoxy silyl groups, substituted or unsubstituted $C_3$-$C_{30}$ cycloalkyl silyl groups, substituted or unsubstituted $C_5$-$C_{30}$ aryl silyl groups, substituted or unsubstituted $C_5$-$C_{30}$ aryl groups, substituted or unsubstituted $C_5$-$C_{30}$ aryl amine groups, substituted or unsubstituted $C_3$-$C_{30}$ heteroaryl groups, a halogen group, a cyano group, a carboxyl group, a carbonyl group, an amine group, and a nitro group,
one or two of $R_3$ and $R_4$ are the functional group represented by the following Chemical Formula 2,
$R_5$ and $R_6$ are the same as or different from each other, and each independently selected from the group consisting of hydrogen, deuterium, substituted or unsubstituted $C_1$-$C_{20}$ alkyl groups, substituted or unsubstituted $C_2$-$C_{20}$ alkenyl groups, substituted or unsubstituted $C_2$-$C_{24}$ alkynyl groups, substituted or unsubstituted $C_1$-$C_{20}$ alkoxy groups, substituted or unsubstituted $C_1$-$C_{20}$ alkyl amine groups, substituted or unsubstituted $C_1$-$C_{20}$ alkyl silyl groups, substituted or unsubstituted $C_1$-$C_{20}$ alkoxy silyl groups, substituted or unsubstituted $C_3$-$C_{30}$ cycloalkyl silyl groups, substituted or unsubstituted $C_5$-$C_{30}$ aryl silyl groups, substituted or unsubstituted $C_5$-$C_{30}$ aryl groups, substituted or unsubstituted $C_5$-$C_{30}$ aryl amine groups, substituted or unsubstituted $C_3$-$C_{30}$ heteroaryl groups, a halogen group, a cyano group, a carboxyl group, a carbonyl group, an amine group, and a nitro group,
o and p are each independently an integer of 0 to 4,
a sum of o and p is equal to or more than 1,

[Chemical Formula 2]

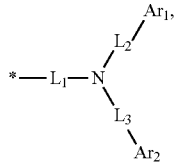

and
in the above Chemical Formula 2,
$L_1$, $L_2$ and $L_3$ are the same as or different from each other, and each independently selected from the group consisting of a single bond, substituted or unsubstituted $C_5$-$C_{30}$ arylene groups, substituted or unsubstituted $C_3$-$C_{30}$ heteroarylene groups, substituted or unsubstituted $C_1$-$C_{20}$ alkylene groups, substituted or unsubstituted $C_3$-$C_{20}$ cycloalkylene groups, substituted or unsubstituted $C_2$-$C_{20}$ alkenylene groups, substituted or unsubstituted $C_3$-$C_{20}$ cycloalkenylene groups, substituted or unsubstituted $C_1$-$C_{20}$ heteroalkylene groups, substituted or unsubstituted $C_3$-$C_{20}$ heterocycloalkylene groups, substituted or unsubstituted $C_2$-$C_{20}$ heteroalkenylene groups and substituted or unsubstituted $C_3$-$C_{20}$ heterocycloalkenylene groups, and $Ar_1$ and $Ar_2$ are the same as or different from each other, and each independently selected from the group represented by the following Chemical Formulas:

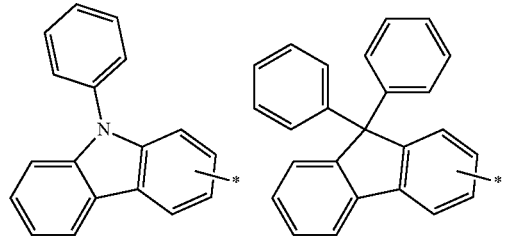

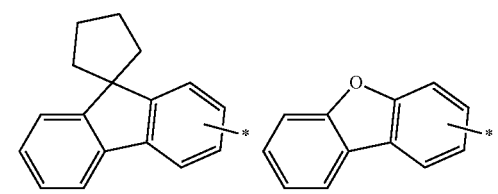

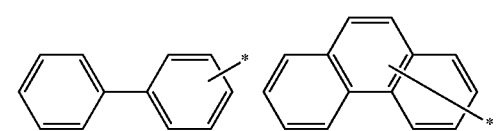

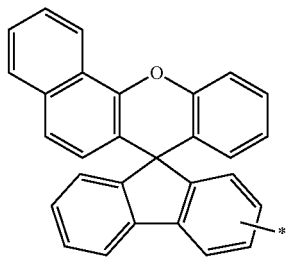

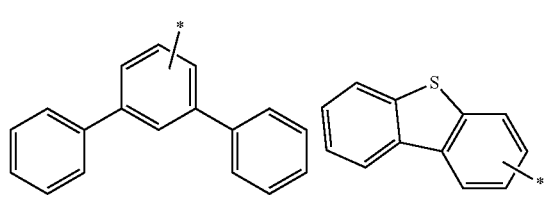

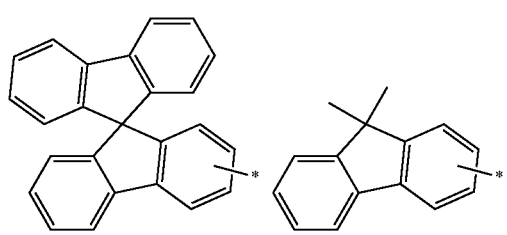

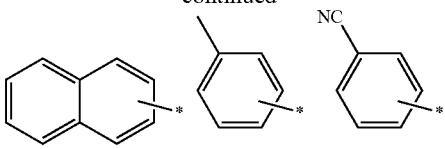

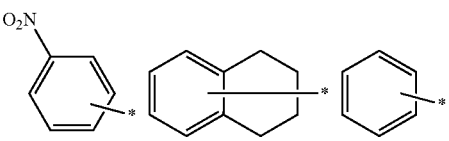

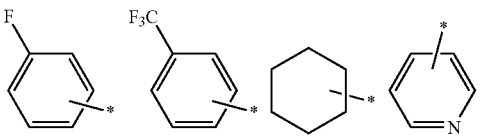

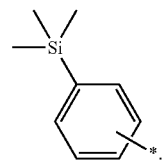

16. The organic compound according to claim 15, wherein the organic compound is represented by the Chemical Formula 3-1.

17. The organic compound according to claim 16, wherein another one of $X_1$ and $X_2$ is O or S.

18. The organic compound according to claim 16, wherein $X_1$ is O, and $R_5$ is hydrogen.

19. The organic compound according to claim 18, wherein:
    $L_1$, $L_2$ and $L_3$ are each independently a single bond or a substituted or unsubstituted $C_6$ arylene group, and
    $Ar_1$ and $Ar_2$ are each independently selected from the group represented by the following Chemical Formulas:

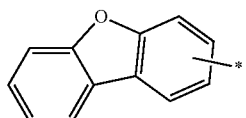

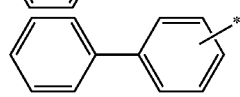

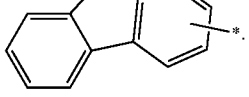

20. The organic compound according to claim 15, wherein the organic compound includes at least one selected from the following compounds:

341
1
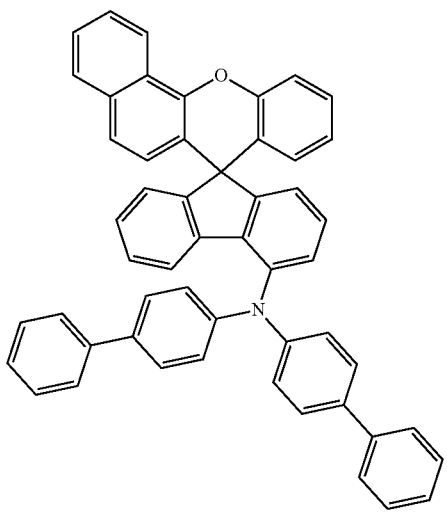
2
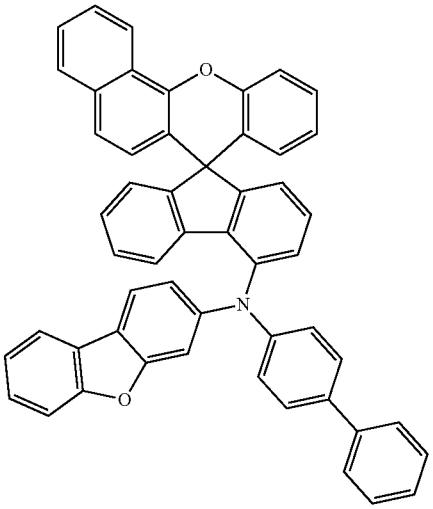
3
342
-continued
4
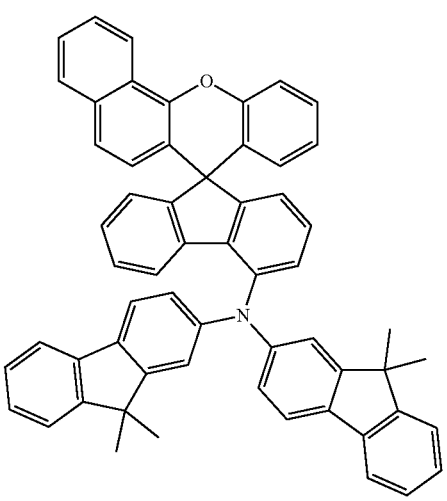
5
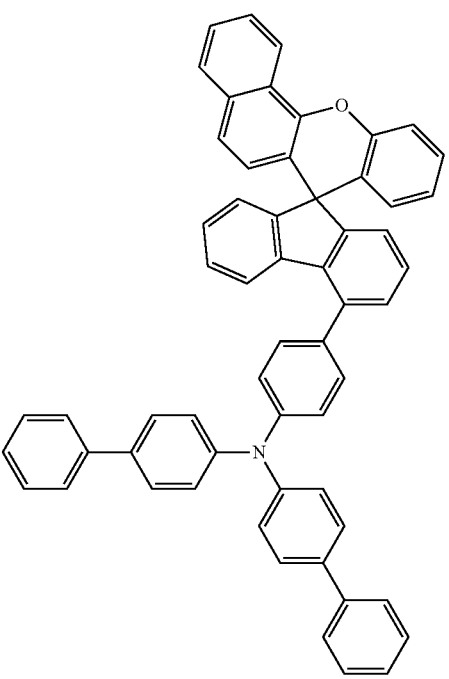
6

343
-continued
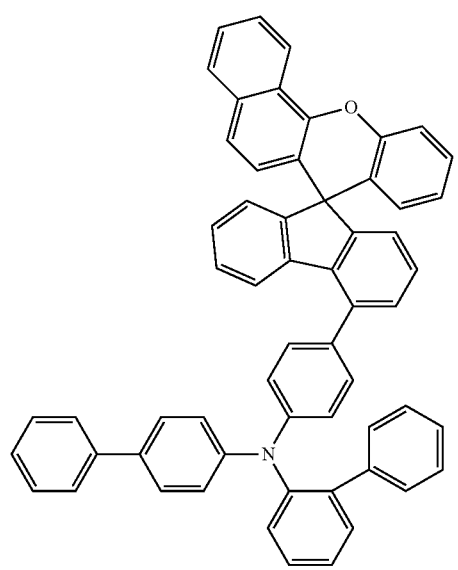
7
344
-continued
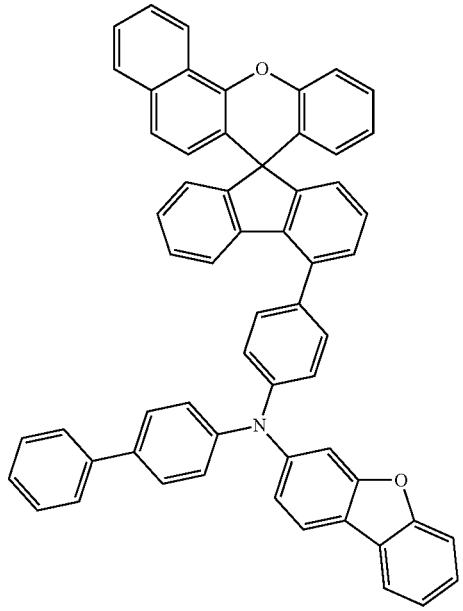
9
8
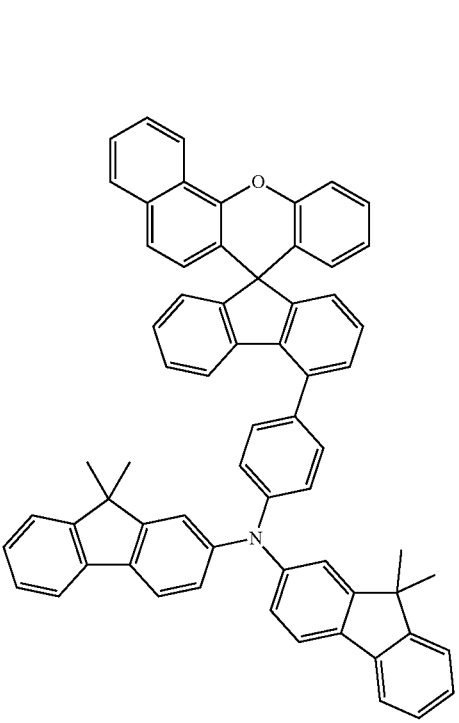
10

11
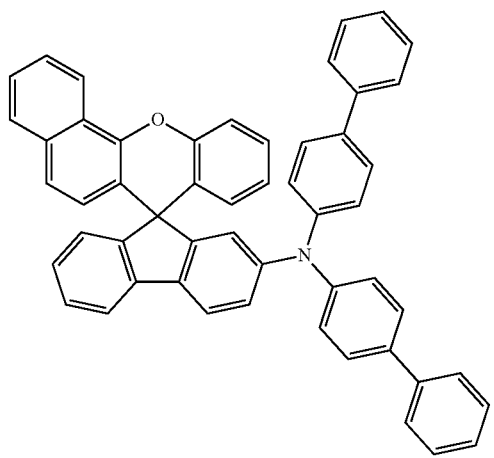
14
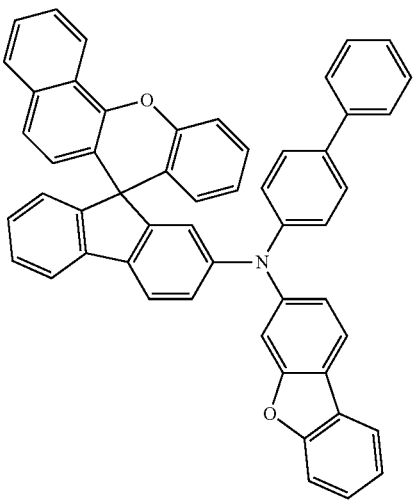
12
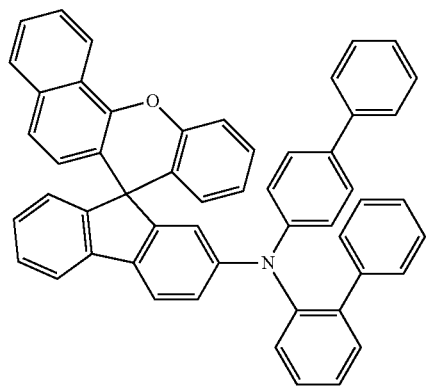
15
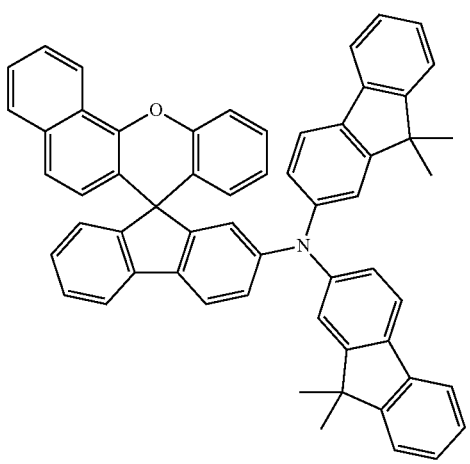
13
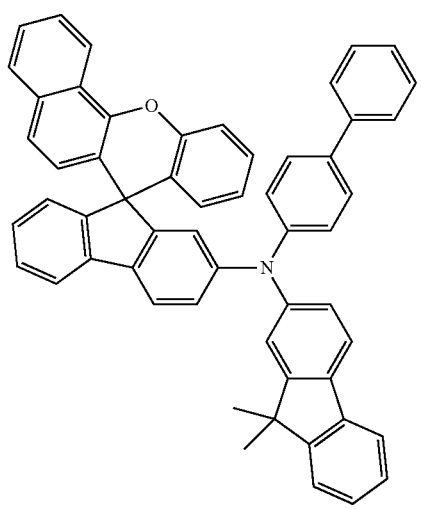
16
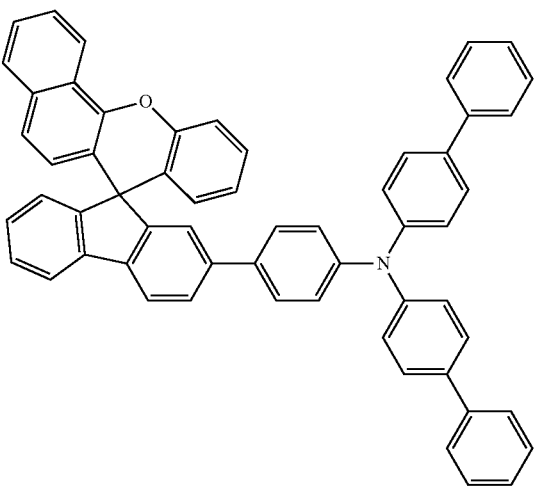

17
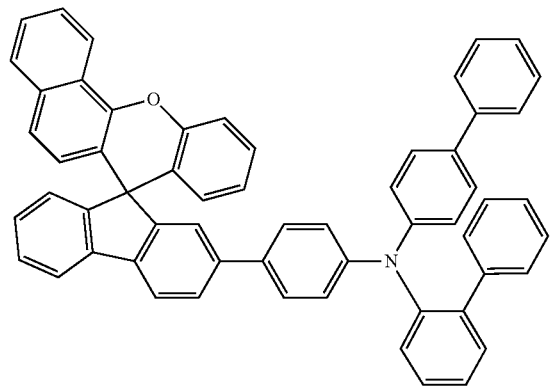
18
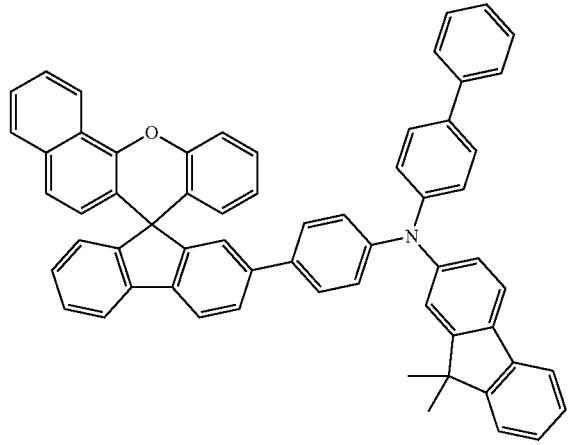
19
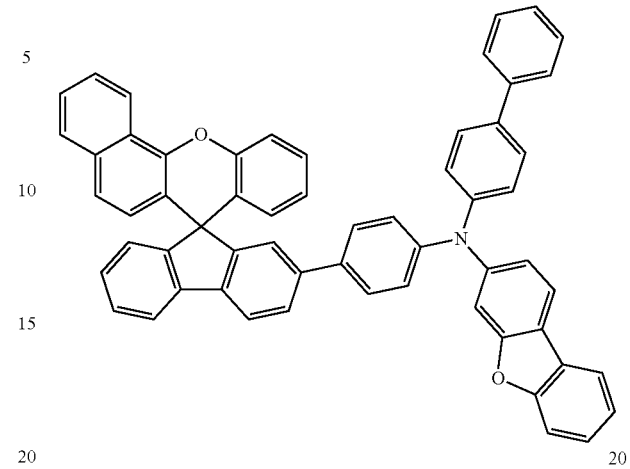
20
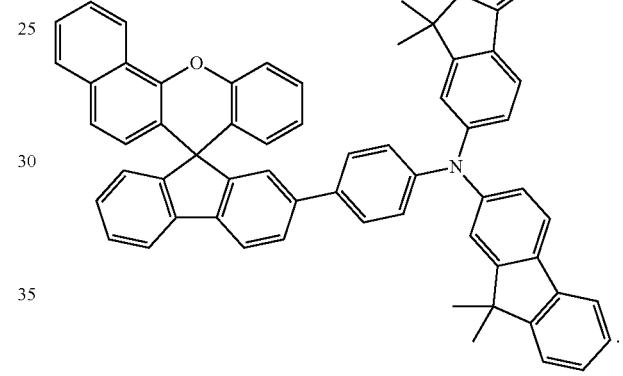
* * * * *